US005693809A

United States Patent [19]
Durette et al.

[11] Patent Number: 5,693,809
[45] Date of Patent: Dec. 2, 1997

[54] SUBSTITUTED 4-AZA-5α-ANDROSTAN-ONES AS 5α-REDUCTASE INHIBITORS

[75] Inventors: Philippe L. Durette, New Providence; William Hagmann, Westfield; Gary H. Rasmusson, Watchung; Richard L. Tolman, Warren; Ihor E. Kopka, Millburn; Soumya P. Sahoo, Old Bridge; Craig K. Esser, Belford; Nathan G. Steinberg, Clark; Donald W. Graham, Mountainside; Bruce E. Witzel, Westfield, all of N.J.

[73] Assignee: Merck & Co., Inc., Rahway, N.J.

[21] Appl. No.: 338,571

[22] Filed: May 12, 1995

Related U.S. Application Data

[63] Continuation-in-part of Ser. No. 886,537, May 20, 1992, abandoned.

[51] Int. Cl.⁶ ...................... C07D 221/02; A61K 31/435
[52] U.S. Cl. .......................... 546/77; 514/284; 546/78; 544/336; 544/405; 544/182
[58] Field of Search .................... 546/77, 78; 514/284

[56] References Cited

U.S. PATENT DOCUMENTS

| | | | |
|---|---|---|---|
| 3,264,301 | 8/1966 | Doorenboos | 546/77 |
| 3,285,918 | 11/1966 | Doorenboos et al. | |
| 4,220,775 | 9/1980 | Rasmusson et al. | 546/77 |
| 4,377,584 | 3/1983 | Rasmusson et al. | 546/77 |
| 4,596,812 | 6/1986 | Chidsey, III et al. | |
| 4,732,897 | 3/1988 | Cainelli | 546/77 |
| 4,760,071 | 7/1988 | Rasmusson et al. | 514/284 |
| 4,859,681 | 8/1989 | Rasmusson et al. | 546/77 |
| 4,882,319 | 11/1989 | Holt et al. | |
| 4,888,336 | 12/1989 | Holt et al. | 514/284 |
| 5,049,562 | 9/1991 | Rasmusson et al. | 514/284 |
| 5,110,939 | 5/1992 | Holt et al. | 546/250 |
| 5,116,983 | 5/1992 | Bhattacharya et al. | 546/77 |
| 5,215,894 | 6/1993 | Arison et al. | 546/77 |
| 5,278,159 | 1/1994 | Bakshi et al. | 546/77 |
| 5,359,071 | 10/1994 | Durette et al. | 546/77 |
| 5,378,710 | 1/1995 | Biollaz | 514/284 |
| 5,380,728 | 1/1995 | Rasmusson | 516/97 |
| 5,494,914 | 2/1996 | Labrie et al. | 514/284 |

FOREIGN PATENT DOCUMENTS

| | | |
|---|---|---|
| 970 692 | 7/1975 | Canada . |
| 0 004 949 | 10/1979 | European Pat. Off. . |
| 0 155 096 | 9/1985 | European Pat. Off. . |
| 0 200 859 | 11/1986 | European Pat. Off. . |
| 0 314 199 | 5/1989 | European Pat. Off. . |
| 0 547 687 | 6/1993 | European Pat. Off. . |
| 93/23376 | 11/1993 | WIPO . |
| 93/23419 | 11/1993 | WIPO . |
| 93/23420 | 11/1993 | WIPO . |

OTHER PUBLICATIONS

The Daily (Tuesday, May 7, 1996), "New Data on Proscar, Abbott's Hytrin Show Conflicting Results".
Wall Street Journal (Tuesday, May 7, 1996), "Study Finds Abbott's Prostate Drug is Much More Effective than Merck's", p. B4.
US News & World Report, May 20, 1996, "Zapping a problem prostate".
Stinson, "Prostate Drug Proscar Cleared for Marketing", Chem. Eng. News, Jun. 29, 1992 pp. 7–8.
Helliker, "Alopecia Sufferers Seek to Suffer Less and Not in Silence", Wall Street Journ. 7 Jun. 91, pp. A1 & A7 (1991).
Diani et al., "Hair Growth Effects of Oral Administration of Finasteride, a Steroid 5alpha–reductase Inhibitor, Alone and in Combination with Topical Minoxidil," J. Clin. & Metab. 74:345–50 (1992).
Burger, Medicinal Chemistry, 2nd Ed. Interscience, NY 1960 p. 42.
Back et al., "N–Chloroazasteroids: A Novel Class of Reactive Steroid Analogues. Preparation, Reaction with Thiols and Photochemical Conversion to Electrophilic N–Acyl Imines", J. Org. Chem., 54(8):1904–10 (1989).
Rasmusson et al., "Azasteroids as Inhibitors of Rat Prostatic 5–alpha–reductase" J. Med. Chem. 27(12):1690–1701 (1984).
Doorenbos et al., "Synthesis & Antimicrobial Properties of 17–Beta–Isopentyloxy–4–Aza–5–alpha Androstane and 4–Methyl Derivative", J. Pharm. Sci. 62(4):638–640 (1973).
Doorenbos et al., "4, 17–Alpha–Dimethyl–4–Aza–5 alpha–Androstan–17–beta–ol–Acetate & Related Azasteroids", J. Pharm. Sci. 60(8): 1234–1235 (1971).
Doorenbos et al., "Synthesis & Evaluation of Antimicrobial Properties of Amidinoaza–androstanes and Guanidinoazaandrostanes", J. Pharm. 63(4):620–622 (1974).
Rasmusson et al., "Azasteroids: Structure Activity Relationships for Inhibition of 5–alpha–reductase and of Androgen Receptor Binding", J. Med. Chem. 29(11): 2298–2315 (1986).
Brooks et al., "5–alpha–Reductase Inhibitory and Antiandrogenic Activities of some Azasteroids in the Rat", Steroids 47(1): 1–19 (1986).
Brooks et al., "Prostatic Effects Induced in Dogs by Chronic or Acute Oral Administration of 5–alpha–reductase Inhibitors", Prostate, 9(1): 65–75 (1986).
Geldof et al., "Consideration of the Use of 17Beta–N, N–Diethyl Carbamoyl–4–Methyl–4–aza–5–alpha–Androstan–3–one (4MA), a 5–alpha–Reductase Inhibitor, in Prostate Cancer Therapy", J. Cancer Res. Clin. Oncol. 118:50–55 (1992).
Rittmaster et al., "The Effects of N,N–Diethyl–4–Methyl–3–Oxo–4–Aza–5–alpha–Androstane–17beta–Carboxamide, a 5–alpha–Reductase Inhibitor and Antiandrogen, or the Development of Baldness in the Stumptail Macaque", J. Clin. Endocrin. & Metabolism 55(1): 188–193 (1987).
LaBrie et al., "Combination Therapy in Prostate Cancer", Lancet No. 8515, 1095–1096 (1986).
Metcalf eta l. "Inhibitors of Steroid 5–alpha–reductase in Benign Prostatic Hyperplasia, male Pattern Baldness & Acne" TIPS, 10:491–495 (1989).
Boyle et al., Urology, "Prostate Volume Predicts Outcome of Treatment of Benign Prostatic Hyperplasia with Finasteride: Meta–Analysis of Randomized Clinical Trials", vol. 48, No. 3, Sep. 1996, pp. 398–405.

*Primary Examiner*—Donald G. Daus
*Attorney, Agent, or Firm*—Catherine D. Fitch; Melvin Winokur

[57] ABSTRACT

Described are new 16-substituted and 7,16-disubstituted 4-aza-5α-androstan-3-ones and related compounds as 5α-reductase inhibitors.

1 Claim, No Drawings

SUBSTITUTED 4-AZA-5α-ANDROSTAN-ONES AS 5α-REDUCTASE INHIBITORS

CROSS REFERENCE TO RELATED APPLICATIONS

This application is a national phase application under 35 U.S.C. § 371 of PCT application PCT/US93/04734, filed May 18, 1993, which in turn is a continuation in part of application Ser. No. 886,547, filed May 20, 1992, now abandoned.

BACKGROUND OF THE INVENTION

The present invention is directed to new 16-substituted and 7,16-disubstituted 4-aza-5α-androstan-3-ones and related compounds and the use of such compounds as 5α-reductase inhibitors.

DESCRIPTION OF THE PRIOR ART

The art reveals that certain undesirable physiological manifestations, such as acne vulgaris, seborrhea, female hirsutism, male pattern baldness and benign prostatic hypertrophy, are the result of hyperandrogenetic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example. 4'-nitro-3'-trifluoromethylisobutyranilide. See Neri, et al., Endo., Vol. 91. No. 2 (1972). However, these products, though devoid of hormonal effects, are peripherally active, competing with the natural androgens for receptor sites, and hence have a tendency to feminize a male host or the male fetus of a female host.

It is now known in the art that the principal mediator of androgenic activity in some target organs is 5α-dihydrotestosterone, and that it is formed locally in the target organ by the action of testosterone-5α-reductase. It is also known that inhibitors of testosterone-5α-reductase will serve to prevent or lessen symptoms of hyperandrogenic stimulation.

For example, a number of 4-aza steroid compounds are known in the an which are 5α-reductase inhibitors. See U.S. Pat. Nos. 4,377,584, 4,220,775, 4,859,681, 4,760,071 (which describes the synthesis of PROSCAR®, finasteride, 17-beta-N-(t-butyl)carbamoyl-5-α-4-aza-androst-1-en-3-one) and the articles J. Med. Chem. 27, p. 1690–1701 (1984) and J. Med. Chem. 29, 2998–2315 (1986) of Rasmusson, et al., U.S. Pat. No. 4,845,104 to Carlin, et al., and U.S. Pat. No. 4,732,897 to Cainelli, et al. which describe 4-aza-17β-substituted-5α-androstan-3-ones said to be useful in the treatment of DHT-related hyperandrogenic conditions.

However, despite the suggestion in the prior an that hyperandrogenetic diseases are the result of a single 5α-reductase, there are reports regarding the presence of other 5α-reductase isozymes in both rats and humans. For example, in human prostate, Bruchovsky, et al. (See J. Clin. Endocrinol. Metab. 67, 806–816, 1988) and Hudson (see J. Steroid Biochem. 26, p 349–353, 1987) found different 5α-reductase activities in the stromal and epithelial fractions. Additionally, Moore and Wilson described two distinct human reductases with peaks of activities at either pH 5.5 or pH 7–9. (See J. Biol. Chem. 251, 19, p. 5895–5900, 1976.)

Recently, Andersson and Russell isolated a cDNA which encodes a rat liver 5α-reductase (see J. Biol. Chem. 264 pp. 16249–55 (1989). They found a single mRNA which encodes both the liver and prostatic reductases of rats. The sequence of this rat gene was later used to select a human prostatic cDNA encoding a 5α-reductase termed "5α-reductase 1". (See Proc. Nat'l. Acad. Sci. 87, p. 3640–3644, 1990.)

More recently, a second, human prostatic reductase (5α-reductase 2) has been cloned with properties identified with the more abundant form found in crude human prostatic extracts. (See Nature. 354, p. 159–161, 1991.)

Further, "Syndromes of Androgen Resistance"—The Biology of Reproduction. Vol. 46, p. 168–173 (1992) by Jean O. Wilson indicates that the 5α-reductase 1 enzyme may be associated with hair follicles.

Thus, the an supports the existence of at least two genes for 5α-reductase and two distinct isozymes of 5α-reductase in humans. Both forms are present in prostatic tissue in which 5α-reductase 2 is the more abundant, and the other isozyme, 5α-reductase 1, is believed to be more abundant in scalp tissue.

In the treatment of hyperandrogenic disease conditions. e.g. benign prostatic hyperplasia (BPH) it would be desirable to have one drug entity which is active against both enzymes 1 and 2 in the prostate to substantially inhibit dihydrotesterone (DHT) production. Alternatively, it would be desirable to have a drug entity which is highly selective for inhibiting the scalp associated enzyme 5α-reductase 1, for use in treating diseases of the skin and scalp, e.g. acne and alopecia. This latter drug could also be used in combination with PROSCAR® (finasteride) which is highly selective for the prostatic enzyme 5α-reductase 2 for combination therapy in the treatment of BPH.

SUMMARY OF THE INVENTION

The present invention discloses novel 16-substituted and 7,16-disubstituted 4-aza-5α-androstan-3-one compounds which are useful for inhibiting the 5α-reductase enzyme and isozymes thereof and are particularly effective in selectively inhibiting the 5α-reductase 1 associated with the scalp and dually inhibiting both isozymes 1 and 2 in the treatment of benign prostatic hyperplasia, acne, female hirsutism, male pattern baldness, androgenetic alopecia, prostatitis, and the treatment of prostatic carcinoma.

In accordance with the present invention there is provided novel 16-substituted and 7,16-disubstituted 4-aza-5α-androstan-3-one compounds of the general structural formula I:

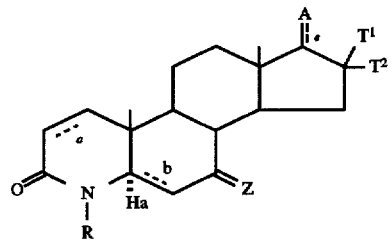

wherein

R is selected from hydrogen, methyl or ethyl; the dashed lines-a, b, e indicate double bonds which can be present, providing that if b double bond is present, then the 5α hydrogen, Ha, is not present:

$T^1$ and $T^2$ are independently selected from the following alpha and beta substituents: hydrogen, $C_1$–$C_6$ alkyl, wherein $T^1$ and $T^2$ can also be taken together to form a $C_1$–$C_6$ alkenyl radical, with the proviso that at least one of $T^1$ or $T^2$ is not hydrogen:

Z can be
1) oxo,
2) α-hydrogen and β-hydrogen or a β-substituent selected from: $C_1$–$C_4$ alkyl, $C_2$–$C_4$ alkenyl, $CH_2COOH$, hydroxy, carboxy, $COOC_1$–$C_4$ alkyl esters; $OCONR^1R^2$, where $R^1$ and $R^2$ are independently H, $C_1$–$C_4$ alkyl, phenyl, benzyl, and $R^1$ and $R^2$ together with the nitrogen can form a 5–6 membered saturated heterocyclic ring, optionally with one other heteroatom; $OC_1$–$C_4$ alkyl, $OC_3$–$C_6$ cycloalkyl, —$OCOCH_3$, halo, hydroxy $C_1$–$C_2$ alkyl, halo $C_1$–$C_2$ alkyl, trifluoromethyl, $C_3$–$C_6$ cycloalkyl;
3) =CH—R' where R' is H, $C_1$–$C_4$ alkyl;
4) spiro:

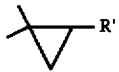

where R' is H, $C_1$–$C_4$ alkyl;

A can be:

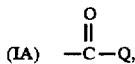

where Q is:
(1) $NR^2R^3$, where $R^3$ is independently hydrogen, methyl or ethyl; and $R^2$ is a hydrocarbon radical, selected from substituted or unsubstituted straight or branched chain alkyl, cycloalkyl, or aralkyl of from 1–12 carbons or monocyclic aryl optionally containing 1 or more lower alkyl substituents of from 1–2 carbon atoms and/or 1 or more halogen substituents with the proviso that Z, $T^1$ or $T^2$ are not beta methyl where $R^2$ is $C^1$–$C^8$ alkyl;
(2) a hydrocarbon radical, being:
 (a) a monovalent aliphatic radical selected from straight or branched chain alkyl, or cycloalkyl, of from 1–12 carbons, which can be substituted by one or more of $C_1$–$C_2$ alkyl or halo, excluding $C_1$–$C_4$ alkyl when Z, $T^1$ or $T^2$ are beta methyl;
 (b) an aralkyl radical selected from benzyl or phenethyl;
 (c) a polycyclic aromatic radical which can be substituted with one or more of: —OH, organosilyl protected —OH, —$OC_1$–$C_4$ alkyl, $C_1$–$C_4$ alkyl, halo or nitro;
 (d) a monocyclic aromatic radical which can be substituted with one or more of:
  (i) —OH, —$OC_1$–$C_4$ alkyl, $C_1$–$C_4$ alkyl, —$(CH_2)_mOH$, —$(CH_2)_nCOOH$, including organo-silyl protected hydroxy, where m is 1–4, n is 1–3, providing $C_1$–$C_4$ alkyl is only present when one of the above oxygen-containing radicals is present;
  (ii) —SH, —$SC_1$–$C_4$ alkyl, —$SOC_1$–$C_4$ alkyl, —$SO_2C_1$–$C_4$ alkyl, —$SO_2N(C_1$–$C_4$-alkyl$)_2$, —$SO_2NH(C_1$–$C_4$alkyl), $C_1$–$C_4$ alkyl-($CH_2$)$_m$SH, —S—($CH_2)_n$—O—$COCH_3$, where m is 1–4, n is 1–3, providing $C_1$–$C_4$ alkyl is only present when one of the above sulfur containing radicals is present;
  (iii) $N(R^3)_2$, which can be protected, where $R^3$ is independently H or $C_1$–$C_4$ alkyl, where the monoaryl ring can also be further substituted with $C_1$–$C_4$ alkyl; and
  (iv) heterocyclic radical selected from 2- or 3- or 4-pyridyl, 2-pyrrolyl, 2-furyl or thiophenyl; and (IIA) where:
A is —$XR^4$, or —$(CHR^1)_n$—$XR^4$;
n is 1–10;
X is —O— or —$S(O)_p$—, wherein p is zero, 1 or 2; and
$R^1$ can be the same or different when n is greater than 1 and is: —H, aryl, or —$C_{1-3}$alkyl unsubstituted or substituted with aryl;
$R^4$ is
 1) hydrogen or —$C_{1-20}$ alkyl, unsubstituted or substituted with one or more of:
  a) —OH,
  b) halo,
  c) —$C_{1-8}$ alkoxy,
  d) —$C_{1-6}$ alkenyl,
  e) —$CONR^5R^5$, wherein $R^5$ is independently
   i) —H,
   ii) —$C_{1-8}$ alkyl unsubstituted or substituted with one or more of $R^7$, aryl or heterocycle, the aryl being unsubstituted or substituted with one or more of $R^7$ or $R^9$,
   iii) aryl unsubstituted or substituted with one or more of $R^7$ or $R^9$, or
   iv) heterocycle, unsubstituted or substituted with one or more of $R^7$ or $R^9$,
  f) —$COOR^6$, wherein $R^6$ is
   i) —H,
   ii) —$C_{1-8}$ alkyl unsubstituted or substituted with one or more of $R^7$ or aryl, the aryl being unsubstituted or substituted with one or more of $R^7$ or $R^9$, or
   iii) aryl, unsubstituted or substituted with one or more of $R^7$ or $R^9$,
  g) —$S(O)_p$—$R^5$, wherein p is defined above,
  h) —$N(R^5)_2$,
  i) aryl, unsubstituted or substituted with one or more of aryl, $R^7$ or $R^9$,
  j) heterocycle, unsubstituted or substituted with one or more of $R^7$ or $R^9$,
  k) —$C_{3-10}$ cycloalkyl, such as cyclohexyl, norbornyl, or adamantyl, unsubstituted or substituted with one or more of $R^7$ or $R^9$, or
  l) —$CONR^8$—CO—$NHR^8$, wherein $R^8$ is —H, —$C_{1-8}$ alkyl, benzyl or cyclohexyl; or
 2) aryl, unsubstituted or substituted with one or more of aryl, $R^7$ or $R^9$, or
 3) heterocycle or —$C_{3-10}$ cycloalkyl, either of which is unsubstituted or substituted with one or more of $R^7$ or $R^9$;
$R^7$ is
 1) —OH,
 2) —$C_{1-3}$ alkoxy,
 3) —CN,
 4) —$COOR^6$
 5) —$C_{1-8}$alkyl-$COOR^6$
 6) —$NO_2$, or
 7) -halo; and
 8) amino, mono $C_1$–$C_4$ alkylamino, di-$C_1$–$C_4$ alkylamino;
$R^9$ is
 1) —$C_{1-8}$ alkyl, unsubstituted or substituted with one or more of aryl or $R^7$, 2) —CO—A, —$C_{1-8}$ alkyl-CO—A, —NHCO—A, or —$S(O)_p$—A, wherein p is defined above and A is
   a) —H,
   b) —$C_{1-8}$ alkyl, unsubstituted or substituted with one or more of
      i) —$R^7$, or
      ii) aryl, unsubstituted or substituted with one or more of $R^7$, or
   c) aryl, unsubstituted or substituted with one or more of $R^7$,
3) —NHCO-heterocycle,
4) —$N(R^{10})_2$ or —$CON(R^{10})_2$ wherein $R^{10}$ is independently —H, heterocycle, or —A,
5) —NHCO—$(CH_2)_q$—CO—Q, wherein q is 1–4, and Q is —$N(R^{10})_2$ or —$OR^{10}$;

(IIIA) where:
A is $$(CHR^1)_n-X-\overset{O}{\overset{\|}{C}}-R^4;$$

$R^1$ can be the same or different when n is greater than 1 and is: —H, aryl, or —$C_{1-3}$alkyl unsubstituted or substituted with aryl;
n is zero through 10;
X is —O— or —S—; and
$R^4$ is
1) hydrogen or —$C_{1-20}$ alkyl, unsubstituted or substituted with one or more of:
   a) —OH,
   b) halo,
   c) —$C_{1-8}$ alkoxy,
   d) —$C_{1-6}$ alkenyl,
   e) —$CONR^5R^5$, wherein $R^5$ is independently
      i) —H,
      ii) —$C_{1-8}$ alkyl unsubstituted or substituted with one or more of $R^7$, aryl or heterocycle, the aryl being unsubstituted or substituted with one or more of $R^7$ or $R^9$,
      iii) aryl unsubstituted or substituted with one or more of $R^7$ or $R^9$, or
      iv) heterocycle, unsubstituted or substituted with one or more of $R^7$ or $R^9$,
   f) —$COOR^6$, wherein $R^6$ is
      i) —H,
      ii) —$C_{1-8}$ alkyl unsubstituted or substituted with one or more of $R^7$ or aryl, the aryl being unsubstituted or substituted with one or more of $R^7$ or $R^9$, or
      iii) aryl unsubstituted or substituted with one or more of $R^7$ or $R^9$,
   g) —$S(O)_p$—$R^5$, wherein p is zero, 1 or 2;
   h) —$N(R^5)_2$,
   i) aryl, unsubstituted or substituted with one or more of aryl, $R^7$ or $R^9$,
   j) heterocycle, unsubstituted or substituted with one or more of $R^7$ or $R^9$,
   k) —$C_{3-10}$ cycloalkyl, such as cyclohexyl, norbornyl, or adamantyl, unsubstituted or substituted with one or more of $R^7$ or $R^9$, or
1) —$CONR^8$—CO—$NHR^8$, wherein $R^8$ is —H, —$C_{1-8}$ alkyl, benzyl or cyclohexyl,
2) aryl, unsubstituted or substituted with one or more of aryl, $R^7$ or $R^9$,
3) heterocycle or —$C_{3-10}$ cycloalkyl, either of which is unsubstituted or substituted with one or more of $R^7$ or $R^9$,
   4) —$NR^5R^5$, or
   5) —$OR^5$;
$R^7$ is
1) —OH,
2) —$C_{1-3}$ alkoxy,
3) —CN,
4) —$COOR^6$
5) —$C_{1-8}$alkyl-$COOR^6$
6) —$NO_2$, or
7) halo; and
8) amino mono $C_1$-$C_4$ alkylamino, di $C_1$-$C_4$ alkylamino;
$R^9$ is
1) —$C_{1-8}$ alkyl, unsubstituted or substituted with one or more of aryl or $R^7$,
2) —CO—A, —$C_{1-8}$ alkyl-CO—A, —NHCO—A, or —$S(O)_p$—A, wherein p is defined above and A is
   a) —H,
   b) —$C_{1-8}$ alkyl, unsubstituted or substituted with one or more of
      i) —$R^7$, or
      ii) aryl, unsubstituted or substituted with one or more of $R^7$, or
   c) aryl, unsubstituted or substituted with one or more of $R^7$,
3) —NHCO-heterocycle,
4) —$N(R^{10})_2$ or —$CON(R^{10})_2$ wherein $R^{20}$ is independently, heterocycle or —A,
5) —NHCO-$(CH_2)_q$—CO—Q, wherein q is 1–4, and Q is —$N(R^{10})_2$ or —$OR^{10}$;

with the provisos that when Z, $T^1$ or $T^2$ are beta methyl, the following are excluded:

when n is 1–12, $R^1$ is —H at each occurrence, X is —O—, and $R^4$ is —$C_{1-6}$alkyl, $R^4$ is not substituted with an unsubstituted phenyl ring;

when n is 1–12, $R^1$ is —H at each occurrence, and X is —O—, $R^4$ is not unsubstituted $C_{5-10}$cycloalkyl, unsubstituted phenyl, amino, —$C_{1-8}$alkyl substituted amino, or —$C_{1-8}$alkoxy; and when n is zero, $R^4$ is not —$CH_3$; and
(IVA) where A is:

$$\underset{R^4}{}\overset{R^2}{\underset{|}{N}}-W-R^3, \quad (a)$$

$$\underset{R^2}{}\overset{}{\underset{N}{}}W-R^3 \quad (b)$$

$$\underset{R^4}{}\overset{R^5}{\underset{|}{}}\overset{R^2}{\underset{|}{}}(CH)_kN-W-R^3; \quad (c)$$

except when Z, T1 or T2 are beta methyl and the 5αH is present, W equals C(O), and R3 cannot be C1–12 alkyl; and
$R^2$ is:
  H, methyl or ethyl;
$R^3$ is:
  H,
  mono $C_1$-$C_4$ alkylaminoaryl,
  di $C_1$-$C_4$ alkylaminoaryl,
  $C_{1-20}$ alkyl,
  $C_6$-$C_{14}$ aryl,
  heteroaryl, as defined below,
  aryl$C_{1-20}$alkyl, heteroarylC$_{1-20}$alkyl,
C$_{1-20}$alkylthioC$_{1-20}$alkyl,
C$_{1-20}$alkylsulfinylC$_{1-20}$alkyl,
C$_{1-20}$alkylsulfonylC$_{1-20}$alkyl,
C$_{1-20}$alkyloxycarbonylC$_{1-20}$alkyl,
carboxylC$_{1-20}$alkyl,
C$_{1-20}$ alkylcarbonylC$_{1-20}$alkyl,
C$_{1-20}$cycloalkyl,
C$_{1-20}$cycloalkylC$_{1-20}$alkyl,
C$_6$–C$_{14}$ arylC$_{1-20}$alkyloxycarbonylC$_{1-20}$alkyl,
heteroarylC$_{1-20}$alkyloxycarbonylC$_{1-20}$alkyl,
haloC$_{1-20}$alkyl,
hydroxylC$_{1-20}$alkyl,
thiosulfatoC$_{1-20}$alkyl,
C$_6$–C$_{14}$ arylC$_{1-20}$alkyloxyC$_{1-20}$alkyl,
C$_{1-20}$alkyloxyC$_{1-20}$alkyl,
C$_6$–C$_{14}$ arylcarbonylarylC$_{1-20}$alkyl,
diarylC$_{1-20}$alkyl,
triarylC$_{1-20}$alkyl,
C$_{2-20}$ alkenyl,
C$_{2-20}$ alkenylC$_{1-20}$alkyl,
heteroarylC$_{2-20}$alkenyl,
arylC$_{2-20}$alkenyl,
C$_{2-20}$alkynylC$_{1-20}$alkyl,
arylC$_{2-20}$alkynylC$_{1-20}$alkyl, or
heteroarylC$_{2-20}$alkynylC$_{1-20}$alkyl;

R$^4$ is:
H,
C$_{1-20}$ alkyl,
C$_6$–C$_{14}$ aryl or
heteroaryl;

R$^5$ can be the same or different when x is greater than 1 and is:
H, or
C$_{1-20}$ alkyl;

W is:

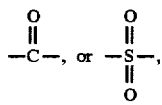

x is an integer from 1–25; and
(VA) where:
A is:

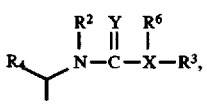 (a)

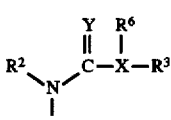 (b)

except when Z, T$^1$ or T$^2$ are beta methyl and R$^2$ equals H, Y equals O, X equals N and 5αH is present, R$^6$ and R$^3$ cannot be independently selected from: H, C$_{1-8}$ alkyl, C$_{3-6}$ cycloalkyl, phenyl and R$^6$ and R$^3$ cannot be taken together with the adjacent N to form a 5–6 membered heterocyclic ring comprising up to one other heteroatom selected from O or N; or

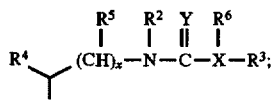 (c)

wherein
R$^2$ is:
H, or
C$_{1-20}$ alkyl;
R$^3$ is:
H,
amino,
mono C$_1$–C$_4$ alkylamino,
di C$_1$–C$_4$ alkylamino
mono C$_1$–C$_4$ alkylaminoaryl,
di C$_1$–C$_4$ alkylaminoaryl,
C$_{1-20}$ alkyl,
C$_6$–C$_{14}$ aryl,
heteroaryl, defined as above,
C$_6$–C$_{14}$ arylC$_{0-20}$alkyl,
C$_{3-20}$ cycloalkyl,
C$_{3-20}$ cycloalkylC$_{1-20}$alkyl,
heteroarylC$_{1-20}$alkyl,
C$_{2-20}$ alkenylC$_{1-20}$alkyl,
haloC$_{1-20}$alkyl,
C$_{1-20}$alkyloxycarbonyl,
C$_{1-20}$alkyl,
C$_{1-20}$ alkyloxyC$_{1-20}$alkyl,
carboxyC$_{1-20}$alkyl,
C$_6$–C$_{14}$ arylcarbonylarylC$_{1-20}$alkyl,
C$_{1-20}$ alkylcarbonylC$_{1-20}$alkyl,
C$_6$–C$_{14}$ arylC$_{1-20}$alkyloxycarbonylC$_{1-20}$alkyl,
heteroarylC$_{1-20}$alkyloxycarbonylC$_{1-20}$alkyl,
hydroxylC$_{1-20}$alkyl,
halohydroxylC$_{1-20}$alkyl,
C$_6$–C$_{14}$ arylC$_{1-20}$alkyloxyC$_{1-20}$alkyl,
heteroarylC$_{1-20}$alkyloxyC$_{1-20}$alkyl,
diarylC$_{1-20}$alkyl,
triarylC$_{1-20}$alkyl,
C$_{2-20}$ alkenyl,
C$_{2-20}$ alkenylC$_{1-20}$alkyl,
C$_{2-20}$ alkynylC$_{1-20}$alkyl,
arylC$_{2-20}$alkynylC$_{1-20}$alkyl,
heteroarylC$_{2-20}$alkynylC$_{1-20}$alkyl,
C$_{1-20}$ alkylthioC$_{1-20}$alkyl,
C$_{1-20}$ alkylsulfonylC$_{1-20}$alkyl, or
C$_{1-20}$ alkylsulfinyl C$_{1-20}$alkyl;
R$^4$ is:
H,
C$_{1-20}$ alkyl,
heteroaryl, or
C$_6$–C$_{14}$ aryl;
R$^5$ can be the same or different when x is greater than 1 and is:
H,
C$_{1-20}$ alkyl,
heteroaryl, as defined below; or
C$_6$–C$_{14}$ aryl;
R$^6$ is present when X equals N and is independently H or C$_{1-20}$ alkyl and can be taken together with R$^3$ and the N to which they are attached to form a heteroaryl ring system as defined below; and (VIA), where A is of the formula:

wherein:

Alk is $C_1$–$C_4$ straight or branched chain alkyl or alkenyl; dashed lines e and f each can independently represent a double bond when present, with the proviso that double bonds formed by e and f are not both present concurrently; and, $R^2$ is (a) $C_6$–$C_{10}$ aryl, or 5–6 membered heteroaryl radical which can contain 1–4 nitrogen atoms, one oxygen or sulfur atoms or combinations thereof with 1–2 nitrogen atoms;

(b) $COR_1$, where $R_1$ is $C_6$–$C_{10}$ aryl, substituted $C_6$–$C_{10}$ aryl, and heteroaryl;

c) $CONHR_2$, where $R_2$ is substituted phenyl, heteroaryl, substituted heteroaryl, or $C_7$ to $C_{12}$ cycloalkyl;

(d) $CO_2R_3$, where $R_3$ is $C_1$–$C_{18}$ linear or branched alkyl, $C_6$–$C_{10}$ aryl, substituted $C_6$–$C_{10}$ aryl, or $C_7$–$C_{12}$ cycloalkyl; providing that in (b), (c) or (d), Alk is only alkenyl;

wherein the above aryl or heteroaryl radicals can also be fused with a benzo or another heteroaryl ring and can further be substituted with one or more substituents;

(VIIA), where A is of the formula:

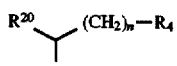

$R^{20}$ is H, methyl;

n is 0–10;

$R^4$ is selected from:
(a) —$COR^1$, where $R^1$ is phenyl or substituted phenyl;
(b) —$CONHR^2$, where $R^2$ is substituted phenyl, heteroaryl, substituted heteroaryl;
(c) —$COOR^3$, where $R^3$ is phenyl, substituted phenyl, heteroaryl, substituted heteroaryl;

wherein said heteroaryl radical is a 5–6 membered ring which can contain 1–4 nitrogen atoms, one oxygen or sulfur atom, or combinations thereof with 1–2 nitrogen atoms, and wherein phenyl and heteroaryl can be substituted with one or more of $C_1$–$C_4$alkyl, $C_1$–$C_4$alkoxy, chloro, fluoro, trifluoromethyl, hydroxy, nitro, mono- and di-$C_1$–$C_4$alkylamino.

(VIIIA), where A is selected from:

1) H; $C_1$–$C_{12}$alkyl;

2) OH; except where $T^1$, $T^2$ or Z is methyl;

3) —$OCOR^1$, —$OCONR^1R^2$, where $R^1$ and $R^2$ are independently selected from:
$C_1$–$C_{10}$alkyl,
$C_3$–$C_{12}$cycloalkyl,
$C_6$–$C_{10}$aryl, or
$C_7$–$C_{11}$aralkyl;

4) —$NHCOR^1$, where $R^1$ is defined above, excluding $R^1$ being $C_1$–$C_{10}$ alkyl where $T^1$, $T^2$ or Z is methyl;

5) —$(CH_3)C$=NOH;

6) —$(CH_3)CH$—OR, where R is H, $COCH_3$, $C_1$–$C_6$ alkyl or alkenyl, $CH(CO_2C_1$–$C_4$alkyl$)_2$, excluding H and $COCH_3$ where $T^1$, $T^2$ or Z is methyl;

7) —$(CH_3)C$=$CH_2$;

8) —$C(CH_3)_2OH$;

9) —$CO_2C_1$–$C_4$alkyl; except where $T^1$, $T^2$ or Z is methyl;

10) —$CONR^1R^2$, where $R^1$ and $R^2$ are defined above and where $T^1$, $T^2$ or Z are not methyl;

11) oxo, and $T^1$ and $T^2$ are both $C_1$–$C_3$ alkyl;

and stereoisomers and pharmaceutically acceptable salts and esters thereof.

Also disclosed are processes or their preparation, pharmaceutical formulations comprising the novel compounds as active ingredients and methods of inhibiting prostatic and scalp 5α-reductases in diseases which occur under hyperandrogenetic conditions, e.g. benign prostatic hyperplasia, androgenetic alopecia, with the novel compounds and their pharmaceutical formulations.

DETAILED DESCRIPTION OF THE INVENTION AND PREFERRED EMBODIMENTS

The description of the novel 16-substituted and 7,16-disubstituted compounds disclosed and encompassed by this invention is conveniently discussed in terms of the 17 position substituents denoted by the symbol "A", that have been placed into categories IA–VIIIA. It is to be noted that there may be some duplication of symbols of radicals which have slightly different meanings, e.g., where A is IA, the $R^3$ radical represents H, methyl or ethyl; however, where A is IVA, $R^3$ represents a long list of possible radicals. Therefore, the discussion of the synthesis, properties and description of the compounds herein must be done with reference to the specific category IA through VIIIA, which categories comprise the definitions of symbol "A" at position 17.

EXAMPLES FOR THE CASE WHEN SUBSTITUENT "A" OF GENERAL FORMULA 'I' IS AS DEFINED IN GROUP "VIII(A)"

The following terms are used in discussing the 17-A radical VIIIA.

By the term "$C_1$–$C_4$ alkyl" as used herein, is meant to include: e.g. methyl, ethyl, propyl, isopropyl, n-butyl, sec-butyl, isobutyl and t-butyl.

By the term "$C_1$–$C_{12}$ alkyl" as used herein is meant to include linear and branched $C_5$–$C_{12}$ alkyl radicals in addition to these encompassed by $C_1$–$C_{10}$ alkyl, e.g., isopentyl, n-hexyl, t-heptyl, n-octyl, isooctyl, n-nonyl, n-decyl, t-decyl, t-undecyl, n-dodecyl, sec-dodecyl, 2-methyl-hept-6-yl (cholestanyl side chain) and the like.

By the term "$C_3$–$C_{12}$ cycloalkyl" is meant mono-, di-, and tri- and tetracyclo saturated hydrocarbon ring systems, e.g., cyclopropyl, cyclobutyl, cyclopentyl, cyclohexyl, 2-norbornyl, bornyl, 1-adamantyl, 2-adamantyl and the like.

By the term "$C_6$–$C_{10}$ aryl" is meant phenyl, naphthyl,

By the term "$C_7$–$C_{11}$ aralkyl" is meant benzyl, phenethyl, phenylpropyl, phenylisobutyl and the like.

Representative 16-substituted compounds of the invention where Z is H,H and the 17-A substituent is of structure VIIIA are:

| Compound No. | Name |
|---|---|
| 7-(20S) | 20(S)-Acetoxy-4,16-β-dimethyl-5α-4- |
| 7-(20R) | 20(R)-Acetoxy-4,16-β-dimethyl-5α-4-aza-pregnan-3-one |
| 9 | 20(-Methyl-20-hydroxy-4,16-β-dimethyl- |

| Compound No. | Name |
|---|---|
| | 5α-4-aza-pregnan-3-one |
| 10-(20R) | 20(R)-Methoxy-4,16-β-dimethyl-5α-4-aza-pregnan-3-one |
| 11-(20R) | 20(R)-Allyloxy-4,16-β-dimethyl-5α-4-aza-pregnan-3-one |
| 12-(20R) | 20(R)-n-propyloxy-4,16-β-dimethyl-5α-4-aza-pregnan-3-one |
| 13-(20R) | 20(R)-(3-methyl-2-butenyloxy)-4,16-β-dimethyl-5α-4-aza-pregnan-3-one |
| 14 | 20(R)-pivaloyloxy-4,16-β-dimethyl-5α-4-aza-pregnan-3-one |
| 15 | 20(R)-benzoyloxy-4,16-β-dimethyl-5α-4-aza-pregnan-3-one |
| 16 | 20(R)-propanoyloxy-4,16-β-dimethyl-5α-4-aza-pregnan-3-one |
| 17 | 20(R)-(1-adamantyl)carbonyloxy-4,16-β-dimethyl-5α-4-aza-pregnan-3-one |
| 18 | 20(R)-aminocarbonyloxy-4,16-β-dimethyl-5α-4-aza-pregnan-3-one |
| 19 | 20(R)-N-methylaminocarbonyloxy-4,16-β-dimethyl-5α-4-aza-pregnan-3-one |
| 20 | 20(R)-(N-isopropyl)aminocarbonyloxy-4,16-β-dimethyl-5α-4-aza-pregnan-3-one |
| 21 | 20(R)-(N,N-dimethyl)aminocarbonyloxy-4,16-β-dimethyl-5α-4-aza-pregnan-3-one |
| 22 | 20(R)-(N-(n-octyl)amino)carbonyloxy-4,16-β-dimethyl-5α-4-aza-pregnan-3-one |
| 23 | 20(R)(N-t-butylamino)carbonyloxy-4,16-β-dimethyl-5α-4-aza-pregnan-3-one |
| 24 | 20(R)-(N-benzyl)aminocarbonyloxy-4,16-β-dimethyl-5α-4-aza-pregnan-3-one |
| 25 | 20(R)-(N-phenyl)aminocarbonyloxy-4,16-β-dimethyl-5α-4-aza-pregnan-3-one |
| 26 | 20-oximino-4,16-β-dimethyl-5α-4-aza-pregnan-3-one |
| 28 | 20(RS)-acetamido-4,16-β-dimethyl-5α-4-aza-pregnan-3-one |
| 29 | 20-methylene-4,16-β-dimetnyi-5α,17a-4-aza-pregnan-3-one |
| 44 | 17β-(Bis-methoxycarbonyl)methoxy-4,16β-dimethyl-5α-4-aza-androst-5-en-3-one |
| 45 | 17β-acetoxy-4,16-β-dimethyl-4-aza-androst-5-en-3-one |
| 46 | 17β-acetoxy-4,16-β-dimethyl-4-aza-androstan-3-one |
| 47 | 17β-(Bis-Benzyloxycarbonyl)-methoxy-4,16β-dimethyl-5α-4-aza-androstan-3-one |
| 48 | 17β-(Bis-carboxyl)methoxy-4,16β-di-methyl-5α-4-aza-androstan-3-one |
| 49 | 17β(carboxymethyloxy)-4,16β-di-methyl-5α-4-aza-androstane-3-one 8 4,16β-dimethyl-5α-4-aza-pregnane-3,20-dione |
| 33 | 20(R,S)-Hydroxy-4,16β-dimethyl-5α-17a-4-aza-pregnan-3-one |
| 34 | 20(R,S)-Acetoxy-4,16β-dimethyl-5α-17a-4-aza-pregnan-3-one |
| 43 | 17β-Hydroxy-4,16β-dimethyl-5α-4-aza-pregnan-3-one |
| 50 | 17β-(N-phenylaminocarbonyl)methoxy-4,16β-dimethyl-5α-4-aza-androstan-3-one |
| 51 | 17β-(N-t-Butylaminocarbonyl)methoxy-4,16β-dimethyl-5α-4-aza-androstan-3-one |
| 52 | 17β-(N-4'-pyridylaminocarbonyl)methoxy-4,16β-dimethyl-5α-4-aza-androstan-3-one |
| 53 | 17β-(methoxycarbonyl)methoxy-4,16β-di-methyl-5α-4-aza-androstan-3-one |
| 54 | 4,16β-dimethyl-5α-4-aza-androstan-3,17-dione |
| 55 | 4,16β-dimethyl-17-oximino-5α-4-aza-androstan-3-one |
| 56 | 17β-amino-4,16β-dimethyl-5α-4-aza-androstan-3-one |
| 57 | 17β-Benzamido-4,16β-dimethyl-5α-4-aza-androstan-3-one |
| 58 | 17β-Acetamido-4,16β-dimethyl-5α-4-aza-androstan-3-one |
| 59 | 17β-Pivalamido-4,16β-dimethyl-5α-4-aza-androstan-3-one |
| 60 | 17β-(S-Mandelamido)-4,16β-dimethyl-5α-4-aza-androstan-3-one |
| 61 | 17β-(R-Mandelamido)-4,16β-dimethyl-5α-4-aza-androstan-3-one |
| 62 | 17β-(N-Benzyl)carbamoyloxy-4,16β-dimethyl-5α-4-aza-androstan-3-one |
| 63 | 17β-Pivaloyloxy-4,16β-dimethyl-5α-4-aza-androstan-3-one |
| 64 | 17β-(N-t-Butyl)carbamoyloxy-4,16β-dimethyl-5α-4-aza-androstan-3-one |
| 65 | 17β-(N-(n-octyl)carbamoyloxy)-4,16β-dimethyl-5α-4-aza-androstan-3-one |
| 66 | 17β-(N-Phenyl)carbamoyloxy-4,16β-dimethyl-5α-4-aza-androstan-3-one |
| 67 | 17β-Benzoyloxy-4,16β-dimethyl-5α-4-aza-androstan-3-one |
| 68 | 16β-ethyl-17β-hydroxy-4-methyl-5α-4-aza-androstan-3-one |
| 69 | 17β-(N-Benzyl)carbamoyloxy-16β-ethyl-4-methyl-5α-4-aza-androstan-3-one |
| 70 | 17β-Pivaloxyloxy-16β-ethyl-4-methyl-5α-4-aza-androstan-3-one |
| 72 | 16-Isopropylidene-4-methyl-5α-4-aza-androstan-3,17-dione |
| 73 | 16β-Isopropyl-4-methyl-5α-4-aza-androstan-3,17-dione |
| 74 | 17β-Hydroxy-16β-isopropyl-4-methyl-5α-4-aza-androstan-3-one |
| 75 | 17β-Acetoxy-16β-isopropyl-4-methyl-5α-4-aza-androstan-3-one |
| 76 | 17β-Pivaloyloxy-16β-isopropyl-4-methyl-5α-4-aza-androstan-3-one |
| 77 | 16β-isopropyl-4-methyl-17-oximino-5α-4-aza-androstan-3-one |
| 78 | 17β-amino-16β-isopropyl-4-methyl-5α-4-aza-androstan-3-one |
| 79 | 17β-Acetamido-16β-isopropyl-4-methyl-5α-4-aza-androstan-3-one |
| 80 | 17β-Pivalamido-16β-isopropyl-4-methyl-5α-4-aza-androstan-3-one |
| 81 | 17β-Benzamido-16β-isopropyl-4-methyl-5α-4-aza-androstan-3-one |
| 82 | 17β-(N'-t-butyl)ureido-16β-isopropyl-4-methyl-5α-4-aza-androstan-3-one |
| 83 | 17β-(N'-Benzyl)ureido-16β-isopropyl-4-methyl-5α-4-aza-androstan-3-one |
| 84 | 16β-(3-propenyl)-4-methyl-5α-4-aza-androstan-3,17-dione |
| 85 | 17β-Hydroxy-16β-(3-propenyl)-4-methyl-5α-4-aza-androstan-3-one |
| 86 | 17β-(N-t-butyl)carbamoyloxy-16β-(3-propenyl)-4-methyl-5α-4-aza-androstan-3-one |
| 87 | 17β-(N-t-butyl)carbamoyloxy-16β-n-propyl-4-methyl-5α-4-aza-androstan-3-one |
| 88 | 16β-n-propyl-4-methyl-5α-4-aza-androstan-3,17-dione |
| 89 | 4-methyl-16-n-propyl-17-(trifluoro-methanesulfonyloxy)-5α-4-aza-16-androsten-3-one |
| 90 | 4-methyl-16-n-propyl-5α-4-aza-16-androsten-3-one |
| 91 | 4-methyl-16β-n-propyl-5α-4-aza-androstan-3-one |
| 92 | 4,16-dimethyl-17-(trifluoromethane-sulfonyloxy)-5α-4-aza-16-androsten-3-one |
| 93 | 4,16-dimethyl-17-methoxycarbonyl-5α-4-aza-16-androsten-3-one |
| 94 | 4,16β-dimethyl-17β-methoxycarbonyl-5α-4-aza-androstan-3-one |
| 95 | 4,16-dimethyl-17-isopropyloxycarbonyl-5α-4-aza-16-androsten-3-one |
| 96 | 4,16β-dimethyl-17-isopropyloxycarbonyl-5α-4-aza-androstan-3-one |
| 97 | 4,16-dimethyl-17-(n-propyloxy)carbonyl-5α-4-aza-16-androsten-3-one |
| 98 | 4,16β-dimethyl-17β-(n-propyloxy)carbonyl-5α-4-aza-androstan-3-one |
| 99 | 4,16-dimethyl-17-(N,N-diethylcarbamoyl)-5α-4-aza-16-androsten-3-one |
| 100 | 4,16β-dimethyl-17-(N,N-diethylcarbamoyl)-5α-4-aza-androstan-3-one |
| 101 | 4,16-dimethyl-17-(N-t-butylcarbamoyl)-5α-4-aza-16-androsten-3-one |

-continued

| Compound No. | Name |
|---|---|
| 102 | 4,16β-dimethyl-17β-(N-t-butylcarbamoyl)-5α-4-aza-androstan-3-one |
| 43 | 17β-Hydroxy-4,16β-dimethyl-5α-4-aza-androstan-3-one |
| 103 | 20-acetoxy-16a-methyl-5α-4-aza-pregnan-3-one |
| 104 | 20-hydroxy-16a-methyl-5α-4-aza-pregnan-3-one |
| 105 | 20-hydroxy-16a-methyl-4-aza-5-pregnen-3-one |
| 106 | 16a-methyl-5α-4-aza-pregnan-3,20-dione |
| 107 | 16β-methyl-5α-4-aza-pregnan-3,20-dione |
| 108 | 20-acetoxy-16β-methyl-5α-4-aza-pregnan-3-one |
| 109 | 20-hydroxy-16β-methyl-5α-4-aza-pregnan-3-one |
| 110 | 20-acetoxy-4,16a-dimethyl-5α-4-aza-pregnan-3-one |
| 111 | 20-hydroxy-4,16a-dimethyl-5α-4-aza-pregnan-3-one |
| 112 | 20-hydroxy-4,16a-dimethyl-4-aza-5-pregnen-3-one |
| 113 | 4,16a-dimethyl-5α-4-aza-pregnan-3,20-dione |
| 114 | 4,16a-dimethyl-4-aza-5-pregnen-3,20-dione |
| 115 | 4,16β-dimethyl-5α-4-aza-pregnan-3,20-dione |
| 116 | 4,16β-dimethyl-4-aza-5-pregnen-3,20-dione |

Unless otherwise indicated, the 17-A substituent is assumed to be in the beta configuration.

The 16-substituted 17-A compounds of this invention where Z is H,H and A is structure VIIIA can be made by procedures outlined in the following Flowsheets:

FLOWSHEET A

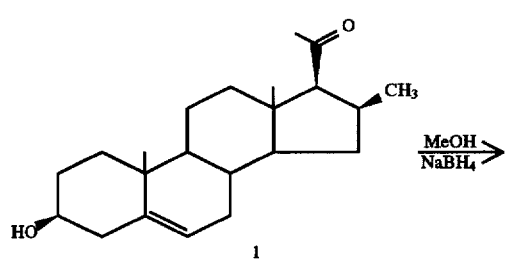

16B-Methyl Pregnenolone

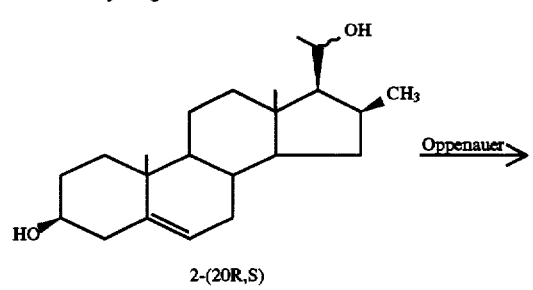

2-(20R,S)

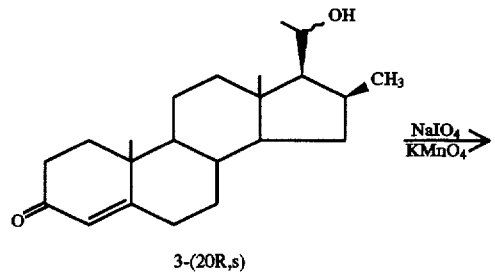

3-(20R,s)

FLOWSHEET A

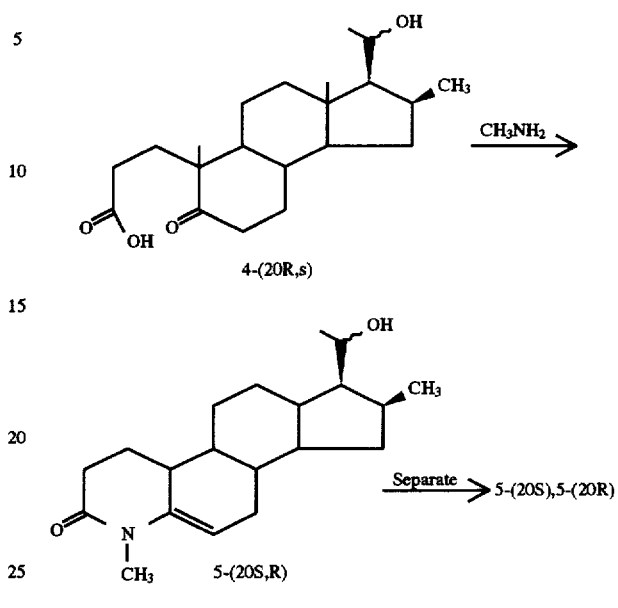

FLOWSHEET B

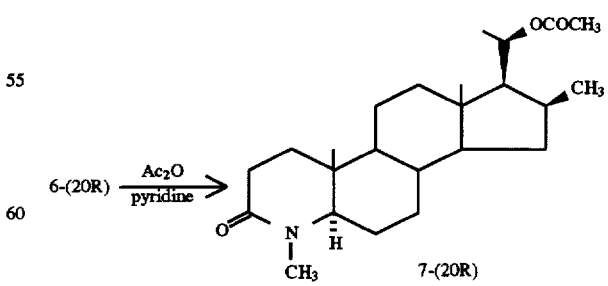

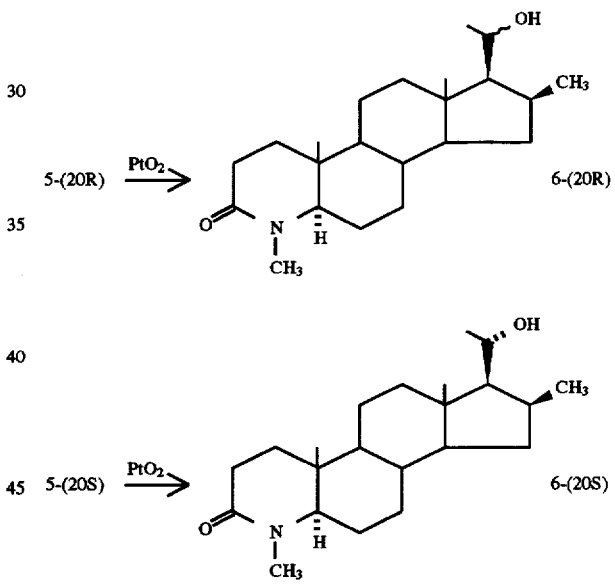

FLOWSHEET B
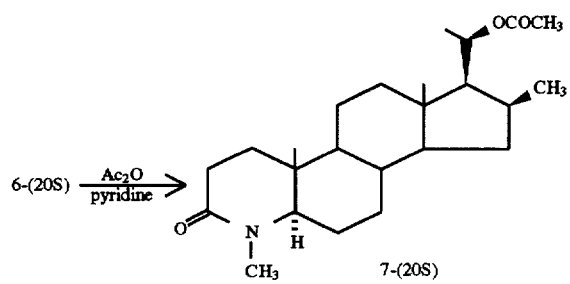
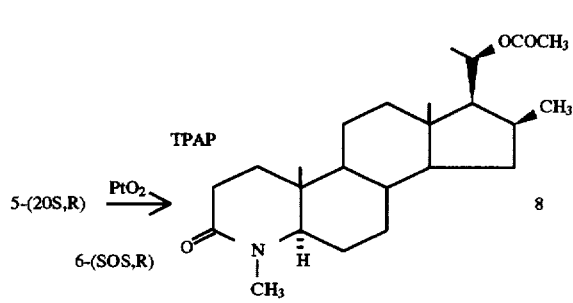
FLOWSHEET C
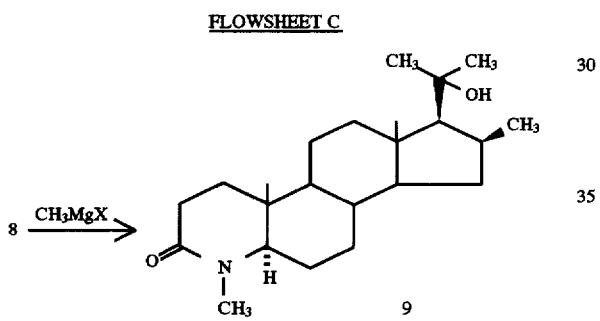
FLOWSHEET D
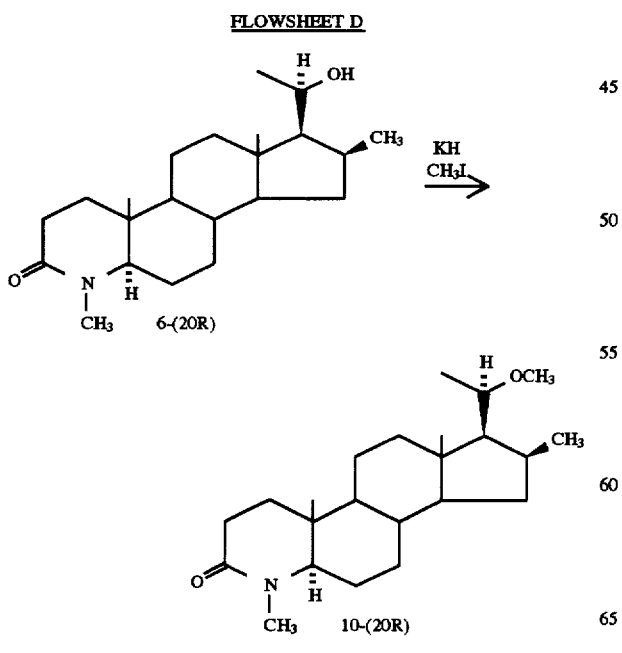
FLOWSHEET D -continued
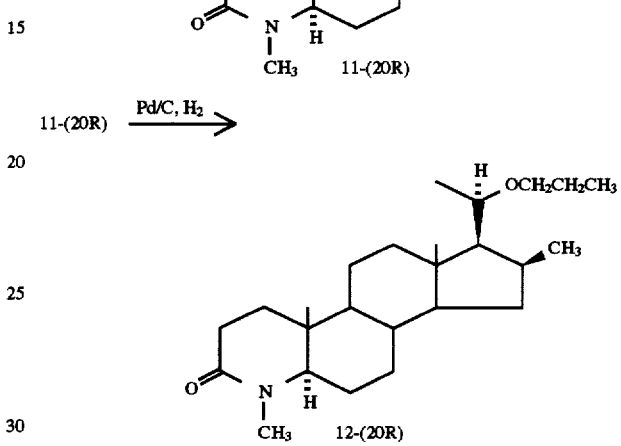
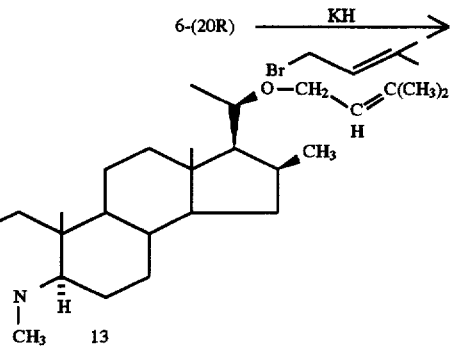
FLOWSHEET E
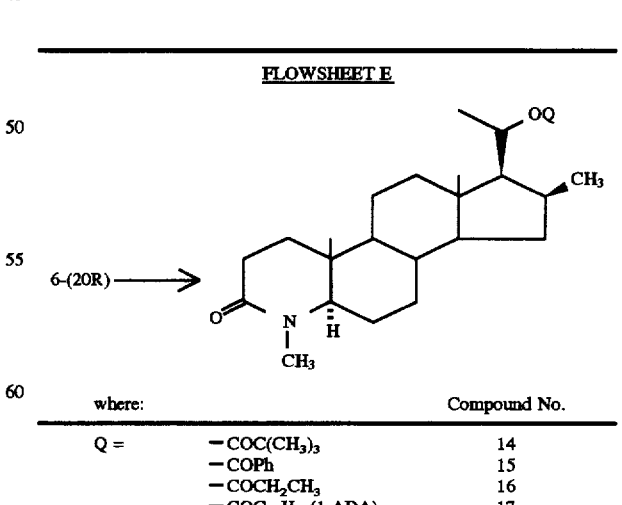
| where: | | Compound No. |
|---|---|---|
| Q = | —COC(CH₃)₃ | 14 |
| | —COPh | 15 |
| | —COCH₂CH₃ | 16 |
| | —COC₁₀H₁₅(1-ADA) | 17 |
| | —CONH₂ | 18 |
| | —CONHCH₃ | 19 |

FLOWSHEET E
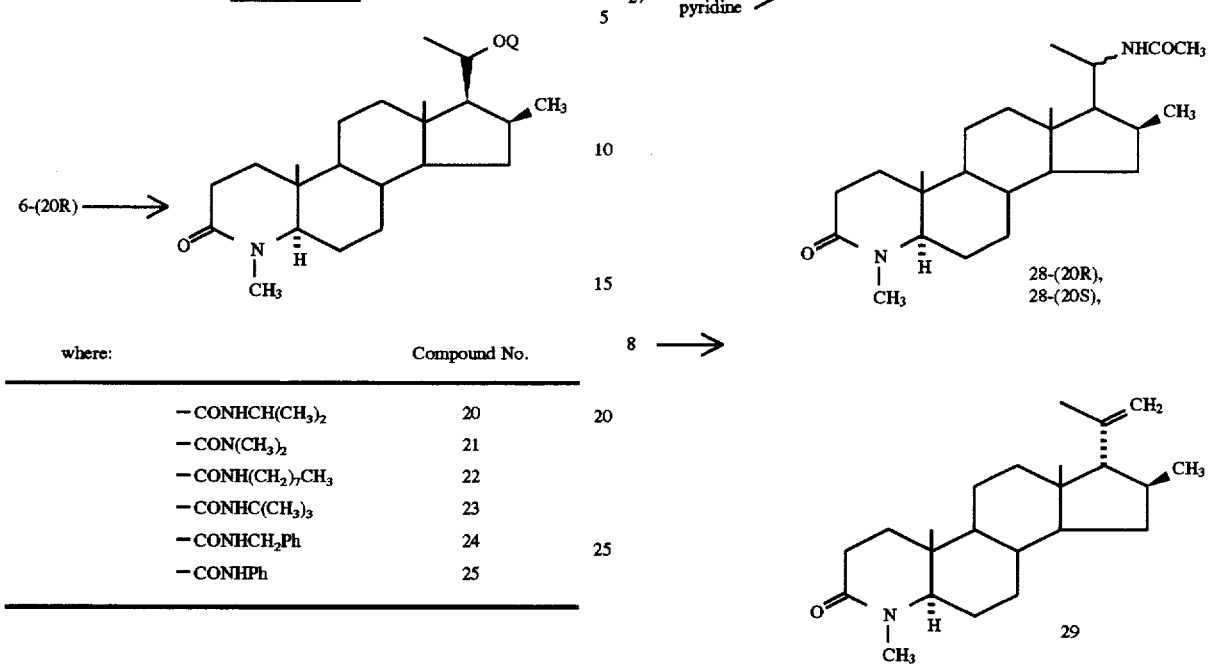
| where: | Compound No. |
|---|---|
| —CONHCH(CH₃)₂ | 20 |
| —CON(CH₃)₂ | 21 |
| —CONH(CH₂)₇CH₃ | 22 |
| —CONHC(CH₃)₃ | 23 |
| —CONHCH₂Ph | 24 |
| —CONHPh | 25 |
FLOWSHEET F
FLOWSHEET G
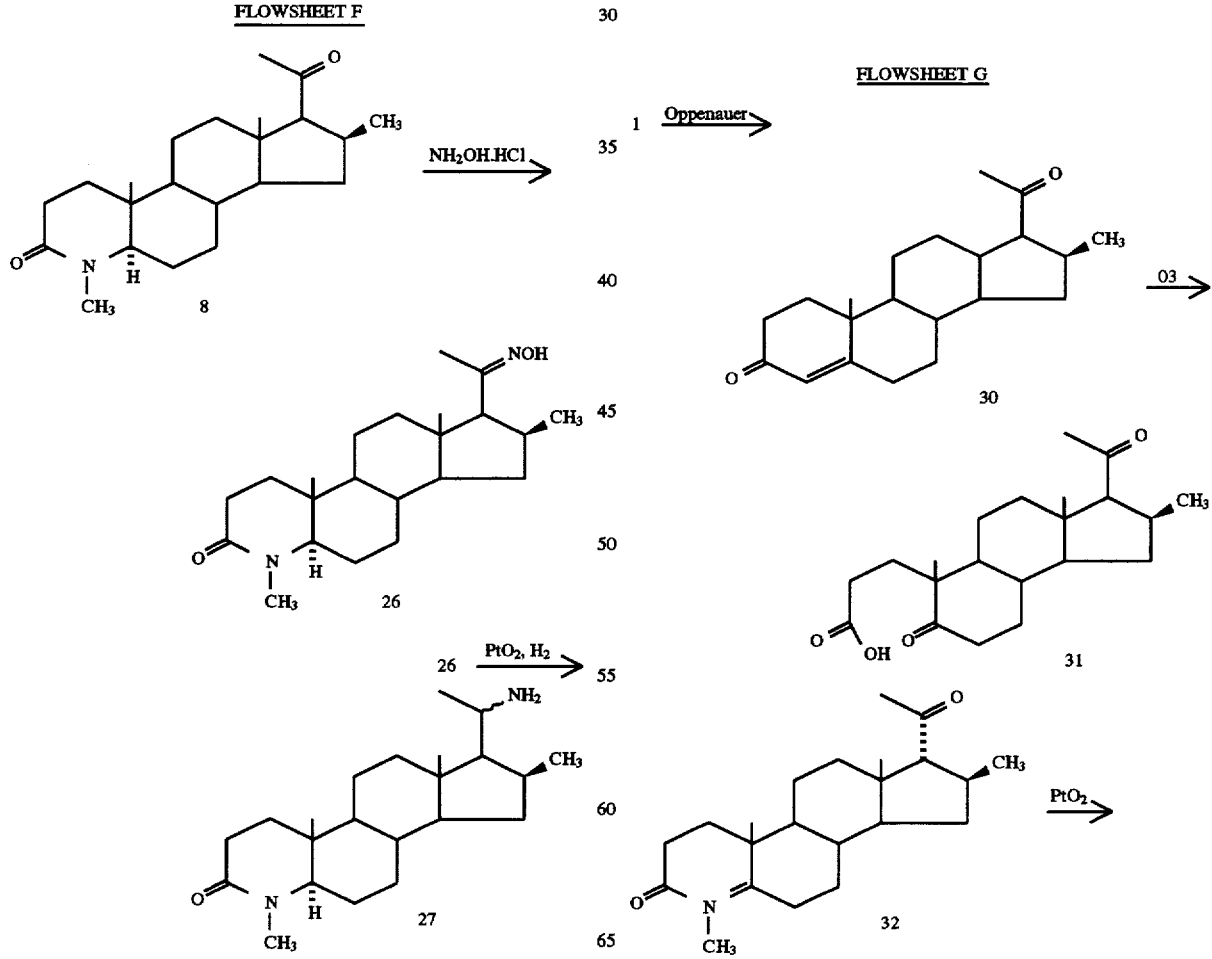

-continued
FLOWSHEET G

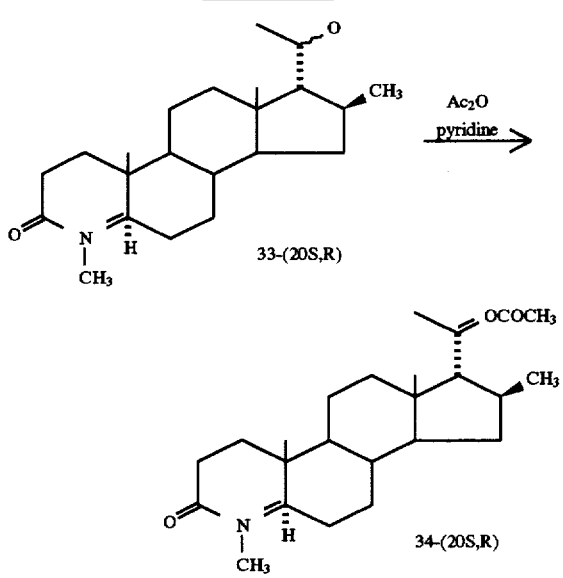

16-Beta-Methyl-17-Pregnane Series

This series of derivatives where structure A is VIIIA, is prepared from 20-hydroxy-16-beta-methyl-4-methyl-4-aza-pregnan-3-one is shown in Flowsheets A–G. As used herein, the 16-methyl group is shown as $CH_3$ and the 5 alpha hydrogen is shown as H. All other straight bond lines e.g. at carbons 18, 19, 21 are assumed to be methyl unless indicated otherwise.

Starting 16-beta methyl pregnenolone (1) is reduced with sodium borohydride in methanol at 6° C. overnight to produce the 20-hydroxy analog 2. (This is a preferred route since the corresponding 16-beta-methyl 17-methyl ketone 1 is unstable during oxidation conditions during the remainder of the procedure and epimerizes to the 17-alpha isomer, which is a route for preparing the 17-alpha analogs.)

Ring A in 2 is oxidized via an Oppenauer oxidation using cyclohexanone, aluminum isopropoxide, in refluxing dry toluene over 1–7 hours to yield the 4-en-3-one 3. This compound 3 was ring opened in a refluxing mixture of sodium periodate, potassium permanganate, in a t-butanol/water solvent over 1–2 hours to form the seco-acid (4).

The seco acid (4) is reacted with methylamine hydrochloride and sodium acetate in ethylene glycol for 2 hours at 185° C. to yield the 4-methyl azasteroid 5, which can be separated into the C-20 stereoisomers 5-(20R) and 5-(20S).

The delta-5 pregnenes can be catalytically hydrogenated to produce the pregnane analogs 6-(20R) and 6-(20S). These are treated with acetic anhydride in dry pyridine/methylene chloride and 4-dimethylaminopyridine (DMAP) at room temperature over an hour to produce the corresponding 20-acetoxy derivatives, 7-(20R) and 7-(20S).

The 5-(20S,R) mixture is hydrogenated to the 6-(20S,R) pregnanes as described above and then treated with TPAP reagent, tetrapropyl perruthenate, See Chem. Commun. 1625, 1987, to produce the 20-one 8.

The ketone 8 can also be subjected to the Grignard reaction, e.g. methylmagnesium bromide in dry THF at 0° C. for about an hour to produce the 20-methyl-20-hydroxy analog 9.

The starting alcohol 6R can be derivatized to the methyl ether 10-(20R), by reacting in dry DMF with methyl iodide and potassium hydride under nitrogen atmosphere at room temperature for 1–3 days.

Similarly, the allyl ether 11-(20R) is formed by reacting allyl bromide in dry DMF and KH under nitrogen. This compound can be hydrogenated in ethyl acetate with 10% palladium on carbon to produce the (20R) propyloxy derivative 12.

Similarly, reacting 6-(20R) and the 4-bromo-2-methyl butane yields the isopentylene ether 13-(20R).

The alcohol 6-(20R) can be reacted with an appropriate acid halide or anhydride in solvent, e.g. dry methylene chloride, dry DMF, in the presence of the proton acceptor, e.g. pyridine, 4-dimethylaminopyridine (DMAP) at room temperature for 1 hour to 2 days followed by conventional chromotographic separation and purification to produce the corresponding 20-acyl derivatives, 14–25.

Specifically, pivaloyl chloride yields 14, benzoic anhydride yields 15, propionyl chloride yields 16, and 1-adamantane carbonyl chloride yields 17.

Reaction of the alcohol 6-(20R) with appropriate isocyanates produces the corresponding carbamates.

Reaction of 6-(20R) with trichloroacetyl isocyanate was carried out in dry methylene chloride at room temperature following the analogous procedure in Tetrahedron Letters, Vol. 27, p 5521 (1986). Alumina was added, stirred overnight to produce after chromatographic elution on silica gel with 1–5% methanol/methylene chloride, the carbamate 18.

Similarly, reacting of the alcohol 6R with other isocyanates in dry methylene chloride or THF, in the presence of a proton acceptor, e.g. DBU (1,8-diazabicyclo[5.4.0]undec-7-ene), at room temperature for 1 hour to 1 day produces the corresponding carbamates.

Specifically, reaction with methyl isocyanate produces 19; with isopropyl isocyanate, 20; with octyl isocyanate, 22; with t-butylisocyanate, 23; with benzyl isocyanate, 24; and with phenyl isocyanate, 25. Also, N-methylation of 19 using sodium hydride and methyl iodide in dry DMF under nitrogen produces the N,N-dimethylcarbamate, 21.

The 20-ketone 8, can be converted into 20-amino derivates by first reacting the 20-ketone 8 with hydroxylamine hydrochloride and sodium acetate in ethanol overnite at 80° C. to produce the oxime 26. This can be hydrogenated, e.g. with platinum oxide in ethanol/acetic acid to yield the (20-R,S) amine 27. This can be derivatized in a like manner to the alcohol described above. For example, reaction with acetic anhydride, pyridine in dry methylene chloride yields the 20-acetamido derivatives 28-(20R) and 28-(20S).

The ketone 8 can be further modified to yield the 17a-20-methylene compound 29 by a Wittig reaction.

The corresponding 4-N—H compounds can be prepared in the series by e.g. refluxing the seco acid 4 with ammonium acetate in glacial acetic acid for 2–4 hours.

The corresponding 1-ene compounds can be prepared by the procedure of Dolling et al., involving dichlorodicyanobenzoquinone, JACS (1988) Vol. 110, pp 3318–3819. Alternatively the delta-one-ene (D') can be formed by reacting the 1,2-dihydro form e.g. 7-(20S) or 7-(20R), where the 20-hydroxy group is protected, with benzeneselenic anhydride in refluxing chlorobenzene.

The corresponding 5-ene compounds, e.g. where 7-(20R) or 7-(20S) further contains a 5-ene double bond ($D^5$) can be formed by directly acylating 5-(20R) or 5-(20S) under the same conditions as used in the acylation to form 7-(20R) or 7-(20S).

FLOWSHEET H
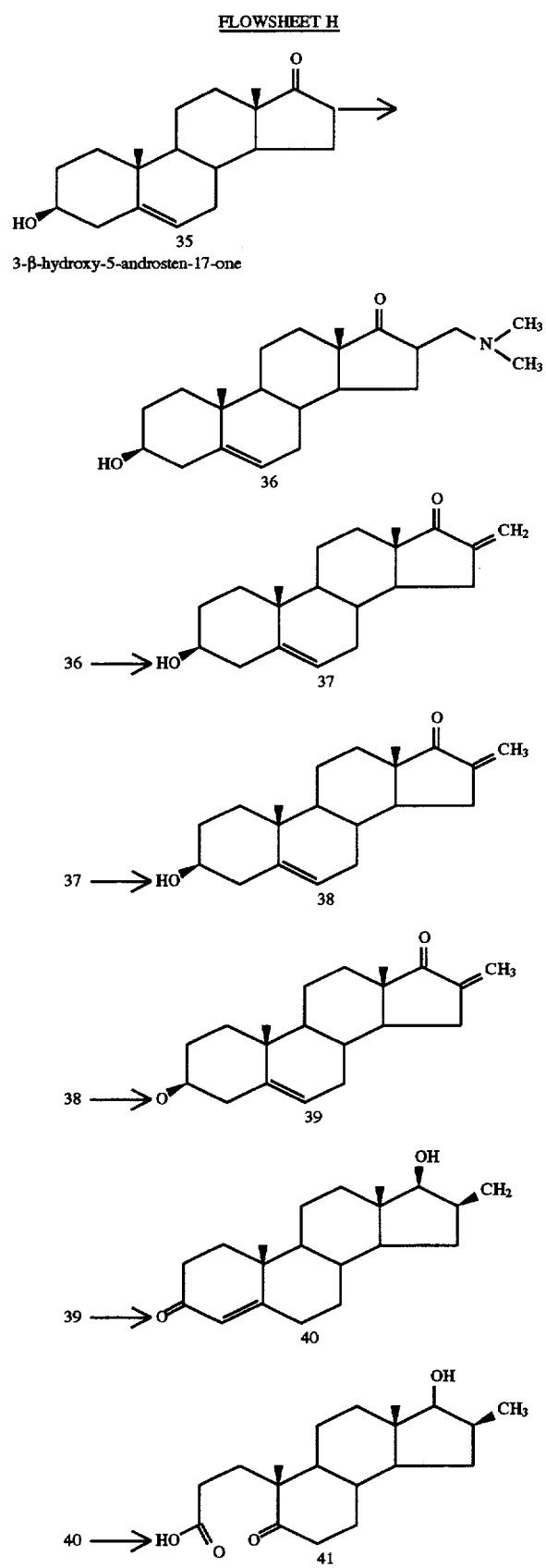
-continued
FLOWSHEET H
FLOWSHEET I
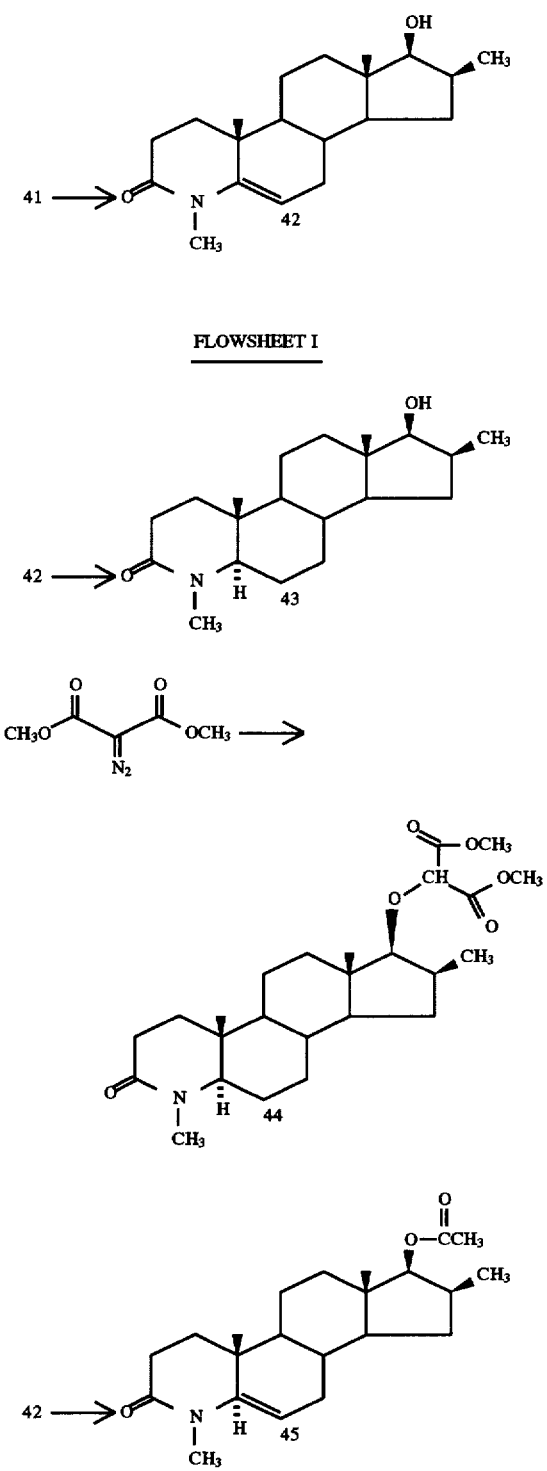

FLOWSHEET I -continued
FLOWSHEET J
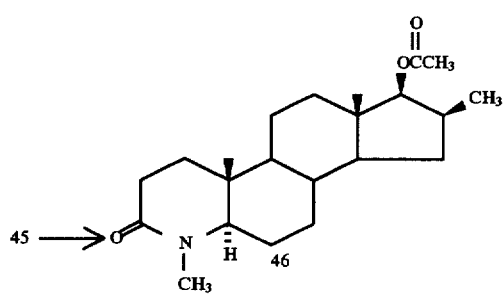
FLOWSHEET K
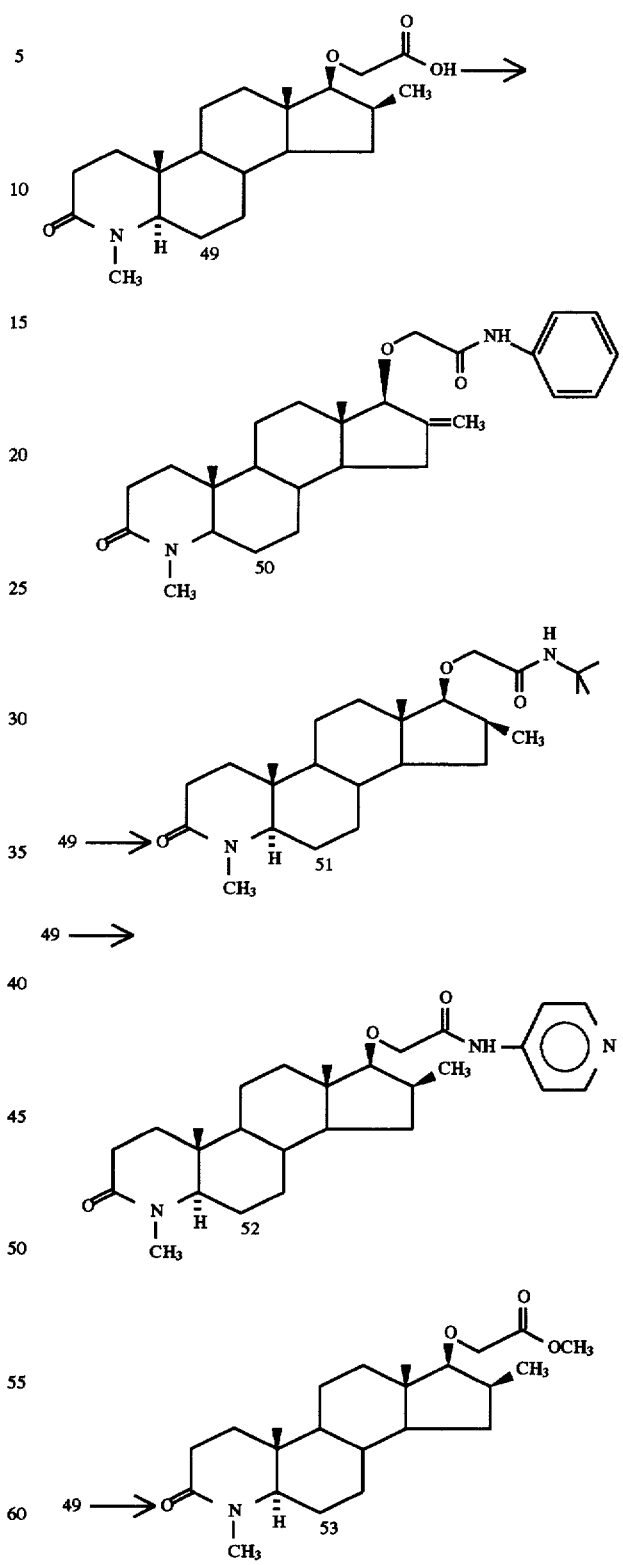

FLOWSHEET L
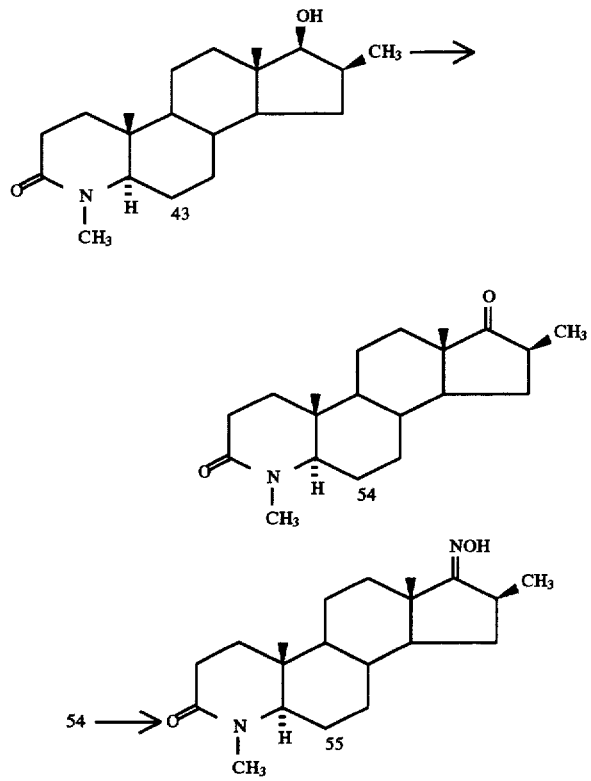
FLOWSHEET M
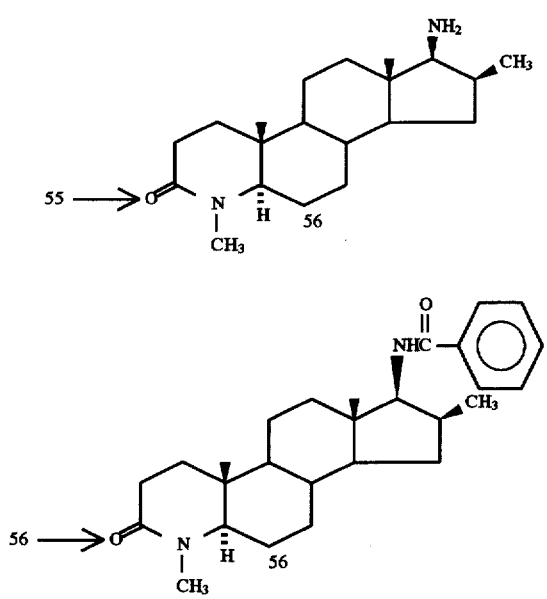
-continued
FLOWSHEET M
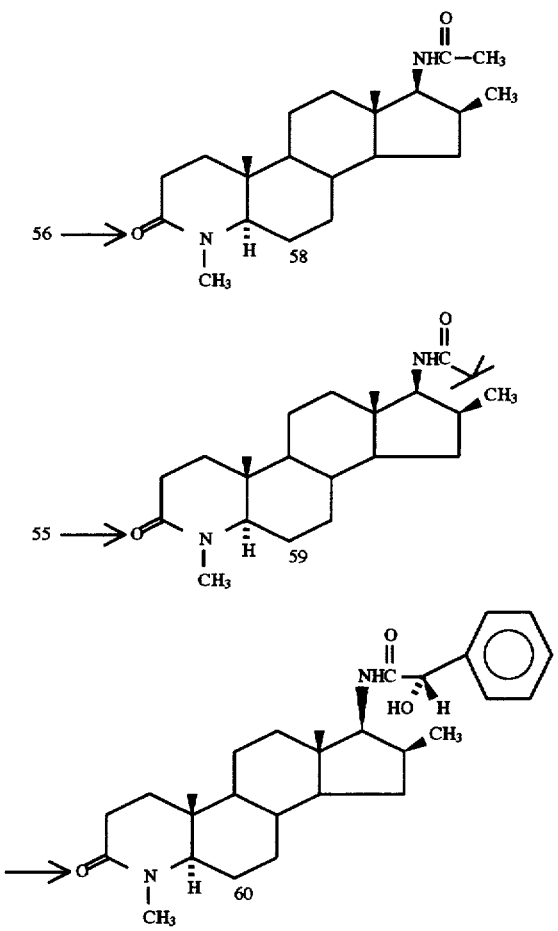
FLOWSHEET N
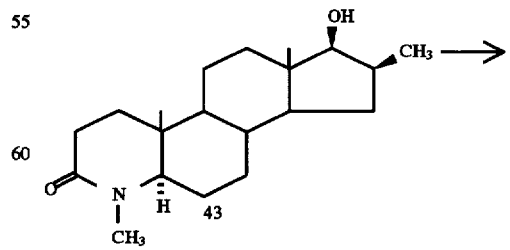

27
-continued
FLOWSHEET N

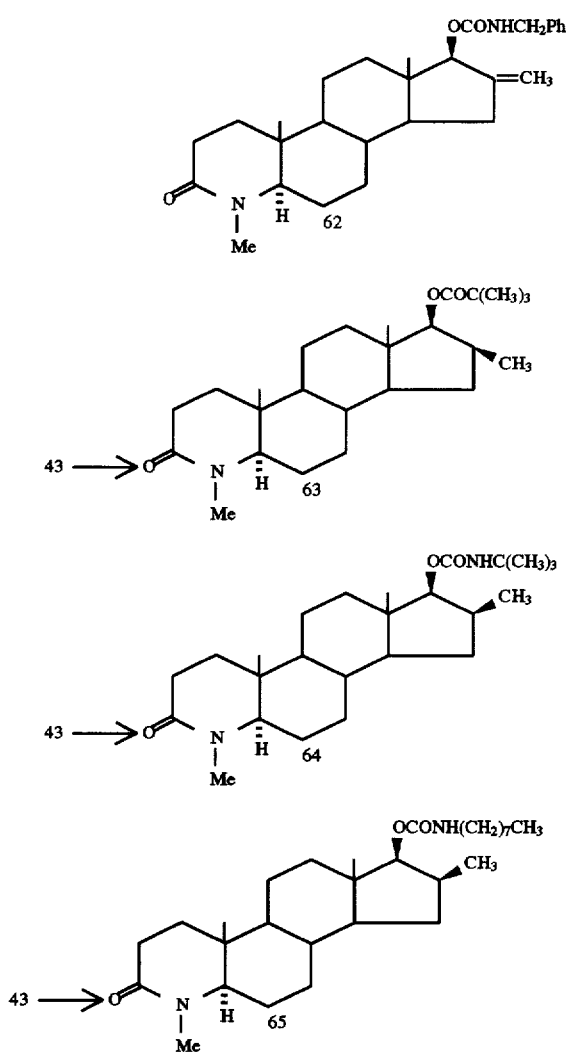

FLOWSHEET O

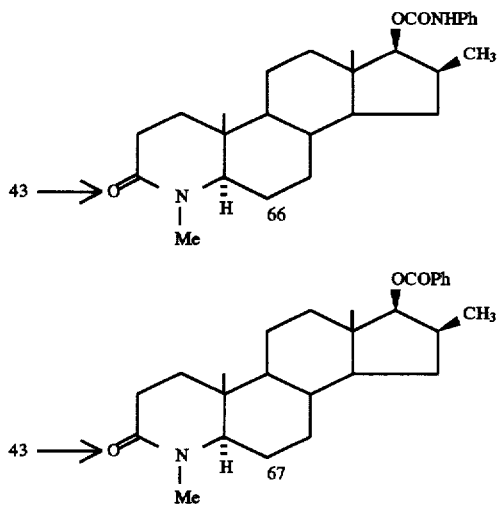

28
17-Oxa and 17-Amino-16β-Methyl Androstane Analogs

The 17-oxygenated and 17-amino compounds in this series where A is structure VIIIA, are prepared from a route starting with the known 3-beta-dehydroisoandrosterone 35 as illustrated in Flowsheets H–O.

Following the procedure in JACS, Vol. 70, p. 3872 (1948), 35 is reacted via a Mannich reaction with paraformaldehyde and dry dimethylamine hydrochloride in isoamyl alcohol under reflux for 2 hours to produce the 16-dimethylaminomethyl derivative 36. This in turn is treated by the procedure in JACS, 77, p. 5677 (1955) via steam distillation to yield the 20-methylene analog 37, which is catalytically hydrogenated selectively from the alpha face at C-16 using 10% Pd/C catalyst in methanol solvent at room temperature under hydrogen balloon pressure for about 5–10 minutes to yield primarily the 16-beta-methyl derivative 38. This is treated under Oppenauer oxidation conditions using aluminum isopropoxide, cyclohexanone, in dry toluene solvent under reflux for 2–4 hours, azeotropically removing water to yield after chromatographic separation the 4-en-3-one derivative 39. The 3- and 17-keto groups in 39 are reduced by treating with 25% DIBAL (diisobutylaluminum hydride) in toluene followed by in situ Oppenauer oxidation of the 3-ol to the 3-one with acetone and 2-propanol at 0° C. for about 6 hours to yield 40 (see also the procedure in Berichte, Vol. 109, p. 2954, 1976). The seco acid 41 is produced by oxidizing 40 with a mixture of sodium periodate, potassium permanganate, sodium carbonate, water, t-butanol at reflux for one hour. (See also the procedure in J. Med. Chem., Vol. 27, p. 1690, 1984). The seco acid 41 is then treated with methylamine hydrochloride, sodium acetate in ethylene glycol at 180° C. for 8 hours to produce the 4-N-methyl analog 42. The 5-ene 42 is catalytically hydrogenated using $PtO_2$ catalyst in glacial acetic acid at 60° C. in a hydrogen atmosphere to yield the 17β-hydroxy-5α analog 43. The steroid 43 is reacted with diazomalonate, and rhodium acetate in dry methylene chloride under nitrogen at 40°–45° C. for about 9 hours to yield 44.

The 5-ene 42 is reacted with acetic anhydride, pyridine, 4-dimethylaminopyridine (DMAP) in methylene chloride at 0° C. for 2 hours to produce the 17-acetoxy analog 45, which in turn can be hydrogenated in glacial acetic acid using $PtO_2$ catalyst at 45° C. for 1 hour under hydrogen pressure to yield the 5α analog, 46.

The saturated 17-hydroxy analog 43 can be further derivatized by analogously using the above procedure described for 44 by reacting with dibenzylmalonate and rhodium diacetate in methylene chloride at 40°–50° C. for 3–4 hours, to yield the bis(dibenzyloxycarbonyl)methoxy analog 47. This in turn is hydrogenated in methanol with 10% Pd/C catalyst over one hour at room temperature to yield the diacid 48 which is decarboxylated in refluxing DMF over one hour containing 4 drops concentrated HCl to yield the 17-oxyacetic acid, 49.

The 17-oxyacetic acid 49 can be converted to amide derivatives by reaction with appropriate amines. Reaction of 49 with aniline, together with N-hydroxy benzotriazole monohydrate, (HOBt), 1-(3-dimethylaminopropyl)-3-ethyl carbodiimide hydrochloride (EDC), N-methyl-morpholine in methylene chloride solvent stirred overnight at room temperature yields the anilide 50. Similarly, t-butylamine yields 51; and 4-aminopyridine yields 52.

The methyl ester 53 of the 17-oxyacetic acid 49 is made by reaction with diazomethane is anhydrous methylene chloride at room temperature under nitrogen for one hour. The 17-amino derivatives are produced by first oxidizing the 17-hydroxy compound 43 with a mixture of TPAP, N-methyl morpholine-N-oxide, 4 Å molecular sieves in methylene chloride at 0° C. for one hour to produce the 17-keto compound 54. This in turn is converted to the N-oxime 55 by reaction with hydroxylamine•HCl, sodium acetate, in refluxing absolute ethanol for 18–24 hours. The oxime 55 is hydrogenated in ethanol/acetic acid with PtO₂ to yield the 17-amino compound 56. The 17-amino derivative 56 can be acylated with various acid chlorides in e.g., dry methylene chloride, using a proton acceptor e.g., pyridine and catalytic 4-dimethylaminopyridine, at room temperature for 4–24 hours. Specifically, reaction of 56 with benzoyl chloride yields 57; reaction with acetyl chloride yields 58; reaction with pivaloyl chloride yields 59.

The 17-amine 56 can also be reacted with acids using the analogous procedure described above for preparation of 50. Specifically, reaction of 56 with (R) mandelic acid produces 60, while reaction with (S) mandelic acid produces 61.

The 17-hydroxy analog 43 can be further derivatized by reacting with various isocyanates in e.g. dry methylene chloride and presence of a proton acceptor, e.g. DBU, at room temperature with stirring for 4–48 hours. Reaction of 43 under these type of conditions with benzyl isocyanate yields the carbamate 62; with t-butylisocyanate. 64; with octylisocyanate, 65; with phenylisocyanate, 66. Reaction of 43 with acyl halides in dry methylene chloride and e.g. pyridine at room temperature for 1–3 days produces the corresponding sterol esters. Reaction of 43 with pivaloyl chloride yields the pivaloate ester 63; with benzoyl chloride, the benzoate 67.

FLOWSHEET P

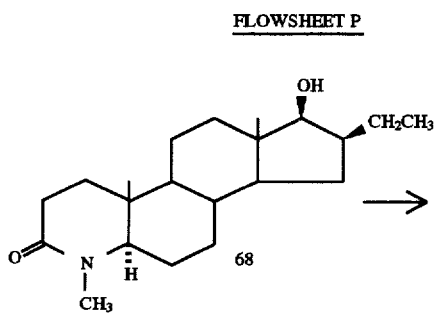

68 ⟶

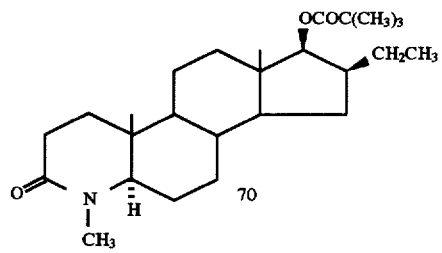

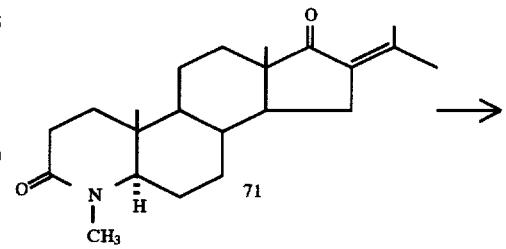

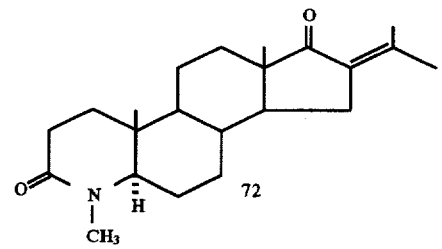

72 ⟶

73 ⟶

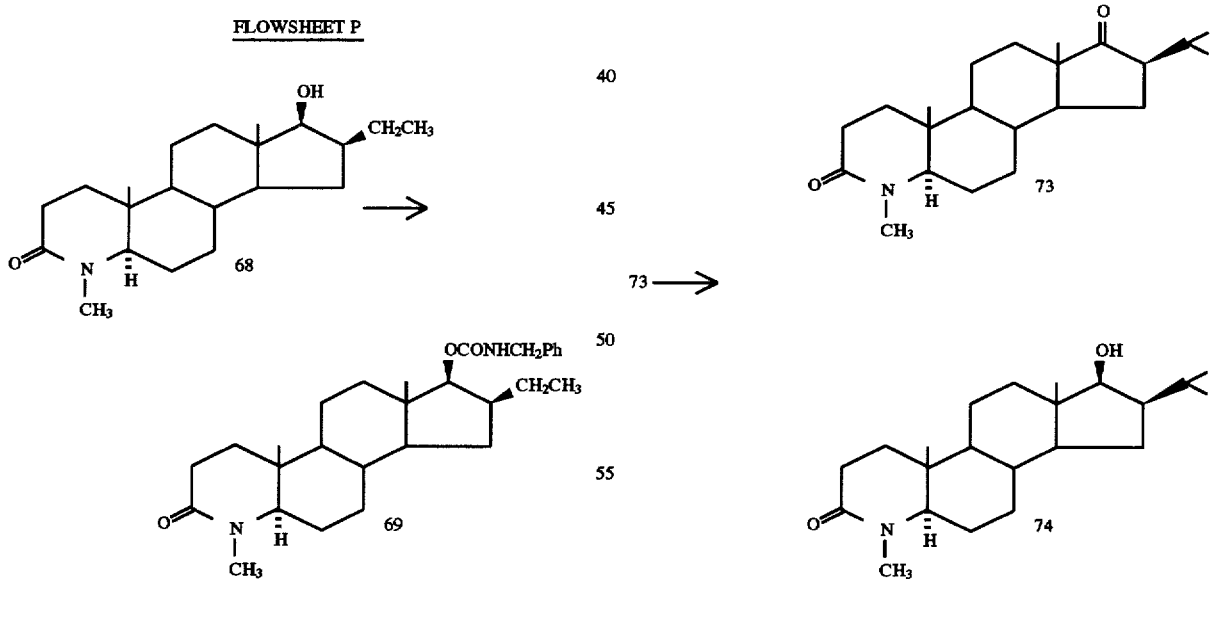

FLOWSHEET O

74 →

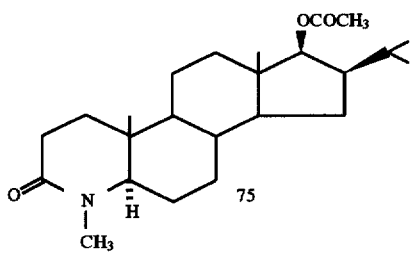
75

74 →

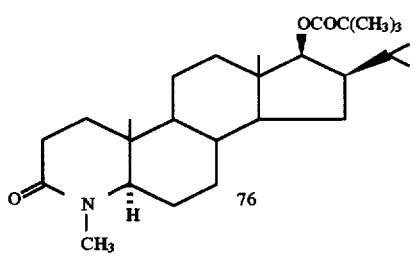
76

73 →

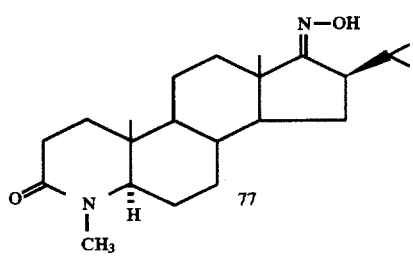
77

77 →

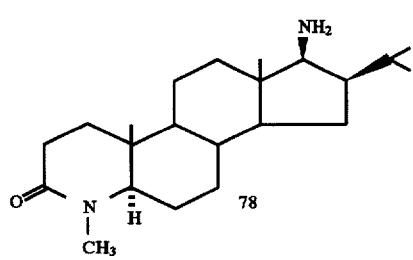
78

78 →

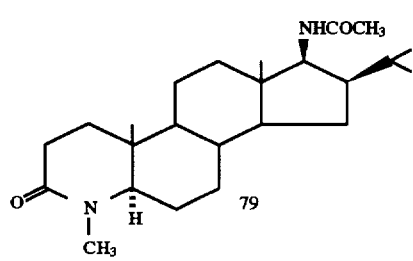
79

FLOWSHEET R

78 →

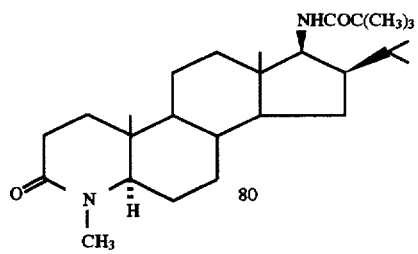
80

78 →

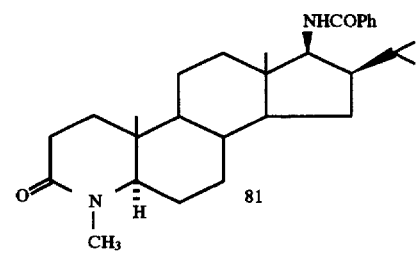
81

78 →

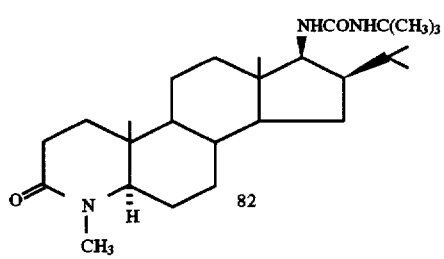
82

78 →

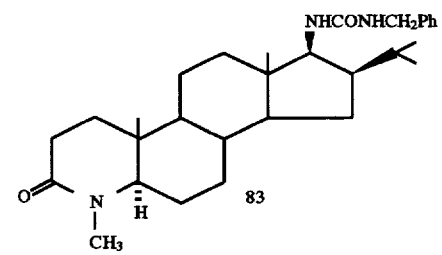
83

The 16-beta-ethyl series where A is structure VIIIA is prepared as illustrated in Flowsheet P.

The starting 16-beta ethyl 17-ol 68, is made by the analogous procedure of K. Yoshioka, *Chem. Pharm. Bull.* (Japan) vol. 23, p. 3203 (1975) wherein the ketone 71, is reacted with acetic anhydride and pyridine overnight at 60° C. to an enol acetate, which is subsequently hydrogenated at high pressure. e.g., 10,000 psig over Raney Nickel at room temperature to yield the 16-beta-ethyl-17-beta-ol, 68.

The 17-hydroxy group can be derivatized to carbamates by reacting with isocyanates, as described above, in dry methylene chloride in the presence of DBU at room temperature for 24–48 hours. Specifically, 68 reacted with benzyl isocyanate in this manner yields 69.

Further derivatization to sterol esters can be carried out by reacting with various acyl halides in e.g., dry methylene chloride with pyridine, 4-dimethylamino-pyridine at room temperature for 24–48 hours. Specifically reaction of 68 with pivaloyl chloride yields the pivaloate 70.

The 16-beta-isopropyl series where A is structure VIIIA is prepared as illustrated in Flowsheets P–R by reacting the 16-unsubstituted 17-one 71, with acetone, potassium hydroxide in methanol under reflux for three days to yield the 16-isopropylidene compound 72, which is hydrogenated in methanol with 10% Pd/C catalyst under one atmosphere $H_2$ pressure for one hour to yield the 16-beta-isopropyl-17-one, 73, which is reduced to the alcohol 74, by treatment with sodium borohydride in methanol overnight at room temperature.

The alcohol 74 can be derivatized to carbamates and esters analogously as described above. Specifically, reacting 74 with acetic anhydride in dry methylene chloride, pyridine and 4-dimethylaminopyridine overnight at room temperature yields the 16-β isopropyl-17β-acetate derivative, 75. Similarly, with pivaloyl chloride, the pivaloate compound 76 is produced.

The 17-amino series where A is structure VIIIA is produced by starting with the 16-beta isopropyl-17-one, 73, converting to the 17-oximino compound 77 by heating at 80° C. for 18 hours with hydroxylamine hydrochloride and sodium acetate in ethanol, and reducing the 17-oximino group to the 17-amino compound 78, by catalytic hydrogenation in ethanol/acetic acid over $PtO_2$ catalyst under hydrogen pressure for 18 hours.

The 17-amino compound 78 can be derivatized by reacting with various acyl halides, anhydrides or isocyanates in a solvent. e.g., methylene chloride at room temperature with pyridine. 4-dimethylaminopyridine over 4–48 hours.

Specifically, reaction of 78 with acetic anhydride yields the 17β-acetate, 79; with pivaloyl chloride, 80; with benzoyl chloride, 81; with t-butylisocyanate, 82; with benzylisocyanate, 83.

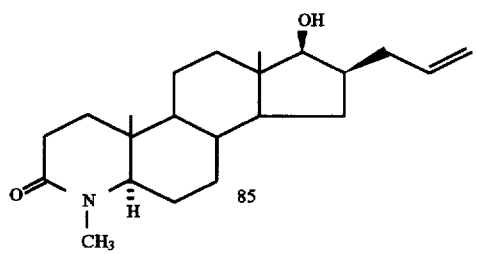

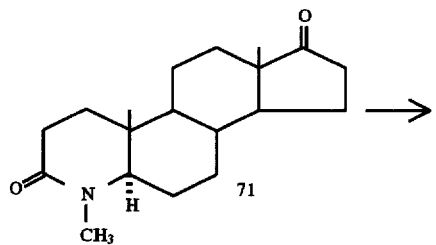

FLOWSHEET S

FLOWSHEET T

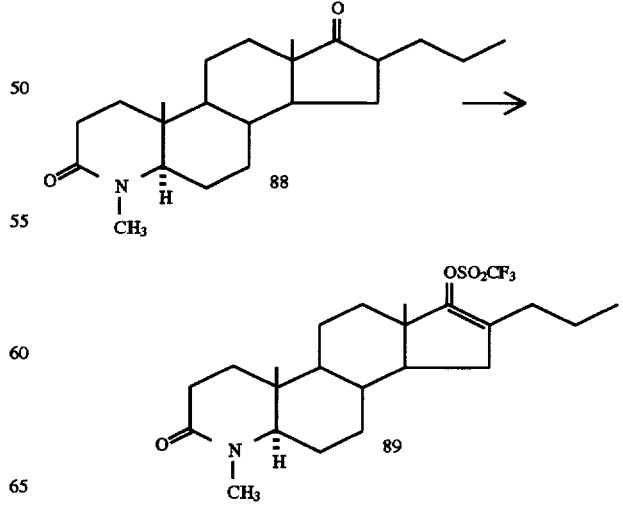

89 →

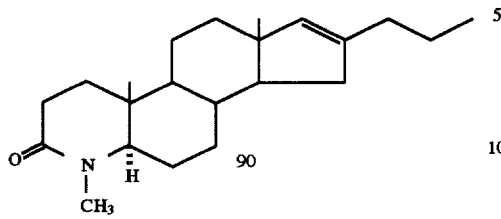

90 →

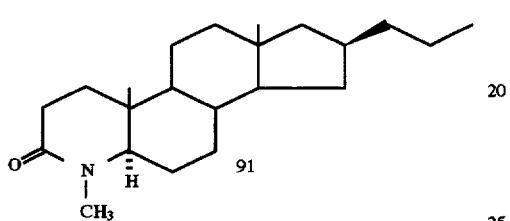

FLOWSHEET U

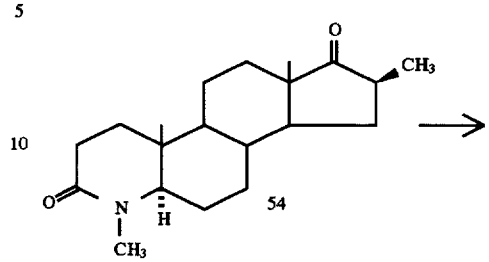

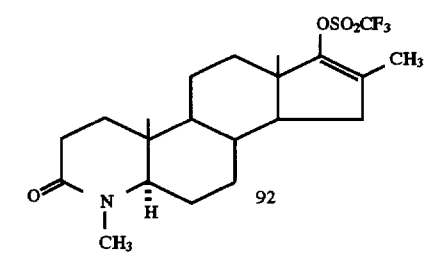

92 →

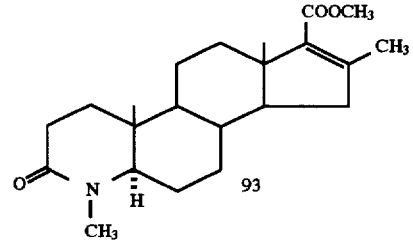

93 →

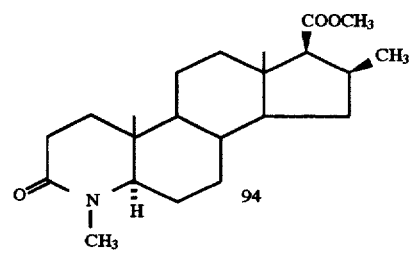

92 →

The 16-propyl and 16-allyl series where A is structure VIIIA are produced as illustrated in Flowsheets S and T by starting with the 17-one, 71, and reacting it with allyl bromide, sodium carbonate, acetone, sodium methoxide, diethyloxalate in methylene chloride stirred overnight at 0° C. to yield the 16-β allyl-17-one, 84. This is known as the oxalate-activation blocking reaction (see Ruggieri. Gaz. Chim. Ital. Vol. 92, p. 972 (1961) and Carothers, J. Org. Chem., Vol. 57, p. 961 (1992)). This is reduced to the 17-beta alcohol, 85, by stirring for 3 hours at 0° C. in a solution of dry THF and L-Selectride (Aldrich).

The alcohol 85 can be derivatized analogously as described above by e.g. reacting with t-butyl isocyanate in dry methylene chloride and DBU at room temperature for 24–48 hours to produce the carbamate, 86, which can be hydrogenated in methanol using 10% Pd/C overnight at room temperature to produce the 16-β propyl analog, 87.

The 17-H series where A is structure VIIIA can be produced as illustrated on Flowsheet T by reacting the 16-β-propyl-17-one, 88, made by catalytic hydrogenation of 84. This is reacted with KHMDS, (potassium hexamethyldisilylazide,) and N-phenyltrifluoromethanesulfonimide (see Tet. Lett. 24, 979, 1983) in dry THF for about 3 hours to yield the 16-propyl-17-enol-triflate, 89. The triflate is treated with tributyl tinhydride, lithium chloride, tetra (triphenylphosphine)palladium, in THF at reflux for 2–4 hours to yield the 16-propyl-16-ene, 90, which can be hydrogenated over 10% Pd/C in methanol at room temperature to yield the 16β-propyl derivative, 91.

FLOWSHEET V

95 →

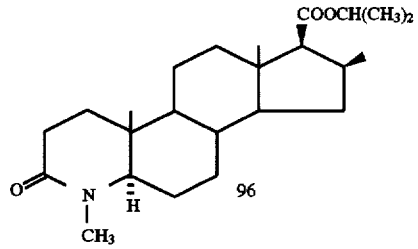

92 →

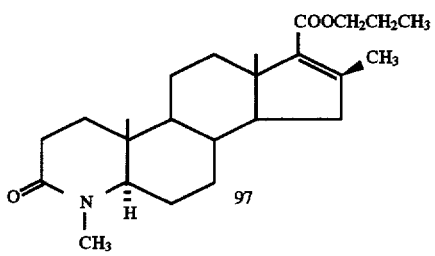

97 →

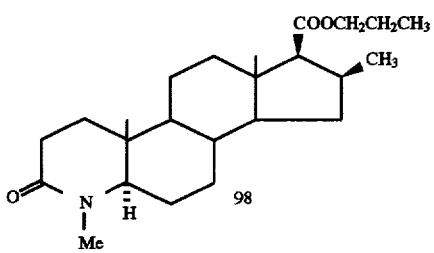

92 →

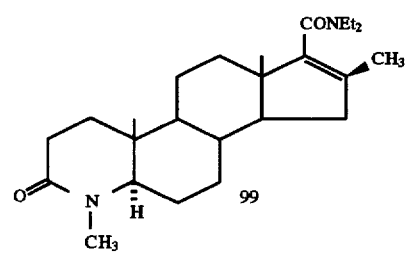

99 →

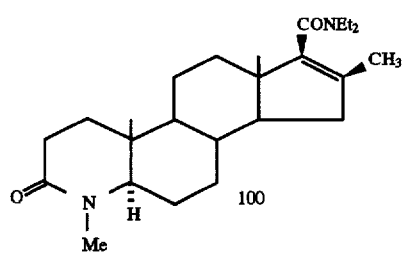

FLOWSHEET W

92 →

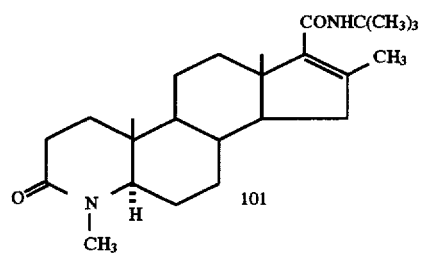

101 →

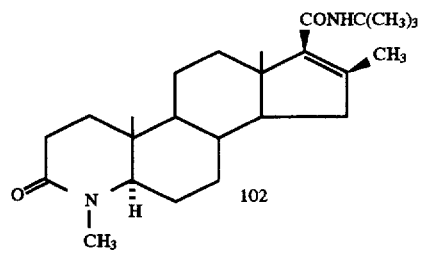

The 17-carboxy series where A is structure VIIIA and Z is (H,H) is prepared as illustrated in Flowsheets V–W through vinyl triflate chemistry analogous to procedures cited below.

The starting point for the 16-beta methyl 17-carboxy series is the 17-one 54, which is converted to the O-triflate analogous to the procedure described above using lithium hexamethyl disilylazide and N-phenyltrifluoromethanesulfonimide in THF to form the 16β-methyl-17-enoltriflate, 92. This is reacted analogous to the prior art procedure in Tet. Lett. 1109 (1985) by treating the enoltriflate 92 with palladium bis(triphenylphosphine) bisacetate, triethylamine, methanol, methylene chloride in a carbon monoxide atmosphere balloon apparatus for 4 hours at room temperature to yield the delta-16-17-methyl carboxylate, 93, which is hydrogenated in ethyl acetate with $PtO_2$ at room temperature under a hydrogen atmosphere to the 16β-methyl-17-carboxylate, methyl ester 94.

Similarly, the enoltriflate, 92, is treated with isopropanol to form the isopropanyl ester 95, which is hydrogenated to yield 96; and with n-propanol to yield the propyl ester 97, which is hydrogenated to yield the 16β-methyl-17-propyl carboxylate, 98.

By using amines in place of the alcohol in the palladium catalyzed carbonylation described above for the preparation of 93, using diethylamine with 92 produced the 17-(N,N-diethyl carboxamide), 99, which was hydrogenated to yield 100.

Similarly, analogously using diisopropylamine in the reaction yielded the 17β-(N,N-diisopropylcarboxamide), 101, which was catalytically hydrogenated to yield 102.

Following are descriptions and methods of synthesis of the other various 17-A radical compounds of structures IA–VIIIA, in this invention which can be used as starting materials to which the methods described herein can be applied to introduce the 16-substituent to yield the corresponding 16-substituted 17-A and 7,16-disubstituted 17-A derivatives.

EXAMPLES THE CASE WHEN SUBSTITUENT "A" OF GENERAL FORMULA "I" IS AS DEFINED IN GROUP "I(A)(1)"

A preferred embodiment of the compound of formula I where A is structure IA (1) applicable in the process of our invention is represented by the general structural formula:

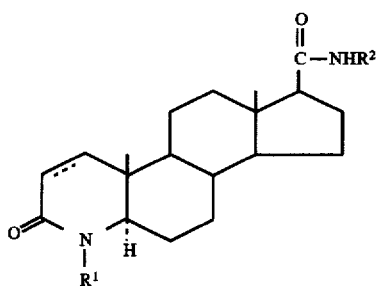

wherein
$R^1$ is hydrogen, methyl or ethyl, and
$R^2$ is branched chain alkyl cycloalkyl, aralkyl of from 4–12 carbons, phenyl, optionally substituted by methyl, chloro or fluoro, substituted or unsubstituted 1-, 2-adamantyl, 1-, 2-adamantylmethyl, 1-, 2- or 7-norbornanyl, 1-, 2- or 7-norbornanymethyl.

Representative compounds to which the 16-substituent may be introduced include the following:
17β-(N-tert-amylcarbamoyl)-4-aza-5α-androst-1-en-3-one,
17β-(N-tert-hexylcarbamoyl)-4-aza-5α-androst-1-en-3-one,
17β-(N-tert-butylcarbamoyl)-4-aza-4-methyl-5α-androst-1-en-3-one,
17β-(N-isobutylcarbamoyl)-4-aza-5α-androst-1-en-3-one,
17β-(N-tert-octylcarbamoyl)-4-aza-5α-androst-1-en-3-one,
17β-(N-t-butylcarbamoyl)-4-aza-5α-androst-1-en-3-one,
17β-(N-neopentylcarbamoyl)-4-aza-5α-androst-1-en-3-one,
17β-(N-2-adamantylcarbamoyl)-4-aza-5α-androst-1-en-3-one,
17β-(N-1-adamantylcarbamoyl)-4-aza-5α-androst-1-en-3-one,
17β-(N-2-norbornylcarbamoyl)-4-aza-5α-androst-1-en-3-one,
17β-(N-1-norbornylcarbamoyl)-4-aza-5α-androst-1-en-3-one,
17β-(N-phenylcarbamoyl)-4-aza-4-methyl-5α-androst-1-en-3-one,
17β-(N-benzylcarbamoyl)-4-aza-4-methyl-5α-androst-1-en-3-one,
17β-(N-tert-amylcarbamoyl)-4-aza-4-methyl-5α-androst-1-en-3-one,
17β-(N-tert-hexylcarbamoyl)-4-aza-4-methyl-5α-androst-1-en-3-one,
17β-(N-tert-butylcarbamoyl)-4-aza-4-methyl-5α-androst-1-en-3-one,
17β-(N-isobutylcarbamoyl)-4-aza-4-methyl-5α-androst-1-en-3-one,
17β-(N-tert-octylcarbamoyl)-4-aza-4-methyl-5α-androst-1-en-3-one,
17β-(N-1,1,3,3-tetramethylbutylcarbamoyl)-4-aza-5α-androst-1-en-3-one,
17β-(N-octylcarbamoyl)-4-aza-4-methyl-5α-androst-1-en-3-one,
17β-(N-1,1-diethylbutylcarbamoyl)-4-aza-4-methyl-5α-androst-1-en-3-one,
17β-(N-neopentylcarbamoyl)-4-aza-4-methyl-5α-androst-1-en-3-one,
17β(N-1-adamantylcarbamoyl)-4-aza-5α-androstan-3-one;
17β(N-1-adamantylcarbamoyl)-4-methyl-4-aza-5α-androst-1-en-3-one;
17β(N-1-adamantylcarbamoyl)-4-methyl-4-aza-5α-androstan-3-one;
17β-(N-1-adamantylmethylcarbamoyl)-4-aza-5α-androst-1-en-3-one;
17β-(N-2-adamantylcarbamoyl)-4-aza-5α-androstan-3-one;
17β-(N-methyl-N-2-adamantylcarbamoyl)-4-methyl-4-aza-androstan-3-one;
17β-(N-2-adamantylcarbamoyl)-4-methyl-4-aza-5α-androstane-3-one;
17β-(N-2-adamantylcarbamoyl)-4-methyl-4-aza-5α-androst-1-en-3-one;
17β-(N-methyl-N-2-adamantyl)carbamoyl-4-methyl-4-aza-androst-1-en-3-one;
17β-(N-(3-methyl)-1-adamantyl-carbamoyl)-4-aza-4-methyl-5α-androst-an-3-one;
17β-(N-exo-2-norbornanylcarbamoyl)-4-aza-4-methyl-5α-androst-1-en-3-one;
17β-(N-exo-2-norbornanylcarbamoyl)-4-aza-5α-androst-1-en-3-one;
17β-(N-2-adamantylcarbamoyl)-4-aza-5α-androst-en-3-one;
17β-(N-methyl-N-2-adamantylcarbamoyl)-4-aza-4-methyl-androstan-3-one;
17β-(N-2-adamantylcarbamoyl)-4-methyl-4-aza-5α-androstan-3-one; and
17β-(N-methyl-N-2-adamantyl)carbamoyl-4-methyl-4-aza-androst-1-en-3-one.

The corresponding compounds of those above wherein the 4-aza substituent is substituted in each of the above named compounds with a hydrogen, methyl or an ethyl radical, to form a different N-substituent, and wherein a double bond can be optionally present as indicated by the dotted line in position 1.

The alkyl, cycloalkyl, aralkyl, monocyclic aryl, 1-, 2-adamantyl or 1-, 2-norbornanyl moieties can be substituted with one or more substituents of the following: $C_1$-$C_4$ linear/branched alkyl, including methyl, ethyl, isopropyl, n-butyl; nitro; oxo; $C_7$-$C_9$ aralkyl, including benzyl; $(CH_2)_n COOR$ where n is 0–2 and R is H or $C_1$-$C_4$ linear/branched alkyl including methyl, ethyl; $CH_2OH$; OH; OR where R is $C_1$-$C_4$ linear/branched alkyl including methyl, ethyl; halo, including fluoro, bromo, iodo; COOH; COOR, where R is linear/branched $C_1$-$C_4$ alkyl; —$CONH_2$; $CH_2NH_2$; $CH_2NHCOR$ where R is $C_1$-$C_4$ linear/branched alkyl including methyl, ethyl; phenyl; o, m, p-substituted phenyl including p-nitro, p-amino and p-sulfo; or cyano. The amino group of the adamantyl or norbornanyl moiety can also be substituted as $R^1$ with methyl and ethyl, as well as hydrogen.

Also included within the scope of this invention are pharmaceutically acceptable salts or esters, where a basic or acidic group is present on the substituted alkyl, cycloalkyl, aralkyl, adamantyl or norbornanyl moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Representative examples include for $R^2$ (where AD is adamantyl):

3,5,7-trinitro-1-AD; 4-oxo-1-AD; 1-benzyl-1-AD; 4,4-dimethyl-1-Ad; 3,7-dimethyl-5-carboxymethyl-1-AD; 3-carboxymethyl-1-AD; 3-chloro-1-AD; 1,3-dihydroxy-6,6-dimethyl-2-AD; 3-chloro-1-AD; 4-carbethoxy-2-AD; 4-carboxy-2-AD; 3-isopropyl-1-AD; 3-n-butyl-1-AD; 3-propyl-1-AD; 3-,5-diethyl-1-AD; 3-hydroxymethyl-1-AD; 2-carboxy-1-AD; 3-methyl-1-AD; 5-hydroxy-2-AD; 2-hydroxy-1-AD; 1-aminomethyl-1-hydroxy-2-AD; 2-oxo-1-AD; 2-phenyl-2-AD; 1-aminomethyl-2-AD; 1-carboxy-2-AD; 1-aminocarbonyl-2-AD; 3-hydroxy-5,7-dimethyl-1-AD; 4-fluoro-1-AD; 3-fluoro-1-AD; 4-hydroxy-2-AD; 3-phenyl-1-AD; 3-(p-aminophenyl)-1-AD; 3-(p-nitrophenyl)-1-AD; 3-methyl-5-hydroxymethyl-1-AD; 3,5-dimethyl-4-hydroxy-1-AD; 2-hydroxymethyl-2-AD; 3-(p-sulfophenyl)-1-AD; 3-methyl-5-ethyl-1-AD; 2-carboxy-2-AD; 3,5-7-trimethyl-1-AD; 4-iodo-2-AD; 4-bromo-2-AD; 4-chloro-2-AD; 1-acetylaminomethyl-2-AD; 1-carboxymethyl-2-AD; 1-methyl-2-AD; 1-aminocarboxylmethyl-2-AD; 1-aminocarboxyl-1-AD; 2-cyano-2-AD; 3,5-dimethyl-7-ethyl-1-AD; 4-hydroxy-1-AD; 1-hydroxy-2-AD; 5-carboxy-3-methyl-1-AD; 3,5-dimethyl-7-carboxy-1-AD; 3-carboxy-1-AD; 3-hydroxy-1-AD; and the like.

Representative examples include for $R^2$ as substituted norbornanyl moieties are (where NB is norbornanyl):

2-NB; 1,7,7-trimethyl-4-phenyl-2-NB; 3-carboxy-2-NB; 3-phenyl-2-carboxy-2-NB; 2-cyano-3-phenyl-2-NB; 3-hydroxy-4,7,7-trimethyl-2-NB; 6-hydroxymethyl-2-NB; 5-cyano-2-NB; 3-allyl-2-NB; 1-NB; 7,7-dimethyl-1-hydroxymethyl-2-NB; 3-methoxy-4,7,7-trimethyl-2-NB; 3-aminocarbonyl-2-NB; 3-ethoxycarbonyl-2-NB; 3,3-dimethyl-2-NB; 7-oxo-1-NB; 3-phenyl-2-NB; 1-carboxymethyl-7,7-dimethyl-2-NB; 1-ethyl-2-NB; 1-methyl-2-NB; 2,2,3,3,5,5,6,6,7,7-decafluoro-1-NB; 3-hydroxy-2-NB; 3-chloro-2-NB; 3-(p-methoxyphenyl)-2-NB; 2,2-dimethyl-3-methylene-7-NB; 3-oxo-2-NB; 1-methoxy-2-NB; 7-NB; 3-isopropyl-2-NB; 2-bromo-1-NB; 3-chloro-1-NB; and the like.

Procedures for preparing the starting compounds of structure IA for introducing the 16-substituent including the above, are well known in the art.

The novel compounds of formula I of the present invention can be prepared by a method starting with the known steroid ester (III) of the general structural formula:

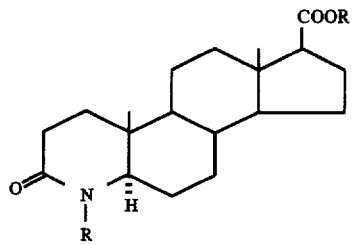

III

17β-(carbomethoxy)-4-aza-5-α-androstan-3-ones which includes the stages of optionally 1) dehydrogenating said starting material to produce the corresponding compound containing a double-bond in the 1,2-position of the A-ring, 2) converting the 17-carbomethoxy substituent into an N-substituted alkyl, cycloalkyl, aralkyl, monocylic acyl, or adamantylcarbamoyl substituent and, if desired, 3) alkylating the A-ring nitrogen to introduce a N-methyl or N-ethyl substituent into the A ring 4-position. For the dehydrogenation step, it is preferable that the 4-aza nitrogen be unsubstituted. The alternate pathways can consist of one or more discrete chemical steps and if desired can take place before step (1) or following step (1) or step (3).

In accordance with the present invention (see flow sheet), the starting materials are formed by optionally: (1) heating a 17β-alkoxycarbonyl-4-aza-5α-androstan-3-ones, compound III, (prepared in the literature as described in the reference U.S. Pat. No. 4,377,584) with a dehydrogenating agent such as benzeneseleninic anhydride in a refluxing inert solvent, e.g. chlorobenzene, to form a 17β-alkoxycarbonyl-4-aza-5α-androst-1-ene-3-one IV (alternately, the dichlorodicyanobenzoquinone process of Dolling, et al., JACS 1988, Vol. 110, pp. 3318–3319, can be used); (2) the formed 5α-androst-1-en-3-one compound from Step 1 can be reacted with, e.g. sodium hydride under anhydrous conditions in a neutral solvent such as dimethylformamide; (3) contacting the resulting reaction mixture with an alkyl (methyl or ethyl) iodide to form the corresponding 17-β-alkoxy-adamantylcarbamoyl-4-alkyl-4-aza-5α-androst-1-en-3-one V; (4)subsequently hydrolyzing said 17β-alkoxycarbonyl-4-alkyl-4-aza-5α-androst-1-en-3-one with a strong base, such as aqueous methanolic potassium hydroxide at the reflux temperature, followed by acidification and isolation of the resulting steroidal acid to yield 17β-carboxy 4-alkyl-4-aza-5α-androst-1-en-3-one VI; (5) said steroidal acid can be then converted to its corresponding 2-pyridylthio ester by refluxing with triphenyl phosphine and 2,2'-dipyridyl disulfide in an inert solvent such as toluene and the resulting product 17β-(2-pyridylthiocarbonyl)-4-alkyl-4-aza-5α-androst-1-en-3-one VII can be isolated by chromatography on e.g. silica gel; and (6) said pyridylthio ester can be then reacted with 1-adamantyl, 2-adamantylamine or norbornanylamine in an inert solvent e.g. tetrahydrofuran, to form the desired product 17β-N-adamantyl-carbamoyl-4-alkyl-4-aza-5α-androst-1-en-3-one VIII which can be isolated by chromatography e.g. on silica gel. When the previous reaction is carried out in the absence of first forming the double bond at position 1, the corresponding 17β-(N-adamantyl-carbamoyl)-4-alkyl-4-aza-5α-androstan-3-one (or N-norbornanyl carbamoyl compound) is prepared.

In accordance with an alternate process of our invention the corresponding N-unsubstituted-17β(N-adamantyl-carbamoyl)-4-aza-5α-androst-1-en-3-one XIV is readily prepared from the 17β(alkoxycarbonyl)-4-aza-5α-androstone-3-one IV by repeating the above series of reaction steps but omitting the alkylation Step 2 herein above, i.e. treatment of the 4-aza-5-α-androst-1-en-3-one with e.g. sodium amide followed by methyl or ethyl iodide via intermediates XII and XIII.

In accordance with a further alternate process of preparing the compounds of our invention having only hydrogen as the sole substituent on the ring A—nitrogen, the double bond in the A ring is introduced as the last step of the process. Thus, a 17β-alkoxycarbonyl 4-aza-5α-androstan-3-one III is hydrolyzed to the corresponding steroidal acid IX 17β-carboxy-4-aza-5α-androstan-3-one which in turn is converted to the corresponding pyridylthio ester, 17β (2-pyridylthiocarbonyl)-4-aza-5α-androstan-3-one, X followed by treatment of the ester with an amine of formula $R^2$—$NH_2$ wherein $R^2$ is as defined hereinabove as 1- or 2-adamantyl or 1-, 2-, or 7-norbornanyl to form a 17β (N-adamantyl-carbamoyl)-4-aza-5α-androstone-3-one XI which is dehydrogenated as previously described to produce compound XIV, 17β-(N-adamantyl-carbamoyl)-4-aza-androst-1-en-3-one or corresponding norbornanyl derivative.

In another alternate method of introducing the 17β-(N-adamantyl-carbamoyl)substituent into a 17β-carboxy androstane compound of formula VI, XII or IX, each is treated in a manner similar to the procedure described in Steroids, Vol. 35 #3, March 1980, p. 1–7 with dicyclohexylcarbodiimide and 1-hydroxybenzo-triazole to form the 17β-(1-benzotriazoloxycarbonyl)-4-aza-5α-androst-1-en-3-one, VII, XIII or compound X, wherein the substituent X is benzotriazoloxy group.
The above reactions are schematically represented in the following flowsheet.
Flowsheet I
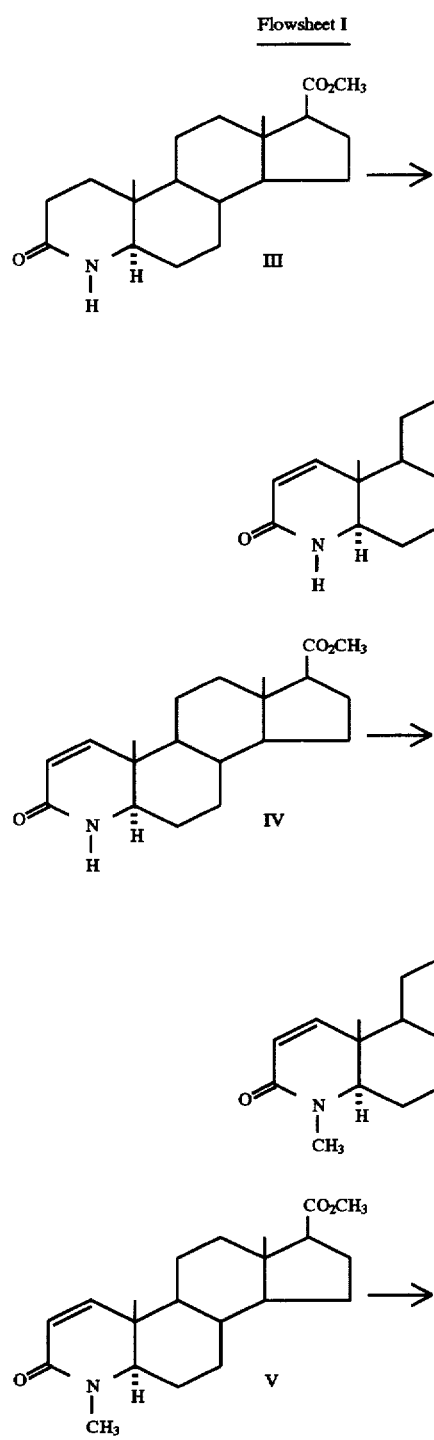
-continued
Flowsheet I
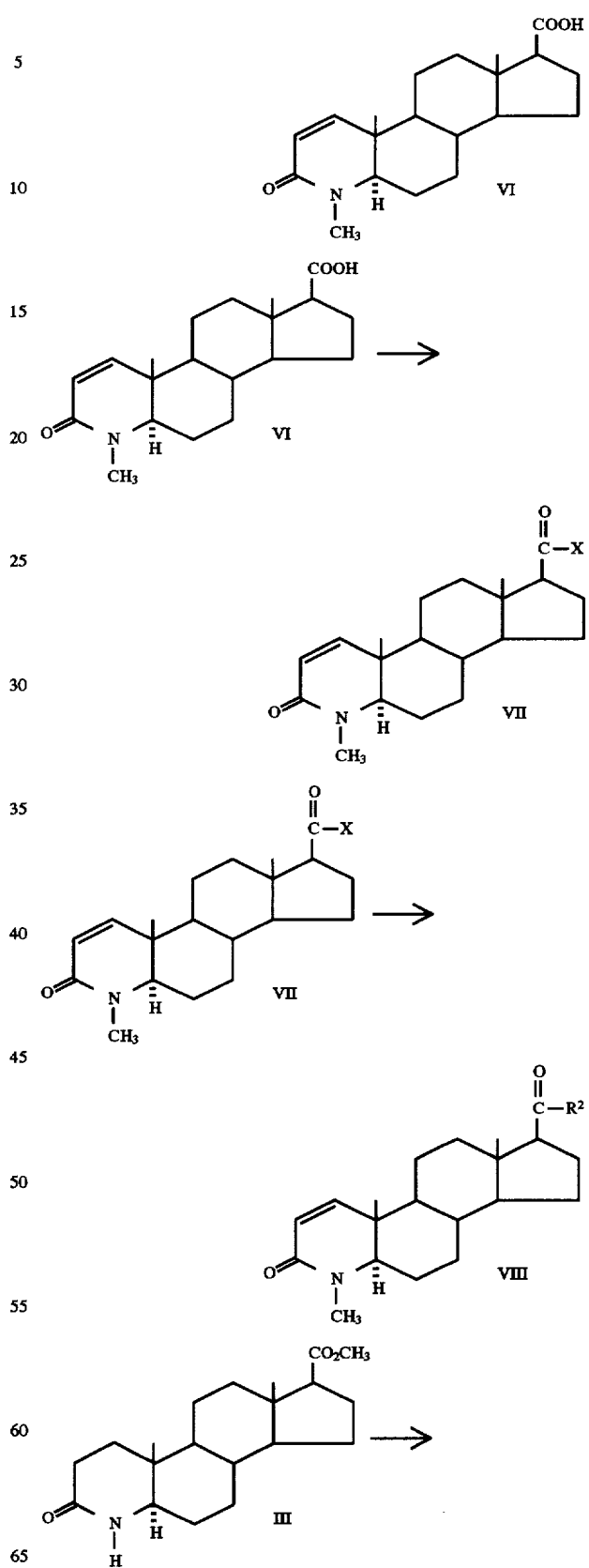

45
-continued
Flowsheet I
46
-continued
Flowsheet I
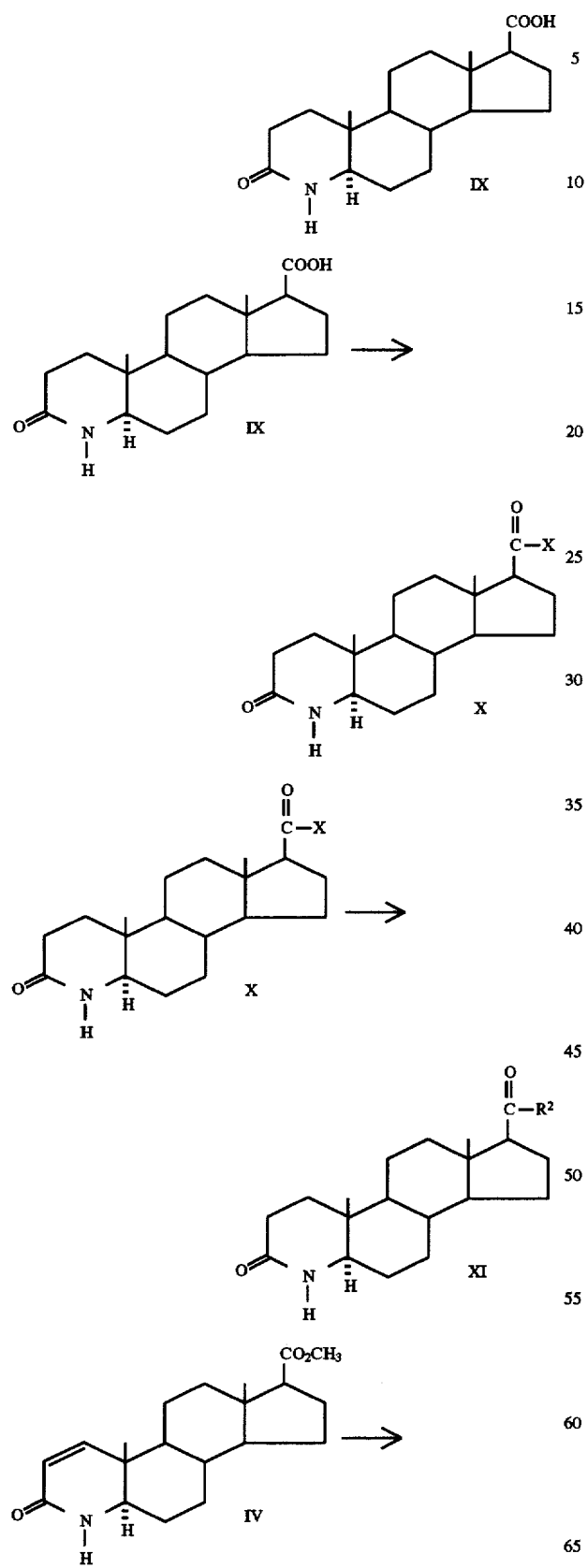
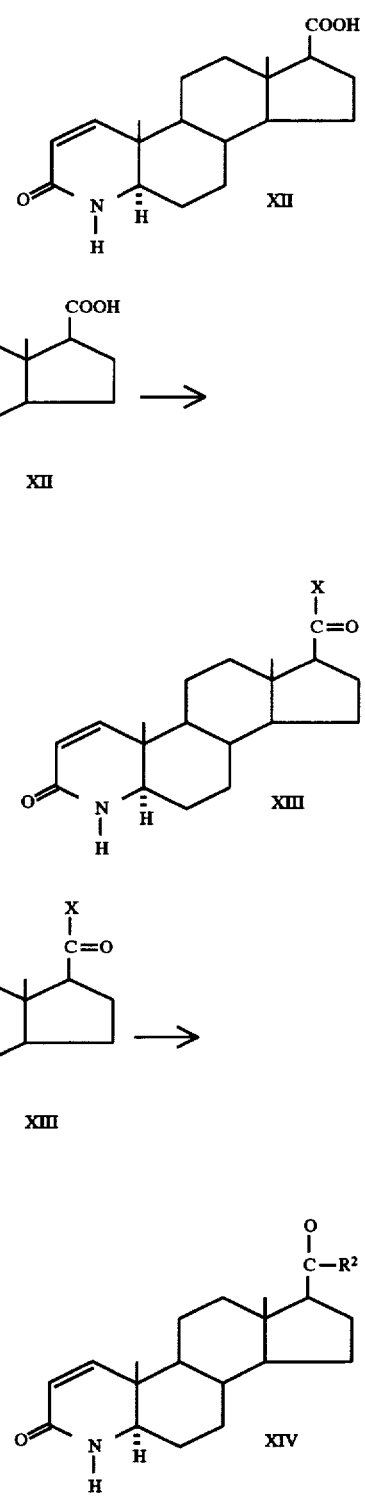

-continued
Flowsheet I

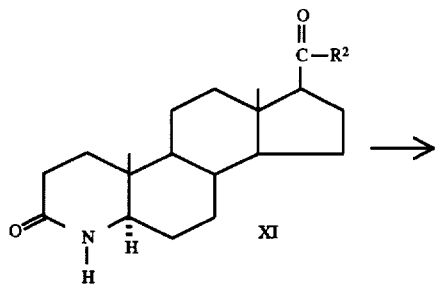

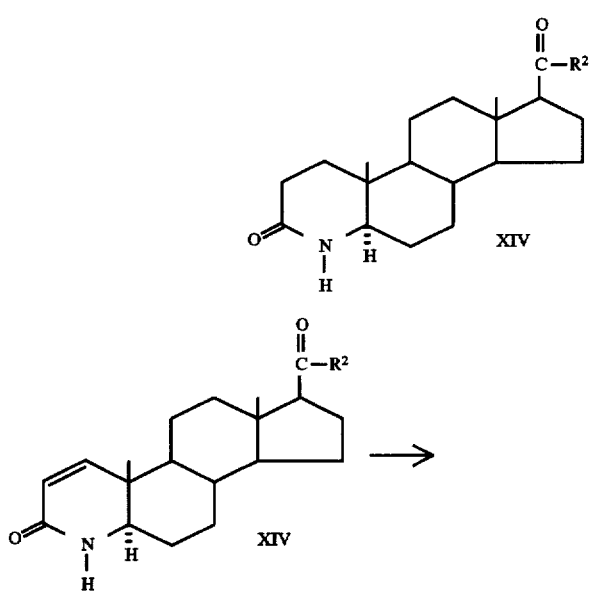

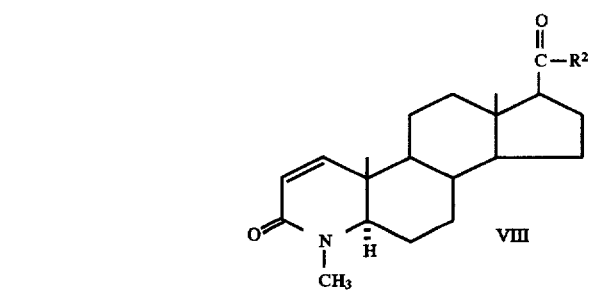

X is 2-pyridylthio or 1-benzotriazoloxy.
R² is 1- or 2-adamantyl or norbornanyl.

EXAMPLES FOR THE CASE WHEN
SUBSTITUENT "A" OF GENERAL FORMULA
"I" IS AS DEFINED IN GROUP "I(A)(2)"

A preferred embodiment of the compounds of our invention process is:
the compound of above Structure I, wherein
the dotted line is a double bond,
R is hydrogen or methyl, and
R² is branched chain alkyl, or cycloalkyl of from 4–10 carbons,
and R" and R'" are hydrogen.

Another embodiment of the invention is the compounds of above Structure I where R² is phenyl, or phenyl substituted by substituents described above, including where R² is phenyl, 2-, 3-, or 4-tolyl, xylyl, 2-bromophenyl, 2-chlorophenyl, 2,6-dichlorophenyl, 2,6-dibromophenyl, aminophenyl, N-alkylaminophenyl, N-N-dialkylaminophenyl, 4-biphenyl, 3-biphenyl, naphthyl, anthracyl, phenanthryl, thiophenyl, methylthiophenyl, methylsulfinyl, phenyl, methylsulfophenyl, aminosulfophenyl, thioethylphenyl, acetoxymethylthiophenyl, 17β-(4-hydroxyphenyl), 17β-(3-hydroxyphenyl), 17β-(3,4-dihydroxyphenyl), or 17β-(3,5-dimethyl-4-hydroxyphenyl).

Representative compounds of the invention are:
17β-(phenylcarbonyl)-4-aza-4-methyl-5α-androst-1-ene-3-one;
17β-(2-tolylcarbonyl)-4-aza-4-methyl-5α-androst-1-ene-3-one;
17β-(3-tolylcarbonyl)-4-aza-4-methyl-5α-androst-1-ene-3-one;
17β-(4-tolylcarbonyl)-4-aza-4-methyl-5α-androst-1-ene-3-one;
17β-(2-bromophenylcarbonyl)-4-aza-4-methyl-5α-androst-1-ene-3-one;
17β-(2-chlorophenylcarbonyl)-4-aza-4-methyl-5α-androst-1-ene-3-one;
17β-(2,6-dichlorophenylcarbonyl)-4-aza-4-methyl-5α-androst-1-ene-3-one;
17β-(2,6-dibromophenylcarbonyl)-4-aza-4-methyl-5α-androst-1-ene-3-one;
17β-(xylylcarbonyl)-4-aza-4-methyl-5α-androst-1-ene-3-one;
17β-(t-butylcarbonyl)-4-aza-5α-androst-1-ene-3-one;
17β-(isobutylcarbonyl)-4-aza-5α-androst-1-ene-3-one;
17β-(isooctylcarbonyl)-4-aza-5α-androst-1-ene-3-one;
17β-(n-octylcarbonyl)-4-aza-5α-androst-1-ene-3-one;
17β-(1,1-diethylbutylcarbonyl)-4-aza-5α-androst-1-ene-3-one;
17β-(neopentylcarbonyl)-4-aza-5α-androst-1-ene-3-one;
17β-(tert-amylcarbonyl)-4-aza-4-5α-androst-1-ene-3-one;
17β-(tert-hexylcarbonyl)-4-aza-4-5α-androst-1-ene-3-one;
17β-(cyclohexylcarbonyl)-4-aza-5α-androst-1-ene-3-one;
17β-(cyclopentylcarbonyl)-4-aza-5α-androst-1-ene-3-one;
17β-(benzylcarbonyl)-4-aza-5α-androst-1-ene-3-one;
17β-(2-pyridylcarbonyl)-4-aza-5α-androst-1-ene-3-one;
17β-(4-pyridylcarbonyl)-4-aza-5α-androst-1-ene-3-one;
17β-(2-pyrrolylcarbonyl)-4-aza-5α-androst-1-ene-3-one;
17β-(2-furylcarbonyl)-4-aza-5α-androst-1-ene-3-one;
17β-(2-thiophenylcarbonyl)-4-aza-5α-androst-1-ene-3-one;
17β-(2-adamantylcarbonyl)-4-aza-5α-androst-1-ene-3-one;
17β-(phenylcarbonyl)-4-aza-5α-androst-1-ene-3-one;
17β-(2-tolylcarbonyl)-4-aza-5α-androst-1-ene-3-one;
17β-(3-tolylcarbonyl)-4-aza-5α-androst-1-ene-3-one;
17β-(4-tolylcarbonyl)-4-aza-5α-androst-1-ene-3-one;
17β-(2-bromophenylcarbonyl)-4-aza-5α-androst-1-ene-3-one;
17β-(2-chlorophenylcarbonyl)-4-aza-5α-androst-1-ene-3-one;
17β-(2,6-dichlorophenylcarbonyl)-4-aza-5α-androst-1-ene-3-one;
17β-(2,6-dibromophenylcarbonyl)-4-aza-5α-androst-1-ene-3-one;
17β-(xylylcarbonyl)-4-aza-5α-androst-1-ene-3-one;
17β-(phenylethyl)carbonyl-4-aza-5α-androst-1-ene-3-one;
17β-(4-dimethylaminophenylcarbonyl)-4-aza-5α-androst-1-en-3-one;
17β-(3-dimethylaminophenylcarbonyl)-4-aza-5α-androst-1-en-3-one,
17β-(3,4-diethylaminophenylcarbonyl)-4-aza-androst-1-en-3-one, 17β-(3,5-dimethyl-4-diethylaminophenylcarbonyl)-4-aza-5α-androst-1-en-3-one;
17β-(4-N-methylaminomethylphenylcarbonyl)-4-aza-5α-androst-1-en-3-one; or
17β-(2-N-ethylamino-4-ethylphenylcarbonyl)-4-aza-5α-androst-1-en-3-one.
17β-(4-phenylbenzoyl)-4-aza-5α-androst-1-en-3-one;
17β-(3-phenylbenzoyl)-4-aza-5α-androst-1-en-3-one;
17β-(4-biphenyl)-4-aza-5α-androst-1-en-3-one;
17β-(3-biphenyl)-4-aza-5α-androst-1-en-3-one;
17β-(1-naphthyl)-4-aza-5α-androst-1-en-3-one;
17β-(2-naphthyl)-4-aza-5α-androst-1-en-3-one;
17β-(1-phenanthryl)-4-aza-5α-androst-1-en-3-one;
17β-(2-phenanthryl)-4-aza-5α-androst-1-en-3-one;
17β-(1-biphenyl)-4-aza-5α-androst-1-en-3-one;
17β-(9-anthracyl)-4-aza-5α-androst-1-en-3-one;
17β-(4-thiophenylcarbonyl)-4-aza-5α-androst-1-en-3-one;
17β-(3-thiophenylcarbonyl)-4-aza-5α-androst-1-en-3-one;
17β-(4-methylthiophenylcarbonyl)-4-aza-5α-androst-1-en-3-one;
17β-(4-methylsulfinylphenylcarbonyl)-4-aza-5α-androst-1-en-3-one;
17β-(4-methylsulfophenylcarbonyl)-4-aza-5α-androst-1-en-3-one;
17β-(3-methylsulfinylphenylcarbonyl)-4-aza-5α-androst-1-en-3-one;
17β-(4-N,N-dimethylaminosulfophenylcarbonyl)-4-aza-5α-androst-1-en-3-one;
17β-(2-ethyl-4-methylthiophenylcarbonyl)-4-aza-5α-androst-1-en-3-one;
17β-(4-thioethylphenylcarbonyl)-4-aza-4-methyl-5α-androst-1-en-3-one;
17β-(4-acetoxymethylthiophenylcarbonyl)-4-aza-4-methyl-5α-androst-1-en-3-one;
17β-(2-methyl-4-methylthiophenylcarbonyl)-4-aza-4-methyl-5α-androst-1-en-3-one;
17β-(2-methyl-4-methylsulfinylphenylcarbonyl)-4-aza-4-methyl-5α-androst-1-en-3-one;
17β-(2-isopropyl-4-methylsulfophenylcarbonyl)-4-aza-4-methyl-5α-androst-1-en-3-one;
17β-(4-methylthiophenylcarbonyl)-4-aza-4-methyl-5α-androstan-3-one;
17β-(4-methylsulfinylphenylcarbonyl)-4-aza-4-methyl-5α-androstan-3-one;
17β-(4-methylsulfophenylcarbonyl)-4-aza-4-methyl-5α-androstan-3-one;
17β-(4-hydroxyphenyl)-4-aza-5α-androst-1-en-3-one;
17β-(3-hydroxyphenyl)-4-aza-5α-androst-1-en-3-one;
17β-(3,4-dihydroxyphenyl)-4-aza-5α-androst-1-en-3-one;
17β-(3,5-dimethyl-4-hydroxyphenyl)-4-aza-5α-androst-1-en-3-one;
17β-(4-hydroxymethylphenyl)-4-aza-5α-androst-1-en-3-one;
17β-(2-hydroxyethylphenylcarbonyl)-4-aza-5α-androst-1-en-3-one;
17β-(4-methoxyphenyl)-4-aza-5α-androst-1-en-3-one;
17β-(4-carboxymethylphenyl)-4-aza-5α-androst-1-en-3-one;
17β-(4-hydroxyphenyl)-4-aza-4-methyl-5α-androst-1-en-3-one;
17β-(3-hydroxyphenyl)-4-aza-4-methyl-5α-androst-1-en-3-one;
17β-(3,4-dihydroxyphenyl)-4-aza-4-methyl-5α-androst-1-en-3-one;
17β-(3,5-dimethyl-4-hydroxyphenyl)-4-aza-4-methyl-5α-androst-1-en-3-one;
17β-(4-hydroxymethylphenyl)-4-aza-4-methyl-5α-androst-1-en-3-one;
17β-(2-hydroxyethylphenylcarbonyl)-4-aza-4-methyl-5α-androst-1-en-3-one;
17β-(4-methoxyphenyl)-4-aza-4-methyl-5α-androst-1-en-3-one;
17β-(4-carboxymethylphenyl)-4-aza-4-methyl-5α-androst-1-en-3-one; and
17β-(4-carboxyphenyl)-4-aza-5α-androst-1-en-3-one.
and the corresponding compounds wherein the 4-hydrogen substituent is replaced in each of the above named compounds by a methyl or an ethyl radical.

The compounds of formula I of the present invention are prepared by a method starting with the known steroid ester of the general structural formula IV:

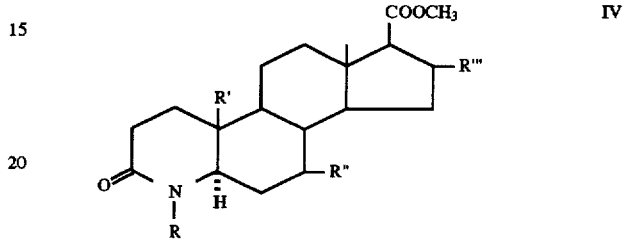

named 17β-(carbomethoxy)-4-aza-5α-androstan-3-one, which includes the stages of (1) dehydrogenating said starting material to produce the corresponding compound containing a double bond in the 1,2-position of the A-ring, (2) converting the 17-carbomethoxy substituent into a 17β-acyl substituent and, if desired (3) alkylating the A-ring nitrogen to introduce 4-methyl or 4-ethyl substituents into the A-ring. For the dehydrogenation step, it is preferable that the 4-aza nitrogen be unsubstituted. The dehydrogenation step can be carried out, e.g. according to the procedure of Dolling, et al. involving dichlorodicyanobenzoquinone, JACS (1988) Vol. 110, pp. 3318–3319. Stage (2) may consist of one or more chemical steps and if desired may take place before stage (1) or following stage (1) or stage (3).

In accordance with the process of the present invention, the products of our invention are formed by (1) heating a 17β-alkoxycarbonyl-4-aza-5α-androstan-3-one compound III with a dehydrogenating agent such as benzeneseleninic anhydride in refluxing chlorobenzene to form a 17β-alkoxycarbonyl-4-aza-5α-androst-1-en-3-one (IV), (2) the formed 5α-androst-1-en-3-one compound from step (1) is reacted with sodium hydride and under anhydrous conditions in a neutral solvent such as dimethylformamide, (2) contacting the resulting reaction mixture with an alkyl (methyl or ethyl) iodide to form the corresponding 17β-alkoxycarbonyl-4-alkyl-4-aza-5α-androst-1-en-3-one (V), (3) subsequently hydrolyzing said 17β-alkoxycarbonyl-4-alkyl-4-aza-5α-androst-1-en-3-one with a strong base such as aqueous methanolic potassium hydroxide at the reflux temperature, followed by acidification and isolation of the resulting steroidal acid, 17β-carboxy-4-alkyl-4-aza-5α-androst-1-en-3-one (VI), (4) said steroidal acid is then converted to its corresponding 2-thiopyridyl ester by refluxing with triphenyl phosphine and 2,2'-dipyridyl disulfide in an inert solvent and the product 17β-(2-pyridylthiocarbonyl)-4-alkyl-4-aza-5α-androst-1-en-3-one (VII) is isolated by chromatography on silica, (5) said pyridylthio ester is then reacted with an $R^2$—Li or an $R^2MgX$ (X=Cl, Br) compound, such as sec-butylmagnesium chloride in tetrahydrofuran, to form the desired product, e.g., 17β-(sec-butylcarbonyl)-4-alkyl-4-aza- 5α-androst-1-en-3-one (VIII) which is isolated by chromatography on silica gel. When the previous reaction is carried out using an $R^2MgX$ or, an $R^2$—Li compound in place of sec-butylmagnesium chloride, the corresponding 17β-(acyl)-4-alkyl-4-aza-5α-androst-1-en-3-one is prepared wherein acyl is $R^2$ carbonyl.

In accordance with the process of our invention, the corresponding 17β-acyl-4-aza-5α-androst-1-en-3-one XV is readily prepared from the 17β(alkoxycarbonyl)-4-aza-5α-androsten-3-one (IV) by repeating the above series of reaction steps but omitting step 2 hereinabove. i.e., treatment of the 4-aza-5α-androst-1-en-3-one with sodium amide followed by methyl or ethyl iodide.

In accordance with a further alternate process of preparing the compounds of our invention, having only hydrogen as the sole substituent on the ring A-nitrogen, the 1,2-double bond in the A-ring is introduced as the last step of the process. Thus, a 17β-alkoxycarbonyl-4-aza-5α-androstan-3-one (III) is hydrolyzed to the corresponding steroidal acid, 17β-carboxy-4-aza-5α-androstan-3-one, (IX) which, in turn, is converted to the corresponding thiopyridyl ester, 17β-(2-pyridylthiocarbonyl)-4-aza-5α-androstan-1-one (X) followed by treatment of the ester with an $R^2MgX$ or $R^2Li$ compound wherein $R^2$ is as defined hereinabove to form a 17β-(acyl)-4-aza-5α-androstan-3-one (XI) which is dehydrogenated as previously described to produce compound XIV, 17β-(acyl)-4-aza-5α-androst-1-en-3-one.

In an additional alternative process for making the compounds of formula I when the starting material is an ester, particularly methyl ester as shown in formula III-V in the schematic, reaction with a Grignard reagent $R^2MgX$, gives the ketone, 17β-$R^2CO$—, corresponding to the $R^2$ moiety associated with the Grignard reagent.

The 16-methyl derivative wherein R''' is methyl are prepared from known 16-methyl-17-acyl-4-methyl-4-aza-5α-androstan-3-ones, e.g. 4,16β-dimethyl-17β-acetyl-4-aza-5α-androstan-3-one by known dehydrogenation procedures for 4-methyl-4-aza compounds to produce the corresponding 4,16β-dimethyl-17β-acetyl-4-aza-5α-androst-1-en-3-one.

The above reactions are schematically represented in the following flowsheet II:

Flowsheet II

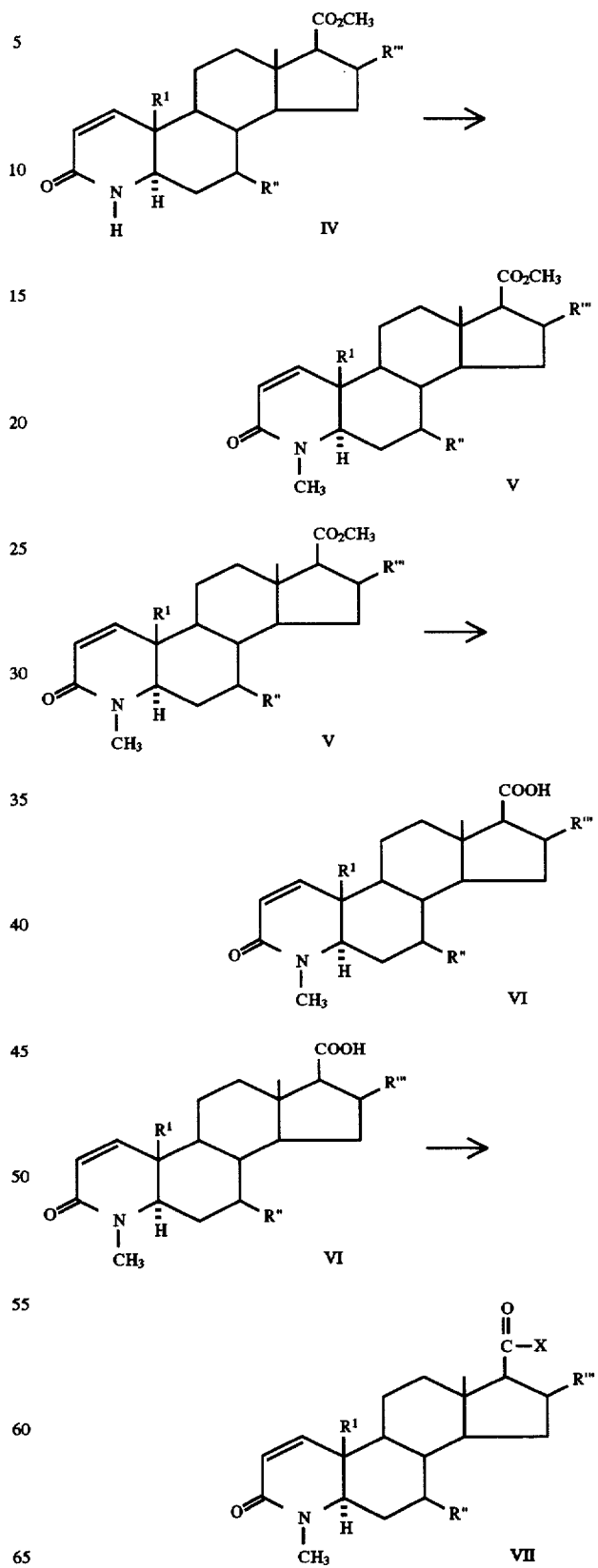

-continued
Flowsheet II
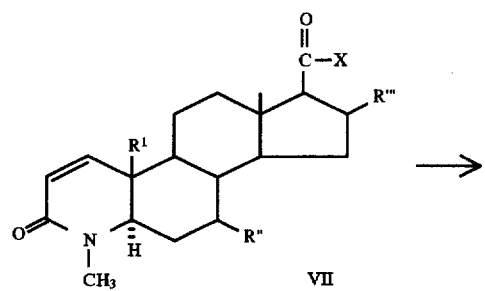
VII
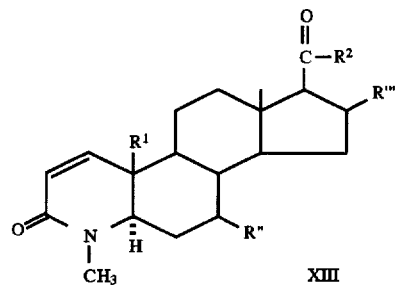
XIII
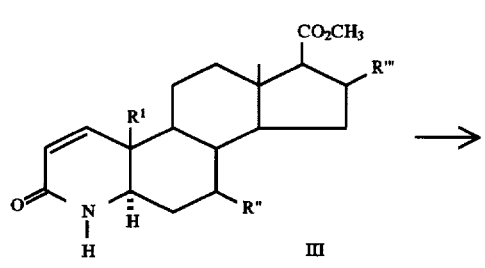
III
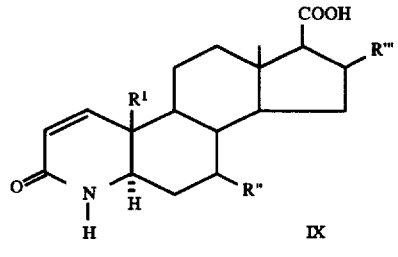
IX
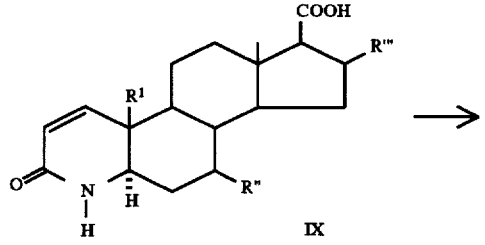
IX
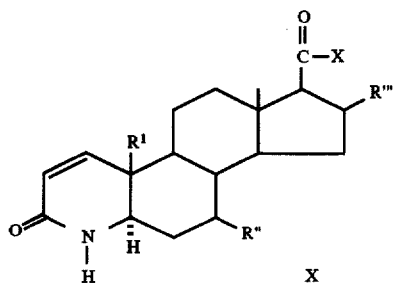
X
-continued
Flowsheet II
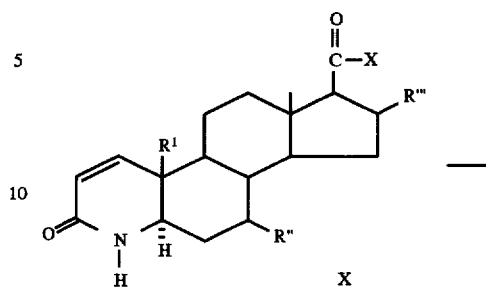
X
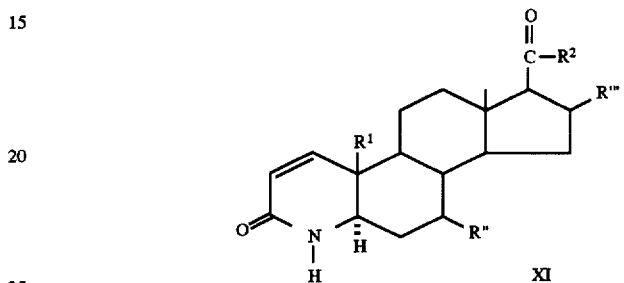
XI
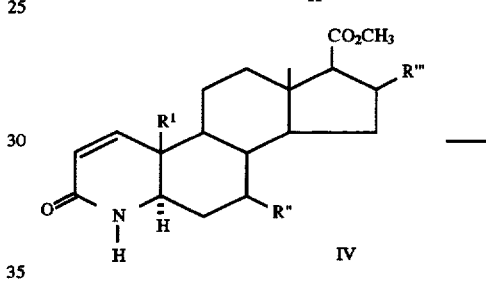
IV
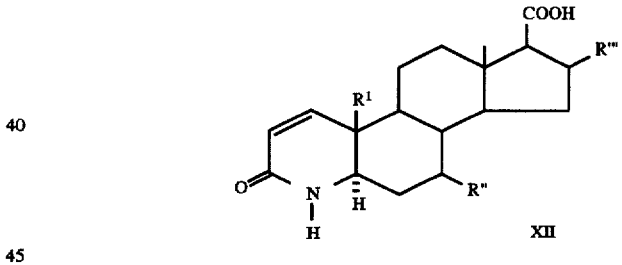
XII
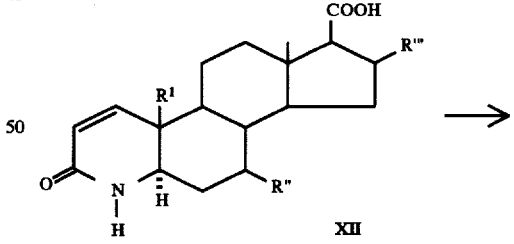
XII
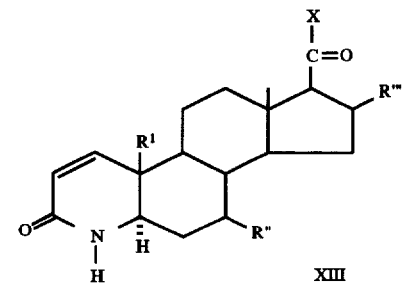
XIII

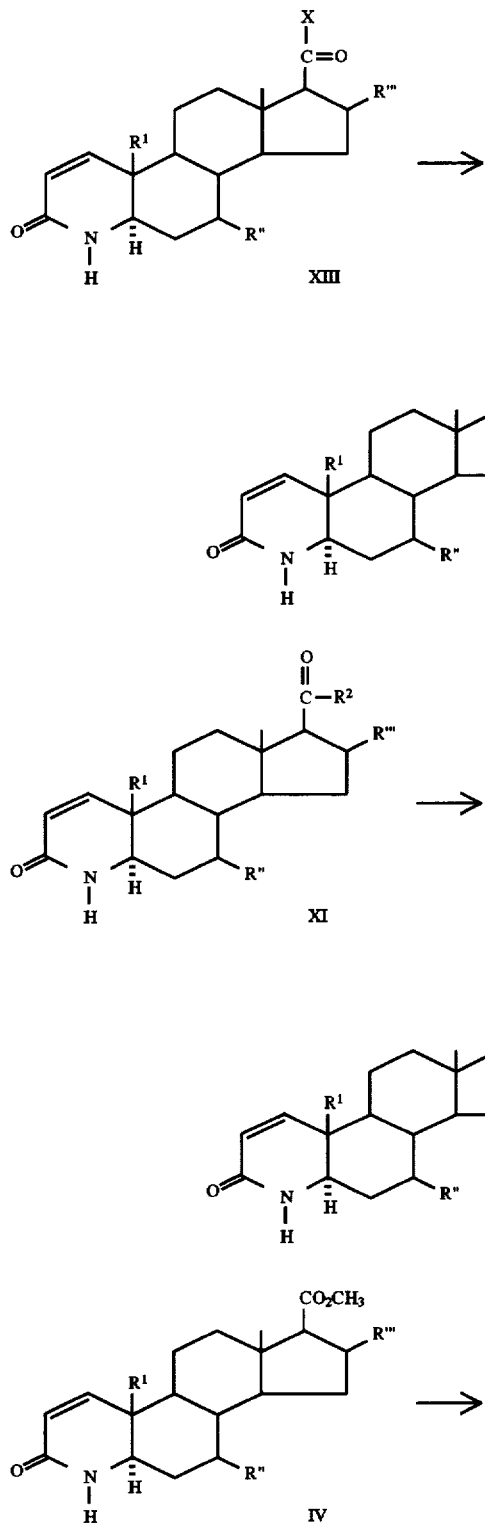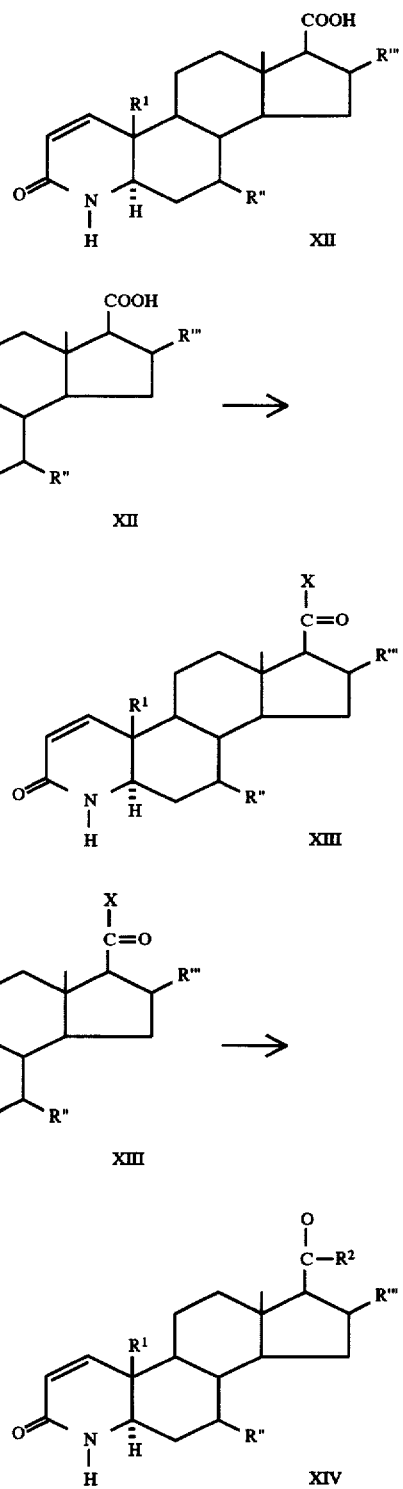

-continued
Flowsheet II

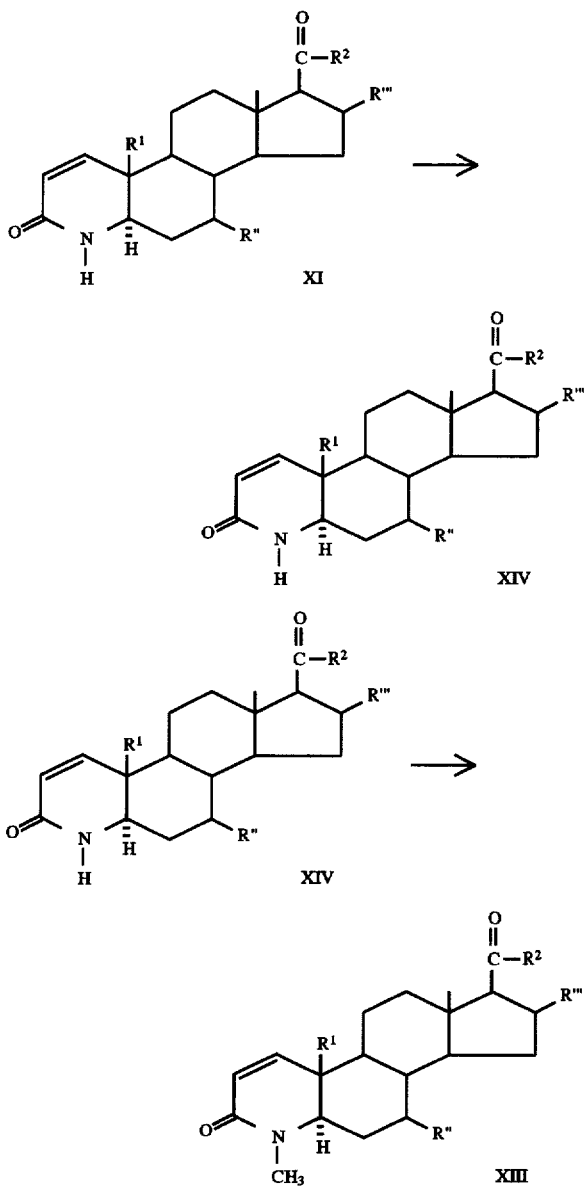

wherein X is a 2-pyridylthio substituent and $R^2$ is defined as hereinabove.

In the above described reaction Scheme, where $R^2$ is p-hydroxybiphenyl, this can be derived by starting with an appropriate bromobiphenylylphenol, e.g. p-bromobiphenylphenol, protecting the phenolic —OH with a conventional blocking group, e.g. trioganosilyl, i.e. t-butyldimethylsilyl, carrying out the Grignard reaction and then deblocking the silyl group by the use of, e.g. refluxing aqueous tetrabutylammonium fluoride.

Other halo substituted benzenes to form the appropriate Grignard reagent useful in the instant invention will be obvious to one skilled in the art from this disclosure.

By the term "protected hydroxy" as used herein, is meant the alcoholic or carboxylic —OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like.

By the term "$C_1$-$C_4$ alkyl" is used herein, is meant linear or branched alkyl, including methyl, ethyl, propyl, isopropyl, n-butyl, isobutyl, sec-butyl and t-butyl.

When this reaction scheme is carded out using an $R^2$MgX or $R^2$—Li compound containing an thiophenyl substituted $R^2$, e.g. p-methylthiophenyl magnesium chloride, the corresponding 17β-(substituted thio-benzoyl)-4-alkyl-4-aza-5α-androst-1-en-3-one is prepared wherein phenyl is $R^2$.

The Grignard reagent, $R^2$MgX, for all the species included within the scope of this invention, are available or can readily be made by one skilled in the art. For example, where $R^2$ is $C_1$-$C_4$ alkyl thiophenyl, can be formed from the appropriate $C_1$-$C_4$ alkyl thiobromobenzene, e.g. p-methylthiobromobenzene.

The formed $C_1$-$C_4$ alkyl thiobenzene can be used to further prepare $C_1$-$C_4$ alkyl sulfoxides by oxidation with e.g. m-chloroperbenzoic acid. The resulting sulfoxide can be further oxidized by the use of the m-chloroperbenzoic acid reaction to proceed for a longer period of time to form the $C_1$-$C_4$ alkyl sulfone.

Further, the sulfoxide can be used in the Pummerer rearrangement to form the corresponding thiol.

The —SO$_2$N($C_1$-$C_4$ alkyl)$_2$ substituted phenyl ($R^2$) is formed from the appropriate bromobenzene, e.g. p-N,N-dimethylaminosulfobromobenzene which is used directly in the Grignard reaction to form the final product.

The thioalkyl groups on the phenyl ring, i.e. —(CH$_2$)$_m$SH, where m is 1–4, are readily formed via a four step procedure from an alkoxy alkyl phenyl bromide, Br—C$_6$H$_4$—(CH$_2$)$_m$OCH$_3$. Direct addition of the Grignard reagent prepared from above-bromoalkyl phenyl derivative to the thiopyridyl ester results in the keto derivative, i.e. 17β(4-methoxyalkyl-benzoyl)-4-aza-5α-androst-1-ene-3-one. This can be readily converted into thio analogue via BBr$_3$ at −70° C. to form the hydroxyalkyl derivative, followed by displacement by halogen, e.g. bromo and then converting the halogenated compound through NaSH displacement to give the final mercapto compound. Where in the Reaction Scheme said pyridylthio ester is reacted with an aminophenyl containing $R^2$—Li or an $R^2$MgX (X=Cl, Br) compound, such as p-dimethylaminophenyl magnesium chloride, this is carried out in tetrahydrofuran to form the desired product 17β-(p-dimethylaminophenyl-carbonyl)-4-alkyl-4-aza-5α-androst-1-en-3-one (VIII) which is isolated by chromatography on silica gel.

The Grignard reagent. $R^2$MgX, for all of the aminophenyl species included within the scope of this invention, are available and can be made readily by one skilled in the art.

Where in the process said Grignard reagent contains a phenolic type $R^2$ moiety, then said pyridylthio ester is then reacted with an $R^2$—Li or an $R^2$MgX (X=Cl, Br) Grignard reagent, such as p-methoxyphenyl-magnesium chloride in tetrahydrofuran to form the desired product, e.g. 17β-(p-methoxy-phenylcarbonyl)-4-alkyl-4-aza-5α-androst-1-en-3-one (VIII) which is isolated by chromatography on silica gel. When this reaction is carried out using another $R^2$MgX or, an $R^2$—Li compound in place of p-methoxyphenylmagnesium chloride, the corresponding 17β-(substituted benzoyl)-4-alkyl-4-aza-5α-androst-1-en-3-one is prepared wherein phenyl is $R^2$.

The Grignard reagent, $R^2$MgX, for all of the species included within the scope of this invention, are available and can be made readily by one skilled in the art.

For example, where $R^2$ is hydroxyphenyl, this can be derived by starting with an appropriate bromophenol, e.g. p-bromophenol, protecting the phenolic —OH with a conventional blocking group, e.g. trioganosilyl, i.e. t-butyldimethylsilyl, carrying out the Grignard reaction and then deblocking the silyl group by the use of, e.g. refluxing aqueous tetrabutylammonium fluoride.

For $R^2$ being hydroxyethylphenyl, the same blocking procedure can be analogously conducted starting with the appropriate hydroxyalkyl bromophenol, e.g. p-hydroxymethylbromobenzene, or p-hydroxyethylbromobenzene.

Where $R^2$ is carboxyphenyl, this can be obtained by the chromic acid oxidation of the appropriate hydroxymethylbenzene, e.g. p-bromohydroxymethylbenzene, formed as described above.

Where $R^2$ is —O—$C_1$-$C_4$ alkyl, the appropriate bromo-O—$C_1$-$C_4$ alkyl benzene, e.g. p-methoxybromobenzene, is utilized for the Grignard reaction.

Other halo substituted benzenes to form the appropriate Grignard reagent useful in the instant invention will be obvious to one skilled in the art from this disclosure.

By the term "protected hydroxy" as used herein, is meant the alcoholic or carboxylic —OH groups which can be protected by conventional blocking groups in the an as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like.

Also within the scope of the present invention is the use of ketone reduction products of I, in combination with minoxidil for treatment of patterned alopecia, being secondary alcohols of the general structural formula V:

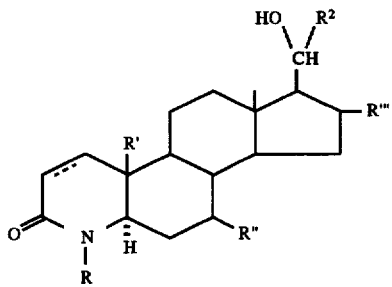

wherein

R is selected from hydrogen, methyl and ethyl;

$R^2$ is (a) a monovalent radical selected from straight or branched chain alkyl, or cycloalkyl, of from 1–12 carbons, which can be substituted by one or more of $C_1$-$C_2$ alkyl or halo;

(b) an aralkyl radical selected from benzyl or phenethyl;

(c) a polycyclic aromatic radical which can be substituted with one or more of: —OH, protected —OH, —O$C_1$-$C_4$ alkyl, $C_1$-$C_4$ alkyl, halo or nitro;

(d) a monocyclic aromatic radical which can be substituted with one or more of:

(1) —OH, —O$C_1$-$C_4$ alkyl, $C_1$-$C_4$ alkyl, —(CH$_2$)$_m$OH, —(CH$_2$)$_n$COOH, including protecting hydroxy, where m is 1–4, n is 1–3, providing $C_1$-$C_4$ alkyl is only present when one of the above oxygen-containing radicals is present;

(2) —SH, —S$C_1$-$C_4$ alkyl, —SO$C_1$-$C_4$ alkyl, —SO$_2$$C_1$-$C_4$ alkyl, —SO$_2$N($C_1$-$C_4$-alkyl)$_2$, $C_1$-$C_4$ alkyl-(CH$_2$)$_m$SH, —S—(CH$_2$)$_n$—O—COCH$_3$, where m is 1–4 n is 1–3, providing $C_1$-$C_4$ alkyl is only present when one of the above sulfur containing radicals is present;

(3) N($R^3$)$_2$, which can be protected, where $R^3$ is independently H or $C_1$-$C_4$ alkyl, where the monoaryl ring can also be further substituted with $C_1$-$C_4$ alkyl; and (4) heterocyclic radical selected from 2- or 4-pyridyl, 2-pyrrolyl, 2-furyl or thiophenyl;

R', R" and R'" are hydrogen or methyl, wherein the dotted line represents a double bond which can be present, and pharmaceutically acceptable salts and esters thereof.

These compounds can be made by conventional sodium borohydride reduction of the carbonyl attached to $R^2$ without reducing the amide carbonyl in Ring A or the 1,2-double bond, if present. If the $R^2$ phenyl contains a carbonyl function, it can be selectively blocked and then regenerated after the borohydride reduction by conventional methods.

The borohydride reduction can be carried out in, e.g. water or aqueous methanol, at a temperature of room temperature to 50° C. and the product then isolated and purified by conventional means. The compounds are also active as 5-alpha reductase inhibitors in the treatment of patterned alopecia.

EXAMPLES FOR THE CASE WHEN SUBSTITUENT "A" OF GENERAL FORMULA "I" IS AS DEFINED IN GROUP "II(A)"

Another preferred embodiment is where:

Z is —$XR^4$, or —(CHR$^1$)$_n$—$XR^4$;

n is 1–10;

X is —O— or —S(O)$_p$—, wherein p is zero, 1 or 2; and $R^1$ can be the same or different when n is greater than 1 and is —H, aryl, or —$C_{1-3}$alkyl unsubstituted or substituted with aryl;

R is —H, methyl or ethyl;

$R^4$ is

1) —$C_{1-20}$ alkyl, unsubstituted or substituted with one or more of:
 a) —OH,
 b) halo,
 c) —$C_{1-8}$ alkoxy,
 d) —$C_{1-6}$ alkenyl,
 e) —CONR$^5$R$^5$, wherein R$^5$ is independently
  i) —H,
  ii) —$C_{1-8}$ alkyl unsubstituted or substituted with one or more of R$^7$, aryl or heterocycle, the aryl being unsubstituted or substituted with one or more of R$^7$ or R$^9$,
  iii) aryl unsubstituted or substituted with one or more of R$^7$ or R$^9$, or
  iv) heterocycle, unsubstituted or substituted with one or more of R$^7$ or R$^9$,
 f) —COOR$^6$, wherein R$^6$ is
  i) —H,
  ii) —$C_{1-8}$ alkyl unsubstituted or substituted with one or more of R$^7$ or aryl, the aryl being unsubstituted or substituted with one or more of R$^7$ or R$^9$, or p4 iii) aryl, unsubstituted or substituted with one or more of R$^7$ or R$^9$,
 g) —S(O)$_p$—R$^5$, wherein p is defined above,
 h) —N(R$^5$)$_2$,
 i) aryl, unsubstituted or substituted with one or more of aryl, R$^7$ or R$^9$,
 j) heterocycle, unsubstituted or substituted with one or more of R$^7$ or R$^9$,
 k) —$C_{3-10}$ cycloalkyl, such as cyclohexyl, norbornyl, or adamantyl, unsubstituted or substituted with one or more of R$^7$ or R$^9$, or 1) —CONR⁸—CO—NHR⁸, wherein R⁸ is —H, —C₁₋₈ alkyl, benzyl or cyclohexyl; or
2) aryl, unsubstituted or substituted with one or more of aryl, R⁷ or R⁹, or
3) heterocycle or —C₃₋₁₀ cycloalkyl, either of which is unsubstituted or substituted with one or more of R⁷ or R⁹;

R⁷ is
1) —OH,
2) —C₁₋₃ alkoxy,
3) —CN,
4) —COOR⁶
5) —C₁₋₈alkyl-COOR⁶
6) —NO₂, or
7) -halo; and
8) amino, mono C₁-C₄ alkylamino, di C₁-C₄ alkylamino;

R⁹ is
1) —C₁₋₈ alkyl, unsubstituted or substituted with one or more of aryl or R⁷,
2) —CO—A, —C₁₋₈ alkyl-CO—A, —NHCO—A, or —S(O)ₚ—A, wherein p is defined above and A is
  a) —H,
  b) —C₁₋₈ alkyl, unsubstituted or substituted with one or more of
    i) —R⁷, or
    ii) aryl, unsubstituted or substituted with one or more of R⁷, or
  c) aryl, unsubstituted or substituted with one or more of R⁷,
3) —NHCO-heterocycle,
4) —N(R¹⁰)₂ or —CON(R¹⁰)₂ wherein R¹⁰ is independently —H, heterocycle, or —A,
5) —NHCO—(CH₂)_q—CO—Q, wherein q is 1–4, and Q is —N(R¹⁰)₂ or —OR¹⁰.

A first preferred embodiment of this invention is represented by compounds of formula VI

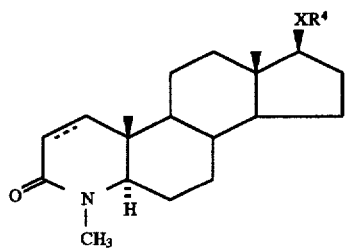

VI wherein
R⁴ is —C₁₋₂₀ alkyl, unsubstituted or substituted with one or more of
—OH, halo, —C₁₋₈alkoxy, —C₁₋₆alkenyl, —S(O)ₚ—R⁵, —N(R⁵)₂, aryl unsubstituted or substituted with one or more of aryl, R⁷ or R⁹, heterocycle unsubstituted or substituted with one or more of R⁷ or R⁹, or —C₃₋₁₀ cycloalkyl unsubstituted or substituted with one or more of R⁷ or R⁹ and X, p, R⁵, R⁷ and R⁹ are all defined as in formula I.

A second preferred embodiment of this invention is represented by compounds of formula VI wherein R⁴ is —C₁₋₂₀ alkyl substituted with —CONR⁵R⁵, —COOR⁶ or —CONR⁸CONHR⁸, and X, R⁵, R⁶ and R⁸ are defined as in formula I.

A third preferred embodiment of this invention is represented by compounds of formula VI wherein R⁴ is aryl unsubstituted or substituted with one or more of aryl, R⁷ or R⁹; heterocycle unsubstituted or substituted with one or more of R⁷ or R⁹; or —C₃₋₁₀ cycloalkyl unsubstituted or substituted with one or more of R⁷ or R⁹;
and X, R⁷ and R⁹ are defined as in formula I.

A fourth preferred embodiment of this invention is represented by compounds of formula VII

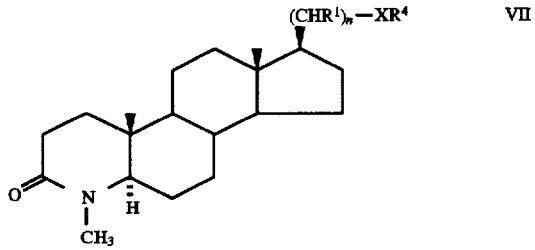

VII wherein
R⁴ is —C₁₋₂₀ alkyl, unsubstituted or substituted with one or more of
—OH, halo, —C₁₋₈alkoxy, —C₁₋₆alkenyl, —S(O)ₚ—R⁵, —N(R⁵)₂, aryl unsubstituted or substituted with one or more of aryl, R⁷ or R⁹, heterocycle unsubstituted or substituted with one or more of R⁷ or R⁹, or —C₃₋₁₀ cycloalkyl unsubstituted or substituted with one or more of R⁷ or R⁹, and X, R¹, n, p, R⁵, R⁷ and R⁹ are defined as in formula I.

A fifth preferred embodiment of this invention is represented by compounds of formula VII wherein R⁴ is —C₁₋₂₀ alkyl substituted with —CONR⁵R⁵, —COOR⁶ or —CONR⁸CONHR⁸, and X, R¹, n, R⁵, R⁶ and R⁸ are defined as in formula I.

A sixth preferred embodiment of this invention is represented by compounds of formula VII wherein R⁴ is aryl unsubstituted or substituted with one or more of aryl, R⁷ or R⁹;

heterocycle unsubstituted or substituted with one or more of R⁷ or R⁹; or

—C₃₋₁₀ cycloalkyl unsubstituted or substituted with one or more of R⁷ or R⁹;

and X, R¹, n, R⁷ and R⁹ are defined as in formula I.

Novel compounds of the present invention include but are not limited to the following compounds:

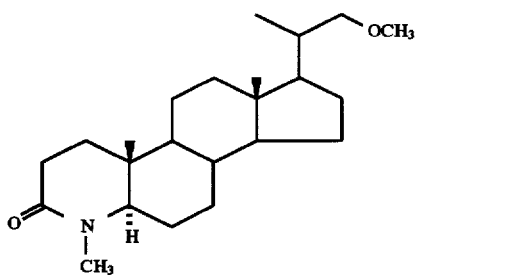

20-(methoxymethyl)-4-methyl-5α-4-azapregnan-3-one.

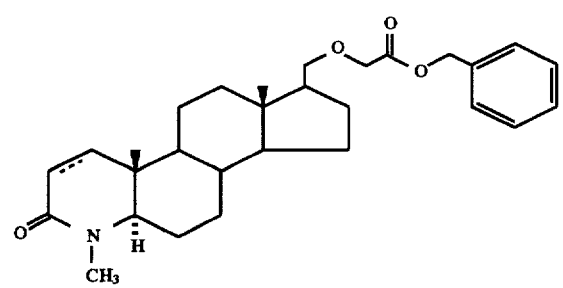

-continued 17-(carbobenzyloxymethoxymethyl)-4-methyl-5α-4-azaandrostan-3-one.

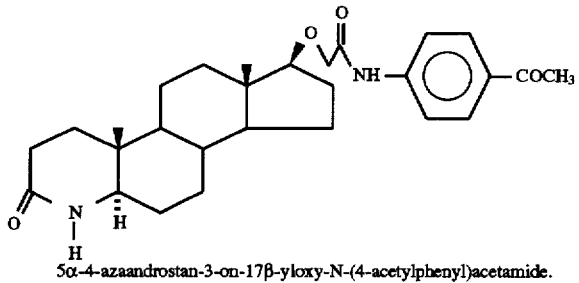

5α-4-azaandrostan-3-on-17β-yloxy-N-(4-acetylphenyl)acetamide.

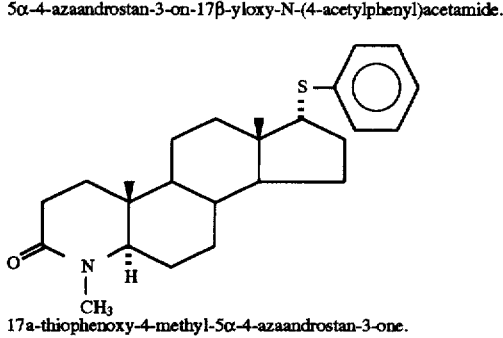

17a-thiophenoxy-4-methyl-5α-4-azaandrostan-3-one.

17-(methoxymethyl)-4-methyl-5α-4-azaandrostan-3-one,
17-(ethylthiomethyl)-4-methyl-5α-4-azaandrostan-3-one,
17-(carboxymethoxymethyl)-4-methyl-5α-4-azaandrostan-3-one,
17-(carboethoxymethoxymethyl)-4-methyl-5α-4-azaandrostan-3-one, 5) 17-(carbobenzyloxymethoxymethyl)-4-methyl-5α-4-azaandrostan-3-one,
17-(diphenylmethoxymethyl)-4-methyl-5α-4-azaandrostan-3-one,
20-(diphenylmethoxy)-4-methyl-5α-4-azapregnan-3-one,
20-(methoxy)-4-methyl-5α-4-azapregnan-3-one,
20-(methoxymethyl)-4-methyl-5α-4-azapregnan-3-one,
20-(diphenylmethoxymethyl)-4-methyl-5α-4-azapregnan-3-one,
20-(ethylthiomethyl)-4-methyl-5α-4-azapregnan-3-one,
20-(isopropylthiomethyl)-4-methyl-5α-4-azapregnan-3-one,
ethyl 4-methyl-5α-4-azaandrostan-3-on-17β-yloxyacetate,
diphenylmethyl 4-methyl-5α-4-azaandrostan-3-on-17β-yloxyacetate,
4-methyl-5α-4-azaandrostan-3-on-17β-yloxy-N-(3,4-dichlorobenzyl)acetamide,
4-methyl-5α-4-azaandrostan-3-on-17β-yloxy-N-phenylacetamide,
4-methyl-5α-4-azaandrostan-3-on-17β-yloxyacetic acid,
4-methyl-5α-4-azaandrostan-3-on-17β-yloxy-N-(4-acetylphenyl)acetamide,
4-methyl-5α-4-azaandrostan-3-on-17β-yloxyacetamide,
17β-(4-biphenyloxy)-4-methyl-5α-4-azaandrostan-3-one,
17β-(2,4-dinitrophenoxy)-4-methyl-5α-4-azaandrostan-3-one,
4-methyl-17a-phenoxy-5α-4-azaandrostan-3-one,
17a-(4-biphenyloxy)-4-methyl-5α-4-azaandrostan-3-one,
17β-diphenylmethoxy-4-methyl-5α-4-azaandrostan-3-one,
4-methyl-17a-thiophenoxy-5α-4-azaandrostan-3-one,
4-methyl-17a-phenylsulfonyl-5α-4-azaandrostan-3-one,
4-methyl-17a-phenylsulfinyl-5α-4-azaandrostan-3-one (isomer a),
4-methyl-17a-phenylsulfinyl-5α-4-azaandrostan-3-one (isomer b),
4-methyl-17β-(4-nitrophenoxy)-5α-4-azaandrostan-3-one,
17β-(4-aminophenoxy)-4-methyl-5α-4-azaandrostan-3-one hydrochloride,
17β-(4-acetamidophenoxy)-4-methyl-5α-4-azaandrostan-3-one,
17β-(4-cyanophenoxy)-4-methyl-5α-4-azaandrostan-3-one,
17β-(4-carboxamidophenoxy)-4-methyl-5α-4-azaandrostan-3-one,
17β-methyleneoxy-[N-cyclohexyl-N-(N-cyclohexylcarbamoyl)carbamoyl]-4-methyl-5α-4-azaandrostan-3-one,
4-methyl-17β-(3-pyridyl)oxy-5α-4-azaandrostan-3-one,
4-methyl-17β-(2-pyridyl)methoxy-5α-4-azaandrostan-3-one,
17β-benzyloxy-4-methyl-5α-4-azaandrostan-3-one,
ethyl 5α-4-azaandrostan-3-on-17β-yloxyacetate,
5α-4-azaandrostan-3-on-17β-yloxyacetic acid,
5α-4-azaandrostan-3-on-17β-yloxy-N-phenylacetamide,
5α-4-azaandrostan-3-on-17β-yloxy-N-(4-acetylphenyl)acetamide,
diphenylmethyl 5α-4-azaandrostan-3-on-17β-yloxyacetate,
17β-methyleneoxy-[N-cyclohexyl-N-(N-cyclohexylcarbamoyl)carbamoyl]-5α-4-azaandrostan-3-one,
5α-4-azaandrostan-3-on-17β-yloxy-N-[4-(1(RS)-hydroxyethyl)phenyl]acetamide,
5α-4-azaandrostan-3-on-17β-yloxy-N-(4-t-butylphenyl)acetamide,
17β-methyleneoxy-[N-isopropyl-N-(N-isopropylcarbamoyl)carbamoyl]-5α-4-azaandrostan-3-one, 17-(4-methylpentyloxy)-4-methyl-5α-4-azaandrostan-3-one,
17-hexyloxy-4-methyl-5α-4-azaandrostan-3-one,
4-methyl-17-propyloxy-5α-4-azaandrostan-3-one,
4-methyl-17-undecyloxy-5α-4-azaandrostan-3-one,
17-allyloxy-4-methyl-5α-4-azaandrostan-3-one,
17-allyloxy-4-methyl-4-azaandrost-5-en-3-one, or
17-hexyloxy-4-methyl-4-azaandrost-5-en-3-one.

Novel compounds of this invention further include, but are not limited to:
17-(4-(isobutyl)benzyloxy)methyl-4-methyl-5α-4-azaandrostan-3-one,
17-(4-acetamidobenzyloxy)methyl-4-methyl-5α-4-azaandrostan-3-one,
4-methyl-17-(3-nitrobenzyloxy)methyl-5α-4-azaandrostan-3-one,
4-methyl-17-(phenoxyethoxymethyl)-5α-4-azaandrostan-3-one,
17-(3-(isopropylthio)propyloxy)methyl-4-methyl-5α-4-azaandrostan-3-one,
17-(2-fluorobenzyloxy)methyl-4-methyl-5α-4-azaandrostan-3-one,
4-methyl-17-(3-(trifluoromethyl)benzyloxy)methyl-5α-4-azaandrostan-3-one,
17-(4-dimethylaminobenzyloxy)methyl-4-methyl-5α-4-azaandrostan-3-one,
17-((N-t-butyl-carboxamido)methoxymethyl)-4-methyl-5α-4-azaandrostan-3-one,
20-(3-(ethylthio)propyl)-4-methyl-5α-4-azapregnan-3-one,
20-(2-(benzyloxy)ethyl)-4-methyl-5α-4-azapregnan-3-one,
20-(3-methoxybenzyloxy)methyl-4-methyl-5α-4-azapregnan-3-one,
17a-(carboethoxymethoxy)benzyl-4-methyl-5α-4-azaandrostan-3-one,
20-(4-(methylthio)benzyloxy)methyl-4-methyl-5α-4-azapregnan-3-one,
4-methyl-17-n-octylthiomethyl-5α-4-azaandrostan-3-one,
20-(t-butylthiomethyl)-4-methyl-5α-4-azapregnan-3-one,
17-(2-furfuryl)thiomethyl-4-methyl-5α-4-azaandrostan-3-one, 17-(geranyloxymethyl)-4-methyl-5α-4-azaandrostan-3-one,
4-methyl-20-(2-(n-nonylthio)ethyl)-5α-4-azapregnan-3-one,
20-(methylthiomethyl)-4-methyl-5α-4-azapregnan-3-one,
17-(4-(benzyloxy)benzyloxy)methyl-4-methyl-5α-4-azaandrostan-3-one,
20-(diphenylmethylthio)methyl-4-methyl-5α-4-azapregnan-3-one,
17-(3-(ethylthio)propyl)-4-methyl-5α-4-azaandrostan-3-one,
4-methyl-20-(phenylthiomethyl)-5α-4-azapregnan-3-one,
17-(ethylsulfonylmethyl)-4-methyl-5α-4-azaandrostan-3-one, or
17-(4-ethoxybenzyloxy)methyl-4-methyl-5α-4-azaandrostan-3-one.

Also included within the scope of this invention are pharmaceutically acceptable salts or esters, where a basic or acidic group is present in a compound of formula I, such as on the substituted alkyl, cycloalkyl, aryl or heterocyclic moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention, may have asymmetric centers and occur as racemates, racemic mixtures and as individual diastereomers, with all isomeric forms being included in the present invention.

When any variable (e.g., aryl, heterocycle, $R^1$, $R^2$, n, X, etc.) occurs more than one time in any constituent or in formula I, II or III, its definition on each occurrence is independent of its definition at every other occurrence. Also, combinations of substituents and/or variables are permissible only if such combinations result in stable compounds.

As used herein "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge. "Cycloalkyl" is intended to include saturated mono-, bi- and tricyclic ring groups, such as cyclopropyl, cyclobutyl, cyclopentyl, cyclohexyl (Cyh), cycloheptyl, norbornanyl and adamantyl. "Alkenyl" is intended to include hydrocarbon groups of either a straight or branched configuration with one or more carbon-carbon double bonds which may occur in any stable point along the chain, such as ethenyl, propenyl, butenyl, pentenyl, and the like. "Halo", as used herein, means fluoro, chloro, bromo and iodo.

As used herein, with exceptions as noted, "aryl" is intended to mean phenyl (Ph) or naphthyl.

The term heterocycle or heterocyclic, as used herein except where noted, represents a stable 5- to 7-membered monocyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl. Preferred heterocycles are piperidinyl, 2-oxopyrrolodinyl, pyrrolyl, pyrazolyl, imidazolyl, pyridyl, pyrazinyl, pyrimidinyl, pyridazinyl, oxazolyl, isoxazolyl, morpholinyl, thiazolyl, isothiazolyl, quinuclidinyl, indolyl, quinolinyl, isoquinolinyl, benzimidazolyl, thiadiazoyl, benzothiazolyl, benzoxazolyl, furyl, tetrahydrofuryl, thienyl, and benzothienyl.

As used herein, "heteroaryl" represents a stable 5-to 7-membered monocyclic unsaturated heterocyclic ring, which consists of carbon atoms and from one to three heteroatoms selected from the group consisting of N, O and S, and wherein the nitrogen and sulfur heteroatoms may optionally be oxidized, and the nitrogen heteroatom may optionally be quaternized.

Further abbreviations that may appear herein are defined as follows:

| | |
|---|---|
| DCC | N,N'-dicyclohexylcarbodiimide |
| DIC | 1,3-diisopropylcarbodiimide |
| DEAD | diethyl azodicarboxylate |
| DMAP | 4-dimethylaminopyridine |
| DMF | N,N-dimethylformamide |
| DMSO | dimethyl sulfoxide |
| EtOAc | ethyl acetate |
| Ph$_3$P | triphenylphosphine |
| m.p (or mp) | melting point |
| THF | tetrahydrofuran |
| m.w. (or mw) | molecular weight |

The compounds of the present invention are made by methods known to those skilled in the art, and are described as follows and in schemes 1-4.

The compounds of this invention are generally made from a steriod alcohol starting material, represented by general structural formula (VIII):

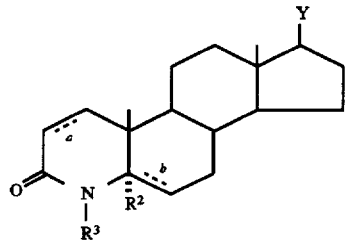

wherein a and b are both single bonds and $R^2$ is hydrogen, or a is a double bond, b is a single bond and $R^2$ is hydrogen, or a is a single bond, b is a double bond and $R^2$ is absent; $R^3$ is —H, methyl or ethyl; Y is —OH or —(CHR$^1$)$_n$—OH; $R^1$ is —H, aryl, or $C_{1-3}$ alkyl unsubstituted or substituted with aryl; and n is 1-10. Methods of making starting alcohols of formula (VIII) are well know to those skilled in the art, and are described, for example, in the following publications: Rasmusson, G. H., et al., *J. Med. Chem.*, 29, 2298–2315 (1986); Rasmusson, G. H., et al., *J. Med. Chem.*, 27 1690–1701 (1984).

Furthermore, the starting 4-azasteroid-20-alcohols of formula (i) may be made by several methods well known to those skilled in the art. For example, 4-azasteroids containing a 17-carbonyl group (e.g. carboxaldehyde) may be reacted with the appropriate organo-metallic reagent to yield the corresponding secondary alcohol, while reduction yields the primary alcohol. Also, an appropriate 17-ketone may be reduced (e.g. with sodium borohydride) to the desired alcohol. The above mentioned ketones may be made by several methods well known in the art; one particularly useful method is that of A. Bhattacharya et al. Synthetic Communications 20 (17), 2683–2690 (1990), in which an activated carbonyl compound is reacted with a suitable Grignard reagent to give the desired ketone. Other activated carbonyl compounds (e.g. pyridine thioesters) may also be used. These alcohol functions may be constructed both before and after the formation of the 4-aza moiety.

For purposes of illustration, schemes III through VI below employ specific steroid alcohol starting materials such as 17-hydroxymethyl-4-methyl-5α-4-azaandrostan-3-one (compound (ii) below) or 17-hydroxy-4-methyl-5α-4-azaandrostan-3-one (compound (v) below) as the starting alcohol. However, the present invention and the synthetic methods described herein are not limited by the use of any particular compounds in any of the schemes or synthetic descriptions presented below, except where otherwise noted, but rather the schemes and synthetic descriptions are presented for illustrative purposes to those skilled in the art. A person skilled in the art would be able to choose the appropriate alcohol starting material to use in the following general synthetic route descriptions to arrive at a target product within the scope of generic formula I.

As depicted in Scheme III below, thioethers (iv) can generally be made by forming the mesylate (iii) of alcohol (ii) by common methods known in the art, e.g. using methanesulfonyl chloride in $CH_2Cl_2$ with pyridine, and then treating the mesylate with $M^+S^-$—$R^4$, wherein $M^+$ is a metal ion, e.g. $Na^+$ or $K^+$, and $R^4$ is as defined in formula I. The $M^+S^-$—$R^4$ reagents are either commercially available, such as sodium thioethoxide or potassium thiophenoxide, or can be generated by methods well known in the art, e.g., as described in *J. Org. Chem.*, 40, p 1181 (1975) or *J. Chem. Soc.*, p 3127 (1928).

SCHEME III

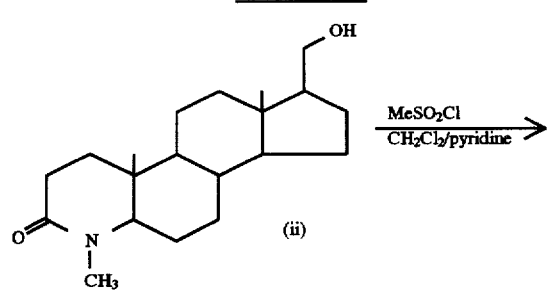

-continued
SCHEME III

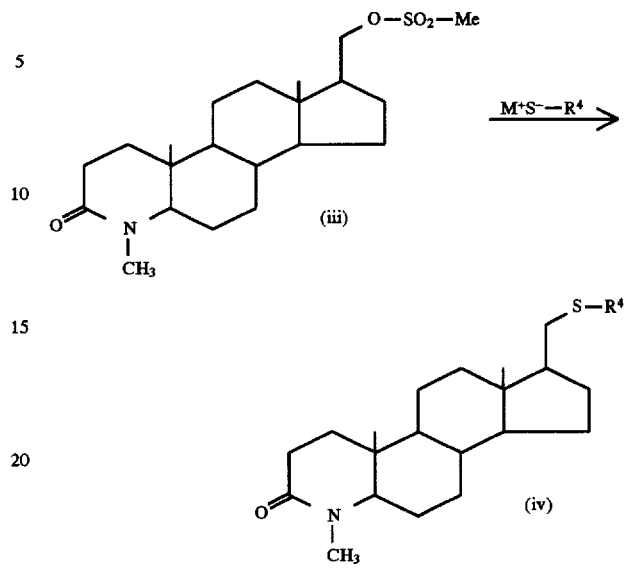

As depicted in Scheme IV, below, the starting alcohol (v) can be treated with a diazo-reagent (vi) using techniques well known in the art, e.g. using boron trifluoride etherate or $Rh_2(OAc)_4$, to obtain ethers of formula (vii). Diazo-reagents, such as diazomethane, diphenyldiazomethane, benzyldiazo-acetate, etc., are generated by methods well know in the art, such as by the methods described in the following publications: British Patent 1,533,381; British Patent 1,459,285; *J. Chem. Soc.*, Perkins I, p. 2030 (1975); *Organic Synthesis*, Collective Vol. III, p. 351 (1955); *J. Org. Chem.*, 24, p. 560 (1959).

When $R^a$ is —H and $R^b$ is —$COOC_2H_5$ in compound (vii), hydrolysis of the ester with base followed by treatment with acid produces compound (viii). The acid (viii) can be coupled with an amine, e.g. an arylamine such as aniline, 4-t-butyl aniline, or p-aminoacetophenone, by common amide coupling procedures well known in the art, e.g., using the carbodiimide method with reagents such as DCC or DIC in the presence of DMAP, to form an amide exemplified by (x).

When DCC is used, the sideproduct (xi) is formed as well: when DIC is used, a sideproduct similar to (xi) is formed except instead of a cyclohexyl urea moiety, it contains an isopropyl urea moiety. Treatment of (viii) with a diazo reagent, such as diphenyl diazomethane, and $Rh_2(Ac)_4$ under conditions well known in the art leads to formation of compounds exemplified by (ix).

The 5α-4-azandrostan-3-on-17-yloxyacetic acid and ethyl 5α-4-azaandrostan-3-on-17β-yloxyacetate analogs can be prepared according to general scheme 2 but are more preferably prepared according to the routes described in Examples 17 and 21 herein.

SCHEME IV

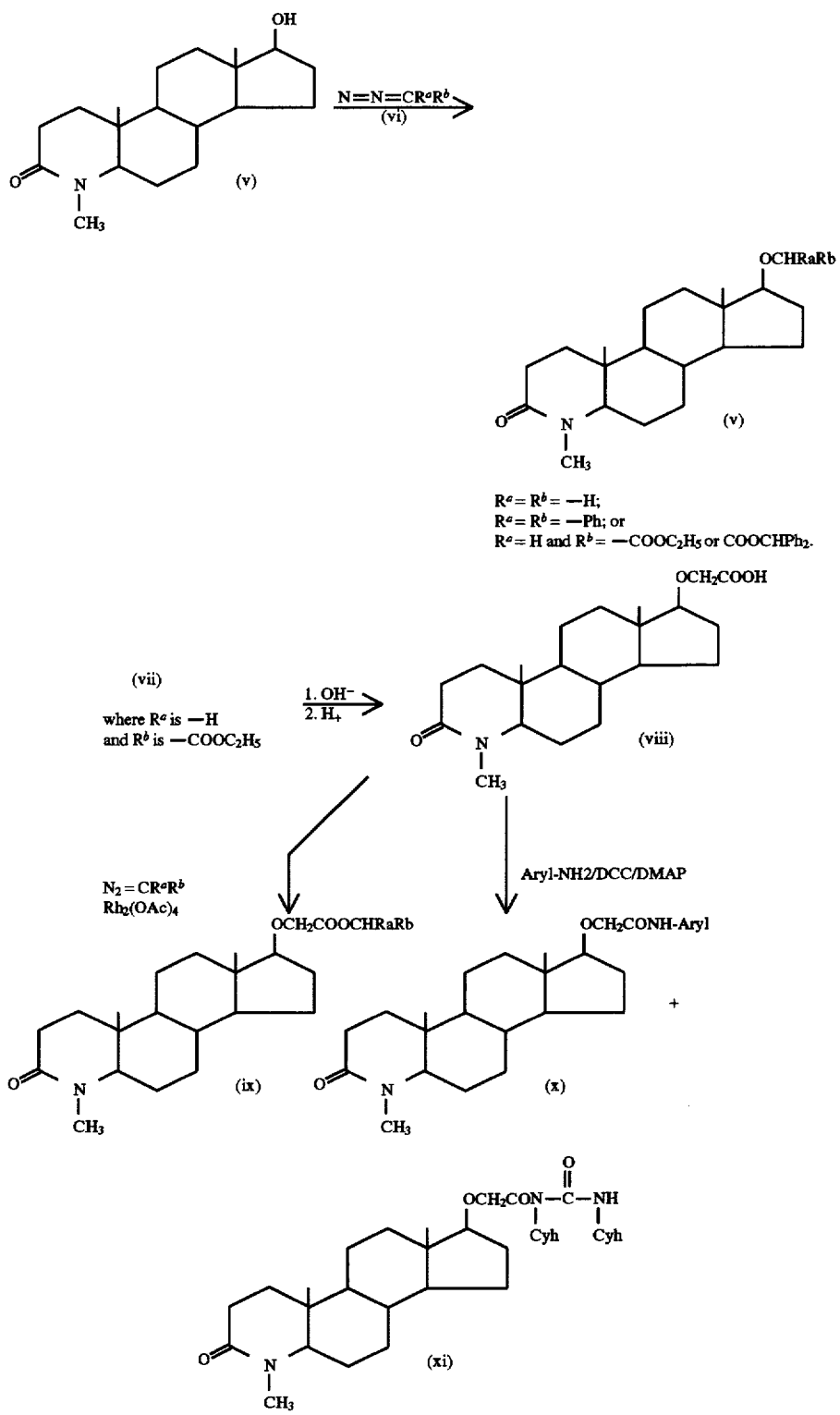

Amide compounds of formula (x) can also be made by alternative methods well known in the art, e.g., by reacting (vii) wherein $R^a$ is —H and $R^b$ is —COOC$_2$H$_5$ directly with an unsubstituted or substituted aryl-NH$_2$ compound and heating the reaction, e.g., to about 170° C.–180° C. (see Example 25). Another method, e.g., is to form a mixed anhydride of acid (viii) and react it with the desired primary amine to obtain compounds of formula (x) (see Example 26).

As depicted in Scheme 3, below, the starting alcohol (v) can be treated with a strong base, such as NaH or KOH, in an appropriate solvent such as DMF or DMSO, followed by treatment with an alkyl- or alkenyl-halide (xii-a), such as hexyliodide or allylbromide for example, to form the corresponding alkyl- or alkenyl-ether product (xiii-a). Use of KOH in DMSO is preferred.

Scheme V

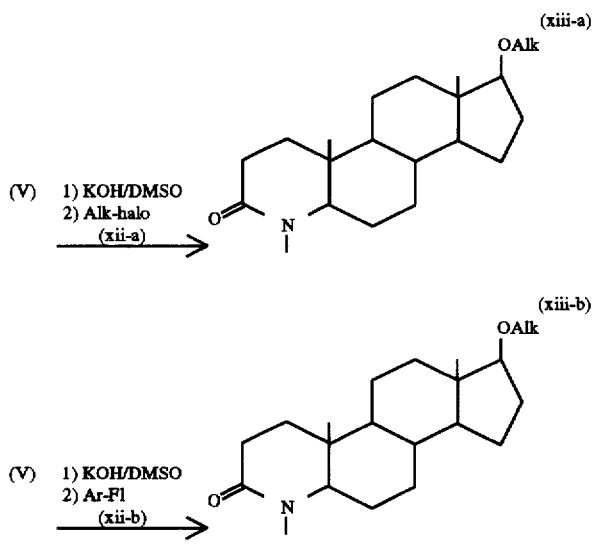

Also as depicted in Scheme V, aryl ether and heteroaryl ether products (xiii-b) can be prepared by treating the steroid alcohol starting material with a fluoroaryl or fluoroheteroaryl compound (xii-b), such as p-nitrofluorobenzene, p-cyanofluorobenzene or 3-fluoropyridine for example, and NaH or KOH in an appropriate solvent such as DMF or DMSO, with KOH/DMF and KOH/DMSO being preferred.

Alternatively, aryl ether and heteroaryl ether products of formula (xiii-b) can be prepared by treating the steroid alcohol starting material with an unsubstituted or substituted hydroxy aryl or hydroxy heteroaryl compound such as phenol or 4-hydroxybiphenyl for example, and triphenylphosphine and diethyl azodicarboxylate (DEAD).

With this method, the ether product will have stereochemistry, at the 17-position that is the opposite of the starting alcohol when Y is —OH in formula (i). For example, using this procedure, 4-methyl-17a-phenoxy-5α-4-azaandrostan-3-one is the product of 17β-hydroxy-4-methyl-5α-4-azaandrostan-3-one and phenol.

Heteroaryl ether products can be reduced by methods well known in the art, e.g., by hydrogenation in an appropriate solvent such as MeOH, in the presence of a catalyst such as palladium or platinum on carbon, to obtain compounds of formula I wherein $R^4$ is a saturated heterocycle.

As depicted in Scheme VI below, compounds of formula (xvii) can be prepared by treating the amino hydrochloride derivative (xv) with the appropriate anhydride reagent using methods well known to those skilled in the art. "$R^d$" in Scheme 4 can be heterocycle, "A" as defined in the generic description of compounds of formula I, or —$(CH_2)_q$—CO—Q, wherein the variables "q" and "Q" are as defined in the generic description of compounds of formula I. Alternatively, compounds of formula (xvii) where $R^d$ is —$(CH_2)_q$—CO—Q can be made by treating (xv) with an anhydride of formula $$\begin{array}{c} CO \\ (CH2)q \quad O \\ CO \end{array}$$

and base, such as pyridine, to make intermediate compounds of formula (xvii) where $R^d$ is —$(CH2)_q$—COOH, and then making amides and esters from the intermediate acid. Compound (xv) is prepared by reduction of the nitro group of compound (xiv) wherein $R^c$ is —$NO_2$, by common techniques well known in the art, e.g., hydrogenation in the presence of a catalyst such as $PtO_2$, and treatment with an acid such as HCl. Compound (xiv) wherein $R^c$ is —$NO_2$ can be prepared by methods described above for making aryl ethers.

Also as depicted in scheme VI, below, the cyano group of compound (xiv), wherein $R^c$ is —CN, can be hydrolyzed by methods well known in the art, e.g., by treatment with $H_2O_2$ and base such as NaOH, to provide compound (xvi). The primary amide of (xvi) can be alkylated by methods well known in the art, such as with methyl iodide, for example, to make the secondary or tertiary amide derivatives.

Scheme VI

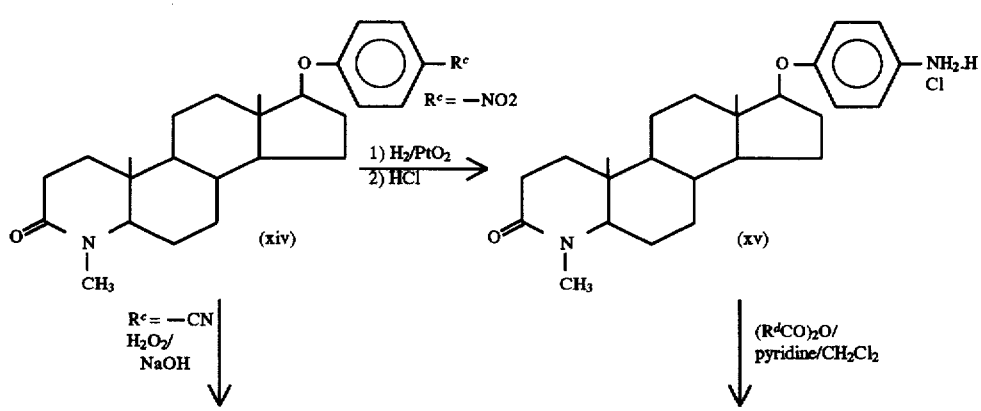

-continued
Scheme VI

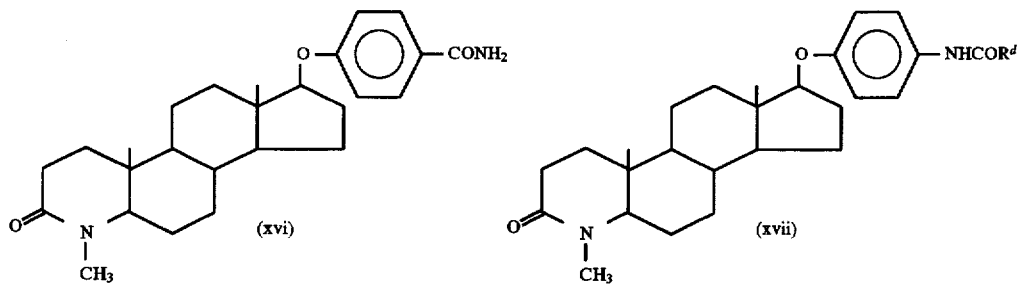

By using methods well known to those skilled in the art, the diazonium salt of compound (xv) can be made by treatment of (xv) with $HNO_2$ or an alkyl nitrite. The resulting diazonium salt can be used as an intermediate in a variety of reactions to replace the diazonium moiety to make other substituted aryl ether derivatives. For example, the diazonium salt moiety can be replaced with a halo, —CN, —OH or alkoxy group by common methods well known to those skilled in the art. Or the diazonium moiety can be replaced with hydrogen to yield the unsubstituted aryl ether derivative.

Alternatively, the ethers of this invention may be obtained by first preparing the desired ether and thioether groups at the desired position in the appropriate non-aza steroid followed by ring opening of the A-ring and subsequent closure to the desired 4-azasteroid. For example, a 20-alkoxy-substituted pregn-4-en-3-one may be oxidized with permanganate-periodate to the corresponding seco-acid which is then reacted with an appropriate amine to give, after reduction of the first obtained 4-aza-5-enesteroid, the desired 20-ether-substituted-5α-4-azapregnan-3-one.

EXAMPLES FOR THE CASE WHEN SUBSTITUENT "A" OF GENERAL FORMULA "I" IS AS DEFINED IN GROUP "III(A)"

A first preferred embodiment of this class is represented by compounds of formula IX

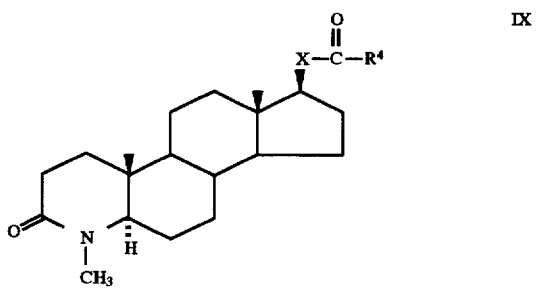

wherein $R^4$ is —$C_{1-20}$alkyl, unsubstituted or substituted with one or more of —OH, halo, —$C_{1-8}$alkoxy, —$C_{1-6}$alkenyl, —$S(O)_p$—$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$, and X, p, $R^5$, $R^7$, and $R^9$ are all as defined in formula I.

A second preferred embodiment of this invention is represented by compounds of formula II wherein $R^4$ is —$C_{1-20}$ alkyl substituted with —$CONR^5R^5$, —$COOR^6$ or —$CONR^8CONHR^8$, and X, $R^5$, $R^6$, and $R^8$ are all as defined in formula I.

A third preferred embodiment of this invention is represented by compounds of formula II wherein $R^4$ is aryl unsubstituted or substituted with one or more of aryl, $R^7$ or $R^9$;

heterocycle unsubstituted or substituted with one or more of $R^7$ or $R^9$;

—$C_{3-10}$ cycloalkyl unsubstituted or substituted with one or more of $R^7$ or $R^9$;

—$NR^5R^5$; or —$OR^5$;

and X, $R^5$, $R^7$, and $R^9$ are all as defined in formula I.

A fourth preferred embodiment of this invention is represented by compounds of formula X

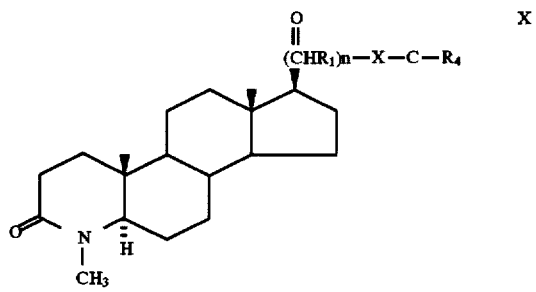

wherein $R^4$ is —$C_{1-20}$ alkyl, unsubstituted or substituted with one or more of —OH, halo, —$C_{1-8}$alkoxy, —$C_{1-6}$alkenyl, —$S(O)_p$—$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$, and X, n, p, $R^1$, $R^5$, $R^7$, and $R^9$ are all as defined in formula I.

A fifth preferred embodiment of this invention is represented by compounds of formula III wherein $R^4$ is —$C_{1-20}$ alkyl substituted with —$CONR^5R^5$, —$COOR^6$ or —$CONR^8CONHR^8$, and X, n, $R^1$, $R^5$, $R^6$, and $R^8$ are all as defined in formula I.

A sixth preferred embodiment of this invention is represented by compounds of formula III wherein $R^4$ is aryl unsubstituted or substituted with one or more of aryl, $R^7$ or $R^9$;

heterocycle unsubstituted or substituted with one or more of $R^7$ or $R^9$;

—$C_{3-10}$ cycloalkyl unsubstituted or substituted with one or more of $R^7$ or $R^9$;

—$NR^5R^5$; or —$OR^5$;

and X, n, $R^1$, $R^5$, $R^7$, and $R^9$ are all as defined in formula I.

Novel compounds of the present invention include but are not limited to the following compounds:

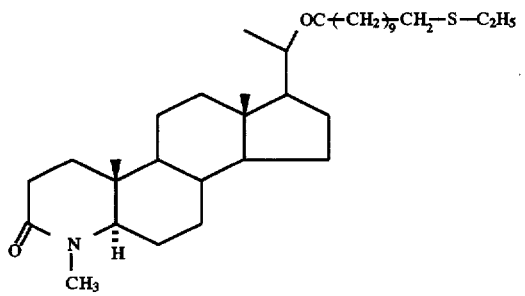

20-(11-(ethylthio)undecanolyloxy-4-methyl-5α-4-azapregnan-3-one,

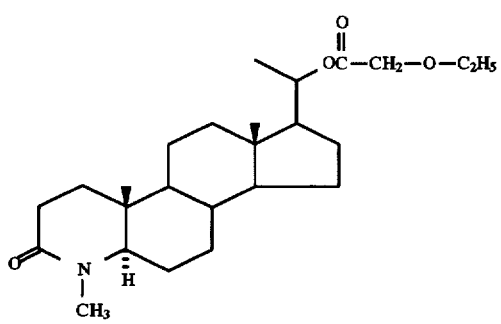

20-ethoxyacetyloxy-4-methyl-5α-4-azapregnan-3-one,

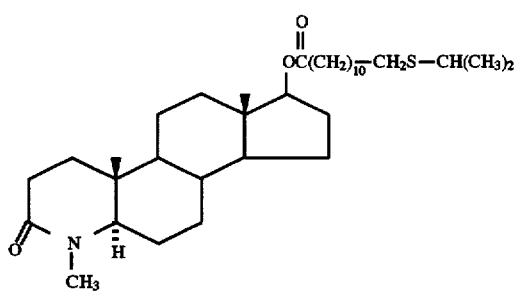

17-(12-(isopropylthio)dodecanoyloxy)-4-methyl-5α-4-azaandrostan-3-one,

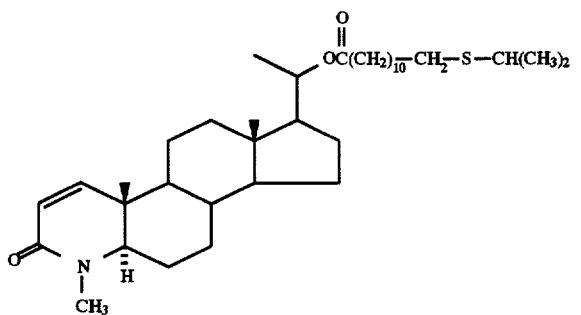

20-(12-(isopropylthio)-dodecanoyloxy)-5α-4-azapregn-1-ene-3-one,

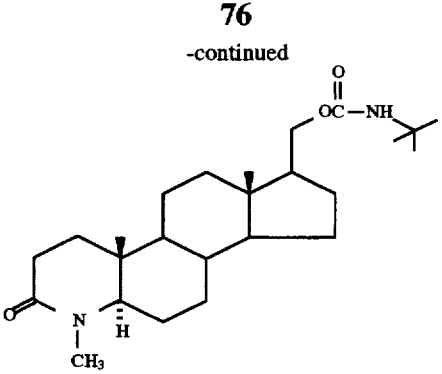

17-(t-butylaminocarbonyloxymethyl)-4-methyl-5α-4-azaandrostan-3-one, 4-methyl-20-tridecanoyloxy-5α-4-azapregnan-3-one,
20-t-butylacetyloxy-4-methyl-5α-4-azapregnan-3-one,
4-methyl-20-trimethylacetyloxy-5α-4-azapregnan-3-one,
4-methyl-20-(10-undecenoyloxy)-5α-4-azapregnan-3-one,
20-(3,7-dimethyl-6-octenoyloxy)-4-methyl-5α-azapregnan-3-one,
20-(3-carboxypropionyloxy)-4-methyl-5α-4-azapregnan-3-one,
20-(11-(carbomethoxy)undecanoyloxy)-4-methyl-5α-4-azapregnan-3-one,
20-(3-(carbobenzyloxy)propionyloxy)-4-methyl-5α-4-azapregnan-3-one,
20-(1-adamantylacetyloxy)-4-methyl-5α-4-azapregnan-3-one
4-methyl-20-(2-norbornylacetyloxy)-5α-4-azapregnan-3-one,
20-(3,4-dimethoxyphenyl)acetyloxy-4-methyl-5α-4-azapregnan-3-one,
20-(4-isopropylphenyl)acetyloxy-4-methyl-5α-4-azapregnan-3-one
20-(isopropylthio)acetyloxy-4-methyl-5α-4-azapregnan-3-one,
20-(9-(isopropylthio)nonanoyloxy)-4-methyl-5α-4-azapregnan-3-one,
20-(12-(isopropylthio)dodecanoyloxy)-4-methyl-5α-4-azapregnan-3-one,
20-(11-(ethylsulfinyl)undecanoyloxy)-4-methyl-5α-4-azapregnan-3-one,
20-(12-(t-butylthio)dodecanoyloxy)-4-methyl-5α-4-azapregnan-3-one
4-methyl-20-(4-thien-2-yl)butyroyloxy-5α-4-azapregnan-3-one,
20-trimethylacetyloxy-5α-4-azapregnan-3-one,
20-(9-(isopropylthio)nonanoyloxy)-5α-4-azapregnan-3-one,
20-(12-(isopropylthio)dodecanoyloxy)-5α-4-azapregnan-3-one,
20-acetoxymethyl-4-methyl-5α-4-azapregnan-3-one,
4-methyl-20-(trimethylacetyloxy)methyl-5α-4-azapregnan-3-one,
20-(12-(isopropylthio)dodecanoyloxy)methyl-4-methyl-5α-4-azapregnan-3-one,
17-acetyloxymethyl-4-methyl-5α-4-azaandrostan-3-one,
4-methyl-17-trimethylacetyloxymethyl-5α-4-azaandrostan-3-one,
17-(2-ethylhexanoyloxy)methyl-4-methyl-5α-4-azaandrostan-3-one,
17-(methylaminocarbonyloxymethyl)-4-methyl-5α-4-azaandrostan-3-one, 17-(12-(isopropylthio)dodecanoyoxy)methyl-4-methyl-5α-4-azaandrostan-3-one, 17β-(benzylaminocarbonyloxy)-4-methyl-5α-4-azaandrostan-3-one, 20-trimethylacetyloxy-5α-4-azapregn-1-ene-3-one, or 20-(t-butylaminocarbonyloxy)-4-methyl-5α-4-azapregnan-3-one.

Novel compounds of the present invention further include, but are not limited to the following compounds:

17-(2-furylacetoxymethyl)-4-methyl-5α-4-azaandrostan-3-one, 17-(4-isopropylphenylacetoxymethyl)-4-methyl-5α-4-azaandrostan-3-one, 17-(cyclohexylacetoxymethyl)-4-methyl-5α-4-azaandrostan-3-one, 17-(3-indolylacetoxymethyl)-4-methyl-5α-4-azaandrostan-3-one, 17-(4-methylcyclohexanecarbonyloxymethyl)-4-methyl-5α-4-azaandrostan-3-one, 17-(4-(3-indolyl)-butyroyloxymethyl)-4-methyl-5α-4-azaandrostan-3-one, 17-(4-isobutylbenzoyloxymethyl)-4-methyl-5α-4-azaandrostan-3-one, 17-(acetoxyacetyloxymethyl)-4-methyl-5α-4-azaandrostan-3-one, 17-(6-bromohexanoyloxymethyl)-4-methyl-5α-4-azaandrostan-3-one, 4-methyl-20-(4-nitrobenzoyloxymethyl)-5α-4-azapregnan-3-one, 20-((3-acetamido)benzoyloxy)-4-methyl-5α-4-azapregnan-3-one, 20-(3,4-dimethoxyphenylacetyloxymethhyl)-4-methyl-5α-4-azapregnan-3-one, 17-(4-ethoxybenzoyloxymethyl)-4-methyl-5α-4-azaandrostan-3-one, 4-methyl-20-(palmitoyloxymethyl)-5α-4-azapregnan-3-one, 17-(iminodibenzyl-5-carbonyloxymethyl)-4-methyl-5α-4-azaandrostan-3-one, 4-methyl-20-(stearoyloxy)-5α-4-azapregnan-3-one, 17-(3,5-bis-(trifluoromethyl)benzoyloxymethyl)-4-methyl-5α-4-azaandrostan-3-one, 17-(3-cyanobenzoyloxymethyl)-4-methyl-5α-4-azaandrostan-3-one, 20-(heptafluorobutyroyloxymethyl)-4-methyl-5α-4-azapregnan-3-one, 20-(4-benzoylbenzoyloxymethyl)-4-methyl-5α-4-azapregnan-3-one, 17-(benztriazol-5-carbonyloxymethyl)-4-methyl-5α-4-azaandrostan-3-one, 20-(3,5-difluorobenzoyloxy)-4-methyl-5α-4-azapregnan-3-one, 17-(bis-(4-isopropyl)phenyl)acetyloxymethyl-4-methyl-5α-4-azaandrostan-3-one, 4-methyl-20-(salicyloyloxymethyl)-5α-4-azapregnan-3-one, 17-((3-hydroxy-4,4,4-trichlorobutyroyloxy)methyl)-4-methyl-5α-4-azaandrostan-3-one, or 17-(cinnamoyloxymethyl)-4-methyl-5α-4-azaandrostan-3-one.

Also included within the scope of this invention are pharmaceutically acceptable salts or esters, where a basic or acidic group is present in a compound of formula I, such as on the substituted alkyl, cycloalkyl, aryl or heterocyclic moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention, may have asymmetric centers and occur as racemates, racemic mixtures and as individual diastereomers, with all isomeric forms being included in the present invention.

When any variable (e.g., aryl, heterocycle, $R^1$, $R^2$, n, X, etc.) occurs more than one time in any constituent or in formula I, II or III its definition on each occurrence is independent of its definition at every other occurrence. Also, combinations of substituents and/or variables are permissible only if such combinations result in stable compounds.

As used herein "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge. "Cycloalkyl" is intended to include saturated mono-, bi- and tricyclic ring groups, such as cyclopropyl, cyclobutyl, cyclopentyl, cyclohexyl (Cyh), cycloheptyl, norbornanyl and adamantyl. "Alkenyl" is intended to include hydrocarbon groups of either a straight or branched configuration with one or more carbon-carbon double bonds which may occur in any stable point along the chain, such as ethenyl, propenyl, butenyl, pentenyl, and the like. "Halo", as used herein, means fluoro, chloro, bromo and iodo.

As used herein, with exceptions as noted, "aryl" is intended to mean phenyl (Ph) or naphthyl.

The term heterocycle or heterocyclic, as used herein except where noted, represents a stable 5- to 7-membered monocyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl. Preferred heterocycles are piperidinyl, 2-oxopyrrolodinyl, pyrrolyl, pyrazolyl, imidazolyl, pyridyl, pyrazinyl, pyrimidinyl, pyridazinyl, oxazolyl, isoxazolyl, morpholinyl, thiazolyl, isothiazolyl, quinuclidinyl, indolyl, quinolinyl, isoquinolinyl, benzimidazolyl, thiadiazoyl, benzothiazolyl, benzoxazolyl, furyl, tetrahydrofuryl, thienyl, and benzothienyl.

"M.p." or "mp" is an abbreviation for melting point: "m.w." or "mw" is an abbreviation for molecular weight.

The compounds of the present invention are made by methods well known to those skilled in the art. The compounds of this invention are generally made from a steriod alcohol starting material, represented by formula (XI)

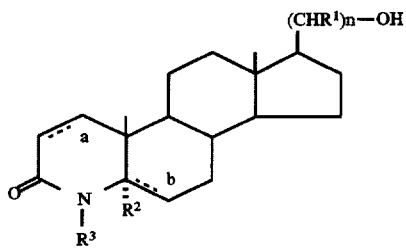

wherein a and b are both single bonds and $R^2$ is hydrogen, or a is a double bond, b is a single bond and $R^2$ is hydrogen, or a is a single bond, b is a double bond and $R^2$ is absent; $R^1$ is —H, aryl, or $C_{1-3}$alkyl unsubstituted or substituted with aryl; $R^3$ is —H, methyl or ethyl; and n is zero through 10.

Methods of making starting alcohols of formula (XI) are well known to those skilled in the an, and are described, for example, in the following publications: Rasmusson, G. H. et al., *J. Med. Chem.*, 29, 2298–2315 (1986); Rasmusson, G. H. et al., *J. Med. Chem.*, 27, 1690–1701 (1984).

Furthermore, the starting 4-azasteroid-20-alcohols of Formula (XI) may be made by several methods well known to those skilled in the art. For example, 4-azasteroids containing a 17-carbonyl group (e.g. carboxaldehyde) may be reacted with the appropriate organo-metallic reagent to yield the corresponding secondary alcohol, while reduction yields the primary alcohol. Also, an appropriate 17-ketone may be reduced (e.g. with sodium borohydride) to the desired alcohol. The above mentioned ketones may be made by several methods well known in the art; one particularly useful method is that of A. Bhattacharya et al., Synthetic Communications 20(17), 2683–2690 (1990), in which an activated carbonyl compound is reacted with a suitable Grignard reagent to give the desired ketone. Other activated carbonyl compounds (e.g. pyridine thioesters) may also be used.

These alcohol functions may be constructed both before and after the formation of the 4-aza moiety.

One method of preparing compounds of formula I is to condense the starting steroid alcohol with an acid of formula (XII)

$$R^4\text{—COOH} \qquad (XII)$$

under conditions known to those skilled in the art, e.g., in an appropriate solvent such as $CH_2Cl_2$, in the presence of 4-(dimethylamino)-pyridine (DMAP) and N,N'-dicyclohexylcarbodiimide (DCC).

Another method of preparing compounds of formula I is to combine the starting alcohol (XI) with an acid chloride of formula (XIII) or acid anhydride or mixed anhydride of formula (XIV)

$$R^4\text{—COCl} \qquad (XIII)$$

$$(R^4CO)_2O \qquad (XIV)$$

under conditions known to those skilled in the art, e.g. under dry conditions using an appropriate solvent such as $CH_2Cl_2$ at a reduced temperature, such as about 0° C., in the presence of a base such as pyridine.

Carbamate derivatives of formula I can be prepared by reacting the starting alcohol (XII) with an isocyanate compound, such as benzyl isocyanate or t-butylisocyanate for example, under conditions known to those skilled in the art, e.g., under dry conditions in an appropriate solvent such as benzene, in the presence of a base such as 1,8-diazabicyclo[5.4.0]undec-7-ene (DBU), with heating e.g. to 60°–70° C.

The thiol esters may be conveniently prepared from the corresponding alcohol via the literature procedure described in Tetrahedron Letters, 22 (1981) pp. 3119–3122, that is, the alcohol and a thiolacid are reacted together in the presence of the preformed adduct from triphenylphosphine and diisopropyl azodicarboxylate. Alternatively, the free thiol obtained from these thiolesters via standard saponification or reduction methods may then be acylated via standard procedures to obtain other thiolesters.

The variable "$R^4$" used in the above synthetic method descriptions is defined in formula I.

EXAMPLES FOR THE CASE WHEN SUBSTITUENT "A" OF GENERAL FORMULA "I" IS AS DEFINED IN GROUP "IVA"

An embodiment of this category is where:
A is:

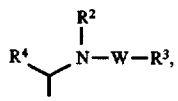  (a)

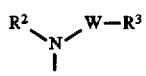  (b)

except when $R^2$ equals H; there is a 5αH and W equals C(O), $R^3$ can not be $C_{1-12}$ alkyl,

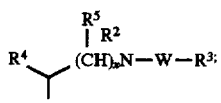

wherein
$R^1$ is:
  H, or
  $C_{1-20}$ alkyl;
$R^2$ is:
  H, or
  $C_{1-20}$ alkyl;
$R^3$ is:
  H,
  $C_{1-20}$ alkyl,
  $C_{6-14}$ aryl,
  heteroaryl,
  $C_{6-14}$ aryl$C_{1-20}$alkyl,
  heteroaryl$C_{1-20}$alkyl,
  $C_{1-20}$ alkylthio$C_{1-20}$alkyl,
  $C_{1-20}$ alkylsufonyl$C_{1-20}$alkyl,
  $C_{1-20}$ alkylsulfinyl$C_{1-20}$alkyl,
  $C_{1-20}$ alkyloxycarbonyl$C_{1-20}$alkyl,
  $C_{1-20}$ alkyl$C_{6-14}$aryl$C_{1-20}$alkyl,
  carboxy$C_{1-20}$alkyl,
  $C_{1-20}$alkyloxy$C_{1-20}$alkyl,
  $C_{1-20}$alkoxycarbonyl$C_{1-20}$alkyl, $C_{1-20}$alkylcarbonyl$C_{1-20}$alkyl,
$C_{3-20}$cycloalkyl,
$C_{3-20}$cycloalkyl$C_{1-20}$alkyl,
$C_{6-14}$ aryl$C_{1-20}$alkyloxycarbonyl$C_{1-20}$alkyl,
heteroaryl$C_{1-20}$alkyloxycarbonyl$C_{1-20}$ alkyl,
halo$C_{1-20}$alkyl,
halohydroxy$C_{1-20}$alkyl,
hydroxy$C_{1-20}$alkyl,
thiosulfato$C_{1-20}$alkyl,
$C_{6-14}$ aryl$C_{1-20}$alkyloxy$C_{1-20}$alkyl,
diaryl$C_{1-20}$alkyl,
triaryl$C_{1-20}$alkyl,
$C_{2-20}$ alkenyl,
$C_{2-20}$ alkenyl$C_{1-20}$alkyl,
$C_{6-14}$ aryl$C_{2-20}$alkenyl,
heteroaryl$C_{2-20}$alkenyl,
$C_{6-14}$ arylcarbonylaryl$C_{1-20}$alkyl,
$C_{2-20}$alkynyl$C_{1-20}$alkyl,
$C_{6-14}$ aryl$C_{2-20}$alkynyl$C_{1-20}$alkyl, or
heteroaryl$C_{2-20}$alkynyl$C_{1-20}$alkyl;

$R^4$ is
  $C_{1-20}$ alkyl,
  $C_{6-14}$ aryl, or
  heteroaryl;

$R^5$ is:
  H, or
  $C_{1-20}$ alkyl;

W is

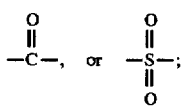

x is an integer from 1 to 25;

and dashes indicate a double bond is optionally present.

Advantageously, compounds of the following general structural formula XV are disclosed.

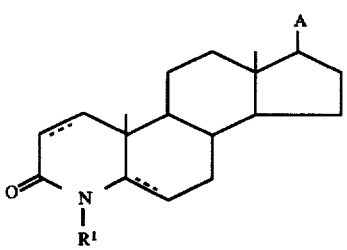

and the pharmaceutically acceptable salts thereof, wherein A is:

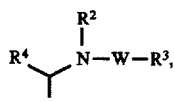 (a)

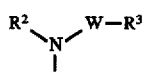 (b)

except when $R_2$ equals H, there is a 5αH and W equals C(O), $R_3$ can not be $C_{1-12}$ alkyl,

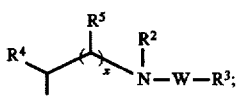 (c)

wherein
  $R^1$ is:
    H, methyl or ethyl;
  $R^2$ is:
    H, or
    $C_{1-20}$alkyl;
  $R^3$ is:
    H,
    $C_{1-20}$alkyl further comprising a straight or branched chain alkane of up to 20 carbon atoms;
    $C_{6-14}$ aryl wherein aryl comprises a mono or polycyclic system composed of 6-membered aromatic rings either unsubstituted or substituted with R wherein R comprises H, $C_{1-6}$alkyl, aryl$C_{1-20}$alkyl with the alkyl groups unsubstituted or substituted with hydroxyl, $C_{1-8}$alkyloxy, carboxy $C_{0-10}$alkyl, or halogen or aryl is directly substituted independently with hydroxyl, halo$C_{1-20}$alkyl, carboamide, benzoyl, $C_{1-20}$alkyloxy, $C_{1-20}$alkyl, $C_{2-20}$alkenyl, cyano, nitro, acetamide or halogen;
    heteroaryl which comprises a mono or polycyclic system composed of 5 or 6-membered aromatic rings containing 1, 2, 3 or 4 heteroatoms chosen from N, O, or S and either unsubstituted or substituted with R or independently with hydroxyl $C_{1-20}$alkyloxy, $C_{1-20}$alkyl, benzoyl, carboamide, acetamide, halogens, $C_{2-20}$alkenyl, cyano, nitro, or haloalkyl directly bonded to the aromatic carbon atom(s);
    $C_{6-14}$ aryl$C_{1-20}$alkyl of the formula:

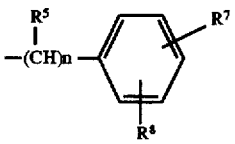

wherein the aromatic ring is optionally and independently substituted with $R^7$ and $R^8$ wherein $R^7$ and $R^8$ comprise:
  H,
  $CH_3$,
  $C_2H_5$,
  carboxamido,
  $OCH_3$,
  $C_1C_6$alkylthio,
  $C_1C_6$alkylsulfinyl,
  $C_1C_6$alkylsulfonyl,
  $NH_2$,
  $CH_3NH$,
  $(CH_3)_2N$—,
  $NO_2$,
  CN,
  OH,
  Fl,
  acetamido,
  Cl,
  $OC_2H_5$,
  $CF_3$,
  isopropyl, or isobutyl;

n equals 1–20 and the $C_{1-20}$alkyl group is optionally substituted with $R^7$;

HeteroarylC$_{1-20}$alkyl further comprising the formula

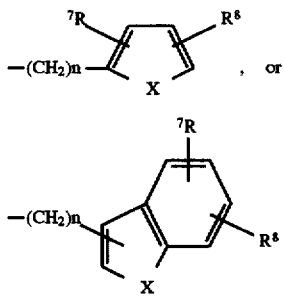, or wherein X equals O, S, or NR; and n equals 1–20;

$C_{1-20}$alkylsulfonylC$_{1-20}$alkyl
$C_{1-20}$alkylthioC$_{1-20}$alkyl
$C_{1-20}$alkylsulfinylC$_{1-20}$alkyl comprising the formula:

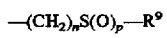

wherein $R^9$ comprises
CH$_3$,
C$_2$H$_5$,
C$_3$H$_7$,
C$_4$H$_9$,
isopropyl,
isobutyl,
sec-butyl,
t-butyl,
isopentyl,
neopentyl, or
isohexyl;

n equals 1–20, p=0–2;

$C_{1-20}$alkyloxycarbonylC$_{1-20}$alkyl further comprising the formula:

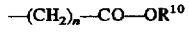

wherein $R^{10}$ comprises:
CH$_3$,
C$_2$H$_5$,
C$_3$H$_7$,
C$_4$H$_9$, or
C$_5$H$_{11}$; and
n equals 1–20;

CarboxylC$_{1-20}$alkyl further comprising:

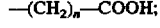

n=1–20;

$C_{1-20}$alkylcarbonylC$_{1-20}$alkyl further comprising the formula

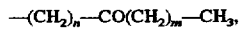

n equals 1–20; m equals 0–19;

C$_{3-20}$cycloalkylC$_{1-20}$alkyl of the formula:

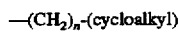

wherein the cycloalkyl portion comprises monocyclic, bicyclic, or polycyclic hydrocarbons of up to 20 carbon atoms wherein the rings are optionally substituted with $R^1$; and n=1–20;

ArylC$_{1-20}$alkyloxycarbonylC$_{1-20}$alkyl of the formula:

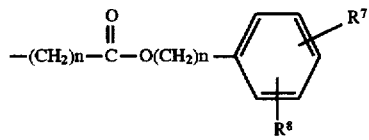

wherein
n=1–20;

HeteroarylC$_{1-20}$alkyloxycarbonylC$_{1-20}$alkyl of the formula:

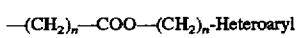

wherein Heteroaryl is as defined and n=1–20;

haloC$_{1-20}$alkyl of the formula:

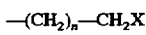

wherein X equals Br, Cl, F or I; n is 1–19;

hydroxylC$_{1-20}$alkyl of the formula:

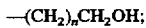

n is 1–19;

halohydroxylC$_{1-20}$alkyl of the formula:

whereto X equals Br, Cl, F or I; n=0–18, q=0–18 n+q=0–18;

ThiosulfatoC$_{1-20}$alkyl of the formula:

n is 1–20;

ArylC$_{1-20}$alkyloxyC$_{1-20}$alkyl of the formula:

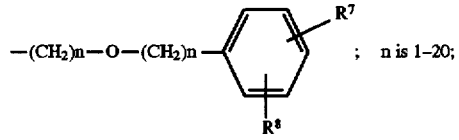 ; n is 1–20;

ArylcarbonylarylC$_{1-20}$alkyl of the formula:

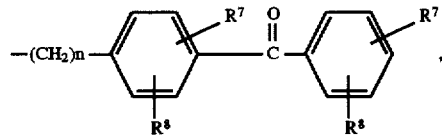

n equals 1–20;

DiarylC$_{1-20}$alkyl of the formula:

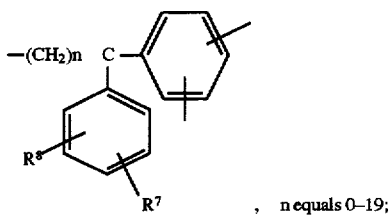, n equals 0–19;

TriarylC$_{1-20}$alkyl of the formula:

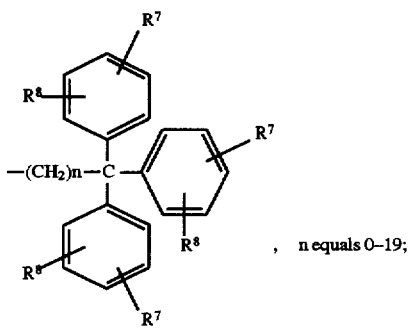, n equals 0–19;

C$_{6-14}$arylC$_{2-20}$alkenyl of the formula:

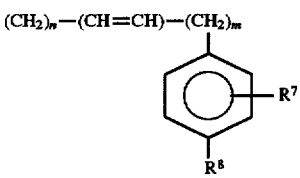

wherein:
n=0–18,
m=0–18,
n+m=0–18;
R$^4$ is
 H,
 C$_{1-20}$alkyl,
 C$_{6-14}$aryl, or
 heteroaryl;
R$^5$ is:
 H, or
 C$_{1-12}$alkyl;
W is:

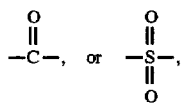

x is an integer from 1–1 0;
and the dashes indicate a double bond is optionally present.
Compounds of the general structural formula XVI

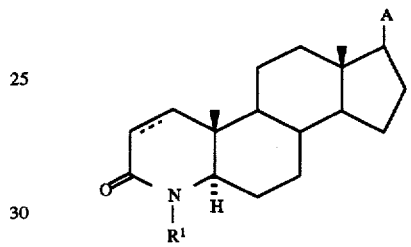

and listed in Table 1 are representative of the compounds claimed in the instant invention. In a preferred embodiment. R$^1$ may be H or CH$_3$ and A may be as indicated in Table 1. Particular representative chemical names are also listed in Table 1 adjacent to the respective side chain and specifically reflect whether the 1 position is saturated or unsaturated. Advantageously, R$^1$ is CH$_3$, A is as indicated in Table 1 and the 1 position is saturated.

TABLE 1

| Side Chain A | Compound(s): |
|---|---|
| (1) ![structure] | 4-methyl-20(trimethylacetamido)-5α-4-aza-pregnen-3-one<br>4-methyl-20(trimethylacetamido)-5α-4-aza-1-pregnan-3-one |
| (2) ![structure] | 4-methyl-17β(trimethylacetamidomethyl)-4-aza-5α-androst-1-en-3-one<br>4-methyl-17β(trimethylacetamido)-4-aza-5α-androstan-3-one |
| (3) ![structure] | 4-methyl-17β(trimethylacetamido)-4-aza-5α-androst-1-en-3-one<br>4-methyl-17β(trimethylacetamido)-4-aza 5α-androstan-3-one |
| (4) ![structure] | 17β(acetamido)-4-methyl-4-aza-5α-androst-1-ene-3-one<br>17β(acetamido)-4-methyl-4-aza-5α-androstan-3-one |

TABLE 1-continued

| Side Chain A | Compound(s): |
|---|---|
| (5) ![H-N-S(=O)(=O)-thiophene] | 4-methyl-17β(2-thiophenesulfonamido-methyl)-4-aza-5α-androst-1-en-3-one<br>4-methyl-17β(2-thiophenesulfonamido-methyl)-4-aza-5α-androstan-3-one |
| (6) H-N-C(=O)-(CH$_2$)$_{10}$CH$_2$-S-CH(CH$_3$)$_2$ | 17β(isopropylthiododecanoylamido-methyl)-4-methyl-4-aza-5α-androst-1-en-3-one<br>17β(isopropylthiododecanoylamido-methyl)-4-methyl-4-aza-5α-androstan-3-one |
| (7) H-N-C(=O)-thiophene | 4-methyl-17β(2-thiophenecarboxamido-methyl-4-aza-5α-androst-1-en-3-one<br>4-methyl-17β(2-thiophenecarboxamido-methyl)-4-aza-5α-androstan-3-one |
| (8) H-N-C(=O)-(CH$_2$)$_7$CO$_2$CH$_3$ | 17β(carbomethoxyoctanoylamido-methyl)-4-methyl-4-aza-5α-androst-1-en-3-one<br>17β(carbomethoxyoctanoylamido-methyl)-4-methyl-4-aza-5α-androstan-3-one |
| (9) H-N-C(=O)-CH(CH$_3$)-phenyl-isobutyl | 17β((2-(4-isobutylphenyl)-propionamidomethyl)-4-methyl-4-aza-5α-androst-1-en-3-one<br>17β((2-(4-isobutylphenyl)-propionamidomethyl)-4-methyl-4-aza-5α-androstan-3-one |
| (10) H-N-C(=O)-(CH$_2$)$_7$COOH | 17β(8-carboxyoctanoylamidomethyl)-4-methyl-4-aza-5α-androst-1-en-3-one<br>17β(8-carboxyoctanoylamidomethyl)-4-methyl-4-aza-5α-androstan-3-one |
| (11) H-N-C(=O)-CH$_2$-C(=O)-CH$_3$ | 17β(acetaocetamidomethyl)-4-methyl-4-aza-5α-androst-1-en-3-one<br>17β(acetoacetamidomethyl)-4-methyl-4-aza-5α-androstan-3-one |
| (12) H-N-C(=O)-CH$_2$-1-Adm | 17β(1-Adamantylacetamidomethyl)-4-methyl-4-aza-5α-androst-1-en-3-one<br>17α(1-Adamantylacetamidomethyl)-4-methyl-4-aza-5α-androstan-3-one |
| (13) H-N-C(=O)-CH$_2$-thiophene | 4-methyl-17β(2-thiopheneacetamidomethyl)-4-aza-5α-androst-1-en-3-one<br>4-methyl-17β(2-thiopheneacetamidomethyl)-4-aza-5α-androstan-3-one |
| (14) HN-C(=O)-(CH$_2$)$_{11}$S-C(CH$_3$)$_3$ | 17β(12-(t-butylthio)dodecanoylamido)-4-methyl-4-aza-5α-androstan-3-one<br>17β(12-(t-butylthio)dodecanoylamido)-4-methyl-4-aza-5α-androstan-3-one |
| (15) H-N-C(=O)-CH$_2$-CH$_2$-C(=O)-OCH$_2$-phenyl | 17β(3-carbobenzyloxy)propionamido-methyl)-4-methyl-4-aza-5α-androst-1-en-3-one<br>17β(3-carbobenzyloxy)propionamido-methyl)-4-methyl-4-aza-5α-androstan-3-one |

TABLE 1-continued

| Side Chain A | Compound(s): |
|---|---|
| (16) ![N(H)-C(=O)-CH2-C6H3(OMe)2] with 3,4-dimethoxyphenyl | 17β(3,4-dimethoxyphenylacetamido-methyl)-4-methyl-4-aza-5α-androst-1-en-3-one<br>17β(3,4-dimethoxyphenylacetamido-methyl)-4-methyl-4-aza-5α-androstan-3-one |
| (17) HN—C(=O)—(CH$_2$)$_7$CO$_2$CH$_3$ | 17β(8-(carbomethoxy)octanoylamido)-4-methyl-4-aza-5α-androst-1-en-3-one<br>17β(8-(carbomethoxy)octanoylamido)-4-methyl-4-aza-5α-androstan-3-one |
| (18) HN—C(=O)—(CH$_2$)$_{11}$—S—CH(CH$_3$)$_2$ | 17β(isopropylthiododecanoylamido)-4-methyl-4-aza-5α-androst-1-en-3-one<br>17β(isopropylthiododecanoylamido)-4-methyl-4-aza-5α-androstan-3-one |
| (19) N(H)—S(=O)$_2$—C$_6$H$_5$ | 17β(benzenesulfonamidomethyl)-4 me-aza-5α-androst-1-en-3-one<br>17β(benzenesulfonamidomethyl)-4-methyl-4-aza-5α-androstan-3-one |
| (20) N(H)—C(=O)—(CH$_2$)$_4$CH$_2$Br | 17β(6-Bromohexanoylamidomethyl)-4-methyl-4-aza-5α-androst-1-en-3-one<br>17β(6-Bromohexanoylamidomethyl)-4-methyl-4-aza-5β-androstan-3-one |
| (21) N(H)—C(=O)—(CH$_2$)$_{11}$OH | 17β(12-hydroxydodecanoylamido-methyl)-4-methyl-4-aza-5α-androst-1-en-3-one<br>17β(12-hydroxydodecanoylamido-methyl)-4-methyl-4-aza-5α-androstan-3-one |
| (22) N(H)—C(=O)—CH(CH$_3$)—C$_6$H$_4$—NO$_2$ | 4-methyl-17β(2-(4-nitrophenyl)pro-pionamidomethyl)-4-aza-5α-androst-1-en-3-one<br>4-methyl-17β(2-(4-nitrophenyl)pro-pionamidomethyl)-4-methyl-4-aza-5α-androstan-3-one |
| (23) N(H)—C(=O)—CH$_2$—S—CH(CH$_3$)$_2$ | 17β(isopropylthioacetamidomethyl)-4-methyl-4-aza-5α-androst-1-en-3-one<br>17β(isopropylthioacetamidomethyl)-4-methyl-4-aza-5α-androstan-3-one |
| (24) N(H)—C(=O)—(CH$_2$)$_4$CH$_2$SSO$_3$Na | 4-methyl-17β(thiosulfatohexanoyl-amido-methyl)4-aza-5α-androst-1-en-3-one<br>4-methyl-17β(thiosulfatohexanoyl-amido-methyl)-4-aza-5α-androstan-3-one |
| (25) N(H)—C(=O)—CH$_2$—O—CH$_2$—C$_6$H$_5$ | 17β(benzyloxyacetamidomethyl)-4-methyl-4-aza-5α-androst-1-en-3-one<br>17β(benzyloxyacetamidomethyl)-4-methyl-4-aza-5α-androstan-3-one |
| (26) N(H)—C(=O)—CH$_2$—CO$_2$CH$_3$ | 17β(carbomethoxyacetamidomethyl)-4-methyl-4-aza-5α-androst-1-en-3-one<br>17β(carbomethoxyacetamidomethyl)-4-methyl-4-aza-5α-androstan-3-one |

TABLE 1-continued

| Side Chain A | Compound(s): |
|---|---|
| (27) ![structure with NH-C(=O)-CH with two phenyl groups] | 17β(diphenylacetamidomethyl)-4-methyl-4-aza-5α-androst-1-en-3-one<br>17β(diphenylacetamidomethyl)-4-methyl-4-aza-5α-androstan-3-one |
| (28) ![structure with NH-C(=O)-CH₂-C with three phenyl groups] | 4-methyl-17β(3,3,3-triphenylpropion-amidomethyl)-4-aza-5α-androst-1-en-3-one<br>4-methyl-17β(3,3,3-triphenylpropion-amidomethyl)-4-aza-5α-androstan-3-one |

The following additional compounds may also be prepared according to the procedures described in the instant specification.

17β-(2-Furylacetamidomethyl)-4-Methyl-4-aza-5α-androstan-3-one;
17β-(4-Isopropylphenylacetamidomethyl)-4-Methyl-4-aza-5α-androstan-3-one;
17β-(Cyclohexylacetamidomethyl)-4-Methyl-4-aza-5α-androstan-3-one;
17β-(3-Indolylacetamidomethyl)-4-Methyl-4-aza-5α-androstan-3-one;
4-Methyl-17β-(4-Methylcyclohexanecarboxamidomethyl)-4-aza-5α-androstan-3-one;
17β-(4-(3-Indolyl)-butyramidomethyl)-4-Methyl-4-aza-5α-androstan-3-one;
17β-(4-Isobutylbenzamidomethyl)-4-Methyl-4-aza-5α-androstan-3-one;
17β-(Acetoxyacetamidomethyl)-4-Methyl-4-aza-5α-androstan-3-one;
17β-(6-Bromohexanoylamidomethyl)-4-Methyl-4-aza-5α-androstan-3-one;
4-Methyl-20-(4-Nitrobenzamidomethyl)-4-aza-5α-pregnan-3-one;
20-((3-Acetamido)benzamido)-4-Methyl-4-aza-5α-pregnan-3-one;
20-(3,4-Dimethoxyphenylacetamidomethyl)4-Methyl-4-aza-5α-pregnan-3-one;
17β-(4-Ethoxybenzamidomethyl)-4-Methyl-4-aza-5α-androstan-3-one;
4-Methyl-20-(Palmitoylamidomethyl)-4-aza-5α-pregnan-3-one;
17β-(Iminodibenzyl-5-carboxamidomethyl)-4-Methyl-4-aza-5α-androstan-3-one;
4-Methyl-20-(Stearoylamido)-4-aza-5α-pregnan-3-one;
4-Methyl-17β-(3,5-Bis-(Trifluoromethyl)benzamidomethyl)-4-aza-5α-androstan-3-one;
17β-(3-Cyanobenzamidomethyl)-4-Methyl-4-aza-5α-androstan-3-one;
20-(Heptafluorobutyramidomethyl)-4-Methyl-4-aza-5α-pregnan-3-one;
20-(4-Benzoylbenzamidomethyl)-4-Methyl-4-aza-5α-pregnan-3-one;
17β-(Benztriazol-5-carboxamidomethyl)-4-Methyl-4-aza-5α-androstan-3-one;
20-(3,5-Difluorobenzamido)-4-Methyl-4-aza-5α-pregnan-3-one;
17β-(Bis-(4-Isopropyl)phenyl)acetamidomethyl-4-Methyl-4-aza-5α-androstan-3-one;
4-Methyl-20-(Salicylamidomethyl)-4-aza-5α-pregnan-3-one;
17β-(Cinnamoylamidomethyl)-4-Methyl-4-aza-5α-androstan-3-one;
17β-((3-Hydroxy-4,4,4-trichlorobutyramido)methyl)-4-Methyl-4-aza-5α-androstan-3-one.

Synthesis of Testosterone 5-a Reductase Inhibitors:

Scheme XII illustrates the synthesis of the intermediate oximes and amines used to produce compounds claimed in the instant invention.

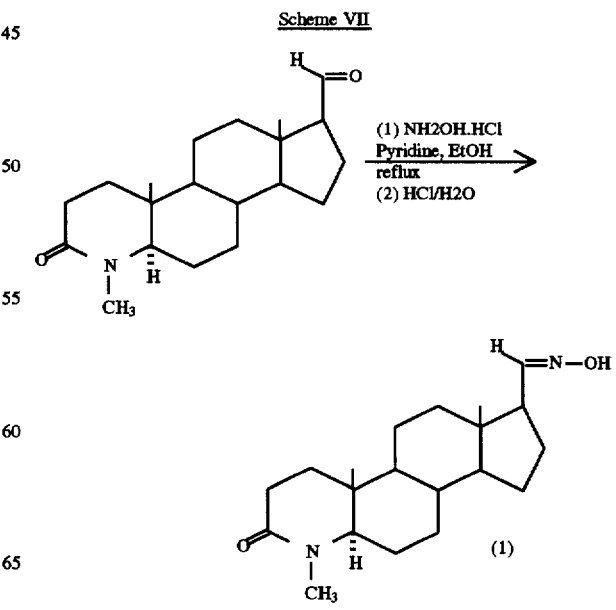

Scheme VII

-continued
Scheme VII

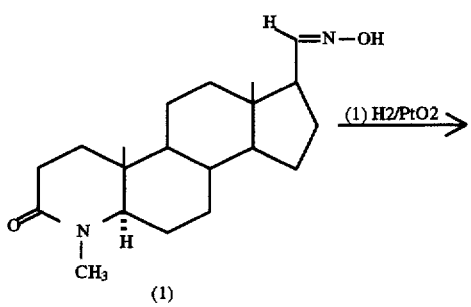

(1)

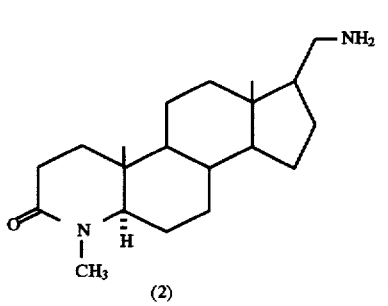

(2)

A stirred mixture of 4-methyl-3-oxo-5-α-4-azaandrostan-17-carboxaldehyde, hydroxylamine hydrochloride, anhydrous pyridine, and anhydrous ethanol is refluxed gently under a nitrogen atmosphere for six to seven hours. After cooling, the ice-cooled mixture is diluted, with stirring, with a slight excess of chilled dilute hydrochloric acid. The suspension is then aged for about twenty minutes, filtered, washed with water and dried to give compound 1.

A mixture of the oxime (1), ethanol, glacial acetic acid and water is reduced in the presence of platinum oxide (PtO₂) until chromatographic analysis (TLC) indicates complete reduction to the amine (2). The filtered reaction mixture is concentrated in vacuo; the resultant residue is dissolved in chloroform (CHCl₃) and washed with fresh dilute sodium hydrogen carbonate solution. The chloroform phase is then dried with sodium sulfate (Na₂SO₄). Concentration of the resultant CHCl₃ solution followed by trituration of the residue with hexane/ether will yield 2 as a white solid.

The following amines are representative of those obtained from the corresponding carbonyl compounds utilizing the basic procedures described in Scheme 1 for preparation of the oximes and amines:

3)

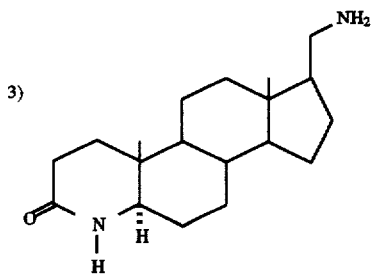

17-Aminomethyl-5-α-4-azaandrostan-3-one;

-continued

4)

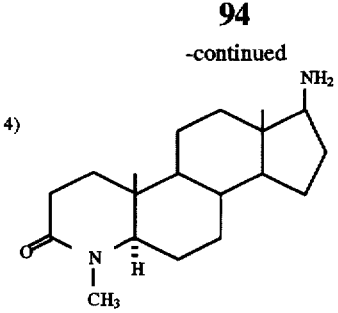

17-Amino-4-methyl-5-α-4-azaandrostan-3-one;

5)

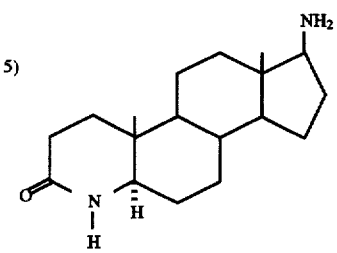

17-Amino-5-a-4-azaandrostan-3-one;

6)

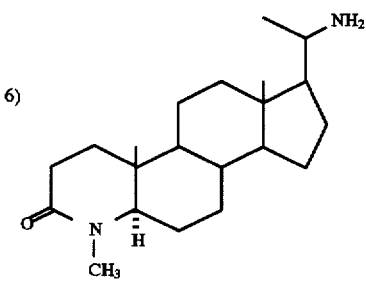

20-Amino-4-methyl-5-a-4-azapregnan-3-one;

7)

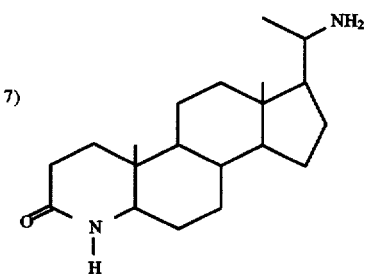

20-Amino-5-a-4-azapregnan-3-one;

8)

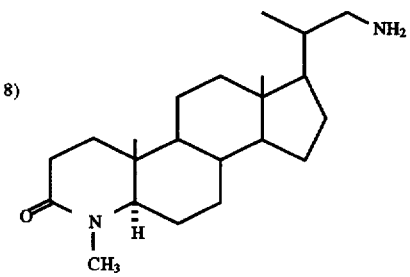

20-(Aminomethyl)-4-methyl-5-a-4-azapregnan-3-one;

9)

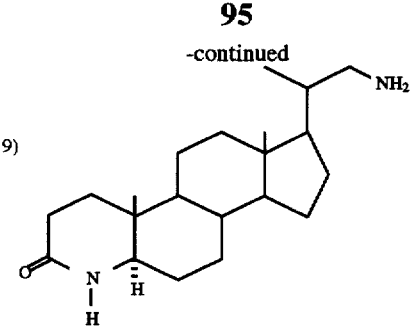

20-(Aminomethyl)-5-a-4-azapregnan-3-one;

As Scheme VII indicates, the oximes useful as intermediates may readily be prepared by reacting 4-azasteroidal aldehyde or ketone with hydroxylamine hydrochloride to form the corresponding oxime. The resultant oximes are subsequently reduced with hydrogen ($H_2$) and platinum oxide ($PtO_2$) or other suitable reducing agent to yield the respective amine. The product amides may be further alkylated with, for example, alkyl halides to give the corresponding $R^2$ alkylated compounds. Alternatively, the primary amines may be alkylated by well known synthetic procedures to the corresponding secondary amines and then acylated to the product amides.

Scheme VIII illustrates the synthesis of the compound 4-methyl-17(trimethylacetylamido)-5-a-4 azaandrostan-3-one and is representative of a basic synthesis of compounds claimed in the instant invention in which an amine is reacted with an acylating agent (or acid equivalent). These reagents include acyl halides and acid anhydrides.

SCHEME VIII

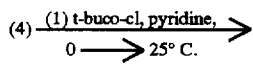

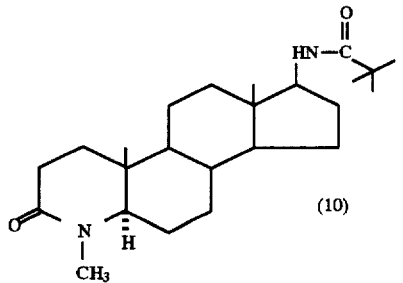

As Scheme VIII illustrates, 4-azasteroidal primary or secondary amines described in the instant invention are reacted with the desired activated carbonyl compound, such as trimethylacetyl chloride, to yield the target amide. Representative acyl halides or acid anhydrides of the formula:

wherein
$R^3$ equals
$C_{1-20}$alkyl,
aryl,
heteroaryl,
aryl$C_{1-20}$alkyl,
heteroaryl$C_{1-20}$alkyl,
$C_{1-20}$alkylaryl$C_{1-20}$alkyl,
$C_{1-20}$alkyloxycarbonylalkyl,
$C_{1-20}$alkylcarbonyl$C_{1-20}$alkyl,
$C_{1-20}$cycloalkyl$C_{1-20}$alkyl,
aryl$C_{1-20}$alkyloxycarbonyl$C_{1-20}$alkyl,
halo$C_{1-20}$alkyl,
aryl$C_{1-20}$alkyloxo$C_{1-20}$alkyl,
diaryl$C_{1-20}$alkyl,
triaryl$C_{1-20}$alkyl,
$C_{2-20}$ alkenyl,
$C_{2-20}$ alkenyl$C_{1-20}$alkyl,
$C_{2-20}$alkynyl$C_{1-20}$alkyl,
aryl$C_{2-20}$alkynyl$C_{1-20}$alkyl,
heteroaryl$C_{2-20}$alkylnyl$C_{1-20}$alkyl,
or aryl$C_{2-20}$alkenyl may be used in the instant invention.

Acyl halides or activated carbonyl compounds disclosed in this invention are commercially available or may be prepared from the corresponding carboxylic acid and thionyl chloride ($SOCl_2$), phosphorous pentahalide ($PX_5$), or phosphorous trihalide ($PX_3$). See Ansell in Patai, "The Chemistry of Acyl Halides", 35–48, Interscience, New York (1972).

The primary or secondary amines disclosed in the instant invention may also be reacted with alkyl and aryl sulfonyl halides or anhydrides to yield compounds claimed in the instant invention.

If a sulfonylhalide or anhydride of the formula $$X-\overset{O}{\underset{O}{\overset{\|}{S}}}-R^3$$

is used, $R^3$ may equal the groups defined above for the carbonyl species.

Amides or sulfonamides representative of those obtained from the corresponding amines utilizing the basic procedure described in Scheme 2 by substituting either the amine or the activated carbonyl compound may be prepared. For example, compound 6 may be substituted for compound 4 in Scheme 2 and reacted with the indicated acylating agent (trimethylacetyl chloride) to yield compound 11 (4-methyl-20-(trimethylacetamido)-5-a-4-azapregnan-3'-one). If compound 2 is reacted with 8-(carbomethoxy)octanoyl chloride using the procedure described in Scheme 2, (17-(8-(Carbomethoxy)octanoylamidomethyl)-4-methyl-5-a-4-aza-androstan-3-one) is produced:

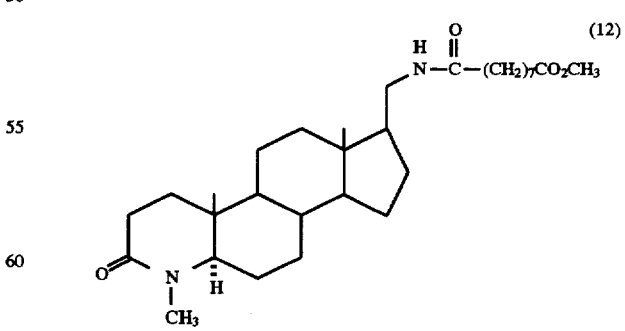

If sulfonyl halide is substituted for an acyl halide and reacted with an amine such as 2, (4-methyl-17-(2-thiophenesulfonylamidomethyl)-5-a-4-azaandrostan-4-one) may be prepared:

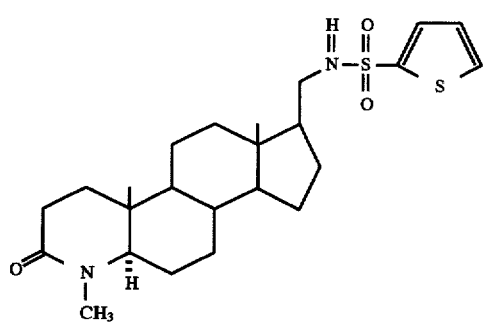

Scheme IX illustrates the synthesis of 17β-(12-(Isopropylthio)dodecanoylamidomethyl)-4-methyl-5α-aza-androstan-3-one (14):

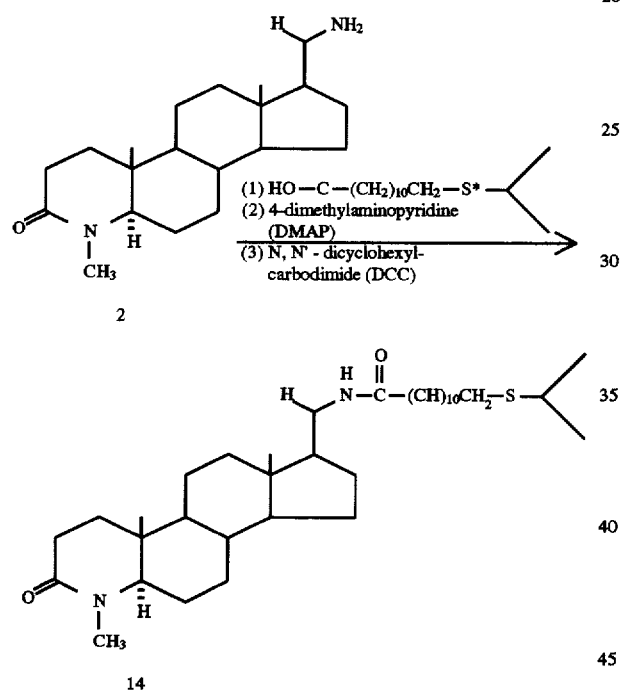

-continued
SCHEME IX

*prepared from 12-bromododecanoic acid and sodium isopropylthiolate

DCC is a well known coupling reagent used in peptide synthesis to generate amide bonds from a free acid and an amine. Coupling reagents may generally be used when the free acid is readily available or when the alternative acid halide is internally labile (e.g., when a thio group is present). An intermediate anhydride of the acid is generated which further reacts with the amine. In Scheme 3, 12-(isopropylthio)-dodecanoic acid is reacted with 2, DCC, and DMAP to produce the corresponding amide (14). For example, DCC is used when $R^3$ is $C_{1-20}$alkylthio$C_{1-20}$alkyl or hydroxyl$C_{1-20}$alkyl. Additionally, dehydrogenation of the 1,2 position or the 5,6 position may readily be accomplished by known synthetic methodology to produce the claimed 1-en or 5-en derivatives. See U.S. Pat. No. 5,061,802; Dolling et al., JACS, 110, 3318–19 (1988).

Schemes X, XI and XII further illustrate how compounds claimed in the instant invention may be prepared. In Scheme X, the staring 4-azasteroid aldehyde or ketone (XV), obtained by known synthetic methods, is reacted to form the oxime (XVI); reduced to the amine (XVII) and reacted with an activated carbonyl or sulfonyl compound and an alkyl-halide (X—$R^2$) to form (XVIII).

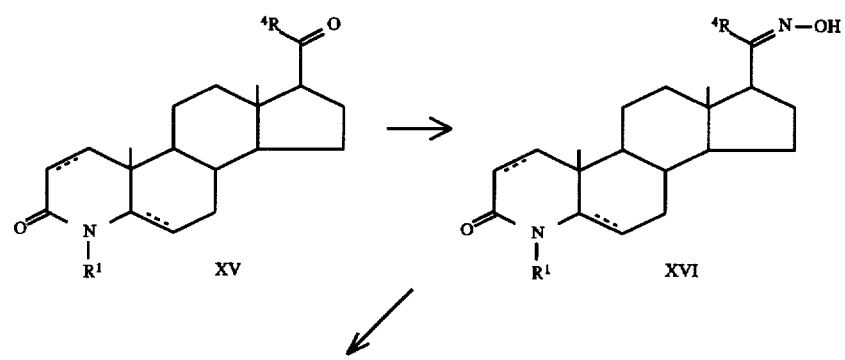

-continued
SCHEME X

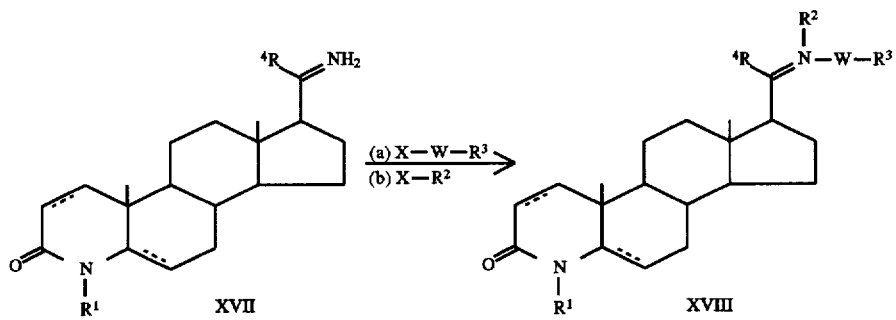

In Scheme XI, the identical procedure is followed using a generic 4-azasteroid (XIX) prepared by known synthetic methods to produce the oxime (XX) which is reduced to the amine (XXI) and reacted with an activated carbonyl or sulfonyl compound (X—W—R³) to yield (XXII).

to form the oxime (XXIV) which is further reduced to form (XXV) and subsequently reacted with an activated carbonyl or sulfonyl compound to form (XXVI).

SCHEME XI

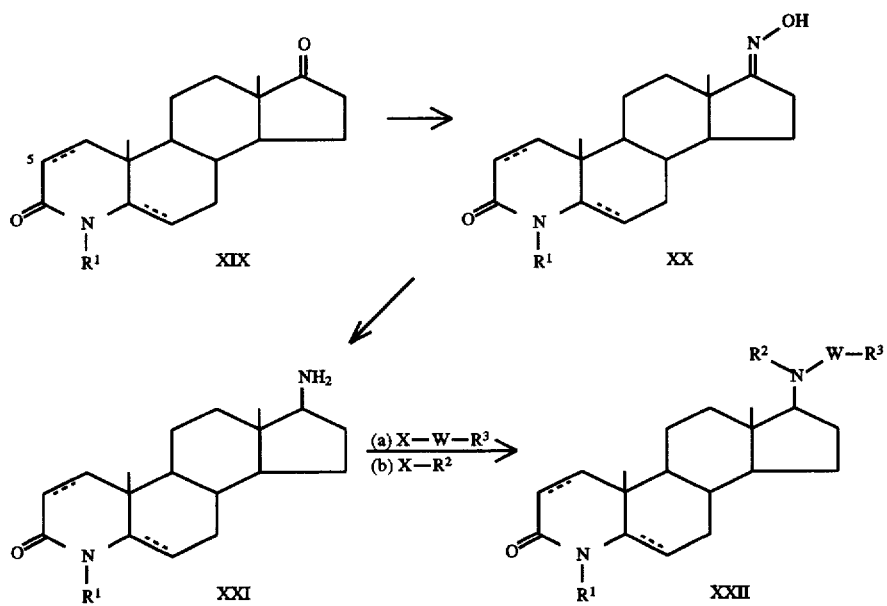

In Scheme 6, the generic 4-azasteroid (XXIII), also obtained from well known synthetic methodology, is reacted

SCHEME XII
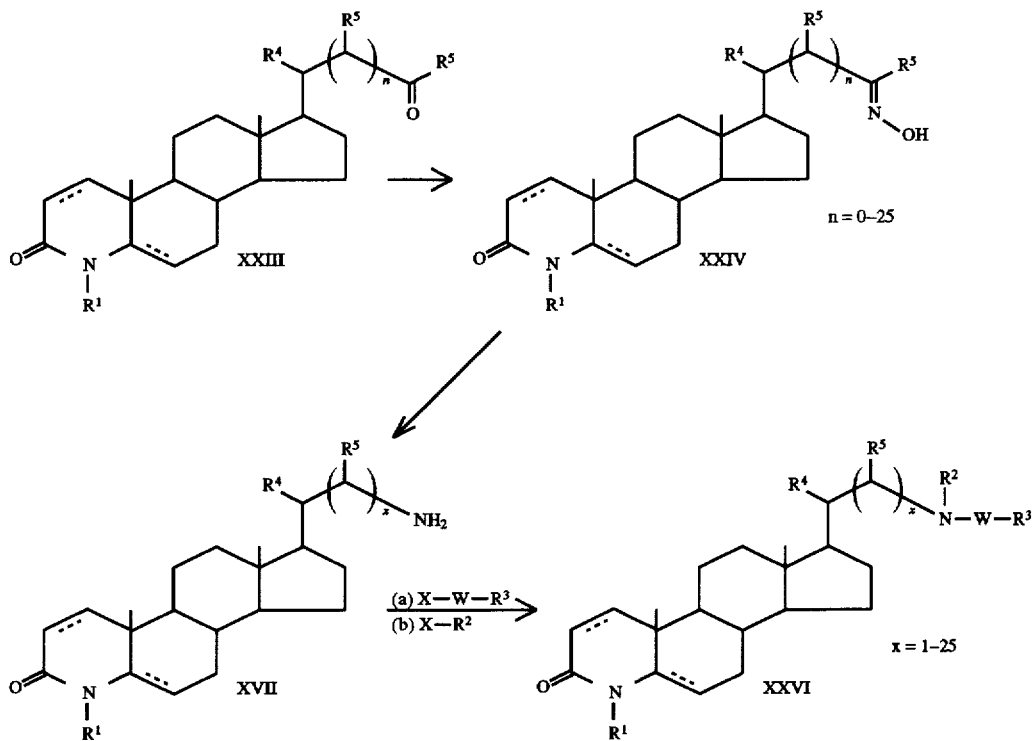
The starting 4-azasteroidal ketones used in the present invention may be prepared according to the well known basic procedures described in Scheme XIII.
SCHEME XIII
(1)
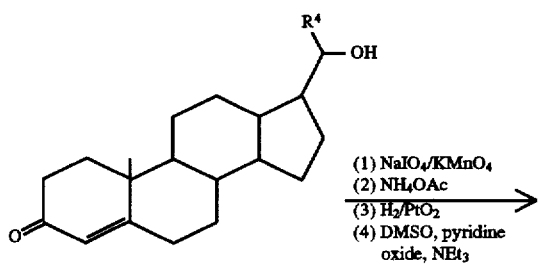
(1) NaIO$_4$/KMnO$_4$
(2) NH$_4$OAc
(3) H$_2$/PtO$_2$
(4) DMSO, pyridine oxide, NEt$_3$
-continued
SCHEME XIII
(2)
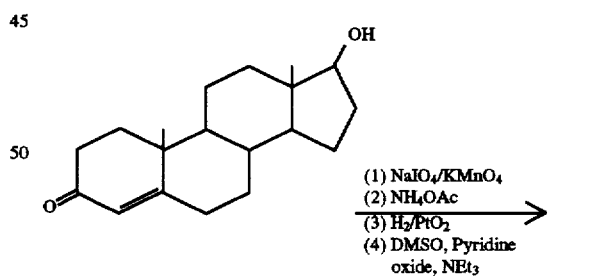
(1) NaIO$_4$/KMnO$_4$
(2) NH$_4$OAc
(3) H$_2$/PtO$_2$
(4) DMSO, Pyridine oxide, NEt$_3$
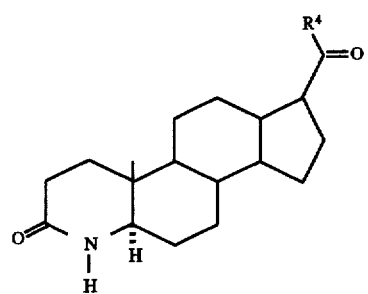
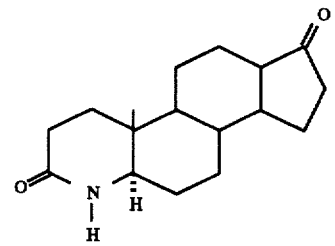

SCHEME XIII -continued (3)

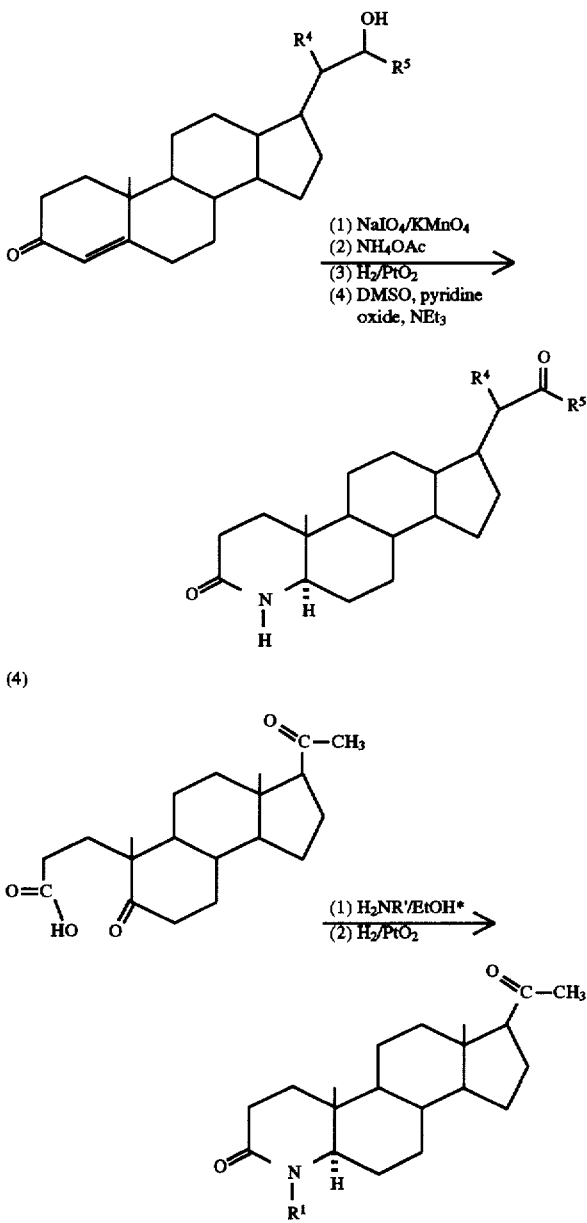

The following examples further describe the synthesis of compounds claimed in the instant invention.
Synthesis of Starting -4-azasteroid oximes:

EXAMPLE 1

4-Methyl-3-oxo-5-a-4-azaandrostan-17-carboxalde-hyde oxime

A stirred mixture of 4-methyl-3-oxo-5-a-4-azaandrostan-17-carboxaldehyde (0.952 g, 3.0 mM), hydroxylamine hydrochloride (1.10 g, 15.8 mM), anhydrous pyridine (6 mL), and anhydrous ethanol (12 mL) was refluxed gently under a nitrogen atmosphere for 6.3 hours. After cooling, the ice-cooled mixture was diluted, with stirring, with a slight excess of chilled dilute hydrochloric acid (ca. 0.3N), the suspension was aged for ca. 20 minutes, filtered, washed with water and dried to give (1) 0.855 g. MS M$^+$ calcd for $C_{20}H_{32}H_2O_2$ 332.48, observed m/e 332.

Synthesis Reactant 4-azasteroid Amines:

EXAMPLES 2-9

2) 17-Aminomethyl-4-methyl-5-a-4-azaandrostan-3-one.

A mixture of (1) (0.67 g, 2.0 mM), ethanol (100 mL), glacial acetic acid (8 mL) and water (4 mL) was reduced in a hydrogen atmosphere (40 p.s.i.) at room temperature in the presence of PtO$_2$ until TLC analysis indicated complete reduction. The filtered reaction mixture was concentrated in vacuo, the residue taken up in chloroform, and the chloroform solution washed with fresh dilute sodium hydrogen carbonate solution and dried (Na$_2$SO$_4$). Concentration of the filtered chloroform solution followed by trituration of the residue obtained with hexane containing a small amount of ether yielded (2) as an off-white solid. MS MH$^+$ calcd for $C_{20}H_{34}N_2O$ 318.49, observed m/e 319.

The following amines are representative of those obtained from the corresponding carbonyl compounds utilizing the above procedures:

3) 17-Aminomethyl-5-a-4-azaandrostan-3-one,
4) 17-Amino-4-methyl-5-a-4-azaandrostan-3-one,
5) 17-Amino-5-a-4-azaandrostan-3-one,
6) 20-Amino-4-methyl-5-a-4-azapregnan-3-one,
7) 20-Amino-5-a-4-azapregnan-3-one.
8) 20-(Aminomethyl)-4-methyl-5-a-4-azapregnan-3-one,
9) 20-(Aminomethyl)-5-a-4-azapregnan-3-one.

Synthesis of Amino substituted azasteroids:

EXAMPLES 10-14

10) 4-Methyl-17β-(trimethylacetamido)-5-a-4-azaandrostan-3-one

To a stirred, ice-cold solution of (4) (0.091 g, 0.3 mM), anhydrous methylene chloride (5 mL), and pyridine (0.1 mL, 1.2 mM), was added trimethylacetyl chloride (0.05 mL, 0.4 mm) dropwise over ca. one minute (nitrogen atmosphere). After an additional 15 min. at ice-bath temperatures the mixture was allowed to warm to room temperature and stir at ambient temperature overnight. The mixture was then transferred to a separatory funnel with additional methylene chloride, washed with dilute (ca. 0.3N) hydrochloric acid, and dried (Na$_2$SO$_4$). Concentration of the filtered solution followed by recrystallization (ethyl acetate) of the residue obtained gave (10) as a white solid. MS M$^+$ calcd for $C_{24}H_{40}N_2O_2$ 388.59, observed m/e 388.

11) 4-Methyl-20-(trimethylacetamido)-5-a-4-azapregnan-3-one

When (4) in the above reaction was replaced by (6), (11) was obtained as a white solid. MS M$^+$ calcd for $C_{26}H_{44}H_2O_2$ 416.65, observed m/e 416.

12) 17β-(8-(Carbomethoxy)octanoylamidomethyl)-4-methyl-5-a-4-azaandrostan-3-one

When (2) was reacted with 8-carbomethoxy-octanoyl chloride using the conditions of Example (10), (12) was obtained as a thick oil. MS M$^+$ calcd for $C_{30}H_{50}N_2O_4$ 502.74, observed m/e 502.

13) 4-Methyl-17β-(2-thiophenesulfonylamidomethyl)-5-a-4-azaandrostan-3-one

When the 8-carbomethoxyoctanoyl chloride in the above example was replaced with 2-thiophene-sulfonyl chloride, (13) was obtained as a white solid. MS M$^+$ calcd for $C_{24}H_{36}N_2O_3S_2$ 464.68, observed m/e 464.

14) 17β-(12-(Isopropylthio)dodecanoylamidomethyl)-4-methyl-5-a-4-aza-androstan-3-one To a stirred solution of (2) (0.028 g, 0.09 mM) and 12-(isopropylthio)dodecanoic acid (0.025 g, 0.09 mM)

(prepared from 12-bromododecanoic acid and sodium isopropylthiolate by heating in 1,2-dimethoxyethane) in methylene chloride (3 mL) was added 4-(dimethylamino)-pyridine (0.011 g, 0.09 mM) followed by a solution of N,N'-dicyclohexylcarbodiimide (0.020 g, 0.097 mM) in a minimum of the same solvent. After stirring for 12–14 hours, the mixture was filtered and the filtrate concentrated in vacuo. Flash chromatography (silica gel, ethyl acetate as eluant) yielded (14) as a very thick oil. MS MH$^+$ calcd for $C_{35}H_{62}N_2O_2S$ 574.95, observed m/e 575.

Examples 15–37 prepared according to the basic procedures described above further exemplify the invention.

15) 4-Methyl-17β(trimethylacetamidomethyl)-4-aza-5α-androstan-3-one;

16) 17β(acetamido)-4-Methyl-4-aza-5α-androstan-3-one;

17) 4-Methyl-17β(2-thiophenecarboxamidomethyl)-4-aza-5α-androstan-3-one;

18) 17β(2-(4-isobutylphenyl)propionamidomethyl)-4-Methyl-4-aza-5α-androstan-3-one;

19) 17β(8-carboxyoctanoylamidomethyl)-4-Methyl-4-aza-5α-androstan-3-one;

20) 17β(acetoacetamidomethyl)-4-Methyl-4-aza-5α-androstan-3-one;

21) 17β(1-Adamantylacetamidomethyl)-4-Methyl-4-aza-5α-androstan-3-one;

22) 4-Methyl-17β(2-thiopheneacetamidomethyl)-4-aza-5α-androstan-3-one;

23) 17β(12-(t-butylthio)dodecanoylamido)-4-Methyl-4-aza-5α-androstan-3-one;

24) 17β(3-(carbobenzyloxy)propionamidomethyl)-4-Methyl-4-aza-5α-androstan-3-one;

25) 17β(3,4-dimethoxyphenylacetamidomethyl)-4-Methyl-4-aza-5α-androstan-3-one;

26) 17β(8-(carbomethoxy)octanoylamido)-4-Methyl-4-aza-5α-androstan-3-one;

27) 17β(isopropylthiododecanoylamido)-4-Methyl-4-aza-5α-androstan-3-one;

28) 17β(benzenesulfonamidomethyl)-4-Methyl-4-aza-5α-androstan-3-one;

29) 17β(6-Bromohexanoxylamidomethyl)-4-Methyl-4-aza-5α-androstan-3-one;

30) 17β(12-hydroxydodecanoylamidomethyl)-4-Methyl-4-aza-5α-androstan-3-one;

31) 4-Methyl-17β(2-(4-nitrophenyl)propionamidomethyl)-4-aza-5α-androstan-3-one, 32) 17β(isopropylthioacetamidomethyl)-4-Methyl-4-aza-5α-androstan-3-one;

33) 4-Methyl-17β(6-(thiosulfato)hexanoylamidomethyl)-4-aza-5α-androstan-3-one;

34) 17β(benzyloxyacetamidomethyl)-4-Methyl-4-aza-5α-androstan-3-one;

35) 17β(carbomethoxyacetamidomethyl)-4-Methyl-4-aza-5α-androstan-3-one;

36) 17β(diphenylacetamidomethyl)-4-Methyl-4-aza-5α-androstan-3-one;

37) 4-Methyl-17β(3,3,3-triphenylpropionamidomethyl)-4-aza-5α-androstan-3-one;

Table 2 illustrates the NMR data of the above examples.

TABLE 2

| | NMR DATA (ppm) | |
|---|---|---|
| Example | Angular Methyls | Miscellaneous |
| 10 | 0.68, 0.88 | 1.20 (—NHCOC(CH$_3$)$_3$) |
| 11 | 0.72 0.88 | 1.17 (—NHCOC(CH$_3$)$_3$) |

TABLE 2-continued

| | NMR DATA (ppm) | |
|---|---|---|
| Example | Angular Methyls | Miscellaneous |
| 12 | 0.67, 0.89 | 3.66 (—CO$_2$CH$_3$) |
| 13 | 0.61, 0.88 | 2.93 (4-NCH$_3$) |
| 14 | 0.67, 0.89 | 1.24 (—SCH(CH$_3$)$_2$) 1.28 |
| 15 | 0.67, 0.88 | 1.18 (—NHCOC(CH$_3$)$_3$) |
| 16 | 0.70, 0.88 | 1.98 (—NHCOCH$_3$) |
| 17 | 0.72, 0.89 | 2.93 (4-NCH$_3$) |
| 18 | 0.57, 0.85 (split) | 2.91 (4—NCH$_3$) |
| 19 | 0.66, 0.88 | 2.92 (4-NCH$_3$) |
| 20 | 0.64, 0.88 | 2.24 (—COCH$_3$) |
| 21 | 0.66, 0.88 | 2.93 (4-NCH$_3$) |
| 22 | 0.61, 0.87 | 3.78 (—COCH$_2$—(C$_4$H$_3$S)) |
| 23 | 0.70, 0.89 | 1.33 (—SC(CH$_3$)$_3$) |
| 24 | 0.64, 0.88 | 5.12 (—CO$_2$CH$_2$Ph) |
| 25 | 0.60, 0.88 | 3.52(d) (—Ph—(OCH$_3$)$_2$) |
| 26 | 0.70, 0.89 | 3.66 (—CO$_2$CH$_3$) |
| 27 | 0.70, 0.89 1.28 | 1.24 (—SCH(CH$_3$)$_2$) |
| 28 | 0.57, 0.87 | 2.91 (4-NCH$_3$) |
| 29 | 0.67, 0.88 | 2.92 (4-NCH$_3$) |
| 30 | 0.66, 0.88 | 2.92 (4-NCH$_3$) |
| 31 | 0.61, 0.86 (split) | 2.92 (4-NCH$_3$) |
| 32 | 0.68, 0.88 1.28 | 1.24 (—SCH(CH$_3$)$_2$) |
| 33 | 0.67, 0.89 | 2.93 (4-NCH$_3$) |
| 34 | 0.65, 0.88 | 4.56 (—OCH$_2$Ph) |
| 35 | 0.68, 0.89 | 3.75 (—CO$_2$CH$_3$) |
| 36 | 0.60, 0.86 | 4.92 (—COCH(Ph)$_2$) |

The above examples are non-limiting and suitable acylating agents may readily be substituted according to the methods described in the present invention and reacted with a described amine to form the claimed amides. The following definitions further clarify the present invention.

The term "pharmaceutically acceptable salts" shall mean non-toxic salts of the compounds of this invention which are generally prepared by the free base with a suitable organic or inorganic acid. Representative salts include the following salts: Acetate, adipate, alginate, aspartate benzenesulfonate, benzoate, bicarbonate, bisulfate borate, butyrate, camsylate, carbonate, camphorate, chloride, citrate, digluconate, fumarate, glucoheptanate, gluconate, glutamate, glycerophosphate, hydrobromide, hydrochloride, hydroiodide, lactate, laurate, malate, maleate, mandelate, mesylate, methylbromide, methylnitrate, methylsulfate, mucate, napsylate, nitrate, oleate, oxalate.

The term "pharmaceutically effective amount" shall mean that amount or quantity of a drug or pharmaceutical agent that will elicit the biological or medical response of a tissue, system or animal that is being sought by a researcher or clinician or physician.

The term "aryl" shall mean a mono- or polycyclic system composed of 5- and 6-membered aromatic rings either unsubstituted or substituted with R wherein R is defined to include H, $C_{1-6}$alkyl, aryl$C_{1-20}$alkyl wherein the alkyl groups are unsubstituted or substituted with $C_{1-8}$ alkyloxy, carboxy$C_{0-10}$alkyl, hydroxy, or halogen. The term "aryl" also encompasses those aromatic systems which independently have hydroxyl, $C_{1-10}$alkyl, $C_{2-20}$alkenyl, $C_{1-20}$alkyloxy, halo$C_{1-20}$alkyl, benzoyl, cyano, nitro, carboamide, acetamide and halogens directly bonded to the aromatic carbon atom(s) or as further defined in the specification.

The term "heteroaryl" shall mean a mono- or polycyclic system composed of 5- and 6-membered aromatic rings containing 1, 2, 3 or four heteroatoms chosen from N, O, or S and either unsubstituted or substituted with R as defined above independently or with hydroxyl, $C_{1-20}$alkyloxy, $C_{1-20}$alkyl, $C_{2-20}$ alkenyl, halo$C_{1-20}$alkyl, benzoyl, cyano, nitro, carboamide, acetamide and halogens directly bonded to the aromatic carbon atom(s).

The term "alkyl" shall mean straight or branched chain alkane.

The term "alkenyl" shall mean straight or branched chain alkene.

The term "alkynl" shall mean straight or branched chain alkyne.

The term "arylalkyl" shall be taken to include an aryl portion as defined above and an alkyl portion as defined above.

The term "heteroarylalkyl" shall mean an heteroaryl portion as defined above and an alkyl portion as defined above.

The "$C_{1-n}$" designation where n may be an integer from 1 to 20 or 3-20 respectively refers to the alkyl portion, the cycloalkyl portion or to the alkyl portion of an arylalkyl or heteroarylalkyl unit. In addition, it refers to alkenyl, aryl or alkynl substituents.

The term "halogen" shall include fluorine, chlorine, iodine and bromine.

The term "oxy" shall mean an oxygen (O) atom.

The term "Thio" shall mean a sulfur atom.

In the schemes and examples described in this disclosure, various reagent symbols have the following meanings:

$PtO_2$ is platinum oxide

TLC is thin layer chromatography $Na_2SO_4$ is sodium sulfate

DMAP is 4-(dimethylamino)pyridine

DCC is N,N'-dicyclohexylcarbodiimide

EXAMPLES FOR THE CASE WHEN SUBSTITUENT "A" OF GENERAL FORMULA "I" IS AS DEFINED IN GROUP "V(A)"

The present invention further comprises compounds of the general structural formula XVII:

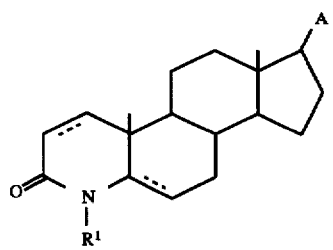

XVII and the pharmaceutically acceptable salts thereof, wherein:

A is:

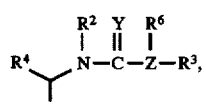  (a)

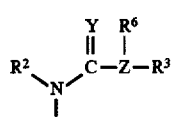  (b)

except when $R^2$ equals H, Y equals O, Z equals N, and there is a 5αH, $R^6$ and $R^3$ cannot be independently selected from H, $C_{1-8}$ alkyl, $C_{3-6}$ cycloalkyl, phenyl or when $R^6$ and $R^3$ are taken together with the adjacent N to form a 5–6 membered ring comprising up to one other heteroatom selected from O or N, or

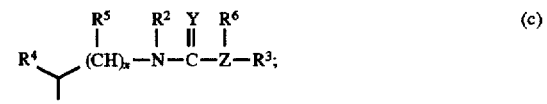  (c)

wherein $R^1$ is:
H,
methyl or ethyl;

$R^2$ is:
H, or
$C_{1-20}$ alkyl;

$R^3$ is:
H,
$C_{1-20}$ alkyl,
$C_{6-14}$ aryl,
heteroaryl,
$C_{6-14}$ aryl$C_{1-20}$alkyl,
$C_{3-20}$ cycloalkyl,
$C_{3-20}$ cycloalkyl$C_{1-20}$alkyl,
heteroaryl$C_{1-20}$alkyl,
$C_{6-14}$ arylcarbonyl$C_{6-14}$aryl$C_{1-20}$alkyl,
$C_{2-20}$ alkenyl$C_{1-20}$alkyl,
halo$C_{1-20}$alkyl,
$C_{1-20}$alkyloxycarbonyl$C_{1-20}$alkyl
$C_{1-20}$ alkyloxy$C_{1-20}$alkyl,
carboxy$C_{1-20}$ alkyl,
$C_{1-20}$ alkylcarbonyl$C_{1-20}$alkyl,
$C_{6-14}$ aryl$C_{1-20}$alkyloxycarbonyl$C_{1-20}$alkyl,
heteroaryl$C_{1-20}$alkyloxycarbonyl$C_{1-20}$alkyl,
hydroxyl$C_{1-20}$alkyl,
halohydroxyl$C_{1-20}$alkyl,
$C_{6-14}$ aryl$C_{1-20}$alkyloxy$C_{1-20}$ alkyl,
heteroaryl$C_{1-20}$alkyloxy$C_{1-20}$alkyl,
diaryl$C_{1-20}$alkyl,
triaryl$C_{1-20}$alkyl,
$C_{2-20}$ alkenyl,
$C_{2-20}$ alkenyl$C_{1-20}$alkyl,
$C_{2-20}$ alkynyl$C_{1-20}$alkyl,
$C_{6-14}$ aryl$C_{2-20}$alkynyl$C_{1-20}$alkyl,
heteroaryl$C_{2-20}$alkynyl$C_{1-20}$alkyl,
$C_{1-20}$ alkylthio$C_{1-20}$alkyl,
$C_{1-20}$ alkylsulfonyl$C_{1-20}$alkyl, or
$C_{1-20}$ alkylsulfinyl$C_{1-20}$alkyl;

$R^4$ is:
H,
$C_{1-20}$ alkyl,
heteroaryl, or
$C_{6-14}$ aryl;

$R^5$ can be the same or different when x is greater than 1 and is:
H,
$C_{1-20}$ alkyl,
heteroaryl, or
$C_{6-14}$ aryl;

$R^6$ is present when Z equals N and is
H, or
$C_{1-20}$ alkyl; or taken together with $R^3$ and the N to which they are attached represent a heteroaryl ring system;

Y is:
O, or
S;

Z is:

N, or

O;

n is an integer from 1–25, and dashes indicate a double bond is optionally present.

Compounds of the following general structural formula XVIII are also disclosed in the present invention.

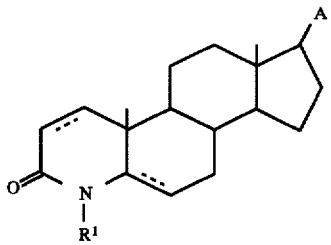

and the pharmaceutically acceptable salts thereof, wherein:

A is:

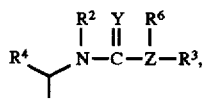  (a)

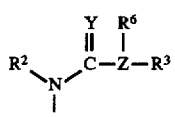  (b)

except when $R^2$ equals H, Y equals O, Z equals N and there is a 5αH, $R^6$ and $R^3$ cannot be independently selected from H, $C_{1-8}$ alkyl, $C_{3-6}$ cycloalkyl, phenyl or when $R^6$ and $R^3$ are taken together with the adjacent N to form a 5–6 membered ring comprising up to one other heteroatom selected from O or N, or

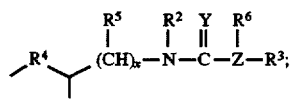  (c)

wherein $R^1$ is:

H, or methyl or ethyl;

$R^2$ is:

H, or $C_{1-20}$ alkyl;

$R^3$ is:

H, $C_{1-20}$ alkyl further comprising a straight or branched chain alkane of up to 20 carbon atoms; $C_{6-14}$ aryl wherein aryl comprises a mono or polycyclic system composed of 6-membered aromatic rings either unsubstituted or substituted with R wherein R comprises H, $C_{1-20}$ alkyl, aryl$C_{1-20}$alkyl with the alkyl groups unsubstituted or substituted with hydroxyl, $C_{1-8}$alkyloxy, carboxy $C_{1-10}$alkyl, or halogen; or aryl can be directly substituted or multisubstituted independently with hydroxyl, halo$C_{1-20}$alkyl, benzoyl, $C_{1-20}$alkyloxy, $C_{1-20}$alkyl, $C_{2-20}$alkenyl, cyano, nitro, carboamide, acetamide, or halogen;

heteroaryl which comprises a mono or polycyclic system composed of 5 and 6-membered aromatic rings containing 1, 2, 3 or 4 heteroatoms chosen from N, O, or S and either unsubstituted or substituted with R as defined for aryl or substituted or multisubstituted independently with hydroxyl, $C_{1-20}$ alkyloxy, $C_{1-20}$alkyl, benzyl, carboamide, acetamide, $C_{2-20}$alkenyl, cyano, nitro, halo$C_{1-20}$alkyl, or halogens, directly bonded to the aromatic carbon atom(s);

$C_{6-14}$ aryl$C_{1-20}$alkyl of the formula:

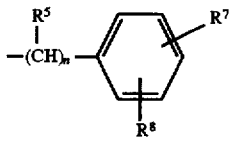

wherein the aromatic ring is optionally and independently substituted with $R^7$ and $R^8$ wherein $R^7$ and $R^8$ comprise

H, $CH_3$, $C_2H_5$, carboamide,

OH, $OCH_3$, $NO_2$,

F,

RS, RSO, $RSO_2$, $R_2N$, where R can be the same or different and is selected from: H, C1–C4alkyl, C6–C14 aryl;

Cl, acetamido, $OC_2H_5$, $CF_3$, isopropyl, or isobutyl; n equals 1–10 and the $C_{1-20}$alkyl portion is optionally substituted with $R^7$;

Heteroaryl$C_{1-20}$alkyl further comprising the formula:

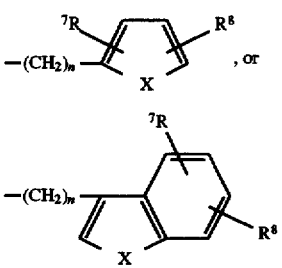

wherein X equals O, S, or NR; and n equals 1–20;

$C_{1-20}$alkylsulfonyl$C_{1-20}$alkyl, $C_{1-20}$alkylthio$C_{1-20}$alkyl, $C_{1-20}$alkylsulfinyl$C_{1-20}$alkyl, comprising the formula:

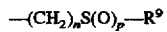

wherein $R^9$ comprises $CH_3$, $C_2H_5$, $C_3H_7$, $C_4H_9$, isopropyl, isobutyl, sec-butyl, t-butyl, isopentyl, neopentyl, or isohexyl; n equals 1–20; p=0, 1, or 2;

$C_{1-20}$ alkyloxycarbonyl$C_{1-20}$alkyl further comprising the formula:

—(CH$_2$)$_n$—COOR$^{10}$ wherein R$^{10}$ comprises:
CH$_3$,
C$_2$H$_5$,
C$_3$H$_7$,
C$_4$H$_9$, or
C$_5$H$_{11}$; n equals 1–20;
carboxylC$_{1-20}$ alkyl further comprising:

—(CH$_2$)$_n$—COOH;

n equals 1–20;
C$_{1-20}$alkylcarbonylC$_{1-20}$ alkyl further comprising

—(CH$_2$)$_n$—CO—(CH$_2$)$_m$—CH$_3$, n equals 1–20; m equals 0–19;
C$_{1-20}$ cycloalkylC$_{1-20}$ alkyl of the formula:

—(CH$_2$)$_n$—(cycloalkyl)

wherein the cycloalkyl portion comprises monocyclic, bicyclic, or polycyclic hydrocarbons of up to 20 carbon atoms wherein the rings are optionally substituted with R$^1$, and n equals 1–20;

C$_{6-14}$ arylC$_{1-20}$ alkyloxycarbonylC$_{1-20}$ alkyl of the formula:

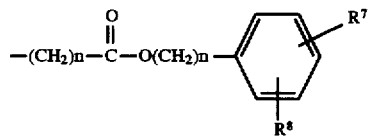

wherein R$^7$ and R$^8$ are as defined; n equals 1–20;
HeteroarylC$_{1-20}$ alkyloxycarbonylC$_{1-20}$alkyl of the formula:

—(CH$_2$)$_n$—C(=O)—O—(CH$_2$)$_n$—Heteroaryl wherein Heteroaryl is as defined: n equals 1–20;
haloC$_{1-20}$ alkyl of the formula:

—(CH$_2$)$_n$—CH$_2$X wherein X equals Br, Cl, F or I; n is 1–19;
hydroxylC$_{1-20}$alkyl of the formula:

—(CH$_2$)$_n$CH$_2$OH;

n equals 1–19;
halohydroxylC$_{1-20}$alkyl of the formula:

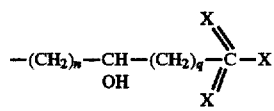

wherein X equals Br, Cl, F or I; n=0–18, q=0–18; n+q=0–18;

C$_{6-14}$ arylC$_{1-20}$alkyloxyC$_{1-20}$ alkyl of the formula:

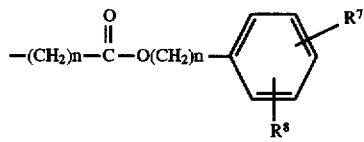

wherein R$^7$ and R$^8$ are as defined; n is 1–20;
ArylcarbonylarylC$_{1-20}$alkyl of the formula:

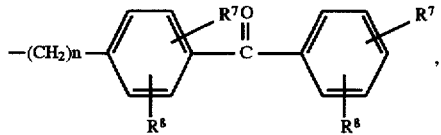

n equals 1–20;
DiarylC$_{1-20}$alkyl of the formula:

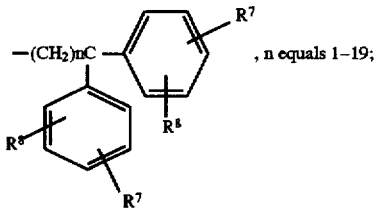

, n equals 1–19;

TriarylC$_{1-20}$alkyl of the formula:

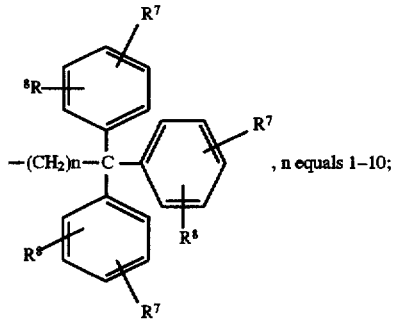

, n equals 1–10;

ArylC$_{2-20}$ alkenyl of the formula:

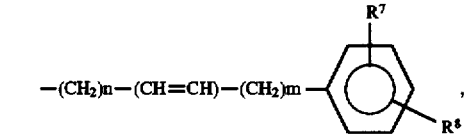

n = 0–18
m = 0–18
n + m = 0–18

R$^4$ is:
H,
C$_{1-20}$alkyl,
C$_{6-14}$ aryl, or
Heteroaryl;
R$^5$ is:
H,
C$_{1-12}$ alkyl;
R$^6$ is present when Z equals N and is independently
H, $C_{1-20}$ alkyl,
equivalent to $R^3$; or taken together with $R^3$ and the N to which they are attached represent a heteroaryl ring system;

Y is:
O, or
S;

Z is
N, or
O;

x is an integer from 1–10,
dashes indicate a double bond is optionally present.

The present invention is also concerned with novel 4-azasteroidal ureas, thioureas, and carbamates and pharmaceutical compositions and formulations thereof that are useful as testosterone 5α-reductase inhibitors of the general structural formula 19:

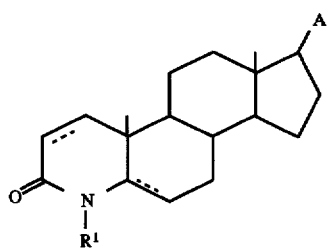

and the pharmaceutically acceptable salts thereof, wherein A is:

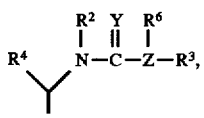 (a)

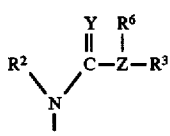 (b)

except when $R^2$ equals H, Y equals O, Z equals N, and there is a 5αH, $R^6$ and $R^3$ may not be independently selected from H, $C_{1-8}$ alkyl, $C_{3-6}$ cycloalkyl, phenyl or when $R^6$ and $R^3$ are taken together with the adjacent N to form a 5–6 membered ring comprising up to one other heteroatom selected from O or N, or

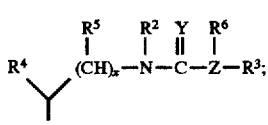 (c)

wherein
$R^1$ is:
H,
methyl or ethyl;
$R^2$ is:
H, or
$C_{1-20}$ alkyl:
$R^3$ is:
H,
$C_{1-20}$ alkyl,
$C_{6-12}$ aryl,
heteroaryl,
$C_{6-12}$ aryl$C_{1-20}$alkyl,
heteroaryl$C_{1-20}$alkyl,
$C_{3-20}$ cycloalkyl,
$C_{3-20}$ cycloalkyl$C_{1-20}$alkyl,
$C_{2-20}$ alkenyl$C_{1-20}$alkyl,
halo$C_{1-20}$alkyl,
$C_{1-20}$ alkyloxy$C_{1-20}$alkyl,
$C_{1-20}$alkyloxycarbonyl$C_{1-20}$alkyl,
$C_{1-20}$ alkylthio$C_{1-20}$alkyl,
$C_{1-20}$ alkylsulfonyl$C_{1-20}$alkyl,
$C_{1-20}$alkylsulfinyl$C_{1-20}$alkyl,
carboxy$C_{1-20}$ alkyl,
$C_{6-12}$ arylcarbonylaryl$C_{1-20}$alkyl
$C_{1-20}$ alkylcarbonyl$C_{1-20}$alkyl,
$C_{6-12}$ aryl$C_{1-20}$ alkyloxycarbonyl$C_{1-20}$alkyl,
heteroaryl$C_{1-20}$alkyloxycarbonyl$C_{1-20}$alkyl,
halo$C_{1-20}$alkyl,
hydroxy$C_{1-20}$alkyl,
halohydroxyl$C_{1-20}$alkyl,
$C_{6-14}$ aryl$C_{1-20}$alkyloxy$C_{1-20}$alkyl,
heteroaryl$C_{1-20}$alkyloxy$C_{1-20}$alkyl,
diaryl$C_{1-20}$alkyl,
triaryl$C_{1-20}$alkyl,
$C_{2-20}$ alkenyl,
$C_{2-20}$ alkenyl$C_{1-20}$alkyl,
$C_{2-20}$ alkynyl$C_{1-20}$alkyl,
$C_{6-14}$ aryl$C_{2-20}$alkynyl$C_{1-20}$alkyl, or
heteroaryl$C_{2-20}$alkynyl$C_{1-20}$alkyl;

$R^4$ is:
H,
$C_{1-20}$ alkyl,
heteroaryl, or
$C_{6-14}$ aryl;

$R^5$ is:
H,
$C_{1-20}$ alkyl,
heteroaryl, or
$C_{6-14}$ aryl;

$R^6$ is present when Z equals N and is
H, or
$C_{1-20}$ alkyl; or taken together with $R^3$ and the N to which they are attached represent a heteroaryl ring system;

Y is:
O, or
S;

Z is:
N, or
O;

x is an integer from 1–25, and dashes indicate a double bond is optionally present.

Compounds of the general structural formula XX:

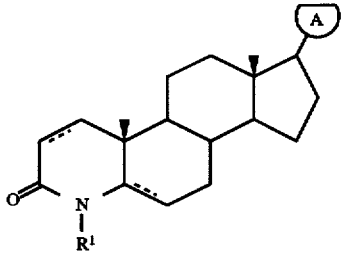

are representative of additional preferred compounds claimed in the instant invention. In a preferred embodiment, $R^1$ may be H or $CH_3$ and A may be as indicated as in Table 3. Particular representative chemical names are also listed in Table 3 adjacent to the respective side chain and specifically reflect whether the 1-position is saturated or unsaturated.

Advantageously, $R^1$ is $CH_3$, A is as indicated in Table 3 and the 1 position is saturated.

TABLE 3

| Side Chain (A) | Compound(s) |
| --- | --- |
| (1) -CH(CH₃)-NH-C(=O)-NH-CH₃ | 4-Methyl-20-(N'-methyluriedo)-5α-4-azapregn-1-en-3-one<br>4-Methyl-20-(N'-methyluriedo)-5α-4-azapregnane-3-one |
| (2) -CH₂-NH-C(=O)-NH-C(CH₃)₃ | 17-(N'-t-butylureidomethyl)-4-methyl 5α-4-azaandrost-1-en-3-one<br>17-(N'-t-butylureidomethyl)-4-methyl 5α-4-azaandrostan-one |
| (3) -CH₂-NH-C(=O)-NH-C₆H₅ | 4-Methyl-17-(N'-phenylureido-methyl)-5α-4-azaandrost-1-en-3-one<br>4-Methyl-17-(N'-phenylureido-methyl)-5α-4-azaandrostan-3-one |
| (4) -CH₂-NH-C(=O)-NH-CH₂-CH₂-CH₃ | 4-Methyl-17-(N'-n-propylureido-methyl)-5α-azaandrost-1-en-3-one<br>4-Methyl-17-(N'-n-propylureido-methyl)-5α-azaandrostan-3-one |
| (5) -CH₂-NH-C(=O)-NH-CH₂-CH₂-CH₃ | 4-Methyl-17-(N'-n-octylureido-methyl)-5α-azaandrost-1-en-3-one<br>4-Methyl-17-(N'-n-octylureido-methyl)-5α-4-azaandrost-an-3-one |
| (6) -C(CH₃)₂-NH-C(=O)-NH-CH₃ | 4-Methyl-17-(N'-methylureido)-5α-4-azaandrost-1-en-3-one<br>4-Methyl-17-(N'-methylureido)-5α-4-azaandrostan-3-one |
| (7) -C(CH₃)₂-NH-C(=O)-NH-C₆H₅ | 4-Methyl-17-(N'-phenylureido)-5α-4-azaandrost-1-en-3-one<br>4-Methyl-17-(N'-phenylureido)-5α-4-azaandrostan-3-one |
| (8) -C(CH₃)₂-NH-C(=O)-NH-C(CH₃)₃ | 17-(N'-t-butylureido)4-methyl-5α-4-azaandrost-1-en-3-one<br>17-(N'-t-butylureido)4-methyl-5α-4-azaandrostan-1-en-3-one |
| (9) -CH₂-NH-C(=O)-NH-CH(CH₃)₂ | 17-(N'-isopropylureidomethyl)4-methyl-5α-4-aza-androst-1-en-3-one<br>17-(N'-isopropylureidomethyl)4-methyl-5α-4-aza-androstan-3-one |
| (10) -CH₂-NH-C(=O)-NH-CH₂-CH₂-CH₃ | 4-Methyl-17β(N'-n-propylureido-methyl)5α-4-azaandrostan-3-one<br>4-Methyl-17β(N'-n-propylureido-methyl)5α-4-azaandrost-1-en-3-one |
| (11) -CH₂-NH-C(=O)-N(CH₂)₇CH₃ | 4-Methyl-17β-(N'-n-octyureido-methyl)5α-4-azaandrost-1-en-3-one<br>4-Methyl-17β-(N'-n-octylureido-methyl)5α-4-azaandrostan-3-one |
| (12) -C(CH₃)₂-NH-C(=O)-NH-C₆H₅ | 4-Methyl-17β-(N'-phenylureido)-5a-4-azaandrostan-3-one<br>4-Methyl-17β-(N'-phenylureido)-5a-4-azaandrost-1-en-3-one |

TABLE 3-continued

| Side Chain (A) | Compound(s) |
|---|---|
| H O H<br>│ ‖ │<br>⊢N—C—N—⟨ | 17β-(N'-Isopropylureidomethyl)-<br>4-methyl-5α-4-azaandrostan-3-one<br>17β-(N'-Isopropylureidomethyl)-4-<br>methyl-5a-4-azaandrostan-3-one |
| (14) structure with iminodibenzyl group<br>⊢N—C(=O)—N | 20-((Iminodibenz-5-yl)carbonyl-<br>aminomethyl)-4-methyl-5a-4-aza-<br>pregan-3-one<br>20-((Iminodibenz-5-yl)carbonyl-<br>aminomethyl)-4-methyl-5a-4-aza-<br>pregn-1-en-3-one |
| (15) structure with iminodibenzyl group<br>⊢N—C(=O)—N | 17β-((Iminodibenz-5-yl)-carbonyl-<br>aminomethyl)-4-methyl-5α-4-aza-<br>androstan-3-one<br>17β-((Iminodibenz-5-yl)-carbonyl-<br>aminomethyl)-4-methyl-5α-4-aza-<br>androstan-3-one |
| (16) H O H O<br>│ ‖ │ ‖          CH₃<br>⊢N—C—N—C—OCH₂—CH⟨<br>                              CH₃ | 17β-(Isobutyloxycarbonylamino-<br>methyl)-4-methyl-5α-4-azaandro-<br>stan-3-one<br>17β-(Isobutyloxycarbonylamino-<br>methyl)-4-methyl-5α-4-azaandrost-<br>1-en-3-one |

The following additional compounds may also be prepared according to the procedures described in the instant specification.

20-(Ethoxycarbonylamino)-4-methyl-5-α-4-azapregnan-3-one,
20-(Benzyloxycarbonylaminomethyl)-5-α-4-azapregnan-3-one,
4-Methyl-17β-(N'-octadecylureidomethyl)-5-α-4-azaandrostan-3-one,
17β-(N'-Benzylureidomethyl)-5-α-4-azaandrostan-3-one,
4-Methyl-17β-(N'-methylureido)-5-'-4-azaandrostan-3-one,
4-Methyl-17β-(Isobutyloxycarbonylamino)-5-α-4-azaandrostan-3-one,
17β-(N'-(2-Ethylphenyl)ureidomethyl)-5-α-4-azaandrostan-3-one,
17β-(N'-Allylureido)-4-methyl-5-α-4-azaandrostan-3-one,
20-(N'-(3-Chlorophenyl)ureido)-5-α-4-azapregnan-3-one,
4-Methyl-20-(N'-phenylureido)-5-α-4-azapregnan-3-one,
20-(N'-p-Tolylureidomethyl)-5-α-4-azapregnan-3-one,
17β-(N'-(2,3,-Dichlorophenyl)ureidomethyl)-4-methyl-5-α-4-azaandrostan-3-one,
17β-(N'-(4-Fluorophenyl)ureido)-5-α-4-azaandrostan-3-one,
20-(N'-(2-Ethoxyphenyl)ureidomethyl)-4-methyl-5-α-4-aza-pregnan-3-one,
17β-(N'-(3-Methoxyphenylureido)-5-α-4-azaandrostan-3-one,
4-Methyl-17β-(N'-(naphth-2-yl)ureidomethyl)-5-α-4-azaandrostan-3-one,
4-Methyl-17β-(N'-thiazol-2-ylureidomethyl)-5-α-4-azaandrostan-3-one,
4-Methyl-20-(N'-thien-2-ylmethylureido)-5-α-4-azapregnan-3-one.

Synthesis of Testosterone 5α Reductase Inhibitors

Scheme XIV illustrates the synthesis of the intermediate oximes and amines used to produce compounds claimed in the instant invention.

SCHEME XIV

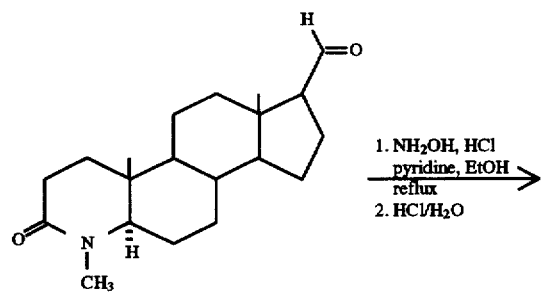

-continued
SCHEME XIV

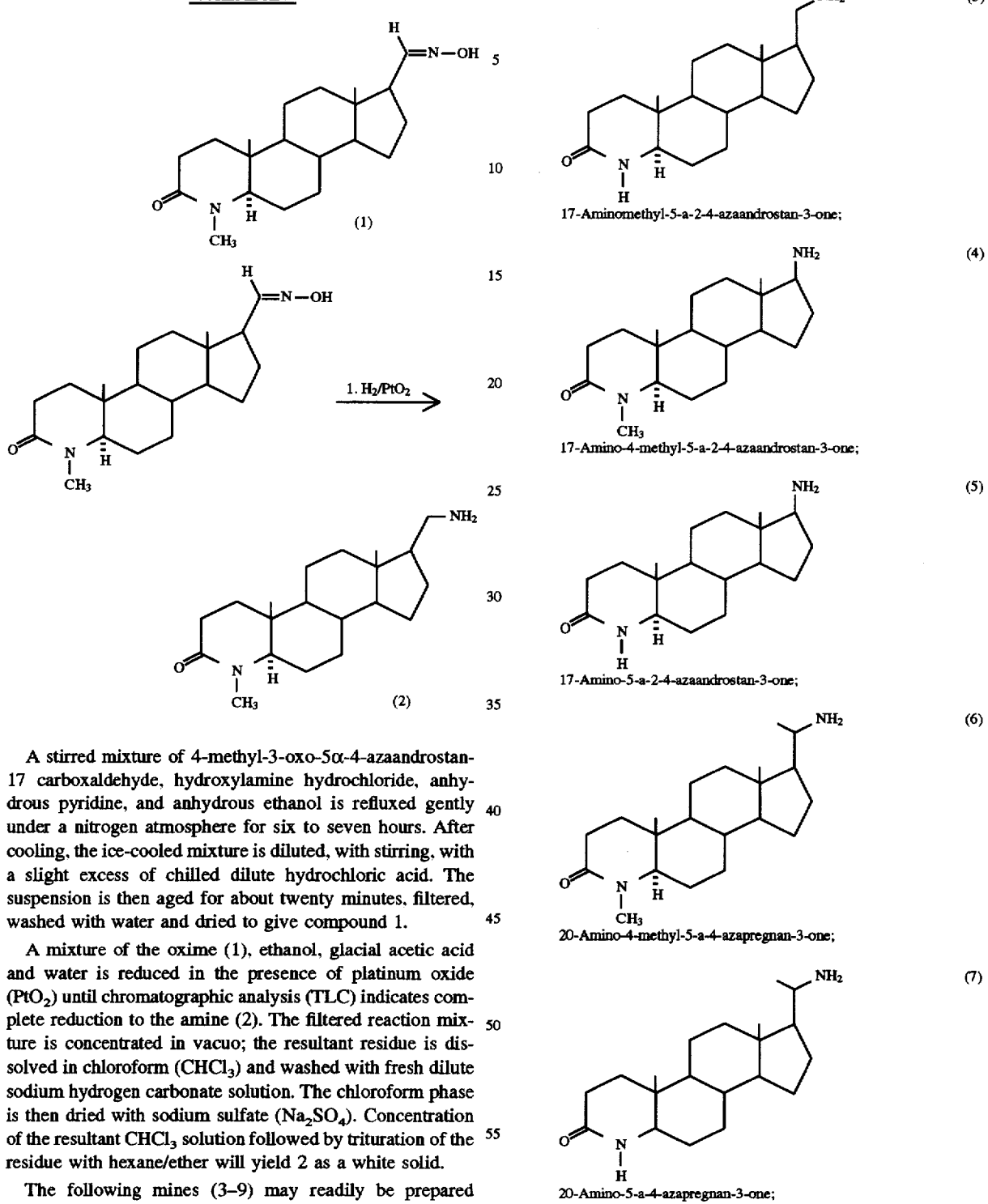

A stirred mixture of 4-methyl-3-oxo-5α-4-azaandrostan-17 carboxaldehyde, hydroxylamine hydrochloride, anhydrous pyridine, and anhydrous ethanol is refluxed gently under a nitrogen atmosphere for six to seven hours. After cooling, the ice-cooled mixture is diluted, with stirring, with a slight excess of chilled dilute hydrochloric acid. The suspension is then aged for about twenty minutes, filtered, washed with water and dried to give compound 1.

A mixture of the oxime (1), ethanol, glacial acetic acid and water is reduced in the presence of platinum oxide (PtO$_2$) until chromatographic analysis (TLC) indicates complete reduction to the amine (2). The filtered reaction mixture is concentrated in vacuo; the resultant residue is dissolved in chloroform (CHCl$_3$) and washed with fresh dilute sodium hydrogen carbonate solution. The chloroform phase is then dried with sodium sulfate (Na$_2$SO$_4$). Concentration of the resultant CHCl$_3$ solution followed by trituration of the residue with hexane/ether will yield 2 as a white solid.

The following mines (3–9) may readily be prepared according to the above process to yield the indicated compounds:

-continued

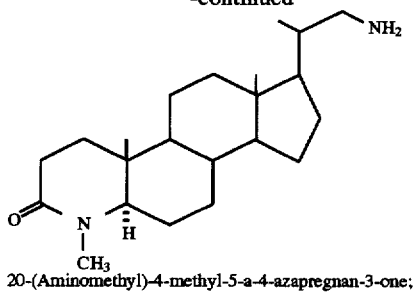

20-(Aminomethyl)-4-methyl-5-a-4-azapregnan-3-one; (8)

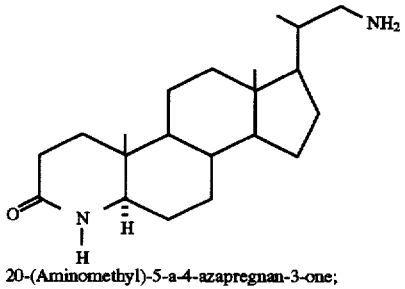

20-(Aminomethyl)-5-a-4-azapregnan-3-one; (9)

As Scheme XIV indicates, the oximes useful as intermediates may readily be prepared by reacting a 4-azasteroidal aldehyde or ketone with hydroxylamine hydrochloride to form the corresponding oxime. The resultant oximes are subsequently reduced with hydrogen ($H_2$) and platinum oxide ($PtO_2$) or other suitable reducing agent to yield the respective amine. Product ureas or thioureas may be further alkylated with, for example, alkyl halides to give the corresponding $R^2$ alkylated compounds.

Scheme XV illustrates the synthesis of the compound 17-(N'-t-butylureidomethyl)-4-methyl-5α-4-azaandrostan-3-one and is representative of a basic synthesis of compounds claimed in the instant invention in which an amine is reacted with a substituted isocyanate.

SCHEME XV

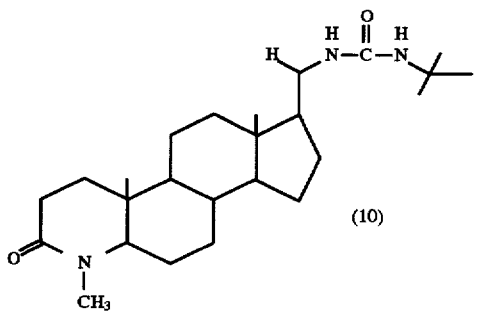

To a stirred solution of 2 in dry benzene at room temperature (25° C.) is added t-butylisocyanate. After stirring for 12-14 hours, the benzene is removed and purified by flash chromatography (silica gel, EtOAc) to give 10 as a white solid. As Scheme XV illustrates, 4-azasteroidal primary or secondary amines described in the instant invention are reacted with the desired substituted isocyanate, such as t-butyl isocyanate, to yield the target ureido derivative.

Representative substituted isocyanates of the formula:

$$R^3-N=C=O$$

wherein $R^3$ equals

H,
$C_{1-20}$ alkyl,
aryl,
heteroaryl,
aryl$C_{1-20}$alkyl,
$C_{3-20}$ cycloalkyl,
$C_{3-20}$ cycloalkyl$C_{1-20}$alkyl,
heteroaryl$C_{1-20}$alkyl,
$C_{2-20}$ alkenyl$C_{1-20}$alkyl,
halo$C_{1-20}$alkyl,
halohydroxyl$C_{1-20}$alkyl
$C_{1-20}$ alkyloxy$C_{1-20}$alkyl,
$C_{1-20}$ alkylcarbonyl$C_{1-20}$alkyl,
$C_{1-20}$alkyloxycarbonyl$C_{1-20}$alkyl,
aryl$C_{1-20}$alkyloxycarbonyl$C_{1-20}$alkyl,
heteroaryl$C_{1-20}$alkyloxycarbonyl$C_{1-20}$alkyl,
hydroxy$C_{1-20}$alkyl,
aryl$C_{1-20}$alkyloxy$C_{1-20}$alkyl,
heteroaryl$C_{1-20}$alkyloxy$C_{1-20}$alkyl,
arylcarbonylaryl$C_{1-20}$alkyl,
diaryl$C_{1-20}$alkyl,
triaryl$C_{1-20}$alkyl,
$C_{2-20}$ alkenyl,
$C_{2-20}$ alkenyl$C_{1-20}$alkyl,
$C_{2-20}$ alkynyl$C_{1-20}$alkyl,
aryl$C_{2-20}$alkynyl$C_{1-20}$alkyl,
heteroaryl$C_{2-20}$alkynyl$C_{1-20}$alkyl,
$C_{1-20}$ alkylthio$C_{1-20}$alkyl,
$C_{1-20}$ alkylsulfonyl$C_{1-20}$alkyl, or
$C_{1-20}$ alkylsulfinyl$C_{1-20}$alkyl;

The primary or secondary amines disclosed in the instant invention may also be reacted with thioisocyantes of the formula $$R^3-N=C=S$$

to yield compounds claimed in the instant invention. In addition, as Scheme XVI shows, the described primary or secondary amines disclosed in the invention (such as 2) may be reacted with activated esters or thioesters to yield compounds claimed in the instant invention. $R^3$ is defined as above.

Substituted isocyanates or thioisocynates may readily be prepared by known synthetic methods. For example, phosgene or thiophosgene may be reacted with a suitable primary amine to give a chloroformamide or chloro sulfamide which loses HCl to form the respective substituted isocyanate or thioisocyanate. For reviews of isocyanate and thioisocyanate preparation, see Patai, "The Chemistry of Cyanates and their thio Derivatives," pt 2, Wiley, New York, pp 619–818 and 1003–1221 (1977). In addition, the isocyanates, thioisocyanates, esters or thioesters used to prepare the claimed compounds are commercially available.

SCHEME XVI

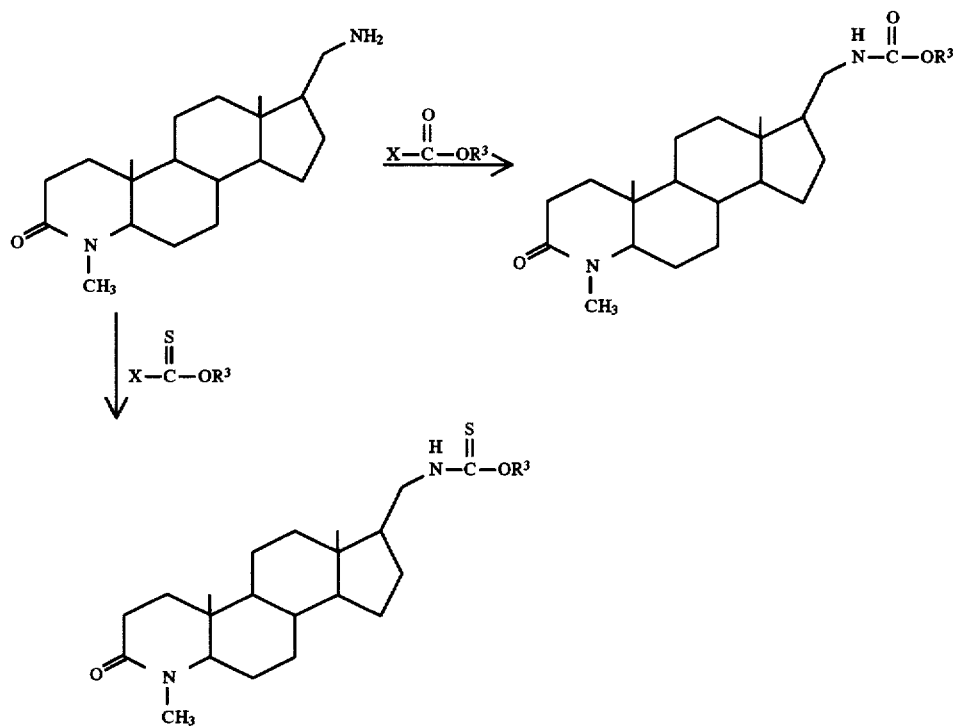

Ureas, thioureas, carbamates, and thiocarbamates claimed in the present invention may readily be obtained by following the basic procedure(s) described in Schemes XV and XVI. To further illustrate, compound 2 may be replaced by the amine (4) and reacted with t-butylisocyanate to yield 17-(N'-t-butylureido)-4-methyl-5α-4-azaandrostan-3-one (11) (Scheme XVII).

SCHEME XVII

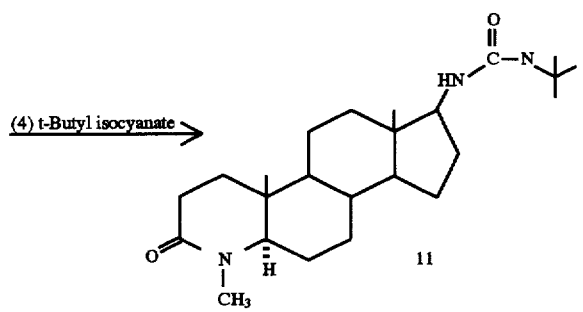

If compound 6 is reacted with methyl isocyante under the conditions described for Scheme XV, 4-methyl-20-(N'-methylureido)-5α-4-azapregnan-3-one is obtained (12) (Scheme XVIII)

SCHEME XVIII

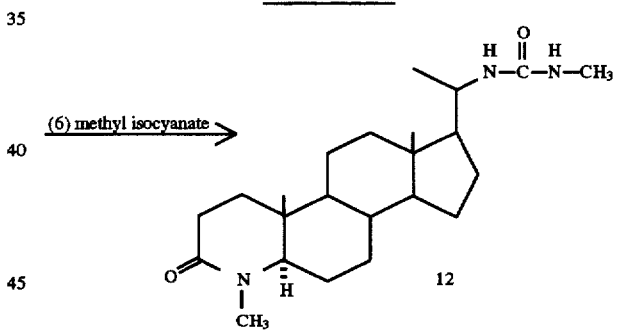

If compound 2 is reacted with phenyl isocyanate under the conditions described in Scheme 2, 4-methyl-17-(N'-phenyluriedomethyl)-5α-4-azaandrostan-3-one is made (13) (Scheme XIX).

SCHEME XIX

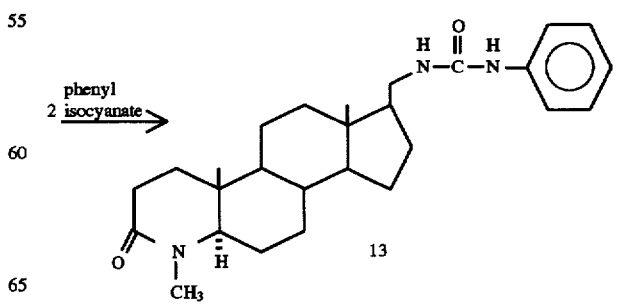

In addition, dehydrogenation of the 1,2 position may readily be accomplished by known synthetic methodology to produce the claimed 1-en derivatives. See U.S. Pat. No. 5,061,802 and Dolling et al., J. Am. Chem. Soc., 110, 3318–19 (1988).

Schemes XX, XXI and XXII further illustrate how compounds claimed in the instant invention may be prepared. In Scheme XX, the starting 4-azasteroid aldehyde or ketone (XIV), obtained by known synthetic methods, is reacted to form the oxime (XV); reduced to the amine (XVI) and reacted with a substituted isocyanate, substituted thioisocyante, activated ester or thioester to form (XVII).

methods, to produce the oxime (XIX) which is reduced to the amine (XX) and reacted with a substituted isocyanate, substituted thioisocyante, activated ester or thioester to form (XXI).

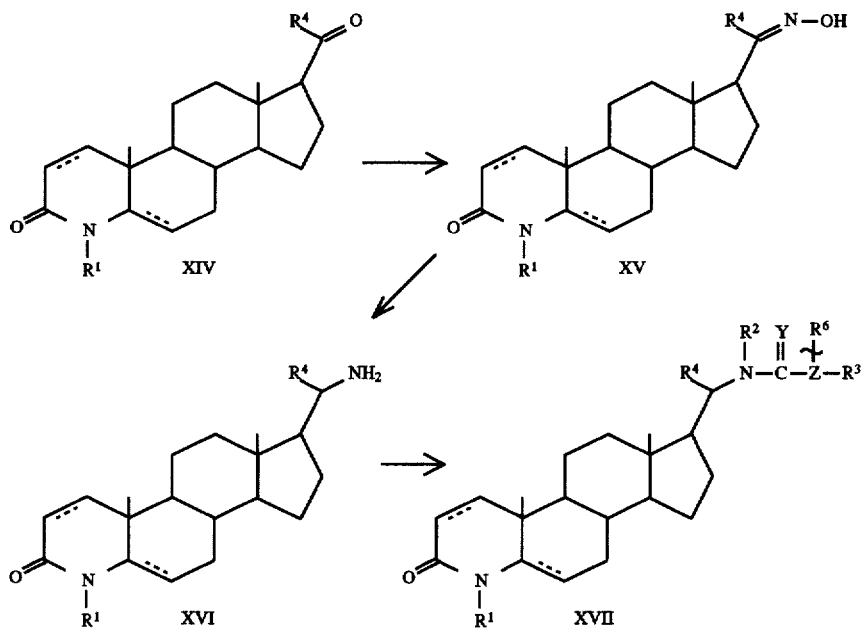

In Scheme XXI, the identical procedure is followed using a generic 4-azasteroid (XVIII), prepared by known synthetic

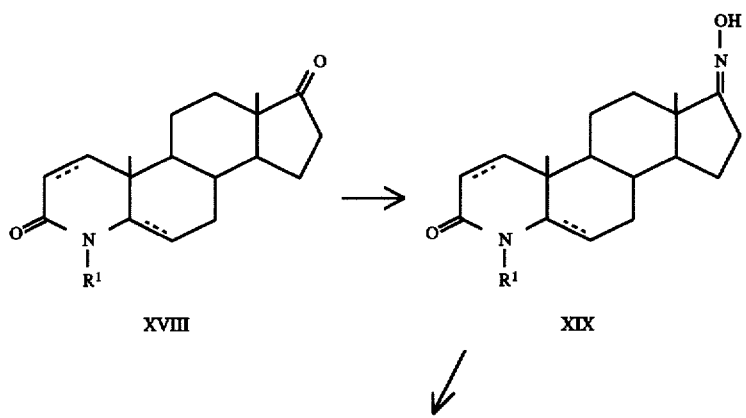

-continued
SCHEME XXI

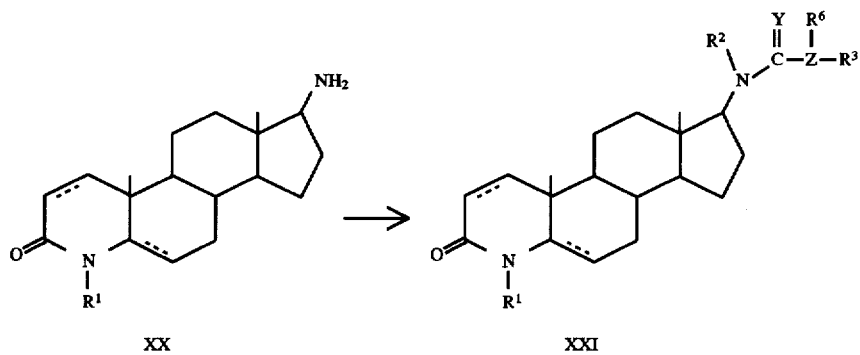

In Scheme XXII, the generic 4-azasteroid (XXII), also obtained from well known synthetic methodology, is reacted to form the oxime (XXIII), which is further reduced to the amine (XXIV), and reacted with a substituted isocyante, substituted thioisocyante, activated ester or thioester to form (XXV).

SCHEME XXII

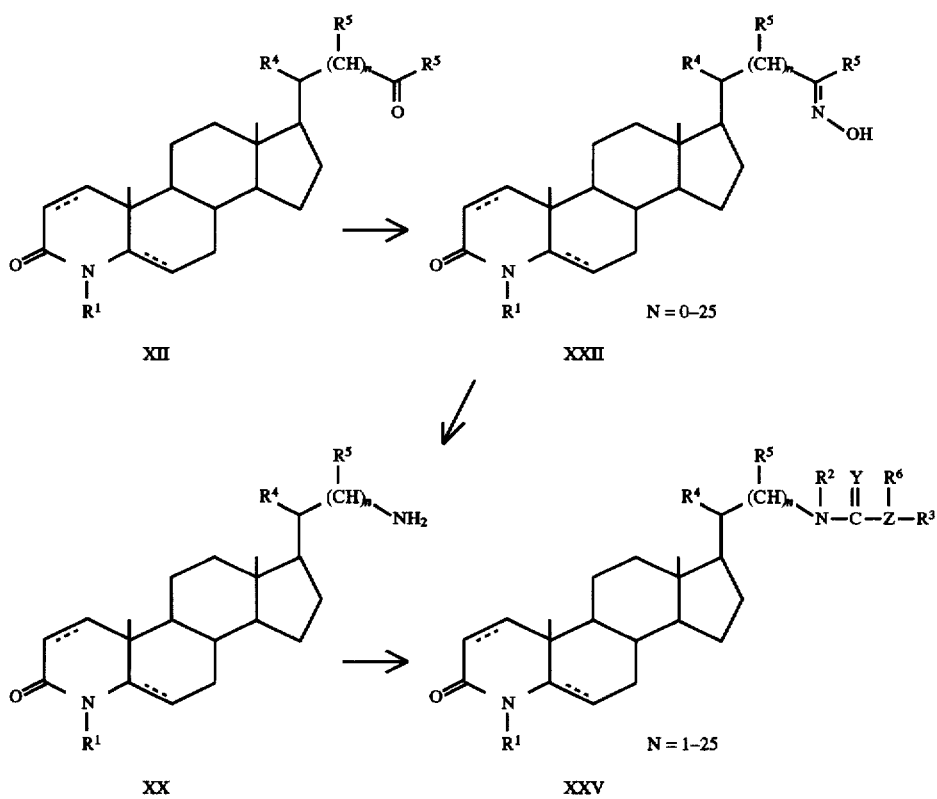

The starting 4-azasteroidal ketones used in the present invention may be prepared according to the basic procedures described in Scheme XXIII via well known synthetic methodology.

SCHEME XXIII

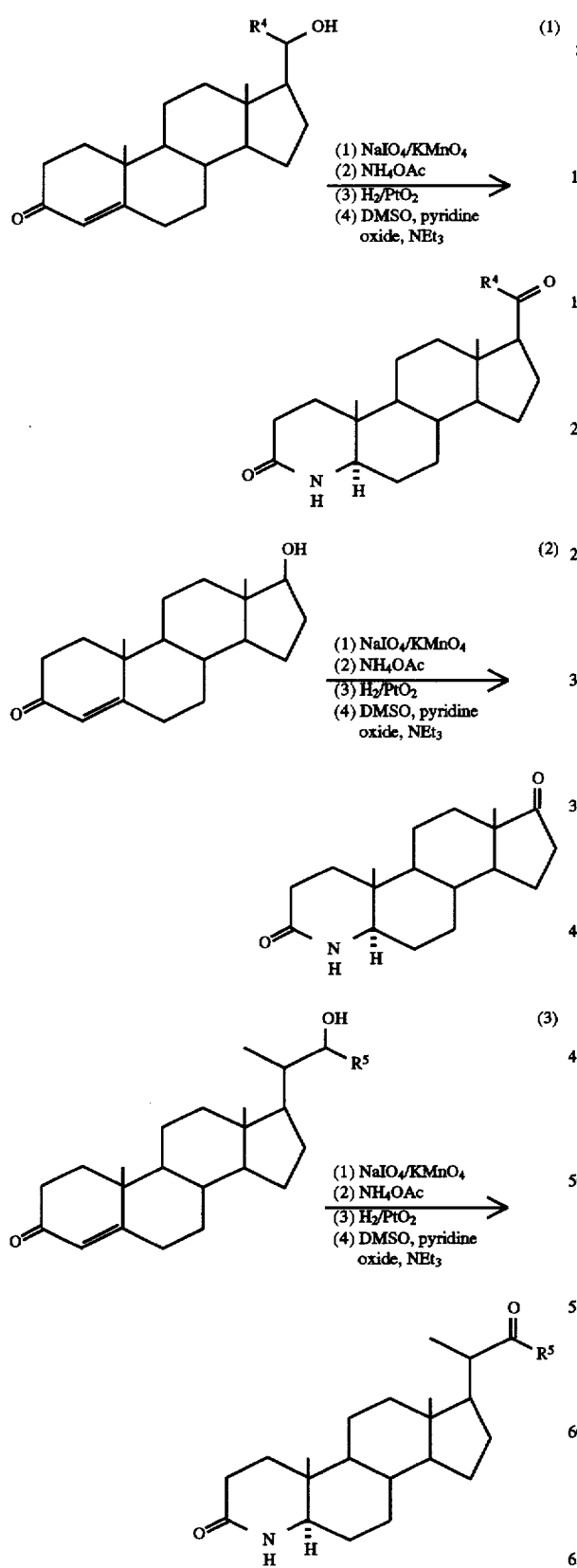

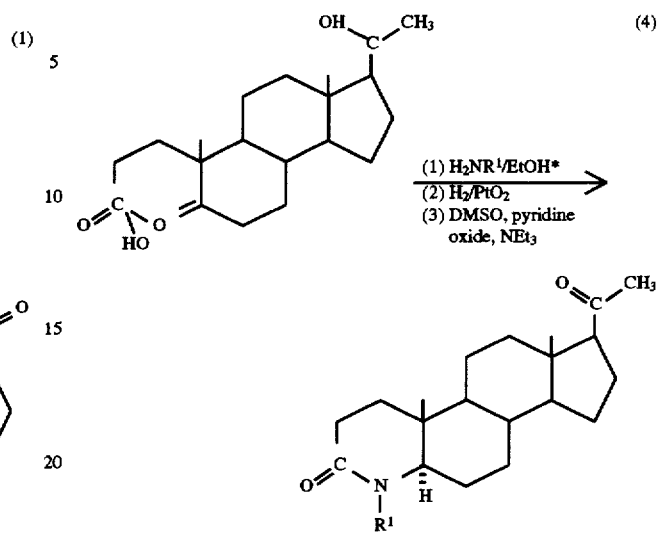

*U.S. Pat. No. 4,377,884

The following examples further describe the synthesis of compounds claimed in the instant invention.

Synthesis of Starting 4-Azasteroid Oximes:

EXAMPLE 38

(38) 4-Methyl-3-oxo-5α-4-azaandrostan-17-carboxaldehyde oxime

A stirred mixture of 4-methyl-3-oxo-5α-4-azaandrostan-17-carboxaldehyde (0.952 g, 3.0 mM), hydroxylamine hydrochloride (1.10 g, 15.8 mM), anhydrous pyridine (6 mL) and anhydrous ethanol (12 mL) was refluxed gently under a nitrogen atmosphere for 6.3 hours. After cooling, the ice-cooled mixture was diluted, with stirring, with a slight excess of chilled dilute hydrochloric acid (ca. 0.3N), the suspension aged for ca. 20 minutes, filtered, washed with water and dried to give (38) 0.855 g. MS M⁺ calcd for $C_{20}H_{32}N_2O_2$ 332.48, observed m/e 332.

Synthesis of Reactant 4-Azasteroid Amines:

EXAMPLES 39–46

(39) 17-Aminomethyl-4-methyl-5α-4-azaandrostan-3-one

A mixture of (38) (0.67 g, 2.0 mM), ethanol (100 mL), glacial acetic acid (8 mL) and water (4 mL) was reduced in a hydrogen atmosphere (40 p.s.i.) at room temperature in the presence of $PtO_2$ until TLC analysis indicated complete reduction. The filtered reaction mixture was concentrated in vacuo, the residue taken up in chloroform, and the chloroform solution washed with fresh dilute sodium hydrogen carbonate solution and dried ($Na_2SO_4$). Concentration of the filtered chloroform solution followed by trituration of the residue obtained with hexane containing a small amount of ether yielded (39) as an off-white solid.

MS MH⁺ calcd for $C_{20}H_{34}N_2O$ 318.49, observed m/e 319.

The following amines are representative of those obtained from the corresponding carbonyl compounds utilizing the above procedures:

(40) 17-Aminomethyl-5α-4-azaandrostan-3-one,
(41) 17-Amino-4-methyl-5α-4-azaandrostane-3-one,
(42) 17-Amino-5α-4-azaandrostan-3-one,
(43) 20-Amino-4-methyl-5α-4-azapregnan-3-one,
(44) 20-Amino-5α-4-azapregnan-3-one,

(45) 20-(Aminomethyl)-4-methyl-5α-4-azapregnan-3-one.
(46) 20-(Aminomethyl)-5α-4-azapregnan-3-one.
Synthesis of Ureido 4-Azasteroids:

EXAMPLES 47–50

(47) 17-(N'-t-Butylureidomethyl)-4-methyl-5α-4-aza-androstan-3-one

To a stirred solution of (39) (0.064 g, 0.2 mM) in dry benzene (8 mL) at room temperature was added t-butyl isocyanate (0.035 mL. 0.3 mM) dropwise over ca. 0.5 min. After stirring overnight the benzene was removed in vacuo and the residue flash chromatographed (silica gel, ethyl acetate as eluant) to give (47) as a white solid.

MS M$^+$ calcd for C$_{25}$H$_{43}$N$_3$O$_2$ 417.64, observed m/e 417.
(48) 17-(N'-t-Butylureido)-4-methyl-5α-4-azaandro-stan-3-one When (39) in the above example was replaced by (41), (48) was obtained as a white solid.

MS M$^+$ calcd for C$_{24}$H$_{41}$N$_3$O$_2$ 403.61, observed m/e 405.
(49) 4-Methyl-20-(N'-methylureido)-5α-4-azapregnan-3-one When (43) was reacted with methyl isocyanate under the conditions of Example 47, (49) was obtained as a white waxy solid.

MS M$^+$ calcd for C$_{23}$H$_{39}$N$_3$O$_2$ 389.58, observed m/e 389.
(50) 4-Methyl-17-(N'-phenyluriedomethyl)-5α-4-azaandrostan-3-one When (39) was reacted with phenyl isocyanate under the conditions of Example 47, (50) was obtained as a white solid.

MS MH$^+$ calcd for C$_{27}$H$_{39}$N$_3$O$_2$ 437.40, observed m/e 438.

Examples 51–58 prepared according to the basic procedures described above further exemplify the claimed invention.

(51) 4-Methyl-17β-(N'-n-propylureidomethyl)-5α-4-azaandrostan-3-one.

MS MH$^+$ calc. for C$_{24}$H$_{41}$N$_3$O$_2$ 403.40, observed m/e 404.

(52) 4-Methyl-17β-(N'-n-octylureidomethyl)-5α-4-azaandrostan-3-one.

MS MH$^+$ calc. for C$_{29}$H$_{51}$N$_3$O$_2$ 473.49, observed m/e 474.

(53) 4-Methyl-17β-(N'-phenylureido)-5α-4-azaandro-stan-3-one.

MS MH$^+$ calc. for C$_{26}$H$_{37}$N$_3$O$_2$ 423.52, observed m/e 424.

(54) 17β-(N'-Isopropylureidomethyl)-4-methyl-5α-4-azaandrostan-3-one.

MS MH$^+$ calcd for C$_{24}$H$_{41}$N$_3$O$_2$ 403.61 observed m/e 404.

(55) 20-(N'-t-Butylureidomethyl)-4-methyl-5α-4-azapregnan-3-one.

MS MH$^+$ calcd for C$_{27}$H$_{47}$N$_3$O$_2$ 445.35, observed m/3 446.

(56) 20-((Iminodibenz-5-yl)carbonylaminomethyl)-4-methyl-5α-4-azapregnan-3-one.

MS MH$_2$$^{++}$ calcd. for C$_{37}$H$_{49}$N$_3$O$_2$ 567.82, observed m/e 569.

(57) 17β-((Iminodibenz-5-yl)carbonylaminomethyl)-4-methyl-5α-4-azaandrostan-3-one.

MS MH$_2$$^{++}$ calcd. for C$_{35}$H$_{45}$N$_3$O$_2$ 539.74, observed m/e 541.

(58) 17β-((Isobutyloxycarbonylaminomethyl)-4-methyl-5α-4-azaandrostan-3-one.

MS MH$^+$ calcd. for C$_{25}$H$_{42}$N$_2$O$_3$ 418.62, observed m/e 419.

TABLE 4

| | NMR DATA (PPM) | |
|---|---|---|
| Example | Angular Methyls | Miscellaneous |
| 47 | 0.66, 0.86 | 1.33 (—NHCONH—C(CH$_3$)$_3$) |
| 48 | 0.67, 0.88 | 1.33 (—NHCONH—C(CH$_3$)$_3$) |
| 49 | 0.73, 0.88 | 2.92 (-4-NCH$_3$) |
| 50 | 0.64, 0.86 | 2.92 (-4-NCH$_3$) |
| 51 | 0.64, 0.88 | 2.90 (-4-NCH$_3$) |
| 52 | 0.65, 0.88 | 2.92 (-4-NCH$_3$) |
| 53 | 0.63, 0.86 | 2.93 (-4-NCH$_3$) |
| 54 | 0.66, 0.88 | 1.12 (—NH—CH(CH$_3$)$_2$ |
| 55 | 0.64, 0.85 | 1.29 (—NHCONH—C(CH$_3$)$_3$) |
| 56 | 0.62, 0.89 | 0.82 —CH(CH$_3$)CH$_2$NHCON— 0.86 |
| 57 | 0.61, 0.88 | 2.92 (-4-NCH$_3$) |
| 58 | 0.66, 0.88 | 2.92 (-4-NCH$_3$) |

The above examples are non-limiting and suitable acylating agents, isocyanates, or thioisocyanates may readily be substituted according to the methods described in the present invention and reacted with a described azasteroidal amine to form the claimed ureas, thioureas, carbamates, and thiocarbamates. The following definitions further clarify the present invention.

PtO$_2$ is platinum oxide
TLC is thin layer chromatography
Na$_2$SO$_4$ is sodium sulfate
DMAP is 4-(dimethylamino)pyridine
DCC is N,N'-dicyclohexylcarbodiimide

EXAMPLES FOR THE CASE WHEN SUBSTITUENT "A" OF GENERAL FORMULA "I" IS AS DEFINED IN GROUP "VI(A)"

For use in the process, further provided are novel 17β-substituted olefinic and saturated 4-aza-5α-androstan-3-one and related compounds of the general structural formula XXI:

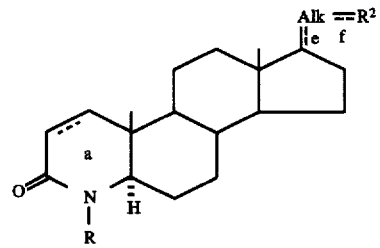

wherein:

Alk is C$_1$–C$_4$ straight or branched chain alkyl or alkenyl; dashed lines a, e and f each can independently represent a double bond when present, with the proviso that double bonds formed by e and f are not both present concurrently;

R is selected from hydrogen, methyl or ethyl;
R$^2$ is
(a) C$_6$–C$_{10}$ aryl, cyano, a 5–6 membered heteroaryl radical, which can contain 1–4 nitrogen atom, one oxygen or sulfur atoms or combinations thereof with 1–2 nitrogen atoms, providing that where R$^2$ is cyano, double bonds e and f are not present;
(b) COR$_1$, where R$_1$ is C$_6$–C$_{10}$ aryl, substituted C$_6$–C$_{10}$ aryl, and heteroaryl;
(c) CONHR$_2$, where R$_2$ is substituted phenyl, heteroaryl, substituted heteroaryl, or C$_7$ to C$_{12}$ cycloalkyl;

(d) $CO_2R_3$, where $R_3$ is $C_1$–$C_{18}$ linear or branded alkyl, $C_6$–$C_{10}$ aryl, substituted $C_6$–$C_{10}$ aryl, or $C_7$–$C_{12}$ cycloalkyl; providing that in (b), (c) or (d), Alk is only alkenyl;

wherein the above aryl or heteroaryl radicals can also be fused with a benzo or another heteroraryl ring and can further be substituted with one or more substituents; and pharmaceutically acceptable salts and esters thereof.

Further provided for are preferred compounds of the general structural formula XXII:

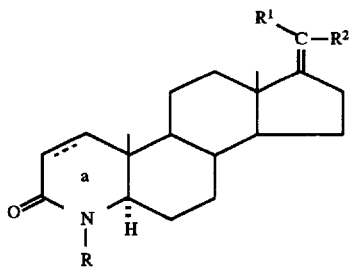

XXII wherein the dashed line a represents a double bond when present,

R and $R^1$ are selected from hydrogen, methyl and ethyl; and $R^2$ is as defined above, including both (E) and (Z) forms, and mixtures thereof.

Also provided for are compounds of the general structural formula XXIII:

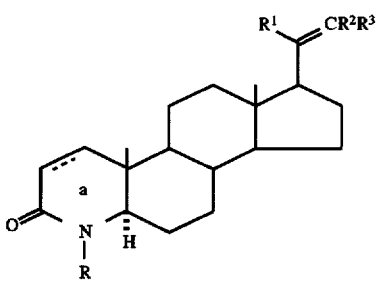

XXIII wherein the dashed line a can represent a double bond when present,

R, $R^1$ and $R^3$ are independently selected from hydrogen, methyl and ethyl, with the proviso that at least one of $R^1$ and $R^3$ is hydrogen, $R^2$ is is $C_6$–$C_{10}$ aryl or heteroaryl as defined above, and $R^2$ and $R^3$ can be in a E or Z bond configuration, and mixtures thereof.

Additionally, there are provided compounds of the general structural formula XXIV:

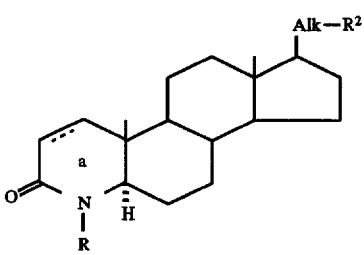

XXIV wherein:

Alk is $C_1$–$C_4$ straight or branched chain alkyl; dashed line a can represent a double bond when present;

R is selected from hydrogen, methyl or ethyl; and
$R^2$ is as defined above.

Also specifically provided for are compounds of general structural formula XXV:

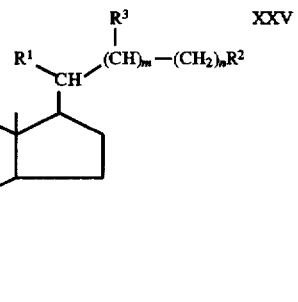

XXV wherein:

the dashed line a can represent a double bond when present, and m is 0–1, n is 0–3; and R, $R^1$ and $R^3$ are independently selected from hydrogen, methyl and ethyl, with the proviso that at least one of $R^1$ and $R^3$ is hydrogen, $R^2$ is is $C_6$–$C_{10}$ aryl, cyano, or heteroaryl as defined above.

Also disclosed are processes for their preparation, pharmaceutical formulations comprising the novel compounds as active ingredients and methods of inhibiting 5α-reductases 1 and/or 2 in diseases which occur under hyperandrogenic conditions, e.g., benign prostatic hyperplasia.

The structures XXI through XXIV above encompass the starting 5α-reductase inhibitor compounds of this invention, where A is group VIA in general structural formula I.

Where the double bond "e" is present, the compounds are delta-17 olefins and where the double bond "f" is present, the compounds are delta-20 olefins. Note that dashed lines "e" and "f" both cannot be double bonds concurrently.

Dashed line "a" can independently be a double bond and when present, the compound is a delta-1-ene.

$R^2$ is a $C_6$–$C_{10}$ aryl including phenyl, benzyl, 1- and 2-phenethyl and naphthyl, and also cyano.

Preferred is where $R^2$ aryl is phenyl or cyano.

$R^2$ can also be 5–6 membered heteroaryl radical being fully unsaturated containing 1–4 nitrogen atoms, e.g. pyridyl, pyrryl, imidazolyl, tetrazolyl, pyrazinyl, pyrimidinyl, pyrazolyl, or triazolyl; containing 1–2 oxygen or sulfur atoms, e.g. thienyl, furanyl; or in combination with 1–2 nitrogen atoms, e.g. isothiazolyl, thiazolyl, isoxazolyl, oxazolyl or thiadiazolyl; or fused with a benzo ring, e.g. quinolyl, isoquinolyl, benzothienyl, isobenzofuryl, indolyl, carbazolyl; or fused with another heteroaryl ring, e.g. purinyl, and the like.

Preferred examples are 2-, 3-, and 4-pyridyl, 2-thienyl; 2-pyrazinyl, 2-, 4-, and 5-thiazolyl.

The $R^2$ aryl or heteroaryl ring can be unsubstituted or substituted with one or more of the following substituents providing the substitution leads to a chemically inert, but biologically active 5α reductase inhibitor.

The $R^2$ ring substituents include:

$C_1$–$C_8$ straight or branched alkyl; e.g. methyl, ethyl, propyl, isopropyl, n-butyl, sec-butyl, isobutyl, t-butyl, n-pentyl, n-hexyl, iso-hexyl, n-butyl, n-octyl, iso-octyl, t-octyl, and the like; $C_2$–$C_8$ straight or branched alkenyl, e.g. ethenyl, 1-propenyl, 2-propenyl, 1-butenyl, 2-butenyl, 3-butenyl, 1-pentenyl, 1-hexenyl, 1-heptenyl, 1-octenyl, 2-octenyl, and the like;

$C_3$–$C_8$ cycloalkyl e.g., cyclopropyl, cyclobutyl, cyclopentyl, cyclohexyl, 1-methylcyclobutyl, cyclopentyl, cyclohexyl, 1-methylcyclohexyl, 2-methylcyclohexyl, 2-ethylcyclohexyl, and the like;

$C_2$–$C_8$ alkynyl e.g., 1-ethynyl; 1-propynyl, 2-propynyl, 2-butynyl, 2-pentynyl, 1-hexynyl, 1-heptynyl, 1-octynyl;

$CONR^4R^5$ where $R^4$ and $R^5$ independently are H, $C_1$–$C_8$ alkyl, as defined above, $C_3$–$C_8$ cycloalkyl as defined above, $C_1$–$C_4$ perhaloalkyl e.g., trifluoromethyl, perfluoromethyl, trichloromethyl, preferably perfluoroalkyl; phenyl, or substituted phenyl, as described below;

$COR^4$, where $R^4$ is defined above, including acetyl, isobutylcarbonyl, benzoyl and the like;

$S(O)_nR^4$, where n is 0–2 and $R^4$ is defined above, including methylsulfinyl, methylsulfonyl, phenylsulfonyl, 4-chlorophenylsulfinyl and the like;

$OCOR^4$, where $R^4$ is defined above, including acetoxy, propionyloxy, benzoyloxy, 4-chlorobenzoyloxy and the like.

$SO_2NR^4R^5$ where $R^4$ and $R^5$ are described above, including sulfonamido, N-methylsulfonamido, N-phenylsulfonamido, N,N-dimethylsulfonamido and the like;

$NR^4(CO)R^5$, wherein $R^4$ and $R^5$ are defined above, including; acetylamino, benzoylamino, N-methylbenzoylamino and the like;

$NR^4(CO)NHR^5$, wherein $R^4$ and $R^5$ are described above, including; ureido, N-methylureido, N-methyl-$N^1$-phenylureido and the like;

$NHSO_2R^4$, $R^4$ being defined above, including methylsulfonylamino, phenylsulfonylamino and the like;

$OR^4$, where $R^4$ is defined above, including methoxy, phenoxy, 4-chlorophenoxy and the like, $NR^4R^5$, wherein $R^4$ and $R^5$ are described above, including amino, methylamino, dimethylamino, anilino and the like;

Cyano, nitro, halo, including: fluoro, chloro, bromo and iodo;

Perhalo $C_1$–$C_4$ alkyl, including: trifluoromethyl, perfluoroethyl, trichloromethyl and the like.

$CO_2R^4$, wherein $R^4$ is defined above, including $CO_2CH_3$, $CO_2Ph$, $CO_2$-(1-adamantyl) and the like; phenyl and substituted phenyl of the formula:

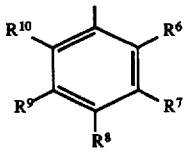

wherein the radicals $R^6$–$R^{10}$ each can represent one or more of the substituents defined above, including; hydrogen, 4-chlorophenyl, 4-fluorophenyl, 4-methoxyphenyl, 4-phenoxy and the like.

Representative compounds of the present invention include the following:

(17E)-17-[phenyl)methylene]-4-methyl-4-aza-5α-androstan-3-one,
(17E)-17-[(4-chlorophenyl)methylene]-4-methyl-4-aza-5α-androstan-3-one,
(17E)-17-[(3-chlorophenyl)methylene]-4-methyl-4-aza-5α-androstan-3-one,
(17E)-17-[(2-chlorophenyl)methylene]-4-methyl-4-aza-5α-androstan-3-one,
(17E)-17-[(4-ethoxycarbonylphenyl)methylene]-4-methyl-4-aza-5α-androstan-one,
(17E)-17-[(4-carboxyphenyl)methylene]-4-methyl-4-aza-5α-androstan-3-one,
(17E)-17-[4-[[(1,1-dimethylethyl)amino)carbonyl]phenyl]methylene]-4-methyl-4-aza-5α-androstan-3-one,
(17E)-17-[(3,4,5-trimethoxyphenyl)methylene]-4-aza-5α-androstan-3-one,
(17E)-17-[(2-methoxyphenyl)methylene]-4-methyl-4-aza-5α-androstan-3-one,
(17E)-17-[(4-methylsulfonylphenyl)methylene]-4-methyl-4-aza-5α-androstan-3-one,
(17E)-17-[(4-biphenyl)methylene]-4-aza-5α-androstan-3-one,
(17E)-17-[(4-nitrophenyl)methylene]-4-methyl-4-aza-5α-androstan-3-one,
(17E)-17-[(4-aminophenyl)methylene]-4-aza-5α-androstan-3-one,
(17E)-17-[(4-acetylaminophenyl)methylene]-4-methyl-4-aza-5α-androstan-3-one,
(17E)-17-(4-pivaloylaminophenyl)methylene)-4-methyl-4-aza-5α-androstan-3-one,
(17E)-17-[(4-phenoxyphenyl)methylene]-4-aza-5α-androstan-3-one,
(17E)-17-[(2-imidazolyl)methylene]-4-methyl-4-aza-5α-androst-1-en-3-one,
(17E)-17-[(2-thiazolyl)methylene]-4-aza-5α-androst-1-en-3-one,
(17E)-17-[(2-pyrazinyl)methylene]-4-methyl-4-aza-5α-androstan-3-one,
(17E)-20-phenyl-4-methyl-4-aza-5α-pregn-17-en-3-one,
(17E)-20-[(4-chloro)phenyl]-4-aza-5α-pregn-17-en-3-one,
(20E)-4-methyl-21-[(4-methoxy)phenyl]-4-aza-5α-pregn-20-en-3-one,
(20E)-4-methyl-21-phenyl-4-aza-5α-pregn-20-en-3-one,
(20E)-4-methyl-21-[(4-methyl)phenyl]-4-aza-5α-pregn-20-en-3-one,
(20E)-4-methyl-21-[(4-chloro)phenyl]-4-aza-5α-pregn-20-en-3-one,
(20E)-4-methyl-21-(4-pyridyl)-4-aza-5α-pregn-20-en-3-one,
(20E)-4-methyl-21-[(3-chloro)phenyl]-4-aza-5α-pregn-20-en-3-one,
(20E)-4-methyl-21-[(2-chloro)phenyl]-4-aza-5α-pregn-20-en-3-one,
(20E)-4-methyl-21-(2-pyridyl)-4-aza-5α-pregn-20-en-3-one,
(20E)-4-methyl-21-(2-thienyl)-4-aza-5α-pregn-20-en-3-one,
(20E)-21-[(4-methoxy)phenyl]-4-aza-5α-pregn-20-en-3-one,
(20E)-4-methyl-21-(3-thienyl)-4-aza-5α-pregn-20-en-3-one,
(20E)-4-methyl-21-(2-furanyl)-4-aza-5α-pregn-20-en-3-one,
(20E)-4-methyl-21-[(2-fluoro)phenyl]-4-aza-5α-pregn-20-en-3-one,
(20E)-21-(4-pyridyl)-4-aza-5α-pregn-1,20-dien-3-one,
(20E)-21-(4-pyridyl)-4-aza-5α-pregn-20-en-3-one,
(20E)-21-[(4-methoxy)phenyl]-4-aza-5α-pregn-1,20-dien-3-one,
(20E)-21-(2-furanyl)-4-aza-5α-pregn-1,20-dien-3-one,
(20E)-21-(2-pyridyl)-4-aza-5α-pregn-1,20-dien-3-one,
(20E)-21-(3-pyridyl)-4-aza-5α-pregn-1,20-dien-3-one
(20E)-21-[(4-ethoxycarbonyl)phenyl]-4-aza-5α-pregn-1,20-dien-3-one, (20E)-21-4-[N-phenyl]benzamido-4-aza-5α-pregn-1,20-dien-3-one,
(20E)-21-(2-pyridyl)-4-aza-5α-pregn-20-en-3-one,
(20E)-21-(3-pyridyl)-4-aza-5α-pregn-20-en-3-one,
(20E)-21-(2-thienyl)-4-aza-5α-pregn-20-en-3-one,
(20E)-4,20-dimethyl-21-phenyl-4-aza-5α-pregn-20-en-3-one,
(20E)-4,20-dimethyl-21-(4-chlorophenyl)-4-aza-5α-pregn-20-en-3-one,
(20E)-4,20-dimethyl-21-(2-thienyl)-4-aza-5α-pregn-20-en-3-one,
(20E)-4,20-dimethyl-21-(2-pyridyl)-4-aza-5α-pregn-20-en-3-one,
(20E)-20-methyl-21-(4-pyridyl)-4-aza-5α-pregna-1,20-dien-3-one,
(20E)-4,20-dimethyl-21-(4-pyridyl)-4pregn-5α-pregn-20-en-3-one,
(20E)-20-methyl-21-(2-furyl)-4-aza-5α-pregna-1,20-dien-3-one,
(20E)-20-methyl-21-(2-pyridyl)-4-aza-5α-pregna-1,20-dien-3-one,
(20E)-20-ethyl-21-phenyl-4-aza-5α-pregna-1,20-dien-3-one,
(20E)-20-ethyl-21-(2-pyridyl)-4-aza-5α-pregna-1,20-dien-3-one,
20(E,Z)-4,21-dimethyl-21-phenyl-4-aza-5α-pregn-20-en-3-one,
20(E,Z)-21-methyl-21-(4-chlorophenyl)-4-aza-5α-pregn-20-en-3-one,
20(E,Z)-4,21-dimethyl-21-(2-pyridyl)-4-aza-5α-pregn-1,20-dien-3-one,
17β-[(4-chlorophenyl)methyl]-4-methyl-4-aza-5α-androstan-3-one,
17β-[(phenyl)methyl]-4-aza-5α-androstan-3-one,
17β-[(2-pyridyl)methyl]-4-methyl-4-aza-5α-androst-1-en-3-one,
17β-[(2-thienyl)methyl]-4-aza-5α-androst-1-en-3-one,
20-phenyl-4-methyl-4-aza-5α-pregnan-3-one,
20-(4-chloro)phenyl-4-aza-5α-pregnan-3-one,
20-(2-pyridyl)-4-methyl-4-aza-5α-pregn-1-en-3-one,
20-(2-thienyl)-4-aza-5α-pregn-1-en-3-one,
21-phenyl-4-aza-5α-pregnan-3-one,
21-(2-pyridyl)-4-methyl-4-aza-5α-pregnan-3-one,
21-[(4-methoxy)phenyl]-4-methyl-4-aza-5α-pregnan-3-one,
21-(2-thienyl)-4-methyl-4-aza-5α-pregnan-3-one,
21-[(4-chlorophenyl)-4-aza-5α-pregn-1-en-3-one,
4-methyl-17β-[3-(phenyl)propyl]-4-aza-5α-androstan-3-one,
17β-[3-(2-pyridyl)propyl]-4-aza-5α-androst-1-en-3-one,
17β-[3-(4-chlorophenyl)propyl]-4-aza-5α-androstan-3-one,
4-methyl-17β-[2-(thienyl)propyl]-4-aza-5α-androst-1-en-3-one,
4-methyl-17β-[4-(phenyl)butyl]-4-aza-5α-androstan-3-one,
17β-[3-(2-pyridyl)butyl]-4-aza-5α-androst-1-en-3-one,
17β-[3-(4-chlorophenyl)butyl]-4-aza-5α-androstan-3-one,
4-methyl-17β-[2-(thienyl)butyl]-4-aza-5α-androst-1-en-3-one,
20-ethyl-21-(2-pyridyl)-4-aza-5α-pregnan-3-one,
20-ethyl-21-phenyl-4-aza-5α-pregnan-3-one,
20-ethyl-21-(2-methoxyphenyl)-4-aza-5α-pregnan-3-one,
4,21-dimethyl-21-(2-pyridyl)-4-aza-5α-pregnan-3-one,
4,21-dimethyl-21-[(4-benzoylamino)phenyl]-4-aza-5α-pregnan-3-one,
4,21-dimethyl-21-(2-thiazolyl)-4-aza-5α-preganan-3-one,
21-phenyl-4-aza-5α-pregnan-3-one,
21-(2-pyridyl)-4-aza-5α-pregnan-3-one,
21-(2-thienyl)-4-aza-5α-pregnan-3-one,
21-(2-methoxyphenyl)-4-aza-5α-pregn-1-en-3-one,
21-(3-pyridyl)-4-aza-5α-pregn-1-en-3-one,
21-(2-thiazolyl)-4-aza-5α)-pregn-1-en-3-one,
4-methyl-21-[4-(methylsulfonyl)phenyl]-4-aza-5α-pregn-1-en-3-one,
4-ethyl-21-(4-fluorophenyl)-4-aza-5α-pregn-1-en-3-one,
4-methyl-21-(4-carboxyphenyl)-4-aza-5α-pregn-1,20-dien-3-one,
4-ethyl-21-(4-carbamoylphenyl)-4-aza-5α-pregn-1,20-dien-3-one,
20-(3-pyridyl)-4-aza-5α-pregna-1,17-dien-3-one,
4-methyl-20-(2-pyrazinyl)-4-aza-5α-pregn-1,17-dien-3-one,
20-ethyl-4-methyl-21-phenyl-4-aza-5α-pregn-20-en-3-one,
4,20-dimethyl-21-(2,6-dimethoxyphenyl)-4-aza-5α-pregna-1,20-dien-3-one,
20-ethyl-4-methyl-21-(s-triazinyl)-4-aza-5α-pregna-1,20-dien-3-one,
4-methyl-20-(phenylmethyl)-4-aza-5α-pregnan-3-one,
20-ethyl-4-methyl-21-(2-pyridyl)-4-aza-5α-pregnan-3-one,
20-(2-thiazolyl)-4-aza-5α-pregnan-3-one,
20-ethyl-21-(3-pyridyl)-4-aza-5α-pregnan-3-one,
20-(4-methylsulfonylphenyl)-4-aza-5α-pregn-1-en-3-one,
20-ethyl-21-(4-methoxyphenyl)-4-aza-5α-pregn-1-en-3-one,
4-methyl-20-(3,4-dimethoxyphenyl)-4-aza-5α-pregn-1-en-3-one,
20-ethyl-4-methyl-21-(2-pyrimidinyl)-4-aza-5α-pregn-1-en-3-one,
4,21-dimethyl-21-(4-pyridyl)-4-aza-5α-pregna-1,20-dien-3-one,
21-methyl-21-(2-thienyl)-4-aza-5α-pregn-1-en-3-one,
21-methyl-21-(1-imidazolyl)-4-aza-5α-pregnan-3-one,
4,21-dimethyl-21-(4-carbamoylphenyl)-4-aza-5α-pregn-1-en-3-one,
4-methyl-21-(4-methoxyphenyl)-4-aza-5α-pregnan-3-one,
4-methyl-17-((4-chloro)phenylmethyl)-4-aza-5α-androstan-3-one,
N-(1,1-dimethylethyl)-4-(4-methyl-3-oxo-4-aza-5α-pregn-21-yl)benzamide,
4-methyl-21-(3-pyridyl)-4-aza-5α-pregn-20-en-3-one,
21-(2-pyrazinyl)-4-methyl-4-aza-5α-preg-20-en-3-one,
4-methyl-21-(2-pyrazinyl)-4-aza-5α-pregnan-3-one,
4-methyl-24-nor-4-aza-5α-cholane-23-nitrile,
4-methyl-3-oxo-4-aza-5α-pregnane-21-carbonnitrile,
24-nor-4-aza-5α-chol-1-ene-23-nitrile,
24-nor-4-aza-5α-cholane-23-nitrile,
4-methyl-24-nor-4-aza-5α-chol-1-ene-23-nitrile,
3-oxo-4-aza-5α-pregn-1-ene-21-carbonitrile,
3-oxo-4-aza-5α-pregnane-21-carbonitrile,
4-methyl-3-oxo-4-aza-5α-pregnane-21-nitrile,
4-methyl-3-oxo-4-aza-5α-cholane-24-nitrile,
3-oxo-4-aza-5α-chol-1-ene-24-nitrile,
4-methyl-3-oxo-21-nor-4-aza-5α-cholane-24-nitrile,
3-oxo-21-nor-4-aza-5α-cholane-24-nitrile, and also including the corresponding compounds whereto the 4-hydrogen substituent is replaced by a methyl or an ethyl radical, and/or a delta-one double bond is present.

The novel compounds of the present invention are prepared by methods starting with appropriate steroid 17-carboxaldehydes and ketones of the following formulae:

FLOWSHEET XXIV

Carboxaldehydes

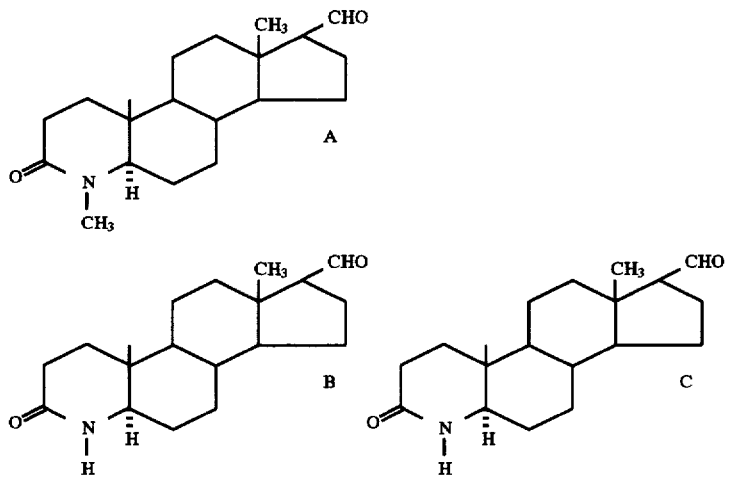

Carboxaldehyde A can be prepared from 17-(2-pyridylthio)carboxylate-4-methyl-5α-androstan-3-one by reaction with Raney nickel to the 17β-carbinol followed by oxidation to the aldehyde with pyridinium chlorochromate. (See J. Med. Chem. 1986, Vol. 29, No. 11, p. 2299, Compound 10bg) The starting 2-pyridylthio ester can be made by hydrolyzing the 17-COOMe derivative to the acid and reacting the acid with 2,2'-dipyridyl disulfide in an inert solvent, e.g. chlorobenzene.

Carboxaldehyde B can be prepared from the lithium aluminum hydride reduction of 17β-(N-methyl-N-methoxy)-carboxamide-5α-4-aza-androst-1-en-3-one (see U.S. Pat. No. 5,061,801 for its preparation, as also described in the following section "Preparation of Starting Materials".

Carboxaldehyde C can be concurrently prepared from the same procedure, as a secondary reaction product, as described above for Carboxaldehyde B (See preparation in "Preparation of Starting Materials").

Note that the corresponding 4-ethyl analogs are also available through conventional alkylation of the 4-NH derivative via, e.g. ethyl iodide, sodium hydride in dry DMF at room temperature.

As seen in Flowsheet XXV, the carboxaldehydes A, B, or C can be reacted with the phosphonate reagent as shown, where $R^2$ is defined above, $R^3$ is hydrogen or methyl and $R_a$ is a conventional ester alkyl radical, e.g. methyl or ethyl, to yield the D-20 olefins IIIa, IIIb & IIIc.

In general, the procedure for reacting the carboxaldehyde with the phosphonate ylid reagent is analogous to the conditions as described for the Wadsworth-Emmons modification of the Wittig reaction (See Chem. Rev. 74, p. 87, 1974 and JACS Vol. 83, p. 1733, 1961). The phosphonate ylid is reacted under anhydrous conditions with the carboxaldehyde in about a 1:1 molar ratio together with a hydride reagent, e.g. sodium hydride, also in a 1:1 molar ratio with the phosphonate reagent in a dry solvent, e.g. dimethylformamide, dimethylacetamide, tetrahydrofuran, dioxane, DMSO and the like, under anhydrous conditions, usually a nitrogen atmosphere, at a temperature of about 50°–100° C. preferably 80°–85° C. for about 1–4 hours. Workup is conventional, e.g. organic liquid extraction followed by drying, evaporating off solvent, followed by chromatography, distillation or recrystallization of the crude material to yield the desired product, being a species of Formula I.

The starting phosphonates can be prepared by known procedures in the art. One procedure that can be used is the modified Arbuzov reaction in which a chloromethyl-aryl or heteroaryl compound, e.g. thienylmethyl chloride, is reacted with an alkyl phosphite, e.g. triethyl phosphite, at 125°–175° C. for 1–10 hours. Conventional workup yields the desired starting phosphonate, e.g. diethyl 2-thienylmethylphosphonate.

FLOWSHEET XXV
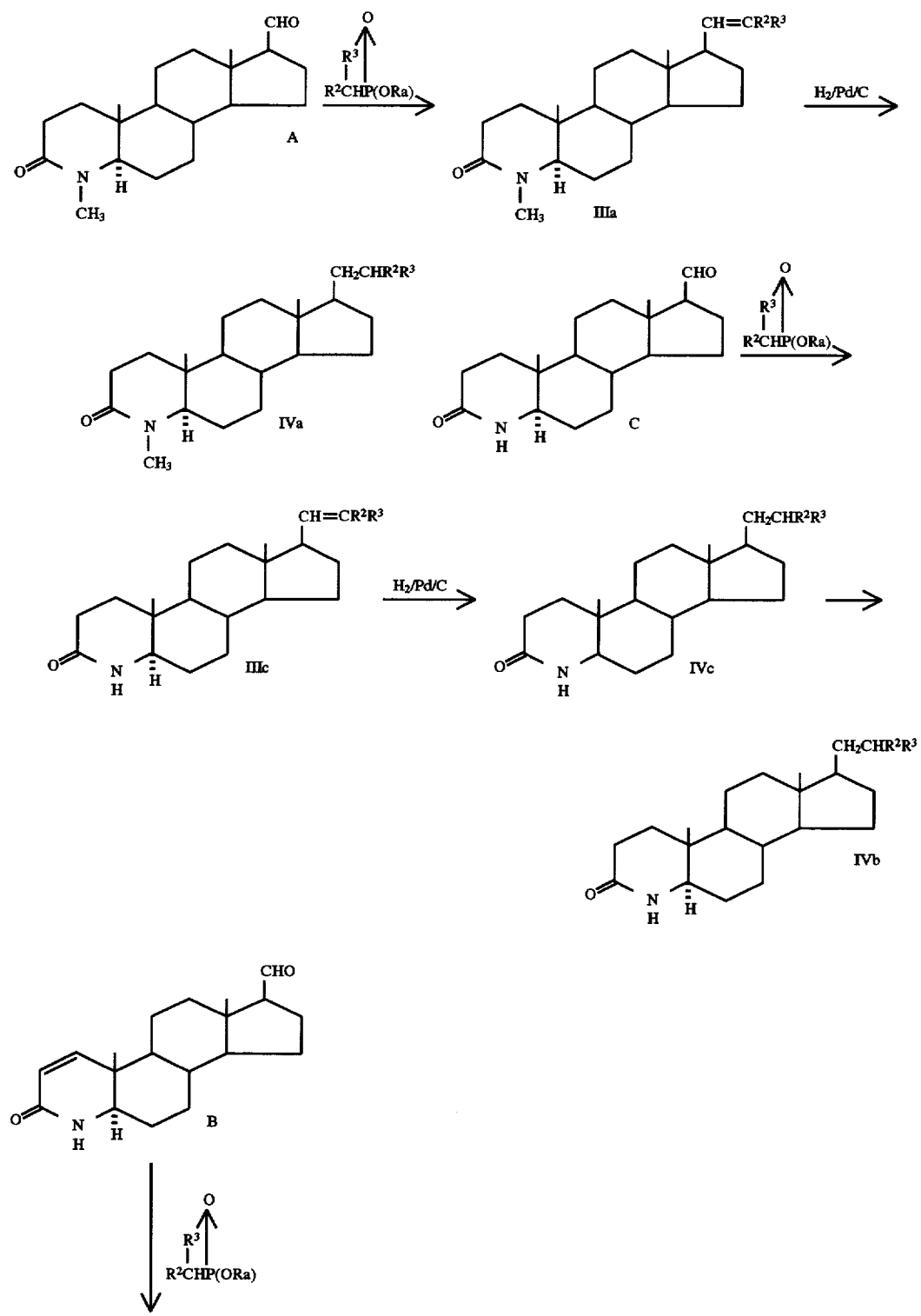

-continued
FLOWSHEET XXV

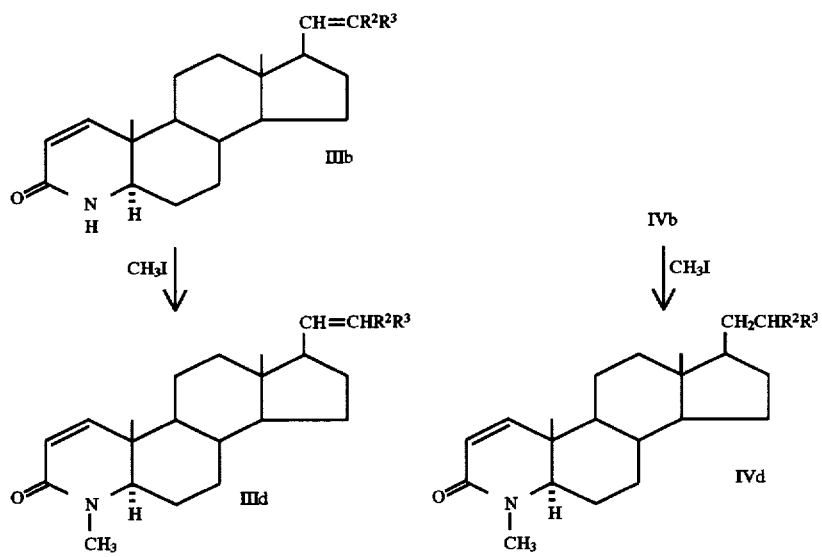

Alternately, the chloromethyl heteroaryl compound, e.g. 4-chloromethylpyridine, can be reacted with diethylphosphite and sodium hydride at about 80°–100° C. for several hours to also produce the desired phosphonate starting materials.

Representative syntheses are given in the "Preparation of Starting Materials" section and representative examples of phosphonate starting materials are:

diethyl 2-thienylmethylphosphonate,
diethyl 4-pyridylmethylphosphonate,
diethyl 4-methylbenzylphosphonate,
diethyl benzylphosphonate,
diethyl 4-chlorobenzylphosphonate,
diethyl 3-chlorobenzylphosphonate,
diethyl 2-chlorobenzylphosphonate,
diethyl 2-pyridylmethylphosphonate,
diethyl 3-thienylmethylphosphonate,
diethyl 2-furanylmethylphosphonate,
diethyl 2-fluorobenzylphosphonate,
diethyl 3-pyridylmethylphosphonate,
diethyl 4-ethoxycarbonylbenzylphosphonate,
diethyl 4-(phenylaminocarbonyl)benzyl phosphonate, As outlined on Flowsheet XXV, the $\Delta^{20}$ olefins IIIa and IIIc can be reduced with e.g. 10% palladium on carbon in a suitable solvent, e.g. methanol, ethanol, dioxane, acetic acid and the like, at room temperature under 1–50 psig hydrogen atmosphere to form IVa and IVc. Compound IVc can be further reacted to form the $\Delta^1$ olefin IVb by the procedure of Dolling et al using dichlorodicyanobenzoquinone, see JACS (1988), Vol 110, pp 3318–3319. Alternatively IVb can be formed by reacting IVc with benzeneselenic anhydride in refluxing chlorobenzene. The 4-nitrogen in IIIb and IVb can be alkylated with methyl iodide in the presence of sodium hydride in e.g. dry dimethylformamide solvent to give IIId and IVd.

Note that the 4-methyl group in the appropriate compounds in Flowsheet XXV can be replaced with a 4-ethyl group to prepare the corresponding 4-ethyl analogs of IIIa, IVa, IIId, and IVd.

The aldehydes A, B and C can be reacted with diethyl $\alpha$-methyl-benzylphosphonate (U.S. Pat. No. 4,515,883) in the Wadsworth-Emmons modification of the Wittig reaction and the corresponding products hydrogenated, alkylated on the 4-nitrogen and dehydrogenated as outlined in Flowsheet XXV to give compounds IIIa–d and IVa–d with $R^2$=phenyl and $R^3$=methyl.

Methyl ketone D (see Chart XXVI) and its preparation is described in J. Med. Chem., 1984, Vol. 27, p. 1690–1701, by G. H. Rasmusson et. al (see Compound 4d.) These compounds can be prepared by reacting the S-(2-pyridyl) androstan-3-one-17β-thio-carboxylate with methylmagnesium chloride under appropriate Grignard conditions.

Methyl Ketone E can be prepared by reacting N-methoxy-N-methyl-3-oxo-4-aza-5α-androst-1-ene-17β-carboxamide (4) with excess methylmagnesium bromide in tetrahydrofuran.

The above 17-methylketones D and E can be reacted with the phosphonate ylids described above in an analogous manner to achieve the 20-methyl pregn-20-en-3-one compounds IIIi and IIIj as illustrated in the following Flowchart XXVI.

FLOWCHART XXVI
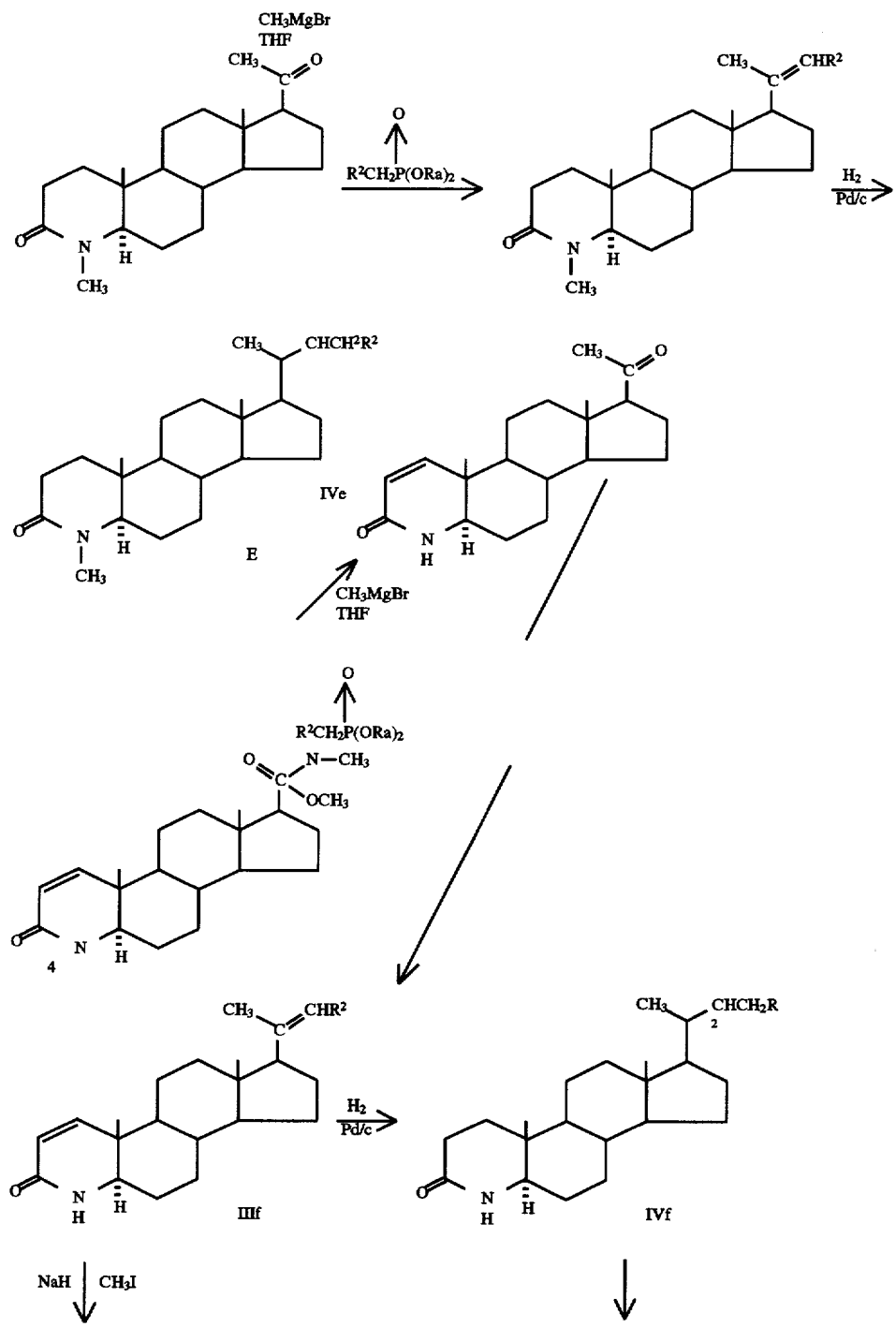

-continued
FLOWCHART XXVI

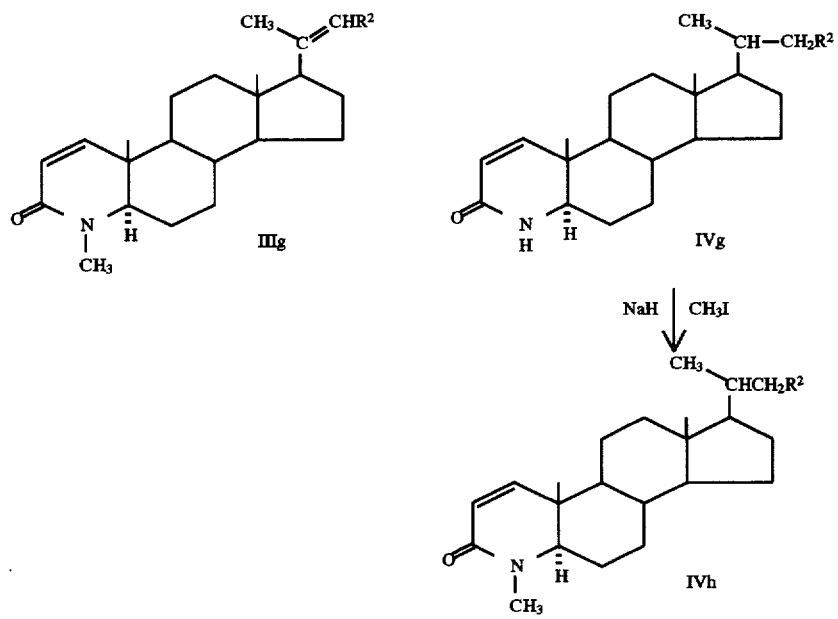

As outlined in Flowsheet XXVI, IIIe and IIIf can be hydrogenated as above to give IVe and IVf. Compound IVf can be dehydrogenated as described above to the D'-compound IVg. Compounds IIIf and IVg can be methylated on the 4-nitrogen to give IIIg and IVh.

Also the amide 4 can be reacted with ethyl-magnesium bromide to give ethyl ketone versions of D and E. Using the reactions outlined in Flowsheet XXVI compounds IIIe–g and IVe–h with the 20-methyl replaced by a 20-ethyl can be prepared.

Ketone F (Flowchart XXVII) can be prepared by conventional techniques, including oxidation of the corresponding 17-β-ol with e.g. Jones reagent, and is known in the art in J. Med. Chem. 1984, Vol. 27, p. 1690–1701 by G. H. Rasmusson et. al. (see Compound 22 on p. 1693).

Ketones G and H can be prepared by Jones reagent oxidation of the corresponding 17b-alcohols described in the above reference. Using the reactions shown in Flowsheet XXVI, the ketones F, G, and H are converted into compounds IIIh–k and IVh–l as seen in Flowsheet XXVII.

The 17β-3-phenyl-propyl compound (53) can be prepared from aldehyde A by a phosphonate olefination with diethyl benzoylmethylphosphonate followed by reduction of the ketone and double-bond by hydrogenation with palladium on carbon catalyst in ethanol. Using the reaction sequences outlined in Flowsheet A, the 4-H, D'-4-H, and 4-CH₃-D' analogs can be prepared starting from aldehydes A or B.

FLOWSHEET XXVIII

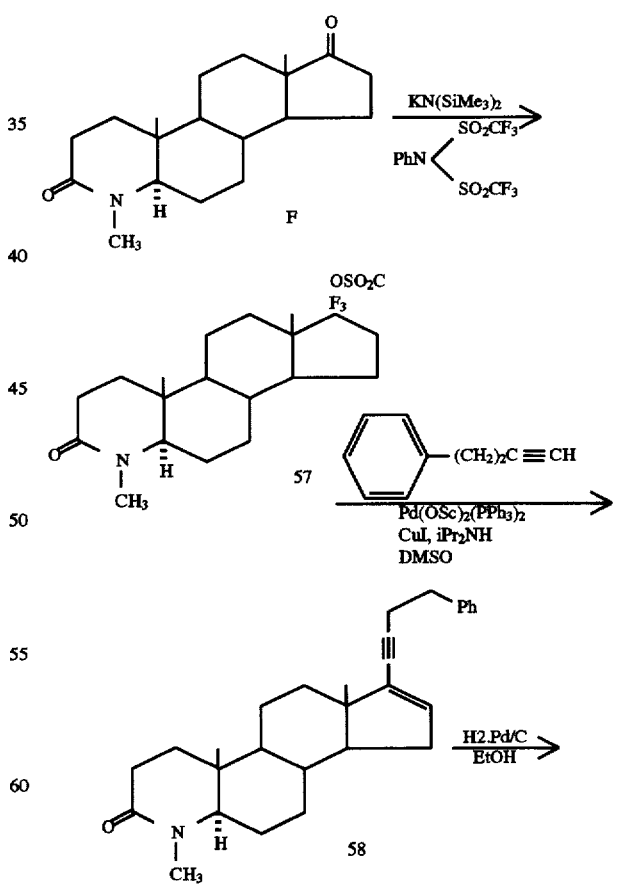

-continued
FLOWSHEET XXVIII

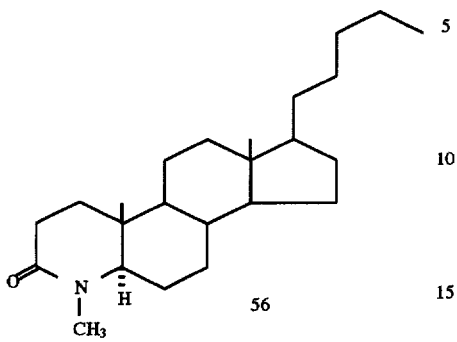

56

As shown in Flowsheet XXVIII, the 17β-3-phenylbutyl compound 56 can be prepared from the ketone F by conversion of the latter to the $D^{16}$-17-trifluoromethylsulfonate 57 with potassium hexamethyldisilazide and N-phenyltrifluoro-methanesulfinimide (*Tetrahedron Lett.* 24, 979 (1983)). Palladium-catalyzed coupling of 57 with 4-phenyl-1-butyne (*Synthesis*, (1986)) can give the en-yne 58 which can be hydrogenated to the desired 17β-3-phenylbutyl compound 56.

FLOWSHEET XXIX

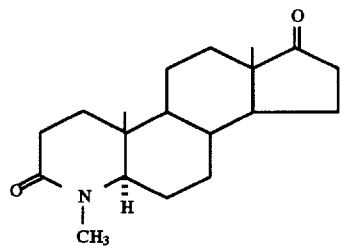
F

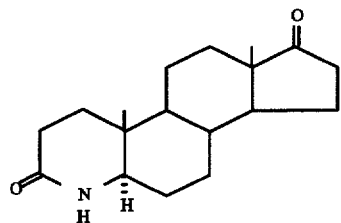
G

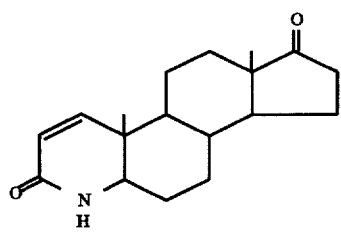
H

-continued

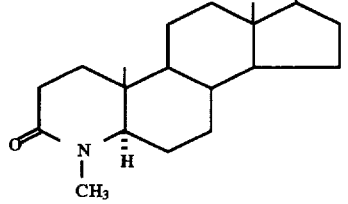
IIa

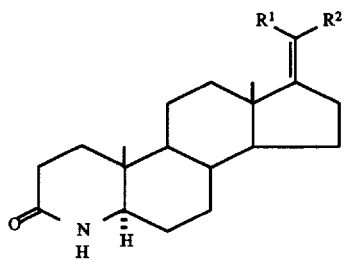
IIb

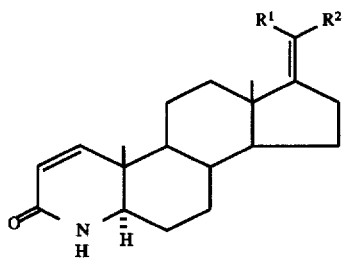
IIc

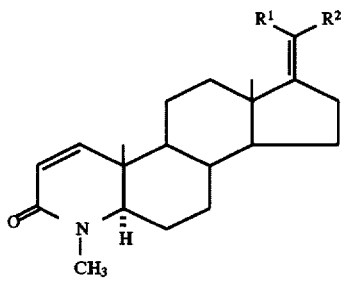
IId

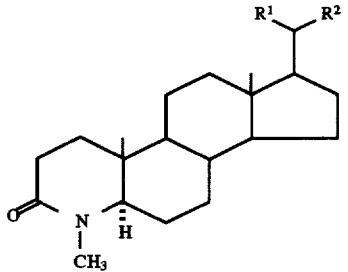
IVi

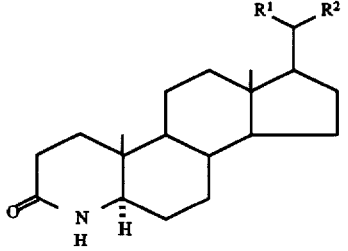
IVj

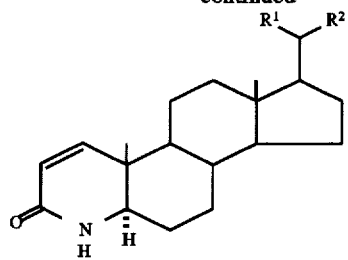
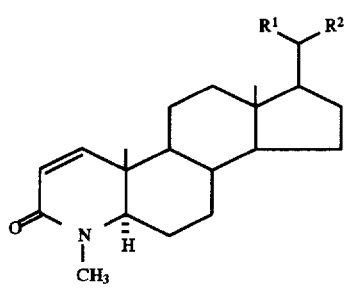
FLOWSHEET XXX
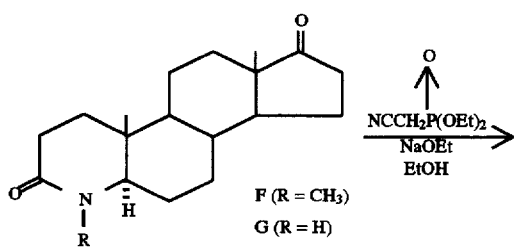
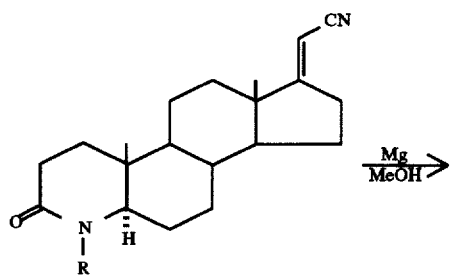
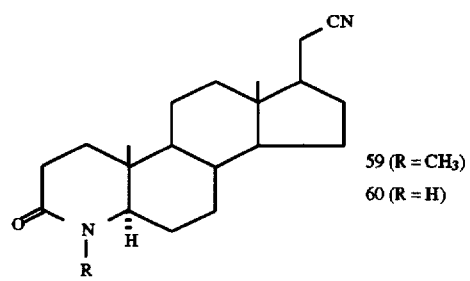
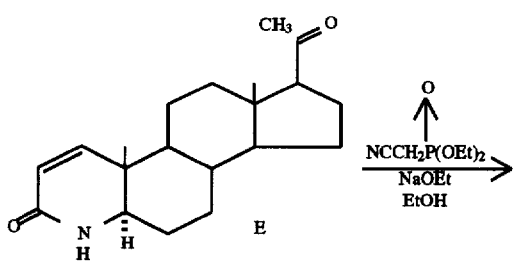
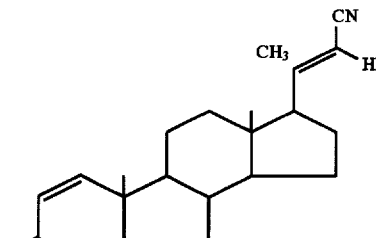
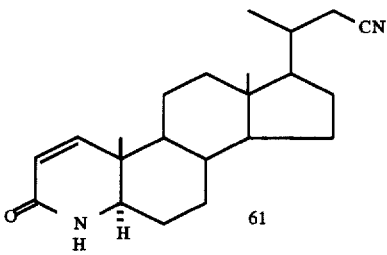
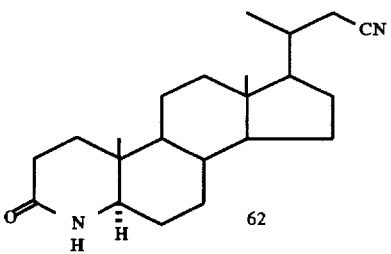
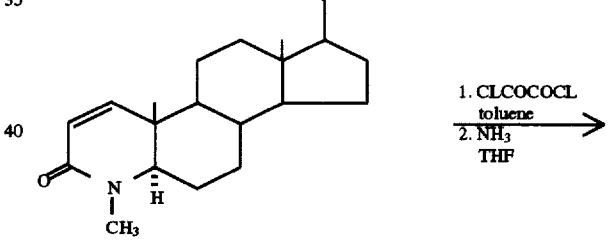
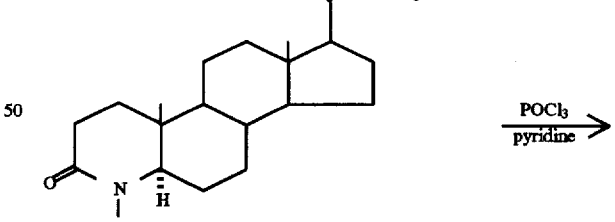
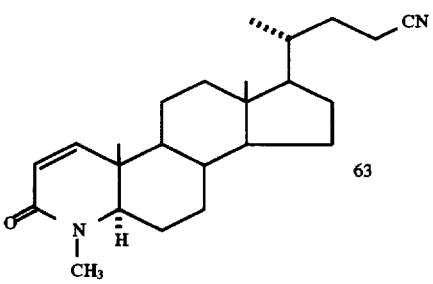

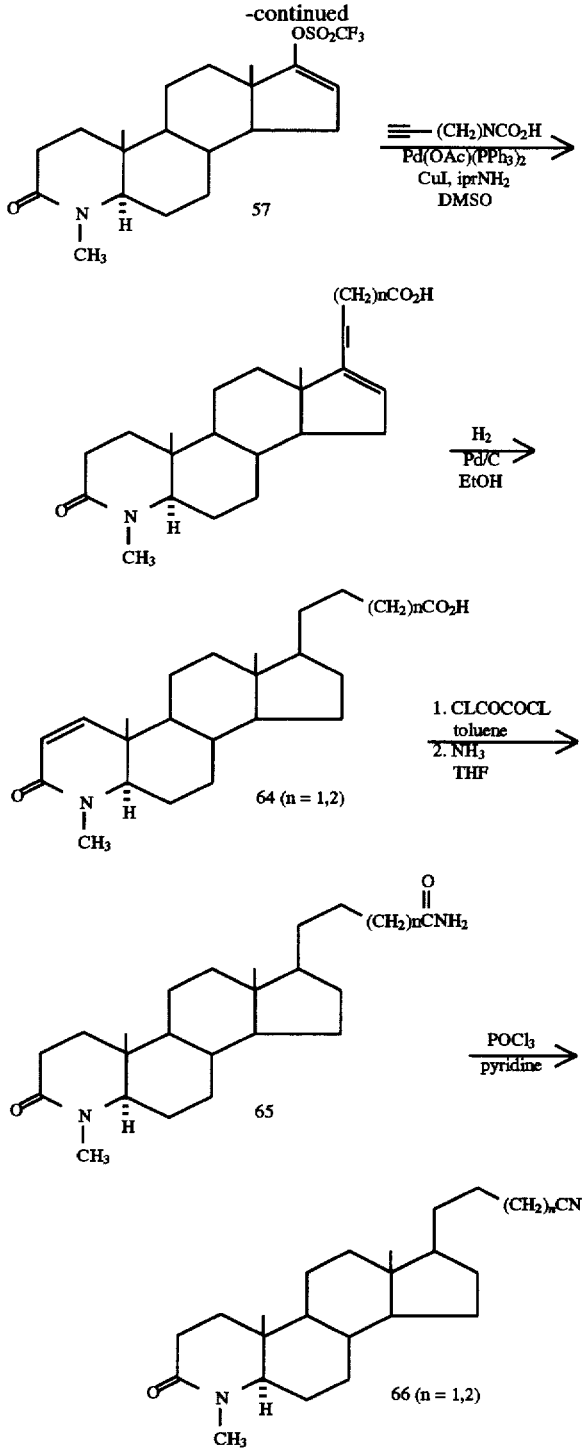

reaction sequence the ketone E can be converted into the D1-4-H-24-norcholane-23-nitrile 61 and its reduction product 62. The 24-cholane-24-carbonitrile 63 can be prepared from the cholanic acid 55 by conversion to the primary amide with oxalyl chloride and ammonia followed by dehydration with POCl$_3$ in pyridine (J. Med. Chem. 29, 2298 (1986)). Similarly the 17-butyric (64, n=1) and valeric (n=2) acids, prepared by palladium-catalyzed coupling of 57 with 3-butynoic and 4-pentynoic acids followed by hydrogenation, can converted into the nitriles 66 (n=1, 2)

FLOWSHEET XXXI

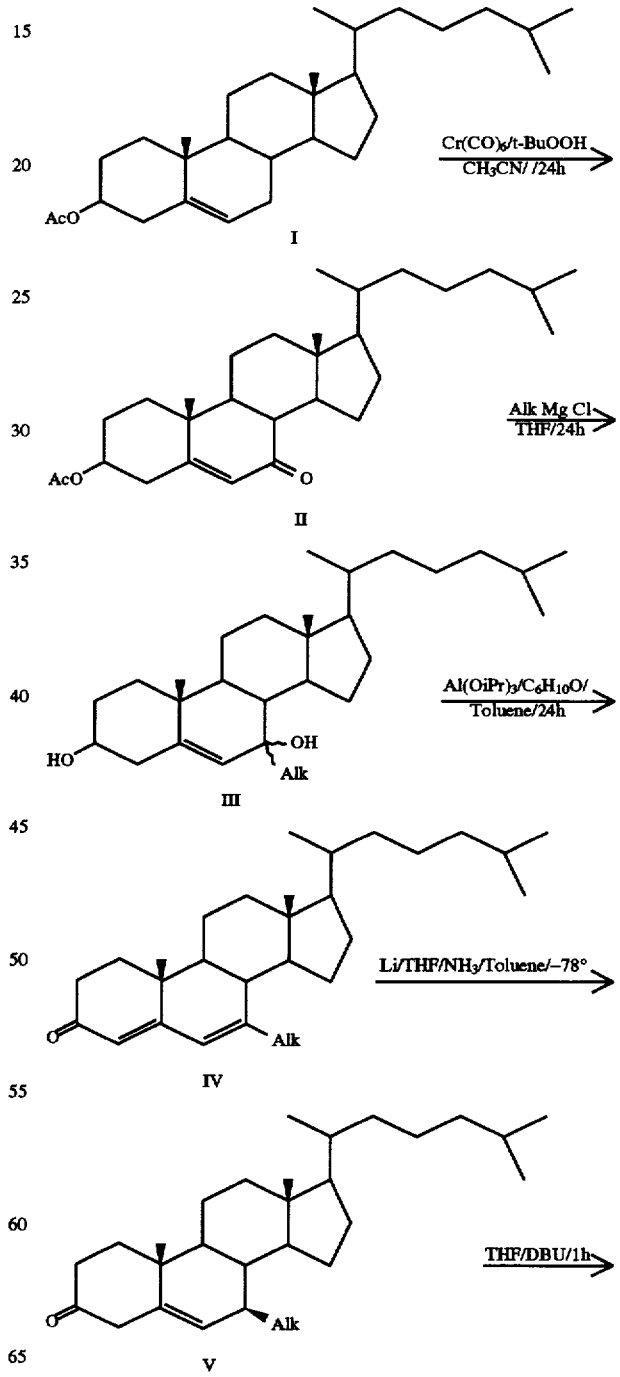

As described above the nitriles (54) (R=CH$_3$, H) were prepared from a "second order" Beckmann treatment on the homologous carboxylic acids (55, R=CH$_3$, H) with sodium nitrite in trifluoroacetic acid and trifluoroacetic anhydride, (J. of Lipid Research 29 1387 (1988)).

The synthesis of other nitriles is outlined in Flowsheet XXX. The pregnane-21-carbonitriles (59) and (60) can be prepared from the ketones F and G by phosphonate olefination with diethyl cyanomethylphosphonate (Steroids 27, 431 (1976)) followed by reduction with magnesium in methanol (J. Org. Chem. 40, 127 (1975)). By the same -continued
FLOWSHEET XXXI

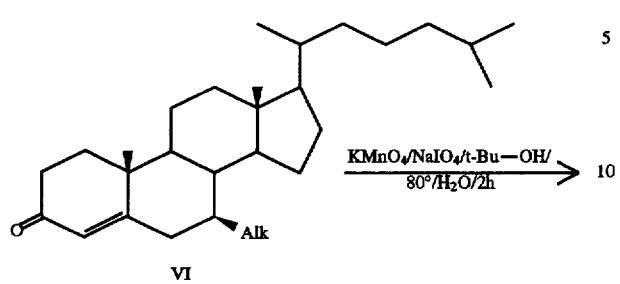

VI

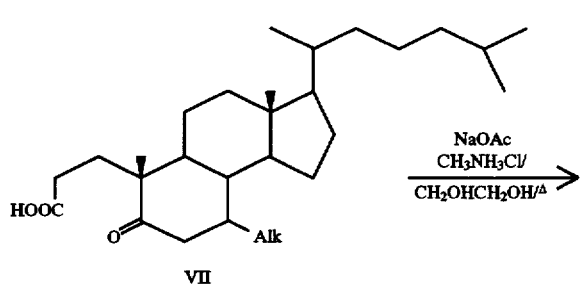

VII

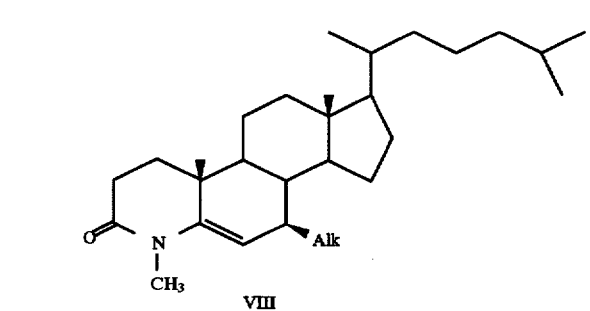

VIII

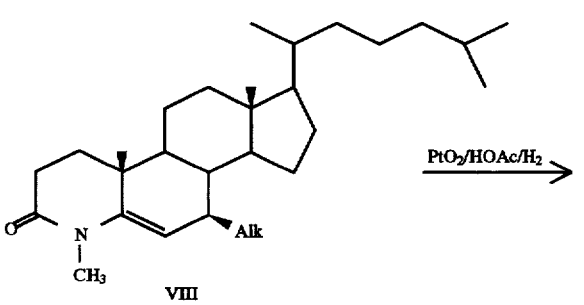

VIII

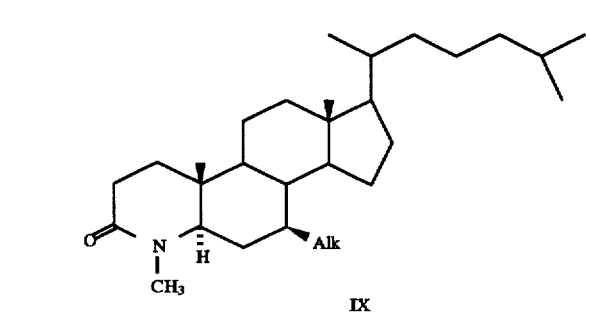

IX

-continued
FLOWSHEET XXXI

VII $\xrightarrow{NH_4OAc/HOAc}$

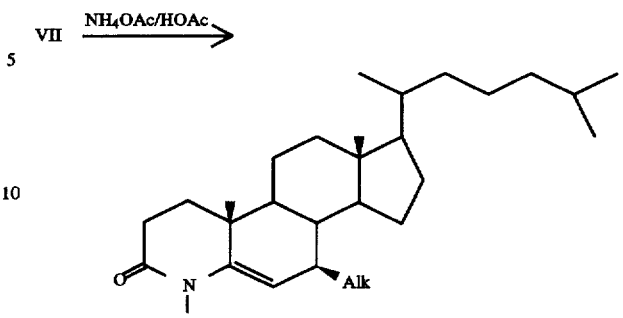

X

X $\xrightarrow[HOAc]{PtO_2/H_2}$

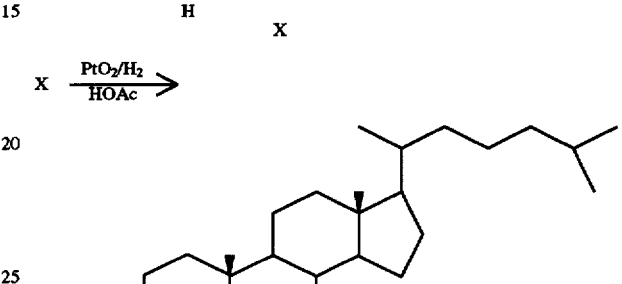

XI

7-Beta Alkyl Series

The compounds of the instant invention comprising Z as a 7b alkyl group, e.g. methyl, ethyl, isopropyl, allyl, can be prepared by the procedure outlined in Flowsheet XXXI.

As seen in the Flowsheet XXXI, the starting 3-acetoxy-cholest-5-ene I is oxidized to the corresponding 5-en-7-one II by treatment with hydrogen t-butyl peroxide and chromium hexacarbonyl in e.g. acetonitrile, at reflux. The $C_1$–$C_4$ alkyl group, designated Alk, e.g. methyl, can be introduced at this point by a Grignard reaction using e.g., alkyl magnesium chloride in e.g., anhydrous THF at 0°–23° C. to produce the 7-alkyl-7-hydroxy adduct III. This is then oxidized with e.g. aluminum isopropoxide and cyclohexanone (Oppenauer oxidation conditions) in refluxing toluene solvent to produce the 7-alkyl-4,6-dien-3-one IV. This in turn is reduced via a e.g., metal-ammonia reduction, using lithium, liquid ammonia. THF and toluene at –78° C., quenching the reaction with dibromoethane and ammonium chloride, to selectively yield the 7-beta-alkyl-5-en-3-one V. In the next step the delta-5 double bond is isomerized to the 4-ene by use of DBU (1,8-diazabicyclo[5.4.0]undec-7-ene) in, e.g. refluxing tetrahydrofuran (THF) to produce the 7-beta-alkyl 4-en-3-one, VI. The A Ring is next cleaved by treatment with e.g. potassium permanganate, sodium periodate in t-butyl alcohol at 80° C. to produce the corresponding seco-acid VII. Treatment of the seco-acid with an appropriate amine e.g., methylamine hydrochloride and sodium acetate in ethylene glycol at 180° C., yields e.g., the 4-methyl-4-aza-cholest-5-en-3-one VIII. This in turn is selectively reduced with e.g., $PtO_2$ catalyst in a hydrogen atmosphere, to remove the 5-position double bond to produce the 5α-hydrogen compound IX. The seco-acid VII can be similarly treated with ammonium acetate in acetic acid to produce the corresponding N—H compound, X, which can then be analogously treated with PtO$_2$ in a catalytic hydrogenation to produce the corresponding 5α-4N—H compound XI. Similarly, use of hydroxylamine or hydrazine for ring A closure of the seco acid will afford the corresponding delta-5-4N—X compounds where —X can be —OH or —NH$_2$, respectively. Reaction of the anion of saturated 4N-compound (generated from the NH precursor by NaH treatment) with methylsulfenyl chloride can provide the corresponding 4N—X compound where —X is —SCH$_3$. Thus, R can also be OH, —OH, —NH$_2$ or SCH$_3$ in the Formula.

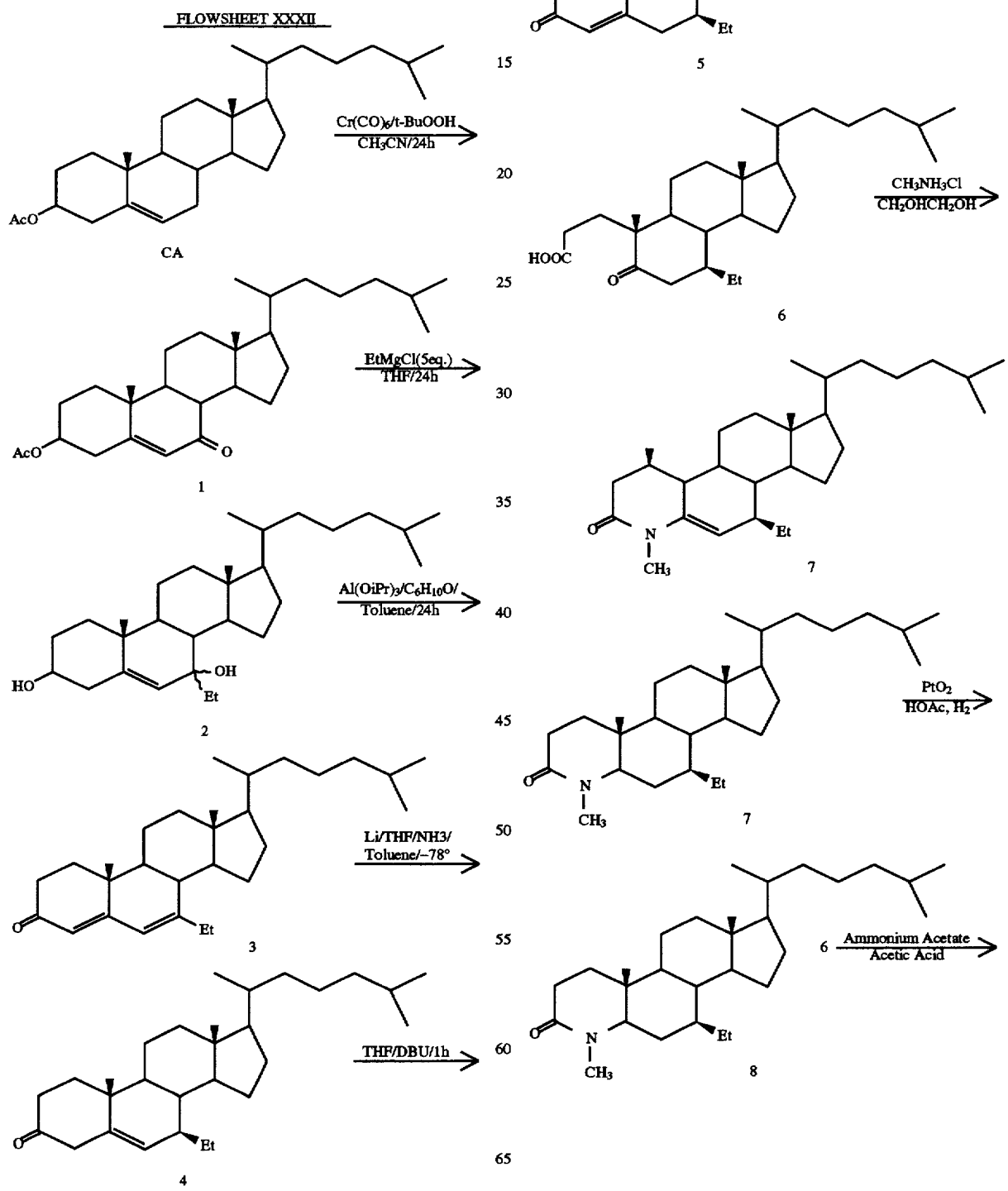

-continued
FLOWSHEET XXXII

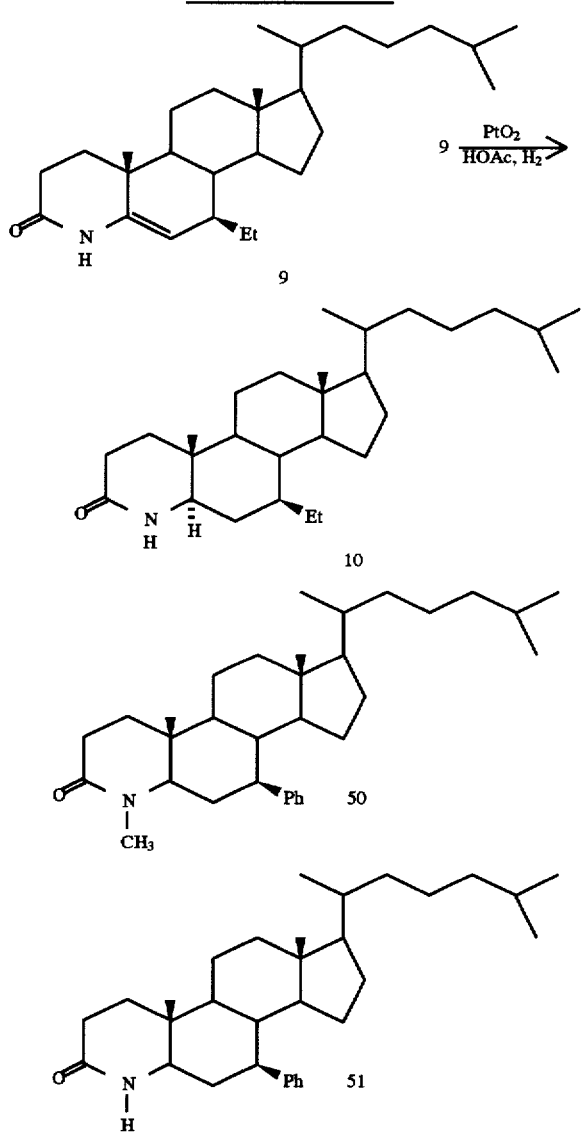

7-Beta-Ethyl-Cholestane Analogues

The 7-ethyl substituent is introduced into the cholestane series as illustrated in Flowsheets XXXIII and XXXIV by the same analogous procedure as described in the Flowsheet XXX.

The starting cholesteryl acetate CA is available commercially (Aldrich). This is treated using the analogous chromium hexacarbonyl/hydrogen t-butylperoxide/acetonitrile oxidation procedure (described in JCS Perkin Trans. 1985, p. 267 by A. J. Pearson) to yield the 3-acetoxy-cholest-5-en-7-one 1. This can be reacted with an alkyl Grignard reagent, e.g. ethyl magnesium chloride to form the adduct 2. This is oxidized under Oppenauer conditions to yield the dienone 3, which then can undergo metal-ammonia reduction to yield the 7b-ethyl-5-en-3-one, 4. This is isomerized using DBU to the 4-en-3-one, 5, which is oxidized to open Ring A to yield the seco-acid 6. This can be treated with amines, e.g. methylamine, to yield the A-ring closed 4-methyl-4-aza compound 2-This in turn can be catalytically hydrogenated to yield the 7-ethyl-5-alpha-4-methyl-4-aza-cholestan-3-one, 8.

Similarly, by treatment of the seco-acid 6 with ammonium acetate/acetic acid, the corresponding 4-NH analog 9, is produced which can be catalytically hydrogenated to yield the 7-beta-ethyl-5α-4-aza-cholestan-3-one, 10.

Following the same procedure but using phenylmagnesium chloride as the Grignard reagent, the corresponding compounds 50 and 51 are produced.

FLOWSHEET XXXIII

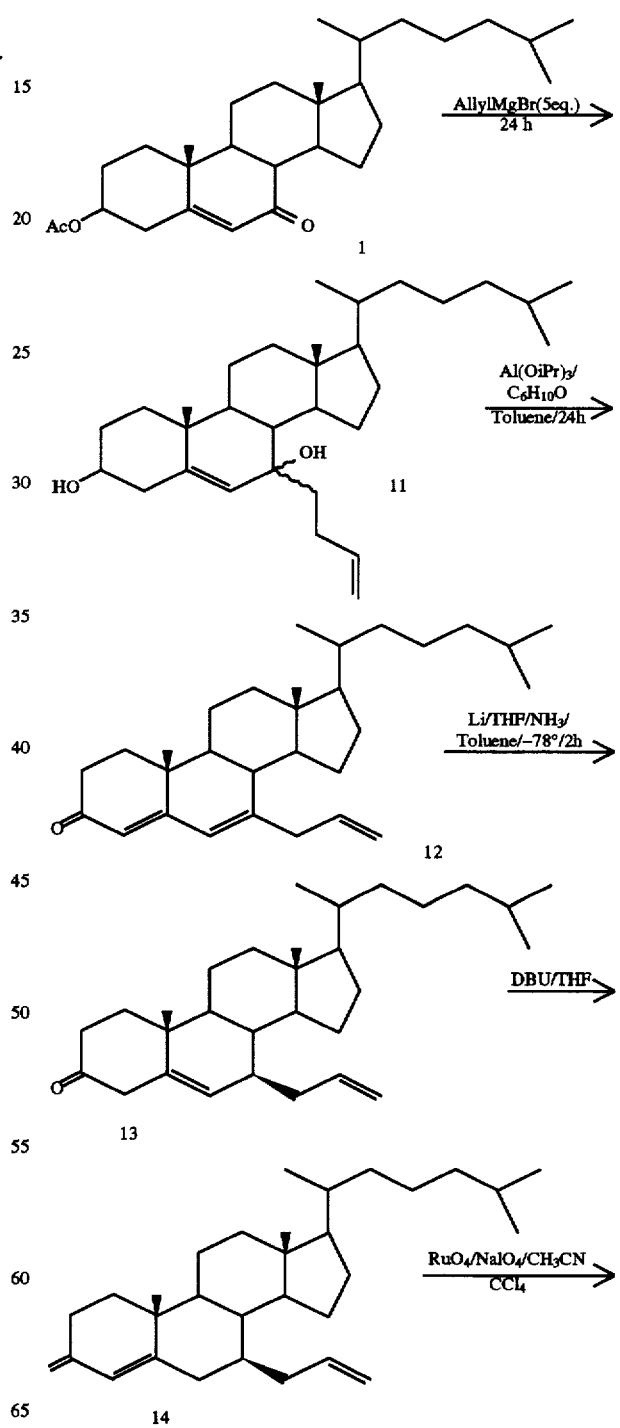

161
-continued
FLOWSHEET XXXIII

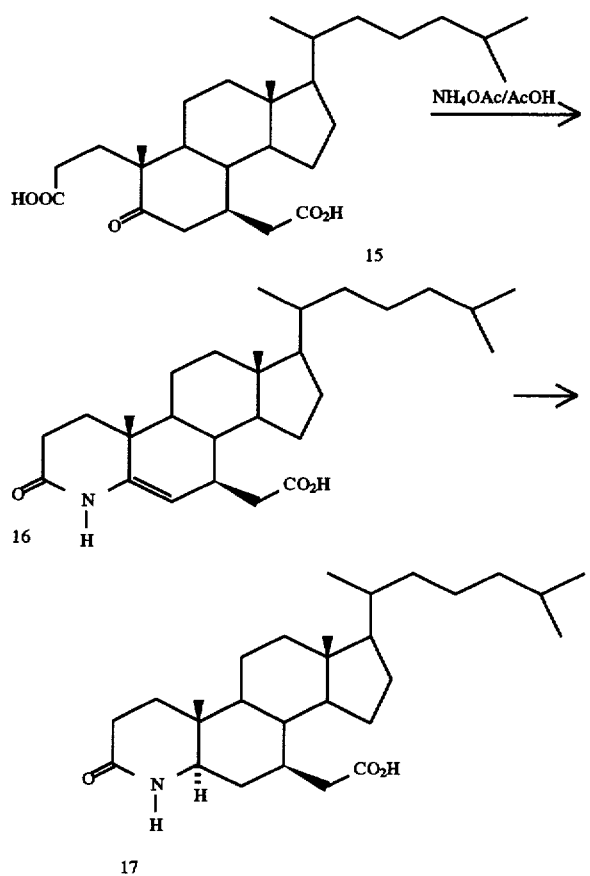

162
-continued
FLOWSHEET XXXIV

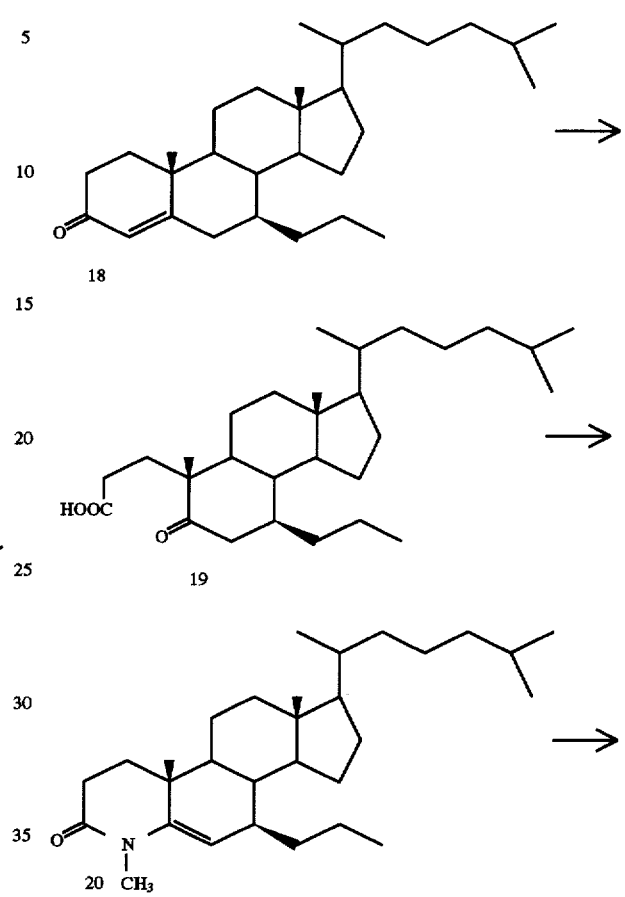

7-Carboxymethyl-Cholestane Series

The 7-carboxy substituent is formed through the corresponding 7-allyl group. As seen in Flowsheet XXXIII, 7-oxo-cholesteryl acetate 1, is reacted with allyl Grignard reagent to form the adduct 11 which is oxidized to the dienone 12 by Oppenauer conditions. Metal-ammonia reduction affords the 5-ene analog 13, followed by DBU-catalyzed double bond isomerization to 14. This in turn can be oxidized in a key step to form the 7-carboxymethyl seco-acid 15. Treatment with amines, e.g. ammonia, forms the 4-aza derivative, 16 which is then reduced to the cholestane 17. Use of methylamine in place of ammonia can yield the corresponding 4-methyl analogs of 16 and 17.

FLOWSHEET XXXIV

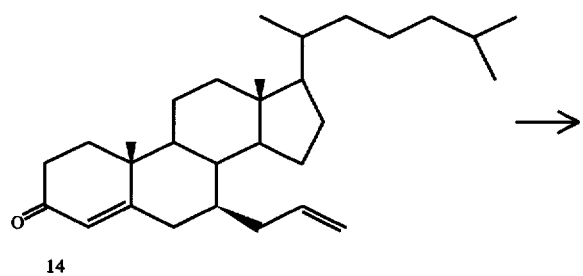

FLOWSHEET XXXV

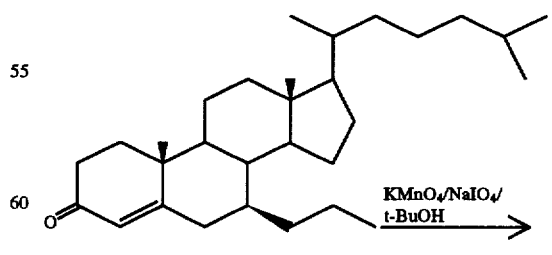

FLOWSHEET XXXV -continued

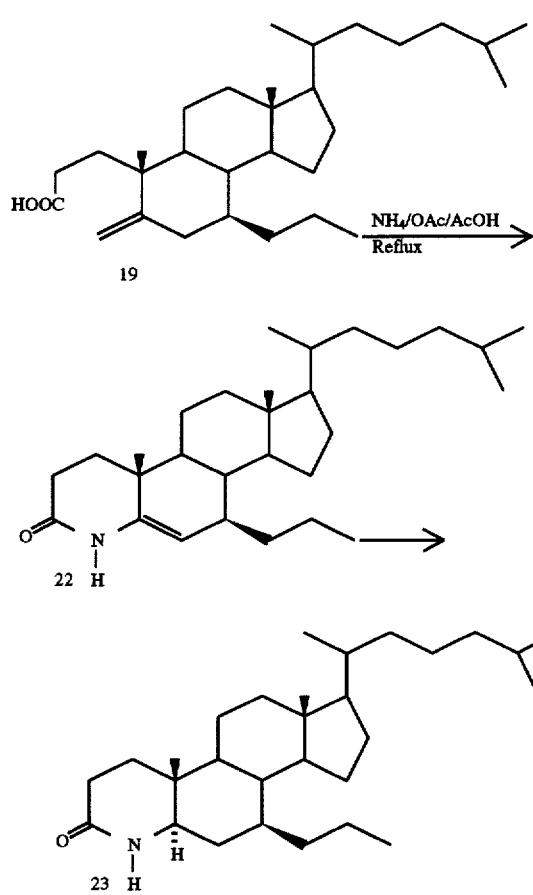

7-Propyl-Cholestane Series

The 7-propyl analogs are made starting with the 7-allyl-4-en-3-one 14, which is reduced by hydrogenation using Wilkinson's catalyst to the propyl derivative 18, oxidized to the seco-acid 19, then condensed with amines, e.g. methylamine, to form the 4-methyl analog 20 and then reduced to the cholestane 21. Corresponding treatment with ammonia is shown in Flowsheet XXXV shows the corresponding unsubstituted 4-aza 22 and cholestane 23 analogs.

FLOWSHEET XXXVI

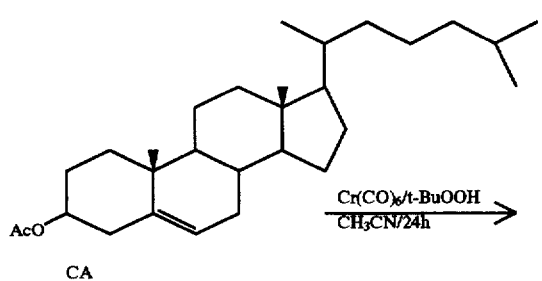

FLOWSHEET XXXVI -continued

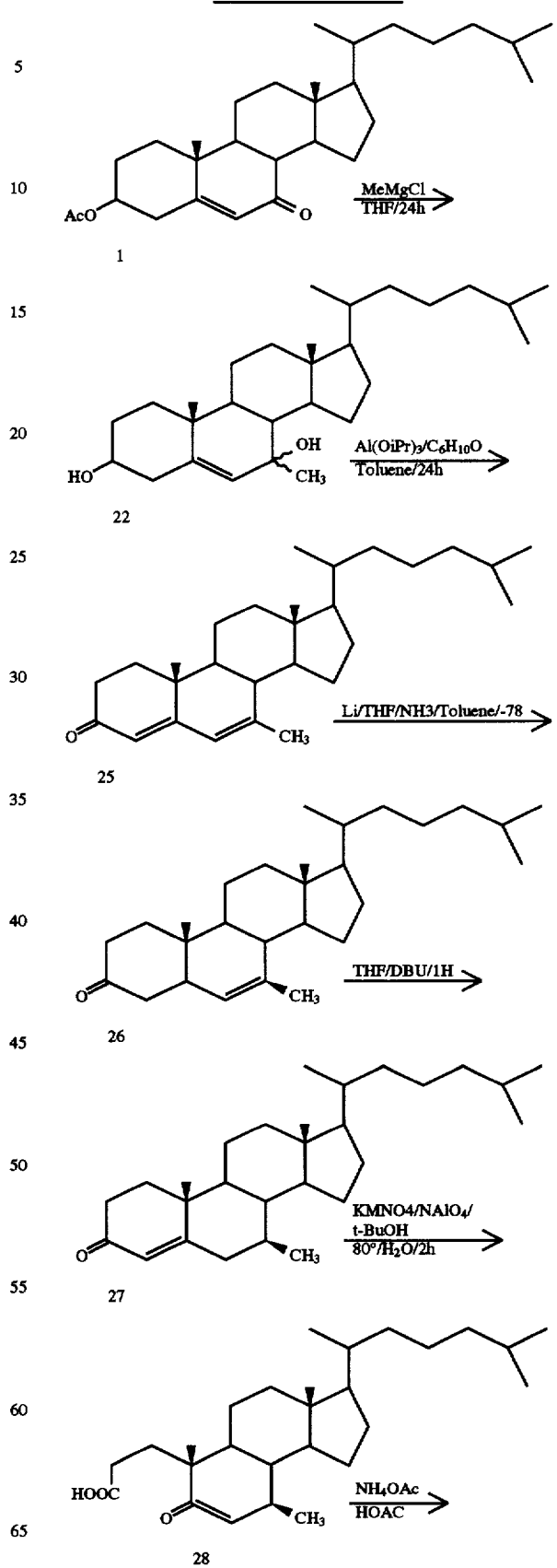

-continued
FLOWSHEET XXXVI

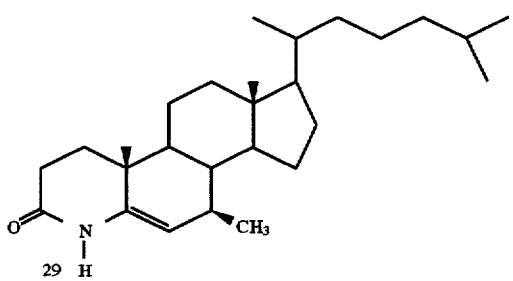
29

FLOWSHEET XXXVII

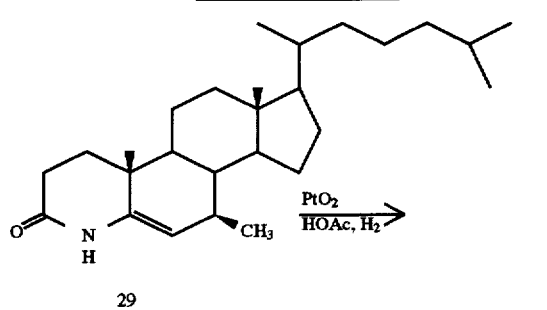
29

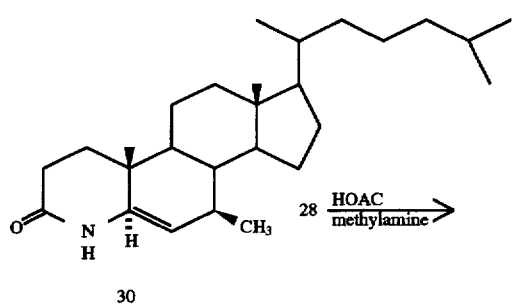
30

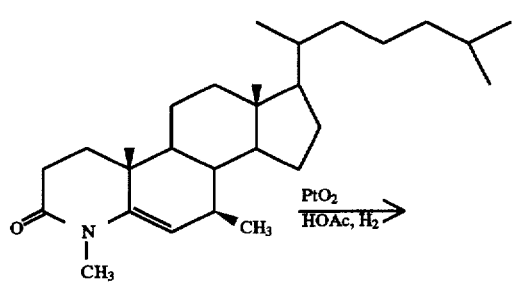
31

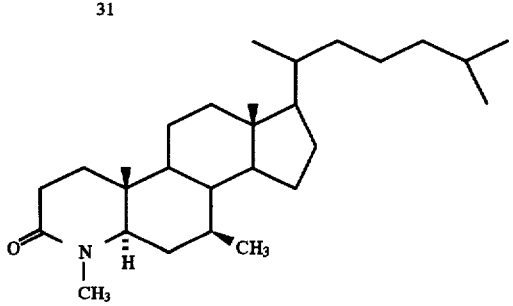
32

7-Beta Methyl Cholestane Series

The 7-beta methyl cholestane series is prepared by the analogously same route as described in Flowsheets A and B for the ethyl derivatives.

The methyl Grignard reagent is used to form the adduct 24, followed by Oppenauer oxidation to form 25, metal-ammonia reduction to form 26, double bond isomerization to form 27, seco-acid oxidation to form 28, and treatment by an ammonium salt to form 29, and reduction to form 30. Corresponding treatment with methylamine produces the corresponding 4-methyl-4-aza compounds, 31 and by reduction, 32.

FLOWSHEET XXXVIII

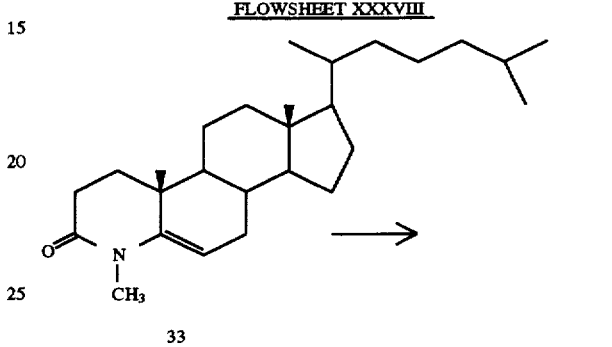
33

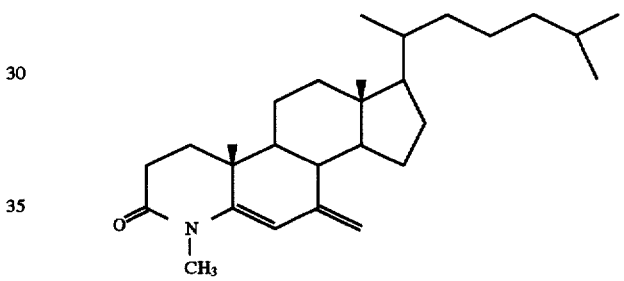
34

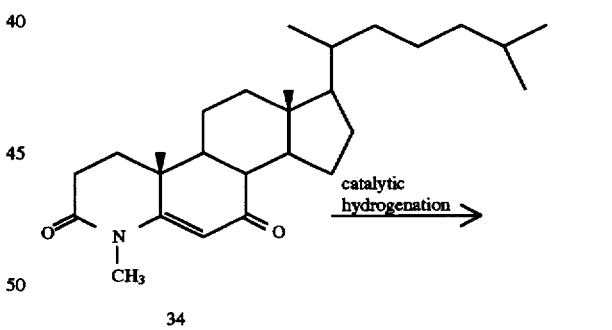
34

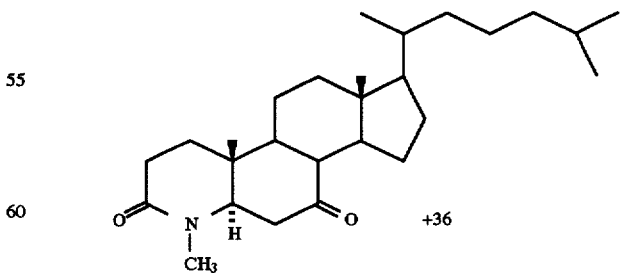
35

FLOWSHEET XXXIX

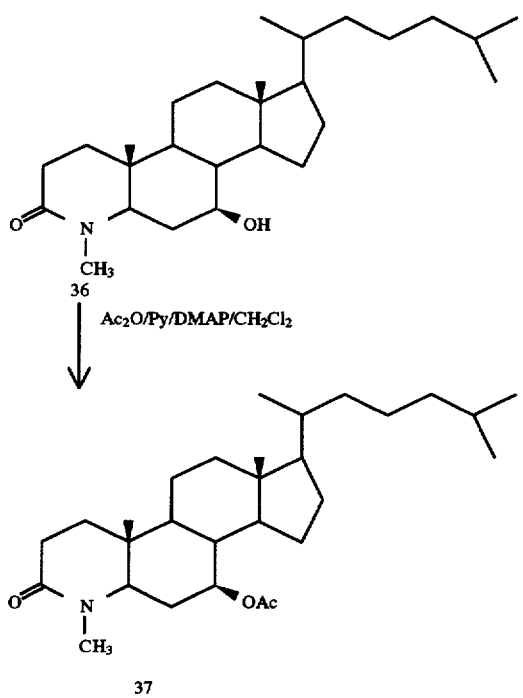

7-Beta Acetoxy Cholestane Series

The 7-beta acetoxy series is prepared by the oxidation of starting 33 to the 5-en-7-one 34 by the chromium hexacarbonyl procedure described for 1, or by pyridine-dichromate/ t-butyl hydroperoxide oxidation as described in the Examples. Subsequent noble metal, e.g. platinum, ruthenium, catalyzed reduction of 34 yields two products, the reduced 7-oxo compound 35, and 7-beta hydroxy compound 36. Acylation of 36 with acetic anhydride yields the 7-beta acetoxy compound 37.

FLOWSHEET XXXX

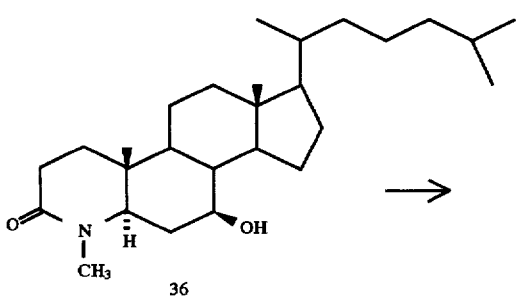

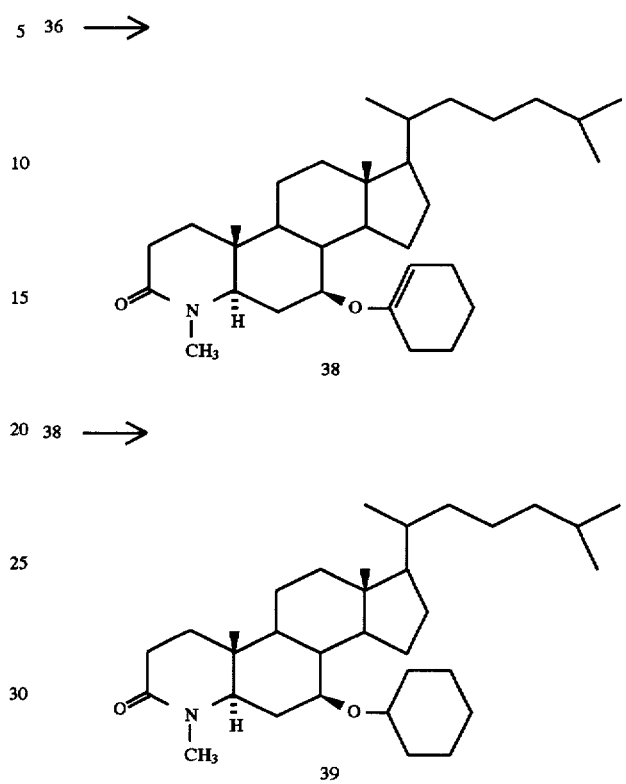

The 7-beta ethers in the cholestane series are prepared from the 7-beta-ol (7-beta hydroxy derivative). As illustrated in Flowsheet XXXX, the 4-N-methyl-7-beta ol 36 can be reacted with e.g. methyl iodide and sodium hydride in e.g., dimethylformamide, to produce the corresponding methyl ether 37. The other $C_1$–$C_4$ ethers can be prepared in the same manner.

The $C_3$–$C_6$ cycloalkyl ethers can be prepared according to the analogous procedure of Steroids, 1972, vol. 19, pp. 639–647 by R. Gardi, et al. For example, 36 can be reacted with 1,1-dimethoxy-cyclohexane to produce the enol ether 38, which can be reduced to the corresponding saturated compound by the use of palladium catalyzed hydrogenation.

FLOWSHEET XXXXI

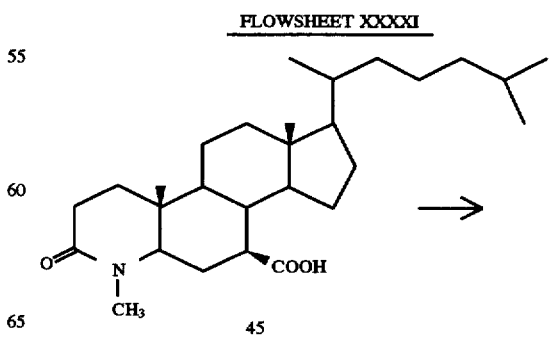

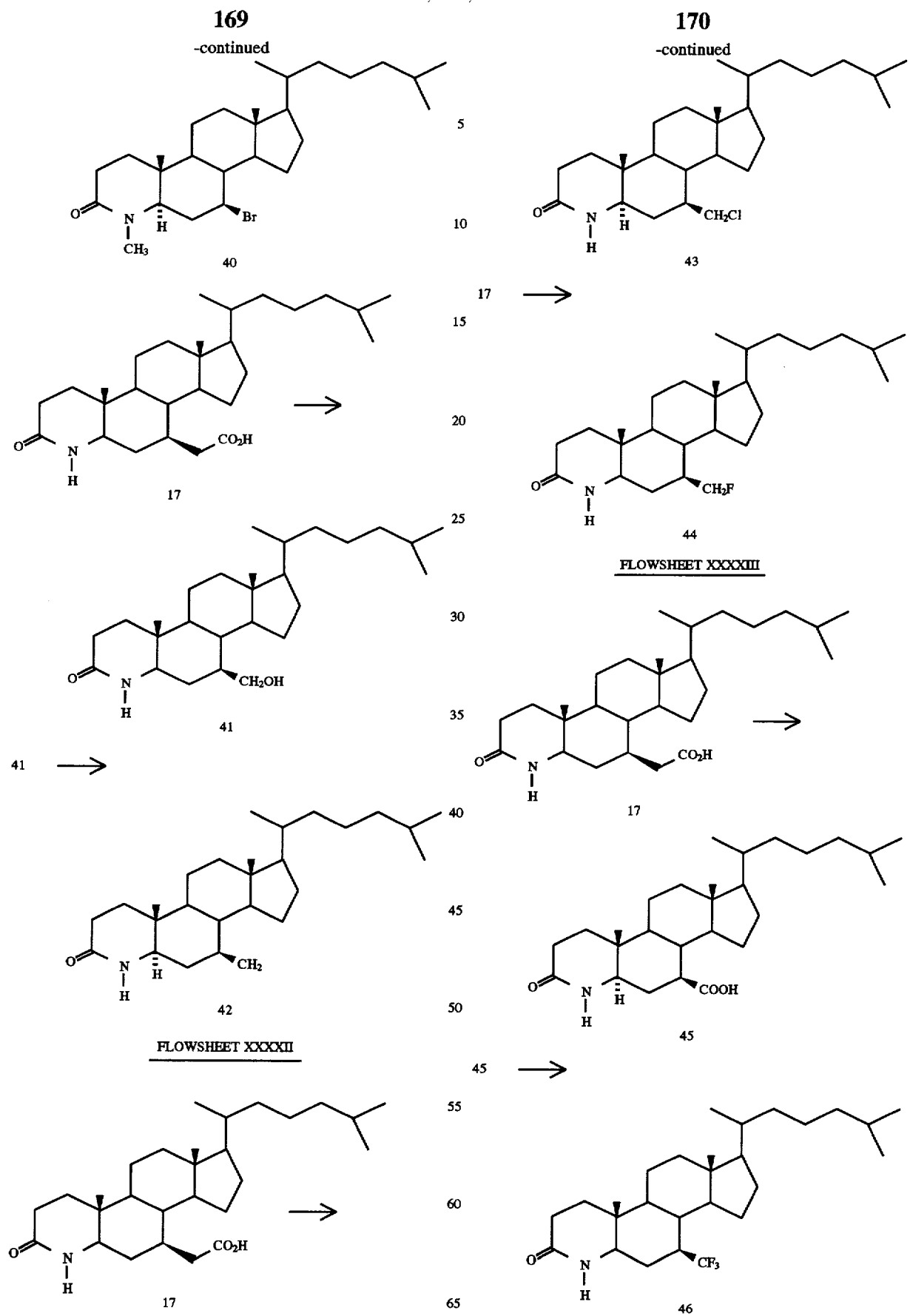

The 7-haloalkyl series is made by the procedure illustrated in Flowsheet K.

Starting with the 7-beta-carboxy, 45, this can be treated under Hunsdiecker reaction conditions, i.e. bromination of a mercury metal salt, to yield the 7-bromo derivative 40. The chloro and iodo derivatives can be made in substantially the same fashion.

The haloethyl compounds can be made by starting with the 7-carboxymethyl analog 17 which can be reacted with a reducing agent, e.g. borane, to produce the primary alcohol 41. This in turn can be reacted with triphenylphosphine and carbon tetrabromide to produce the bromoethyl derivative 42.

The halomethyl compounds can be produced starting with the carboxymethyl derivative 17. This is treated with lead tetraacetate under oxidative decarboxylation/halogenation conditions, with a chloride, bromide or iodide salt to yield, e.g. the 7-chloromethyl analog 43. The carboxymethyl compound 17 can be treated with a fluorinating agent ($XeF_2$) to yield the 7-fluoromethyl analog 44.

The 7-trifluoromethyl derivative can be made from the 7-carboxy derivative 45, by conventional Dast halogenation conditions using $SF_4$ to yield the 7-trifluoromethyl analog 46.

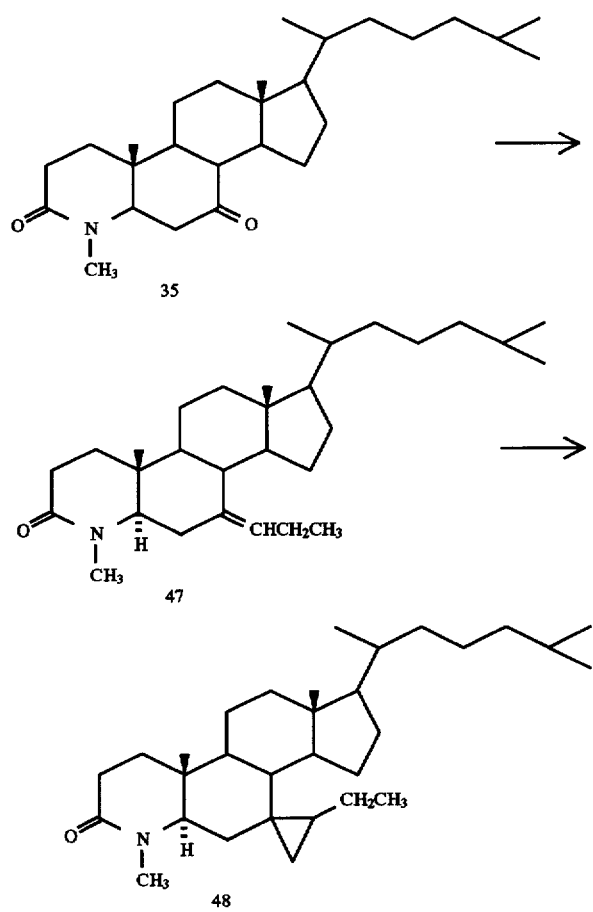

Flowsheet XXXXIV illustrates the 7-methylene series. As seen, the Wittig reaction,using e.g. $Ph_3PCH(CH_2CH_3)$, carried out on the 7-oxo compound 35, leads to the 7-(ethyl) methylene compound 47.

Subsequent treatment of 47 with the cyclopropyl forming reagents, $CH_2I_2$ and zinc, produces the ethyl cyclopropyl spiro compound 48, which is a mixture of stereoisomers.

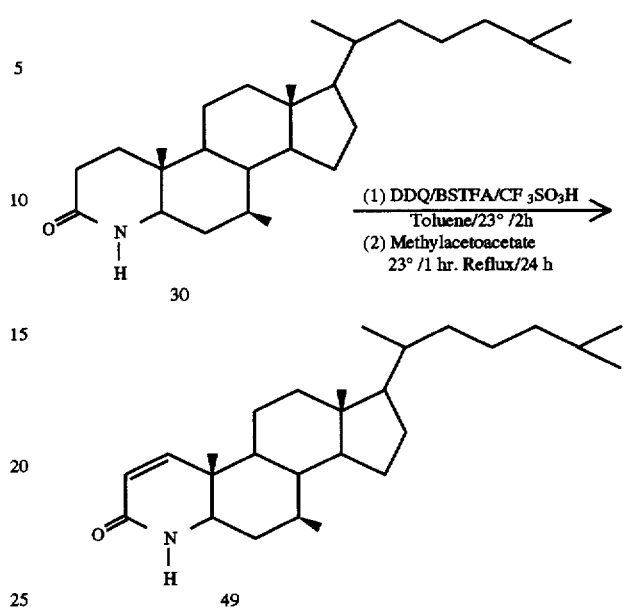

Flowsheet XXXXV illustrates the synthesis of the 1-ene 7-substituted analogs. For example compound 30 is stirred with DDQ, BSTFA (bis-trimethylsilyltrifluoroacetamide) and trifluoromethyl sulfonic acid in toluene at room temperature for 24 hours, methyl acetoacetate is added and the mixture refluxed for 24 hours and purified by preparative thin layer chromatography on silica gel using 3:1 chloroform/acetone to yield 49.

EXAMPLE 59

Synthesis of 7-Oxo-Cholesterol-3-acetate (59)

Cholesteryl acetate (CA) is known in the art and can be oxidized to the known 7-oxo-derivative 1 by the analogous procedure described in the JCS Perkins article by Pearson, supra.

EXAMPLE 60

Synthesis of 7-Ethyl-7-Hydroxy-cholesterol, (60)

To a solution of 59 from Example 59, being 5.0 g (11.32 mmol) in dry tetrahydrofuran at 0° C. was added dropwise 56.6 ml ethyl magnesium bromide (1M) over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield a yellowish-white foam. The Rf value was 0.2 (30% EtOAc/hexane). Proton NMR confirmed the assigned structure of the title compound 60 which was used in the next step without further purification.

EXAMPLE 61

Synthesis of 7-Ethyl-Cholest-4,6-Dien-3-one, (61)

The above Grignard product 2, 5.13 g (11.9 mmol) was dissolved in 50 ml toluene and cyclohexanone and about 40 ml of solvent distilled off under vacuum. To this was added 7.2 g aluminum isopropoxide and the reaction mixture refluxed overnight for 15 hours. The mixture was cooled, diluted with ethyl acetate, washed with sodium potassium tartarate, brine, and the organic layer was concentrated under vacuum and the residue steam distilled. The residue was extracted with ethyl acetate, the ethyl acetate layer, washed with brine, dried and purified by column chromatography on silica gel, eluting with 5% EtOAc/hexane to yield the title compound 3. Rf=0.58 (20% EtOAc/hexane). Mass spec: 412(M=1) by FAB, Calc'd. 411.9.

EXAMPLE 62

Synthesis of 7β-cholest-5-en-3-one, (62)

To a solution of 3.1 g of 61, from Example 61, in 46 ml ammonia, 10 ml THF, 10 milliliters toluene, was added 449 mg of metallic lithium in small pieces. After stirring the blue solution for 2 hours at −78° C., a solution of 1,2-dibromethane in 2 ml THF was added. After stirring the solution at −78° C. for 10 minutes, 2.1 g of ammonium chloride was added and the mixture stirred for 10 minutes. The excess ammonia was removed by evaporation under a nitrogen stream. The reaction mixture was diluted with brine, extracted with ethyl acetate. The organic layer was washed with brine, dried and concentrated to yield crude brown viscous liquid 4 which was used as such in Example 63.

Rf=0.70 (20% EtOAc/hexane). Mass Spec. 412 (EI); calculated MW 412.70.

EXAMPLE 63

Synthesis of 7β-ethyl-cholest-4-en-3-one (63)

To a solution of 62, from Example 62, being 3.1 g in 30 ml THF was added 1.1 ml DBU (1,8-diazabicyclo[5.4,0]undec-7-ene under nitrogen with stirring. The mixture was refluxed for 1.5 hours, then cooled and diluted with $NH_4Cl$. Then THF solvent was removed under vacuum and the residue extracted with ethyl acetate. The organic layer was then washed with water, brine, dried and concentrated under reduced pressure to yield a crude viscous oil. The titled product 63 was purified by chromatography on silica gel using 10% EtOAc/hexane as eluant.

Mass Spec 412 (EI), calc'd MW 412.70.

Rf=0.6 (20% EtOAc/hexane).

EXAMPLE 64

Synthesis of 7-ethyl-17β-(6-methyl-2-heptyl)-5-oxo-A-nor-3,5-secoandrostan-3-oic acid, (64)

To a solution of 1.0 g of 63 in 18 ml t-butyl alcohol at 80° C. was added 300 mg sodium carbonate in 1.8 ml water followed by a dropwise addition over 15–20 minutes of a mixture of 2.74 g sodium periodate with 20.3 mg potassium permanganate in 15 ml water. The reaction mixture was heated at 80° C. for 2 hours, cooled, filtered, the residue washed with water, and then the filtrate concentrated under vacuum, acidified with aqueous HCl, extracted with ethyl acetate and the organic layer washed with aqueous $NaHSO_3$, brine, dried and concentrated to yield crude 64. The proton NMR continued the assigned structure. Fast atom bombardment yielded an m/z molecular ion of 434(m+2); calculated 432.69.

EXAMPLE 65

Synthesis of 7-Ethyl-4-methyl-4-aza-cholest-5-en-3-one, (65)

To a solution of 64, 500 mg in 10 ml ethylene glycol was added 1.3 g sodium acetate and 1.0 g methylamine hydrochloride. After stirring the reaction mixture 4 hours at 180° C., the mixture was cooled, diluted with water, extracted with ethyl acetate, dried and concentrated to afford crude title compound 65. Proton NMR confirmed the assigned structure.

Rf=0.70 (20% EtOAc/hexane).

Mass Spectral m/z ion (FAB) showed 429 (M+2), calculated, 427.72.

Analysis: Calc. for $C_{29}H_{49}NO$ Calc.: C; 81.44; H, 11.55; N, 3.27 Found: C, 82.19; H, 10.92; N, 3.11.

EXAMPLE 66

Synthesis of 7-Ethyl-4-methyl-4-Aza-Cholestan-3-one, (66)

To a solution of 7 from Example 65, being 180 mg in 5 ml acetic acid was added 54 mg platinum dioxide and the resulting mixture was evacuated and flushed with hydrogen. The reaction was shaken overnight at room temperature under hydrogen. Filtered, washed solid with EtOAc, combined EtOAc layers were washed with aqueous $NaHCO_3$, brine, dried, concentrated to yield the title compound 66.

Mass spectral analysis by FAB yielded m/z ion of 431 (m+2), calculated 429.74.

Analysis for $C_{29}H_{51}NO$ Calc: C, 81.06; H, 11.96, N, 3.26 Found: C, 81.42; H, 12.24; N, 3.16

EXAMPLE 67

Synthesis of 7-Ethyl-4-Aza-Cholest-5-en-3-one, (67)

The seco acid 64, 0.5 g, and ammonium acetate, 0.5 g., in 3.5 ml acetic acid were refluxed for 3 hours. The reaction mixture was cooled, water added and then extracted with ethyl acetate. The organic layer was dried over sodium sulfate and concentrated to yield a residue which was eluted on a silica gel column with 10% EtOAc/hexane to give pure title compound 67, mp. 147°–149° C.

Mass Spec. 414 (Mtl). Calc'd; 413.69. Rf=0.45 (30% EtOAc/hexane).

Analysis for $C_{28}H_{49}NO$, MW 413.69 Calc.: C, 81.30; H, 11.45; N, 3.39 Found: C, 81.30: H, 11.87; N, 3.45

EXAMPLE 68

Synthesis of 7β-Ethyl-4-aza-5α-cholestan-3-one, (68)

Following the general analogous procedure described in Example 66, 67 was catalytically hydrogenated to yield the titled compound, 68. Chromatography on silica gel with 50% EtOAc:hexane eluant yielded pure product, mp. 169°–170° C.

Analysis for $C_{28}H_{49}NO$, MW=415.17. Calcd: C; 80.90; H, 11.88; N, 3.37 Found: C; 81.02; H, 12.57; N, 3.47.

Mass Spec.: 416 (M+1)

Rf=0.30 (30% EtOAc/hexane)

EXAMPLE 69

Synthesis of 7-Allyl-3,7-dihydroxy-cholest-5-ene (69)

Following the analogous general Grignard procedure of Example 2, allyl magnesium bromide was reacted with Compound 1 in dry THF to yield the titled product 69. Proton NMR confirmed the assigned structure.

Mass Spec. 441 (M+1). Calc'd. 440.71. Rf=0.25 (30% EtOAc/hexane).

EXAMPLE 70

Synthesis of 7-allyl-cholest-4,6-dien-3-one, (70)

Following the analogous general Oppenauer oxidation procedure of Example 61, compound 69 was oxidized to yield the titled compound 70. Proton NMR confirmed the assigned structure as well the (FAB) mass spec. (M+1) Calc'd. 422.35. Rf=0.78 (30% EtOAc/hexane).

EXAMPLE 71

Synthesis of 7-Allyl-Cholest-5-en-3-one, (71)

Compound 70, was subjected to the analogous metal-ammonia reduction conditions of Example 62 to yield the title compound 71.

Rf=0.5 (5% EtOAc/hexane).

EXAMPLE 72

Synthesis of 7-Allyl-Cholest-4-en-3-one, (72)

Following the general DBU catalyzed isomerization conditions of Example 63, compound 71 was analogously treated to yield the title compound 72.

Mass Spec. 425 (M+1) by FAB. Calc'd.: 424.37

Rf=0.45 (5% EtOAc/hexane).

EXAMPLE 73

Synthesis of 7-Propyl-cholest-4-en-3-one, (76)

1.0 g. of the 7-allyl-enone 72, 5 ml. EtOAc and 50 mg. triphenylphosphine rhodium chloride (Wilkinson's catalyst) were allowed to stir two hours (under $H_2$ atmosphere). The reaction products were filtered through 25 ml. silica gel, and evaporated to dryness to yield fairly pure title product, 76, as confirmed by proton NMR.

Mass Spec. 427 (M+1). Calc'd.: 426.39 Rf=0.15 (5% EtOAc/hexane).

EXAMPLE 74

Synthesis of 7-Propyl-5-oxo-A-nor-3,5-seco-cholestanoic acid, (77)

Following the general procedure of Example 64 for the oxidative Ring A cleavage, compound 76 (7-propyl analogue) was analogously treated to yield the above-titled seco-acid 77. The assigned structure was confirmed by proton NMR. Mass Spec.: 447 (M+1) (FAB). Calc'd.: 446.38 Rf=0.1 (20% EtOAc/hexane).

EXAMPLE 75

Synthesis of 7-Propyl-4-methyl-4-aza-cholest-5-en-3-one, (78)

Following the general procedure of Example 65, compound 77, was analogously treated with methylamine hydrochloride and sodium acetate in ethylene glycol to yield the above-titled liquid product 78. The assigned structure was continued by proton NMr.

Mass Spec. 442 (M+1) (FAB), Calc'd.: 441.74 C, H, N analysis for C H N O as 0.2 $H_2O$, MW=441.74; Calcd: C, 80.91; H, 11.63; N, 3.15. Found: C, 81.00; H, 12.06; N, 2.93.

Rf=0.3 (20% EtOAc/hexane).

EXAMPLE 76

Synthesis of 7-Propyl-4-methyl-4-aza-5a-cholestan-3-one, (79)

Following the analogous general procedure of Example 66, compound 78 was catalytically hydrogenated in HOAc to yield the title liquid compound 79. Proton NMr continued the assigned structure. Mass spec. 444 (M+1) (FAB), C, H, N analysis for C H N; Calcd: C, 81.19; H, 12.05; N, 3.16. MW=443.41. Found: C, 80.78; H, 12.06; N, 3.22.

Rf=0.17 (20% EtOAc/hexane).

EXAMPLE 77

Synthesis of 7-Propyl-4-aza-cholest-5-en-3-one, (80)

Following the analogous procedure of Example 67, compound 77 was treated with ammonium acetate in acetic acid to yield the titled compound, 80. Recrystallized from EtOAc/$Et_2O$ to yield a white crystalline solid, mp. 91°–94° C., C, H, N analysis as the 0.25 $H_2O$ hydrate: Calc'd MW 427.39 Calcd: C, 80.59; H, 11.54; N, 3.24. Found: C, 80.59; H, 11.69; N, 3.36.

Mass Spec. 428 (M+1).

EXAMPLE 78

Synthesis of 7-Propyl-4-aza-5α-cholestan-3-one, (81)

Following the analogous procedure described in Example 66, compound 80 was catalytically hydrogenated to yield the title compound 23, mp. 65°–68° C.

Analysis for C, H, N, calc'd as 0.25 $H_2O$ hydrate: Calcd: C, 80.21; H, 11.95; N, 3.23. Found: C. 80.20: H, 12.14; N, 3.07.

Proton nmr

Mass Spec.=430 (M+1) calc'd MW 429.40.

Rf=0.12 (20% EtOAc/hexane).

EXAMPLE 79

Synthesis of 7-Methyl-7-Hydroxy-cholesterol, (82)

Following the analogous Grignard procedure of Example 59, cholesteryl acetate-7-one 59 was reacted with methyl magnesium bromide under standard Grignard conditions to yield title compound 82, a solid. NMR confirmed the assigned structure and mass spectral analysis confirmed the molecular weight.

EXAMPLE 80

Synthesis of 7-Methyl-Cholest-4,6-Dien-3-one, (83)

Following the analogous procedure of Example 60, the above Grignard product 82, was subjected to Oppenauer oxidation conditions to yield the title compound, 7β-methyl-cholest-4,6-dien-3-one, 83.

EXAMPLE 81

Synthesis of 7β-methyl-cholest-5-en-3-one, (84)

Following the analogous procedure of Example 62 for the metal-ammonia reduction, 83 was similarly treated with lithium in ammonia/THF/toluene to yield title compound 84.

EXAMPLE 82

Synthesis of 7β-methyl-cholest-4-en-3-one (85)

Following the general isomerization procedure of Example 63 using DBU in THF, 84 was analogously treated to yield the title compound 85.

EXAMPLE 83

Synthesis of 7-methyl-17β-(2,6-Dimethylhexyl)-5-oxo-A-nor-3,5-secoandrostan-3-oic acid, (86)

Following the general procedure of Example 64 for the oxidative Ring A cleavage, compound 85 was analogous

177 treated to yield the above titled seco-acid 86. The proton NMR confirmed the assigned structure.

EXAMPLE 84

Synthesis of 7-Methyl-4-aza-cholest-5-en-3-one, (87)

Following the general procedure of Example 67, compound 86 was analogously treated with ammonium chloride in acetic acid to yield the above-titled product 87.

Mass Spectral m/z ion (FB) showed 400.2 (M+1) (M+2), calculated, 399.

EXAMPLE 85

Synthesis of 7-Methyl-4-Aza-Cholestan-3-one, (88)

Following the analogous general procedure of Example 66, compound 87 was catalytically hydrogenated in HOAc to yield the title compound 8.8.

Mass spectral analysis by EI yielded m/z ion of 401 calculated 401.

EXAMPLE 86

Synthesis of 7-Methyl-4-methyl-4-Aza-Cholest-5-en-3-one, (89)

The seco acid 86, was treated analogously as in Example 65 to give pure title compound 89.

Mass Spec. 414 (m+1) by FAB, calc'd., 413.

EXAMPLE 87

Synthesis of 7β-Methyl-4-methyl-4-aza-5a-cholestan-3-one, (90)

Following the general analogous procedure described in Example 66, 89 was catalytically hydrogenated to yield the titled compound, 90. Chromatography on silica gel with 30% EtOAc/hexane, eluant yielded pure product.

Mass Spec. (EI) 415, calc'd., 415.

EXAMPLE 88

Synthesis of 4-methyl-4-aza-cholest-5-en-3,7-dione, (92)

An oxidation procedure is carded out on 4-methyl-4-aza-cholest-5-en-3-one 91 to yield the title compound, 92. (See U.S. Pat. No. 3,264,301 by Doorenboos and J. Org. Chem. 1961, Vol. 26, p.4548.) The compound 91 was heated at 70° C. with a mixture of pyridinium dichromate/t-butyl hydroperoxide in benzene over a 3–4 hour period to produce 92.

EXAMPLE 89

Synthesis of 7β-Acetoxy-4-methyl-4-aza-5a-cholestan-3-one (95)

Compound 92 is hydrogenated by the analogous procedure of Example 66 to produce the 7-H analog 93, and the 7β-ol, 94. Acylation of 94 with acetic anhydride, in the presence of pyridine, 4-dimethyl-aminopyridine in methylene chloride at 23° C. for 24 hrs. produces the title compound 95.

EXAMPLE 90

Synthesis of 7-Beta Methyl-4-aza-5α-cholest-1-en-3-one (107)

To a solution of 280 mg. (0.698 mmol) of 88 in 4 milliliters toluene, was added 178.8 mg. DDQ, 0.7186 mg. BSTFA and 8.163 mg. triflic acid and the reaction contents allowed to stir at room temperature for 24 hours. Methyl acetoacetate, 8.1 mg., was added and the reaction refluxed for 24 hours. The contents were cooled, diluted with ethyl acetate, washed with aqueous sodium carbonate, aqueous sodium bisulfite, brine, dried over magnesium sulfate and concentrated to yield an oil. The crude compound was purified by preparative TLC on silica gel, eluting with 3:1 $CHCl_3$/acetone to yield pure 107, whose proton NMR confirmed the assigned structure.

The following Table lists the unique proton NMR values (400 MHz in $CDCl_3$) for each compound. The data are reported as: s=singlet, d=doublet, m=multiplet, J=coupling constant. The absorption values are given del (δ) units and are illustrated for the C-18, C-19 and C-21 angular ring methyl protons and protons associated with unique portions of the molecule.

The numbering of the 4-aza steroid is given by the following structure;

TABLE

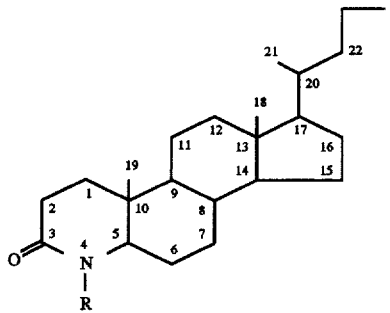

| Compound No. | 18-CH₃ | 19-CH₃ | 21-CH₃ | Others |
|---|---|---|---|---|
| 60 | s 0.660 0.662 | s 1.030 1.060 | d 0.940 J = 7 | 6H s 6.120 (values given for second isomer) |
| 61 | s 0.755 | s 1.061 | d 0.915 J = 7 | 4H and 6H s 5.61, 5.97 |
| 62 | s 0.720 | s 1.110 | d 0.930 J = 7 | 4 CH₂ m 2.83–3.28 |
| 63 | s 0.730 | s 1.12 | d 0.930 J = 7 | 4H s 5.74 |
| 64 | s 0.66 | s 0.963 | d 0.894 J = 7 | |
| 65 | s 0.692 | s 0.977 | d 0.908 J = 7 | N—CH₃ s 3.153 |
| 66 | s 0.690 | s 0.830 | d 0.900 J = 7 | N—CH₃ s 2.93 |
| 67 | s 0.653 | s 0.991 | d 0.903 J = 7 | 6H d 4.91 J = 4 |
| 68 | s 0.675 | s 0.808 | d 0.893 J = 7 | 5H, m, 2.97 3.13 |
| 69 | s 0.66 | s 0.90 | d 0.915 J = 7 | allylic H m(5.8–5.94) |
| 70 | s 0.78 | s 1.07 | d 0.96 J = 7 | allylic H m(5.73–5.85) |
| 71 | s 0.70 | s 1.08 | d 0.90 J = 7 | 6H, s(5.23) |
| 72 | s 0.73 | s 1.13 | d 0.93 J = 7 | 4H s 5.72 |
| 73 | s 0.71 | s 1.13 | d 0.93 J = 7 | 4H s 5.71 |
| 77 | s 0.65 | s 0.963 | d 0.91 J = 7 | |
| 78 | s 0.691 | s 0.974 | d 0.902 J = 7 | (6H)-d, 4.92 (J = 4)(N— CH₃) s 3.16 |
| 79 | s 0.665 | s 0.795 | d 0.883 J = 7 | (N—CH₃) s 2.92 5H m(2.96–3.00) |
| 80 | s 0.680 | s 1.01 | d 0.890 J = 7 | (6H) d 4.86 J = 4 |
| 81 | s 0.680 | s 0.808 | d 0.884 J = 7 | 5H m(3.0–3.1) |

TABLE-continued

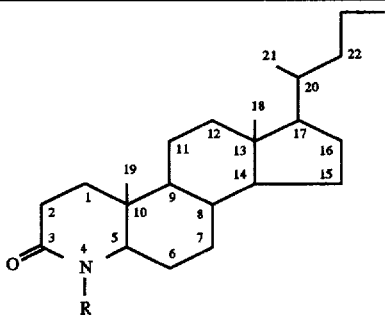

| Compound No. | 18-CH₃ | 19-CH₃ | 21-CH₃ | Others |
|---|---|---|---|---|
| 82 | s, 0.68, 0.69 | s, 0.94, 1.04 | d 0.91 J = 7 | 6H, s, 5.19, 5.21 |
| 83 | s, 0.76 | s, 1.07 | d 0.92 J = 7 | 4H, 6H 5.59, 5.92 |
| 85 | s, 0.70 | s, 1.15 | d 0.92 J = 7 | 7-CH₃, d, 1.04, J = 6.5 4H, s, 5.71 |
| 86 | s, 0.69 | s, 1.12 | d 0.92 J = 7 | 7-CH₃, d, 0.96, J = 6.5 |
| 87 | s, 0.69 | s, 1.04 | d 0.91 J = 7 | 7-CH₃, d, 0.97, J = 6.5 6H, d, 4.59, J = 3.0 |
| 88 | s, 0.67 | s, 0.835 | d 0.91 J = 7 | 7-CH₃, d, 1.00, J = 6.5 5H, dd, J = 3.3, 12.63 |
| 89 | s, 0.69 | s, 1.00 | d 0.95 J = 7 | 7-CH₃, d, 1.05, J = 6.5 6H, d, J = 3.0 |
| 90 | s, 0.68 | s, 0.825 | d 0.91, J = 7H | 7-CH₃, d, 1.05, J = 6.5 4-CH₃, s, 3.92 |
| 91 | s, 0.69 | s, 1.23 | d 0.91 J = 7 | C6-s, 5.42 N—CH₃, s, 3.14 Mass Spec (EI) = 413 |
| 107 | s, 0.69 | s, 0.90 | d 0.915 J = 7 | C-7CH₃, 1.02, d, J = 6, C-2, 1H, 5.79, dd J = 2.5 J = 9.1 |
| 108 | s, 0.62 | s, 1.01 | d 0.86 J = 7 | C-5, 1H, 3.08, dd J = 3.87 J = 12.9 C-7Ph, 5H, m, 7.1–7.3 |
| 109 | s, 0.63 | s, 1.02 | d 0.8 J = 7 | C-5, 1-H, 3.2, dd J = 5.88 J = 10.5 C-7Ph, 5H, m, 7.08–7.3 |

EXAMPLE 91

Synthesis of 20(R)-hydroxy-16β-Methyl-preg-4-en-3-one (92)

To a suspension of 3β-Hydroxy-16β-methyl-preg-5-en-20(R)-ol (2.4 g, 7.22 mmol) in cyclohexanone (22 mL) and toluene (36 mL) heated to reflux in an oil bath (140° C.) and collecting 15 mL of distillate, was added a solution of aluminum isopropoxide (1.5 g. 7.22 mmol) in toluene (10 mL). The mixture was heated to reflux while collecting distillate over 1 h, cooled to room temperature, added water (2.5 mL) and Celite (1.3 g), stirred 10 minutes, filtered, washed Celite with hot ethyl acetate (100 mL), and concentrated to give solid. Purification by flash chromatography on silica gel (20% ethyl acetate/hexane) gave 2.10 g (88%) of 92.

EXAMPLE 92

Synthesis of 20(R)-Hydroxy-5-oxo-A-nor-3,5-secopregnan-3-oic acid (93)

To a suspension of 3 (2.1 g, 6.35 mmol) in tert-butyl (25 mL) at 50° C. (oil bath) was added a solution of sodium carbonate (0.73 g, 6.89 mmol) in water (4 mL) and the mixture was heated to 80° C. while adding a hot solution of sodium periodate (6.98 g, 32.6 mmol) and potassium permanganate (0.078 g, 0.49 mmol) in water (25 mL) over 15 minutes. The reaction mixture was heated at reflux temperature for 40 minutes, cooled to room temperature, filtered through celite, washed with hot water (20 mL, containing a trace of sodium bisulfite) and concentrated to a small volume. To this residue was added water (100 mL), acidified to pH ~2–3 (hydrochloric acid), extracted with methylene chloride (2×50 mL) and washed with a 5% sodium chloride solution (25 mL). The organic layer was dried (MgSO₄) and evaporated to give 1.68 g (75%) of 93 of sufficient purity for the next step.

EXAMPLE 93

Synthesis of 20(R)-Hydroxy-4,16β-dimethyl-4-aza-preg-5-en-3-one (5-(20R))

A suspension of 93 (1.68 g, 4.79 mmol), methylamine hydrochloride (1.78 g, 26.4 mmol) sodium acetate (2.16 g, 26.4 mmol) in ethylene glycol (20 mL) was slowly heated to 185° C. over 2 h. After 2.5 h the reaction mixture was cooled to 30° C., water (200 mL) was added to afford a solid that was filtered, washed with water, and dried. Purification by flash chromatography on silica gel (1% methanol/methylene chloride as eluent) gave 1.05 g (63%) of pure isomer 5-(20R).

EXAMPLE 94

Synthesis of 20(R)-Hydroxy-4,16β-dimethyl-4-aza-5α-pregnan-3-one (6-(20R))

A solution of 5-(20R) (1.05 g, 3.04 mmol) in glacial acetic acid (30 mL) was hydrogenated at atmospheric pressure in the presence of platinum oxide (200 mg) for 3.5 h at room temperature. The catalyst was removed by filtration, the filtrate evaporated to dryness, coevaporated with toluene (3×50 mL) and evaporated to give a solid. The solid was purified by recrystallization from ethyl acetate (80 mL) to give 843 (81%) of pure 6-(20R).

EXAMPLE 95

Synthesis of 20(R)-acetoxy-4,16β-dimethyl-4-aza-5α-pregnan-3-one (7-(20R))

To a suspension of 6-(20R) (50 mg, 0.14 mmol) in dry pyridine (0.50 mL) was added acetic anhydride (0.25 mL) and 4-dimethylaminopyridine (5 mg, 0.04 mmol) and the reaction mixture was stirred for 1 h. The reaction mixture was concentrated to dryness, methylene chloride (25 mL) was added, washed with water (2×10 mL), dried (MgSO₄), and concentrated to give a solid. Purification by flash chromatography on silica gel (80% ethyl acetate/hexane) gave 50 mg (89%) of 7-(20R).

EXAMPLE 96

Synthesis of 4,16β-Dimethyl-4-aza-5α-pregnane-3,20-dione (97)

To a solution of 6-(20R,S) (46.5 mg, 0.134 mmol) in 2 ml dry CH₂Cl₂ was added N-Methylmorpholine N-oxide (23.5 mg, 0.201 mmol), powdered 4A molecular sieves (67 mg), and Tetrapropylammonium perruthenate (TPAP, 2.4 mg, 0.007 mmol). The mixture was stirred at room temperature under $N_2$ for two hours. The reaction mixture was then diluted with ethyl acetate (10 ml), filtered thru a pad of silica gel, and eluted with ethyl acetate. The ethyl acetate was evaporated in vacuo to obtain the product 97.

EXAMPLE 97

Synthesis of 20-Hydroxy-4,16β,20-trimethyl-4-aza-5a-pregnane-3-one (98)

102 mg of 97 were dissolved in 5 ml of distilled THF and cooled to −60° C. under $N_2$. Methyl Grignard (0.125 ml, 0.382 mmol) was added and the reaction was stirred at −60° C. for five minutes before being allowed to warm to room temperature. After 90 minutes, TLC (4% $CH_3OH/CH_2Cl_2$) showed approximately 50% conversion of the staring material 97. The reaction mixture was cooled to 0° C., another portion of methyl Grignard was added (0.125 ml), and the reaction was stirred for 90 minutes at room temperature. The reaction was quenched with saturated $NH_4Cl$ and the THF was evaporated in vacuo. The residue was dissolved in 100 ml $CH_2Cl_2$/25 ml $H_2O$. The organic layer was separated, washed with brine, dried with $MgSO_4$, and evaporated. Pure 9 was obtained via HPLC of the reaction product (8 m silica, 19 mm×300 mm, 0% to 5% $CH_3OH/CH_2C_{12}$).

EXAMPLE 98

Synthesis of 20(R)-methoxy-4,16β-dimethyl-4-aza-5α-pregnan-3-one (99)

To a suspension of compound 6-(20R) (40 mg, 0.115 mmol) in N,N-dimethylformamide (0.65 mL) was added potassium hydride (25 mg, 0.23 mmol) and stirred for 10 min at room temperature. Iodomethane (36 μL, 0.58 mmol), and the reaction mixture was stirred overnight at room temperature. An additional amount of iodomethane (36 μL, 0.58 mmol) was added, and the reaction mixture was stirred for 3 days at room temperature. The mixture was diluted with methylene chloride (30 mL), and the solution was washed with 2N hydrochloric acid, saturated sodium hydrogencarbonate solution, dried (magnesium sulfate), and evaporated. The product was purified by means of flash silica gel chromatography using 1% methanol/methylene chloride as eluant; yield 15 mg (36%).

EXAMPLE 99

Synthesis of 20(R)-allyloxy-4,16β-dimethyl-4-aza-5α-pregnan-3-one (100)

Following the analogous procedure as in Example 98, but substituting allyl bromide in place of iodomethane, the 20(R)-allyloxy derivative 100 was obtained.

EXAMPLE 100

Synthesis of 20(R)-n-propyloxy-4,16β-dimethyl-4-aza-5α-pregnan-3-one (101)

Hydrogenation of 100 in ethyl acetate in the presence of 10% palladium-on-charcoal for 40 min at room temperature afforded the 20(R)-n-propyloxy derivative 101.

EXAMPLE 101

Synthesis of 4,16β-dimethyl-3-oximino-4-aza-5α-pregnan-3-one

A mixture of 4,16β-dimethyl-4-aza-5a-pregnan-3,20-dione (300 mg, 0.87 mmol), sodium acetate (240 mg, 2.93 mmol), and hydroxylamine hydrochloride (195 mg, 2.81 mmol) in ethanol (12 mL) was heated overnight at 80° C. The cooled mixture was diluted with water, and the resulting white solid was filtered, washed with water, and dried by suction and then in a desiccator under high vacuum; yield 260 mg (83%).

EXAMPLE 102

Synthesis of 20(R,S)-amino-4,16β-dimethyl-4-aza-5α-pregnan-3-one

A solution of the product of Example 101 (220 mg, 0.61 mmol) in ethanol (17.5 mL) and glacial acetic acid (7.5 mL) was stirred for 24 h in the presence of platinum oxide (68 mg) under an atmosphere of hydrogen gas. The catalyst was removed by filtration through a pad of Celite and the filter washed with ethanol. The combined filtrate and washings were evaporated under diminished pressure and coevaporated with toluene. The residue was taken up in methylene chloride, and the solution was washed with saturated sodium hydrogencarbonate solution, saturated brine solution, dried (sodium sulfate), and evaporated to afford the desired 20-amino derivative as a mixture of R and S diastereoisomers (185 mg). This material was employed without further purification in the preparation of Example 103 below.

EXAMPLE 103

Synthesis of 20(R) and 20(S)-Acetamido-4,16β-dimethyl-4-aza-5α-pregnan-3-one

A sample of the crude amine product of Example 102 (75 mg) was dissolved in methylene chloride (3 mL) and treated with pyridine (75 μL) and acetic anhydride (50 μL) for 3 h at room temperature. The solution was then diluted with methylene chloride, washed with 1N hydrochloric acid, saturated sodium hydrogencarbonate solution, saturated brine solution, dried (sodium sulfate), and evaporated. The product was obtained as a mixture of 20R and 20S isomers, which were resolved by means of flash silica gel chromatography using 30% acetone in methylene chloride as eluant. The products were characterized by mass and 400 MHz NMR spectroscopy. Analysis of their NMR spectra in chloroform-d continued that the β-configuration was maintained at the 17-position.

EXAMPLE 104

Synthesis of 4,16β-dimethyl-2-methylene-4-aza-5α17α-pregnane-3-one

Sodium hydride (NaH, 60% in mineral oil) was washed with hexane and dried over $N_2$. To 1.5 mL of DMSO is added the washed NaH (30 mg, 1.24 mmol) and stirred with heating at 75° for 30 minutes. A light green solution resulted. Add to this a solution of triphenylphosphine methylbromide (443 mg, 1.24 mmol) in 2.5 mL of DMSO. A darker yellow solution resulted. Then add to this a solution of the pregnanone 97 (100 mg, 0.29 mmol) in 1.5 mL of DMSO/benzene. Stir at 60° for 16 hours. Allow to cool to room temperature and dilute with $CH_2Cl_2$ and $H_2O$. Extract the aqueous layer with $CH_2Cl_2$. Wash organic layers with saturated solution of NaCl. Dry over $MgSO_4$. Filter and concentrate in vacuo. The resulting oil was purified by medium pressure column chromatography on silica gel by eluting a gradient from 0 to 4% MeOH in $CH_2Cl_2$. Medium pressure chromatography did not separate product cleanly, so elute through a 23×250 mm 10 m Whatman silica column with an HPLC gradient from 0 to 4% MeOH in $CH_2CH_2$. $^1H$ NMR 14848-135B ($CDCl_3$, 400 MHz) indicates product with the α-configuration at $C_{17}$-Mass spectrometry gives M+1=344.

There is next presented Table 5, which gives representative physical data for specific compounds synthesized by the methods of the preceeding examples. The values for variables $R_4$, $R_{16}$ and $R_{17}$ are with reference to the following general structural formula XX:

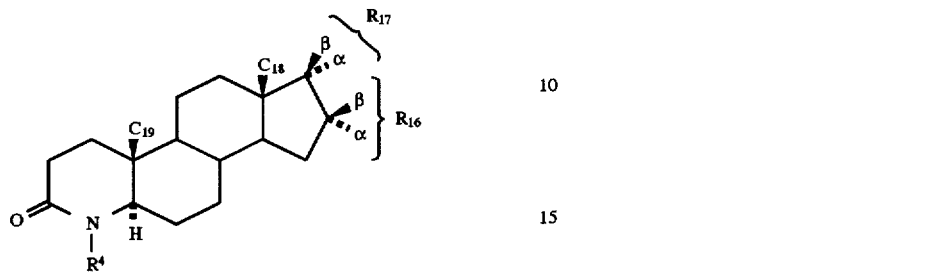

| $R_4$ | $R_{16}$ | $R_{17}$ | | $^1$H-NMR $C_{18}$ | $C_{19}$ | other | Melting pt. °C. | Mass spec. |
|---|---|---|---|---|---|---|---|---|
| $CH_3$ | β-$CH_3$ | β-$CO_2$-n-$C_3H_7$ | | 0.85 | 0.92 | 4.00 (m) | | |
| $CH_3$ | β-$CH_3$ | β-CON($C_2H_5$)$_2$ | | 0.87 | 1.12 | 3.01, 3.12, 3.35, 6.65 (m) | | |
| $CH_3$ | β-$CH_3$ | β-CONH-t-$C_4H_9$ | | 0.87 | 0.96 | 1.31 (s), 5.08 (s) | | |
| H | α-$CH_3$ | β-CH(OCOCH$_3$)CH$_3$ | | 0.55 | 0.80 | 0.99 (d) | 244–5 | 375 (M+) |
| H | α-$CH_3$ | β-CG(OH)CH$_3$ | | 0.78 | 0.89 | 1.00 (d) | 275–6 | 333 (M+) |
| H | α-$CH_3$ | β-CH(OH)CH$_3$ | Δ5 | 0.80 | 1.10 | 1.02 (d) | 220–2 | 331 (M+) |
| H | α-$CH_3$ | β-COCH$_3$ | | 0.61 | 0.83 | 0.92 (d) | | 331 (M+) |
| H | β-$CH_3$ | β-COCH$_3$ | | 0.93 | 0.97 | 1.03 | 210–1 | 332 (M+) |
| H | β-$CH_3$ | β-CH(OCOCH$_3$)CH$_3$ | $C_{20}$ isomer A | 0.65 | 0.86 | 1.99 (s) | 301–2 | 376 (M + 1) |
| H | β-$CH_3$ | β-CH(OCOCH$_3$)CH$_3$ | $C_{20}$ isomer A | 0.82 | 0.84 | 1.98 (s) | 248–9 | 376 (M + 1) |
| H | β-$CH_3$ | β-CH(OH)CH$_3$ | | 0.83 | 0.88 | 1.46 | 334–5 | 334 (M+) |
| $CH_3$ | α-$CH_3$ | β-CH(OCOCH$_3$)CH$_3$ | | 0.58 | 0.74 | 1.02 (d) | 160–1 | 389 (M+) |
| $CH_3$ | α-$CH_3$ | β-CH(OH)CH$_3$ | | 0.78 | 1.03 | 1.08 | 218–9 | 347 (M+) |
| $CH_3$ | α-$CH_3$ | β-CH(OH)CH$_3$ | Δ5 | 0.82 | 1.10 | 1.08 (d) | 220–1 | 346 (M + 1) |
| $CH_3$ | α-$CH_3$ | β-COCH$_3$ | | 0.82 | 1.03 | 1.08 | 178–81 | |
| $CH_3$ | α-$CH_3$ | β-COCH$_3$ | Δ5 | 0.78 | 1.02 | 0.99 (d), 2.08 (s) | 160–2 | |
| $CH_3$ | β-$CH_3$ | β-COCH$_3$ | | 0.98 | 1.10 | 2.08 (s) | 128–32 | |
| $CH_3$ | β-$CH_3$ | β-COCH$_3$ | Δ5 | 0.98 | 1.09 | 2.08 (s) | 145–7 | |
| $CH_3$ | β-$CH_3$ | β-(R)-CH(OH)CH$_3$ | | 0.80 | 0.85 | 3.90 (m) | 206–8 | 348 (M + 1) |
| $CH_3$ | β-$CH_3$ | β-(S)-CH(OH)CH$_3$ | | 0.70 | 0.85 | 3.90 (m) | | 348 (M + 1) |
| $CH_3$ | β-$CH_3$ | β-(R)-CH(OCOCH$_3$)CH$_3$ | | 0.65 | 0.85 | 2.00 (s) | 169–70 | 390 (M + 1) |
| $CH_3$ | β-$CH_3$ | β-(S)-CH(OCOCH$_3$)CH$_3$ | | 0.70 | 0.85 | 2.00 (s) | | 391 (M + 2) |
| $CH_3$ | β-$CH_3$ | β-C(OH)(CH$_3$)$_2$ | | 0.86 | 0.95 | 1.32 (s), 1.25 (d) | | |
| $CH_3$ | β-$CH_3$ | β-(R)-CH(OCH$_3$)CH$_3$ | | 0.75 | 0.85 | 3.27 (s) | | 361 (M+) |
| $CH_3$ | β-$CH_3$ | β-(R)-CH(OCH$_2$CH=CH$_2$)CH$_3$ | | 0.75 | 0.85 | 3.50 (m); 5.93 (m) | | 387 (M+) |
| $CH_3$ | β-$CH_3$ | β-(R)-CH(O-n-$C_3H_7$)CH$_3$ | | 0.75 | 0.85 | 0.90 (t) | | 390 (M + 1) |
| $CH_3$ | β-$CH_3$ | β-(R)-CH(OCH$_2$CH-C(CH$_3$)$_2$)CH$_3$ | | 0.75 | 0.85 | 1.70 (s); 1.65 (s) | | 415 (M + 2) |
| $CH_3$ | β-$CH_3$ | β-(R)-CH(OCO-t-$C_4H_9$)CH$_3$ | | 0.70 | 0.85 | 1.15 (s) | | 433 (M + 2) |
| $CH_3$ | β-$CH_3$ | β-(R)-CH(OCOPh)CH$_3$ | | 0.70 | 0.80 | 5.35 (m) | | 453 (M + 2) |
| $CH_3$ | β-$CH_3$ | β-(R)-CH(OCOC$_2H_5$)CH$_3$ | | 0.70 | 0.85 | 1.13 (t); 2.25 (q) | | 403 (M+) |
| $CH_3$ | β-$CH_3$ | β-(R)-CH(OCO-1-adamantyl)CH$_3$ | | 0.65 | 0.85 | 1.85 (s) | | 509 (M+) |
| $CH_3$ | β-$CH_3$ | β-(R)-CH(OCONH2)CH$_3$ | | 0.72 | 0.87 | 4.92 (m) | | 390 (M+) |
| $CH_3$ | β-$CH_3$ | β-(R)-CH(OCONHCH$_3$)CH$_3$ | | 0.75 | 0.85 | 2.77 (d) | | 406 (M + 2) |
| $CH_3$ | β-$CH_3$ | β-(R)-CH(OCONH-i-C3H7)CH$_3$ | | 0.75 | 0.85 | 1.10 (d) | | 434 (M + 2) |
| $CH_3$ | β-$CH_3$ | β-(R)-CH(OCON(CH$_3$)2)CH$_3$ | | 0.75 | 0.85 | 2.88 (s) | | 419 (M + 1) |
| $CH_3$ | β-$CH_3$ | β-(R)-CH(OCONH-n-$C_8H_{17}$)CH$_3$ | | 0.75 | 0.85 | 1.25 (m) | | 503 (M + 1) |
| $CH_3$ | β-$CH_3$ | β-(R)-CH(OCONH-t-$C_4$H9)CH$_3$ | | 0.75 | 0.85 | 1.30 (s) | | 447 (M + 1) |
| $CH_3$ | β-$CH_3$ | β-(R)-CH(OCONHCH$_2$Ph)CH$_3$ | | 0.75 | 0.85 | 4.35 (d) | | 482 (M + 2) |
| $CH_3$ | β-$CH_3$ | β-(R)-CH(OCONHPh)CH$_3$ | | 0.75 | 0.85 | 5.06 (m); 4.98 (m) | | 468 (M + 2) |
| $CH_3$ | β-$CH_3$ | β-CH(NHCOCH$_3$)CH$_3$ | $C_{20}$ isomer A | 0.73 | 0.87 | 1.91 (s); 4.16 (m) | | 389 (M+) |
| $CH_3$ | β-$CH_3$ | β-CH(NHCOCH$_3$)CH$_3$ | $C_{20}$ isomer A | 0.75 | 0.87 | 1.92 (s); 4.01 (m) | | 389 (M+) |
| $CH_3$ | β-$CH_3$ | α-C(=CH$_2$)CH$_3$ | | 0.86 | 0.87 | 4.61 (s) | | 344 (M + 1) |
| $CH_3$ | β-$CH_3$ | α-CH(OH)CH$_3$ | | 0.84 | 0.84 | 3.67 (qd) | | 349 (M+) |
| $CH_3$ | β-$CH_3$ | α-CH(OCOCH$_3$)CH$_3$ | $C_{20}$ isomer A | 0.80 | 0.85 | 1.98 (s) | | 391 (M+) |
| $CH_3$ | β-$CH_3$ | α-CH(OCOCH$_3$)CH$_3$ | $C_{20}$ isomer A | 0.84 | 0.84 | 1.97 (s) | | 391 (M+) |
| $CH_3$ | β-$CH_3$ | β-OH | | 0.73 | 0.87 | 3.59 (d) | | 319 (M+) |
| $CH_3$ | β-$CH_3$ | β-OCH(CO$_2$CH$_3$)$_2$ | | 0.82 | 0.86 | 3.77 (s), 1.00 (d) | | 461 (M+) |
| $CH_3$ | β-$CH_3$ | β-OCOCH$_3$ | | 0.80 | 0.86 | 2.06 (s) | | 361 (M+) |
| $CH_3$ | β-$CH_3$ | β-OCH$_2$CO$_2$H | | 0.81 | 0.84 | 1.00 (d) (CD$_3$OD) | | 372 (M+) |
| $CH_3$ | β-$CH_3$ | β-OCH$_2$CONHPh | | 0.85 | 0.88 | 1.06 (d) | | 452 (M+) |
| $CH_3$ | β-$CH_3$ | β-OCH$_2$CONH-t-$C_4H_9$ | | 0.78 | 0.87 | 1.35 (s) | | 432 (M+) |

-continued

| R$_4$ | R$_{16}$ | R$_{17}$ | $^1$H-NMR C$_{18}$ | C$_{19}$ | other | Melting pt. °C. | Mass spec. |
|---|---|---|---|---|---|---|---|
| CH$_3$ | β-CH$_3$ | β-OCH$_2$CONH-4-pyr | 0.85 | 0.88 | 1.06 (d) | | 453 (M+) |
| CH$_3$ | β-CH$_3$ | β-OCH$_2$CO$_2$CH$_3$ | 0.79 | 0.86 | 3.72 (s) | | 391 (M+) |
| CH$_3$ | β-CH$_3$ | β-C(=NOH)CH$_3$ | | | | | 361 (M + 1) |
| CH$_3$ | β-CH$_3$ | β-NHCOPh | 0.80 | 0.87 | 0.98 (d) | | 422 (M+) |
| CH$_3$ | β-CH$_3$ | β-NHCOCH$_3$ | 0.71 | 0.86 | 2.01 (s) | | 360 (M+) |
| CH$_3$ | β-CH$_3$ | β-NHCO-t-C$_4$H$_9$ | 0.70 | 0.86 | 1.35 (s) | | 402 (M+) |
| CH$_3$ | β-CH$_3$ | β-NHCO-(S)-CH(OH)Ph | 0.45 | 0.82 | 5.04 (s) | | 452 (M+) |
| CH$_3$ | β-CH$_3$ | β-NHCO-(R)-CH(OH)Ph | 0.64 | 0.84 | 5.05 (s) | | 452 (M+) |
| CH$_3$ | β-CH$_3$ | β-OCONHCH$_2$Ph | 0.77 | 0.86 | 5.01 (t) | | 452 (M+) |
| CH$_3$ | β-CH$_3$ | β-OCO-t-C$_4$H$_9$ | 0.82 | 0.87 | 1.20 (s) | | 403 |
| CH$_3$ | β-CH$_3$ | β-OCONH-t-C$_4$H$_9$ | 0.76 | 0.86 | 1.31 (s) | | 418 (M+) |
| CH$_3$ | β-CH$_3$ | β-OCONH-n-C$_8$H$_{17}$ | 0.77 | 0.86 | 3.13 (m) | | 474 (M+) |
| CH$_3$ | β-CH$_3$ | β-OCONHPh | 0.83 | 0.87 | 7.04 (t) | | 438 (M+) |
| CH$_3$ | β-CH$_3$ | β-OCOPh | 0.88 | 0.95 | 8.04 (d) | | 423 (M+) |

1H NMR were obtained in CDCl$_3$ unless otherwise noted. The C$_5$-C$_6$ double bond analogs are denoted as Δ5.

EXAMPLES FOR THE CASE WHEN SUBSTITUENT "A" OF GENERAL FORMULA "I" IS AS DEFINED IN GROUP "I(A)-(1)"

EXAMPLE 105

Methyl 3-oxo-4-aza-5α-androst-1-ene-17β-carboxylate

A suspension of 83.7 g of methyl 3-oxo-4-aza-5α-androstane-17-carboxylate* and 126.5 g of benzeneseleninic anhydride in 2.09 l of chlorobenzene was heated at reflux for 2 hours. The reflux condenser was switched to a distillation head and the mixture was distilled slowly to remove water that had formed in the reaction (2 hours). The solution was evaporated to leave 198 g of wet residue. The residue as a solution in dichloromethane was washed with saturated aqueous NaHCO$_3$ solution and saturated NaCl solution, then dried and evaporated to leave 172.4 g. This material was chromatographed on 2.56 kg of silica gel eluting first with dichloromethane (5 l) and then with 4:1 dichloromethane acetone. The desired product eluted after 8 l and amounted to 53.4 g. It was rinsed with diethyl ether and dried to leave 49.5 g, of the title compound m.p. 278°–280° C. In a similar fashion the following compounds were converted to their corresponding 1,2-unsaturated derivatives:

| | m.p. |
|---|---|
| 17 substituent = CONHC(CH$_3$)$_3$ | 252–254° C. |
| 17 substituent = CONHC(CH$_3$)$_2$CH$_2$C(CH$_3$)$_3$ | 224–226° |

*Rasmusson Johnston and Arth.
U.S. Pat. No. 4,377,584, March 22, 1983.

EXAMPLE 106

Methyl 4-methyl-3-oxo-4-aza-5α-androst-1-ene-17β-carboxylate

A suspension of 25 g of the product of Example 105 and 2.25 g of sodium hydride in 500 ml of dry dimethylformamide was stirred under nitrogen for 15 minutes. Methyl iodide (15 ml) was added dropwise and the mixture was stirred for 30 minutes at room temperature. Additional (5 ml) methyl iodide was added and the mixture was heated at 50° C. for 2 hours. After cooling the mixture was diluted with water to a volume of 2 liters. The solid was separated after cooling and amounted to 25.4 g, m.p. 159°–161° C.

In a similar fashion the following compounds were converted to their corresponding 4-methyl derivatives:

| | m.p. |
|---|---|
| 2a R = CONHC(CH$_3$)$_2$CH$_2$C(CH$_3$)$_3$, androstane | 148–150° C. |
| 2b = CONHC(CH$_3$)$_3$; Δ-1-androstene | 153–155° |
| 2c = CONHC(CH$_3$)$_2$CH$_2$C(CH$_3$)$_3$ Δ-1-androstene | 168–170° |

EXAMPLE 107

S-(2-Pyridyl) 4-methyl-3-oxo-4-aza-5α-androst-1-ene 17β-thiocarboxylate

A suspension of 25 g of the product of Example 106 in 125 ml of methanol was treated with a solution of KOH (*12.5 g) in 12.5 ml of water. After refluxing for 4 hours, the solution was acidified with 6 NHCl and then was diluted with water. The crude acid (23.32 g) was separated, dried and had m.p. 300° C.

The crude, dry acid (23 g), triphenylphosphine (36.45 g) and 2,2'-dipyridyldisulfide (30.4 g) were suspended in 138 ml of toluene with stirring for 3 hours at room temperature. The reaction mixture was directly chromatographed on a column of 4.5 kg of silica gel eluting with 9:1 ethyl acetate-acetone to give 20.4 g of the desired product, m.p. 218°–220° C.

Continued elution with acetone gave 5.2 g of the methanol addition product, S-(2-pyridyl) 1α-methoxy-4-methyl-3- oxo-4-aza-5α-androstane-17β thiocarboxylate, m.p. 221°–223° C. as a by-product.

3A. In a similar fashion the product of Example 105 was converted into S-(2-pyridyl) 3-oxo-4-aza-5α-androst-1-ene-17β-thiocarboxylate, m.p. 230°–232° C.

3B. In a similar manner methyl 3-oxo-4-aza-5α-androstane 17-carboxylate was converted into S-(2-pyridyl) 3-oxo-4-aza-5α-androstane-17β-thiocarboxylate, m.p. 232°–234° C.

EXAMPLE 108

N-t-butyl 4-methyl-3-oxo-4-aza-5α-androst-1-ene-17β-carboxamide

Anhydrous t-butylamine was added to a suspension of 2.5 g of the pyridylthioester of Example 107 in 70 ml of tetrahydrofuran. After 60 minutes exposure, the resulting solution was evaporated and the residue was chromatographed on 125 g of silica gel. Elution with 20:1 ethyl acetate dichloromethane afforded 1.5 g of the product, m.p. 152°–154° C.

When the example is repeated using an appropriate amine and an appropriate pyridylthioester, the following products were obtained:

4b: N-t-butyl 3-oxo-4-aza-5α-androstane-17β-carboxamide, m.p. 275°–276° C.

4c: N-(2,4,4-trimethyl-2-pentyl) 4-methyl-3-oxo-4-aza-5α-androst-1-ene-17β-carboxamide, m.p. 168°–170° C.

EXAMPLE 109

5-Oxo-3,5-secoetian-3,20-dioic acid

To a solution of 200 g of 3-oxo-4-etien-17β-oic acid in 3.5 l of t-butanol at 80° was added a solution of 198.4 g of sodium carbonate in 474 ml of water. A warm (65° C.) solution of 948.5 g of sodium metaperiodate and 6.95 g of permanganate in 3.5 l of water was added at such a rate that the reaction mixture was maintained at 80° C. After addition the mixture was heated at reflux for one hour. The mixture stood at room temperature overnight. The inorganic salts were removed by filtration and the cake was washed with 225 ml of water. A solution of 5% aqueous sodium bisulfite was added to reduce the iodine that was present. The t-butanol was removed under reduced pressure and the aqueous residue was acidified with conc. hydro-chloric acid. The separated gum was extracted into dichloromethane and was washed with 5% aqueous sodium bisulfite, saturated sodium chloride solution, then dried and concentrated to an off-white residue (214 g). Crystalline material was obtained by suspending the residue in ether and diluting with hexane to give 152 g, m.p. 189°–192° C.

EXAMPLE 110

3-Oxo-4-aza-5-etien-20-oic acid

A suspension of 64.7 g of the dioic acid of Example 109 in 350 ml of ethylene glycol was treated with 80 ml of liquid ammonia. The resulting solution was heated at a rate of 3°/min. up to 180° C. and was held at that temperature for 15 minutes. After cooling, 1 liter of water was added and the mixture was acidified with 10% hydrochloric acid to a pH of 1.5. The product was removed and washed with water, then air dried to leave 57.5 g of the product, m.p. 310° C.

EXAMPLE 111

3-Oxo-4-aza-5α-etian-20-oic acid

A solution of 136 g of the 5-acid of Example 110 in 16.32 ml of acetic acid was hydrogenated at 60° C. in the presence of platinum catalyst (from 16.32 g of PtO$_2$) at 40 psig for 3 hours. The catalyst was removed and the solution concentrated to give 128.2 g of crude product. The material was washed well with 3 l of water then filtered an air dried to leave 125 g of the white solid, m.p. 310°.

This material is also obtained by saponification of methyl 3-oxo-4-aza-5α-androstane-17β-carboxylate (methyl 3-oxo-4-aza-5α-etien-17β-oate) in 7% methanolic potassium hydroxide followed by an acidic work-up.

EXAMPLE 112

N-(2,4,4-trimethyl-2-pentyl)3-oxo-4-aza-5α-androstane-17β-carboxamide

A solution of 5.0 g of the product of Example 111, 3.35 g of dicyclohexylcarbodiimide and 3.18 g of 1-hydroxybenztriazole in 500 ml of dichloromethane was stirred at room temperature overnight. The solid was separated by filtration and the filtrate was treated with 2,4,4-trimethyl-2-pentylamine (t-octylamine). This solution stood at room temperature for 64 hours. A small amount of solid was removed and the solution was washed successively with 10% aqueous sodium hydroxide, water, 10% hydrochloric acid and saturated aqueous sodium chloride. After drying and concentration the crude product was eluted through 240 g of silica gel with 3:7 acetone-dichloromethane to give 5.5 g of the product, m.p. 250°–251° C.

EXAMPLE 113

Example 112 is repeated using t-butylamine in place of 2,2,4-trimethyl-2-pentylamine to obtain N-t-butyl 3-oxo-4-aza-5α-androstane-17β-carboxamide, m.p. 274°–276° C.

EXAMPLE 114

Synthesis of 17β(N-1-adamantyl-carbamoyl)-4-aza-5α-androst-1-en-3-one 100 mg of the 17-methyl ester (0.305 mmoles) from Example 1 was suspended in 3.0 ml of THF (dried over molecular sieves 3A), and then was added 183.0 mg of 1-adamantanamine (1.2 mmoles). The suspension was cooled to 5°–10° C. and then 590 μl of 2.0M solution, of EtMgBr in THF was added. The resulting mixture was allowed to stir for 10 minutes, and then refluxed for 1–2 hours under N$_2$. The mixture was cooled to 0° C. and then quenched with saturated solution of NH$_4$Cl (about 10 ml.). The organic layer was separated and the aqueous layer extracted with three volumes CH$_2$Cl$_2$.

The organic layers were combined, washed 2 times with H$_2$O, twice with saturated sodium chloride, and dried over MgSO$_4$, filtered and evaporated to dryness in vacuum. Crystallization from EtOAc afforded 75.0 mg of product. Recrystallization from MeOH and drying at 110° C. for 2 hours/0.1 mm gave product, mpt. 305°–306° C. Molecular weight (by FAB) showed M+=451: Calculated=451.

Analysis Calculated for C$_{29}$H$_{42}$N$_2$O$_2$ C, 77.28; H, 9.40; N, 6.21. Found: C, 76.84; H, 9.73; N, 5.93.

EXAMPLE 114

Synthesis of 17β(N-2-adamantyl-carbamoyl)-4-aza-5α-androst-1-en-3-one

Following the above-described general procedure of Example 113 but utilizing 2-adamantamine (prepared by aqueous neutralization of the hydrochloride and EtOAc extraction and isolation) in place of 1-adamantamine, and carrying out the reflux for 7 hours rather than 1–2 hours, the title compound is prepared, mpt. 284°–285° C.

EXAMPLE 115

Synthesis of 17β(N-1-adamantylcarbamoyl-4-aza-5α-androstane-3-one 100.0 mg of the adamantyl derivative produced in Example 113 was dissolved in 5.0 ml of dry THF. 300 mg of 5% Pd/C was added and the mixture was hydrogenated for 6.0 hrs. at R.T. at 40 psi. The mixture was filtered through celite, the cake washed with THF (3 times) and solvent evaporated under vacuum to yield 97.0 mg. of crude abovetitled product. NMR showed absence of olefins. The crude material was placed on 15.0 g silica gel column, and eluated with 1:1 ($CH_2Cl_2$:acetone).

Collected fractions afforded a single spot material by TLC weighing 77.98 mg. NMR was in excellent agreement with the proposed structure. Recrystallized from EtOAc to yield 65.59 mg of the above-titled product, mp. 323°–324° C.

Analysis Calculated for $C_{29}H_{44}O_2N_2$ 1/4 $H_2O$: C, 76.18; H, 9.81; N, 6.13. Found: C, 75.91; H, 9.97; N, 6.06.

EXAMPLE 116

Synthesis of 17β(N-1-adamantylcarbamoyl)-4-methyl-4-aza-5α-androst-1-en-3-one 120 mg of the thiopyridyl ester of Example 107 was suspended in 20 ml of dry THF, to the suspension was added 175.0 mg of 1-adamantanamine under $N_2$. The reaction was carried out at R.T. for 16 hours under $N_2$. The reaction was monitored by silica gel TLC, using 1:1 acetone:hexane. The product was separated on TLC 20 cm×20 cm, 1000 μm silica gel plate, eluted with 1:1 (acetone/hexane). The product was crystallized from ethyl acetate, to give 50.0 mg of pure material m. pt. 202°–205° C. Molecular Weight (FAB) showed 465; Calc: 465. Recrystallization afforded 19.14 mg of the above-titled product, m.pt. 202°–202.5° C.

Analysis Calculated for $C_{30}H_{44}N_2O_2 \cdot H_2O$: C, 74.64; H, 9.60; N, 5.80. Found: C, 74.32; H, 9.47; N, 5.89.

EXAMPLE 117

Hydrolysis of Methyl-3-oxo-4-aza-5α-androstane-17β-carboxylate

The 17β-androstane carboxylate starting material of Example 105 was hydrolyzed with 7% KOH in isopropanol or aqueous methanol, followed by an acidic work-up to give the corresponding 17β carboxylic acid which was utilized in Example 118.

EXAMPLE 118

N-(1-adamantyl-3-oxo-4-aza-5α-androstane-17β-carboxamide

A solution of 5.0 g of the product of Example 117, 3.35 g of dicyclohexylcarbodiimide and 3.18 g of 1-hydroxybenztriazole in 500 ml of dichloromethane was stirred at room temperature overnight. The solid was separated by filtration and the filtrate was treated with 1-adamantamine. This solution stood at room temperature for 64 hours, then filtered, and the solution was washed successively with 10% hydrochloric acid and saturated aqueous sodium chloride. After drying with $MgSO_4$, it was filtered and concentrated. The crude product was eluted through 240 g of silica gel with 3:7 (acetone-dichloromethane) to give 5.5 g of the above-titled product, m.p. 323°–324° C.

EXAMPLE 119

Synthesis of Benztriazol-1-yl-3-oxo-4-methyl-4-aza-5α-androstan-17β-carboxylate

A suspension of 83.7 g of methyl-3-oxo-4-methyl-4-aza-5α-androstane-17β-carboxylate. (See Rasmusson, et al. J. Med. Chem 29, 2298–2315, 1986) was hydrolyzed with 7% KOH in aqueous methanol, followed by an acidic work up to give the corresponding 17β-carboxylic acid.

The acid was readily converted into benzotriazyl-1-yl-3-oxo-4 methyl-4-aza-5α-androstane 17β carboxylate as described in Example 120. The activated ester (the benzotriazoyl derivative) was purified on TLC (4 plates, 20 cm×20 cm×20 cm×1000 μm silica gel) eluted with 4:96 (MeOH-$CHCl_3$). The isolated product was washed with ether to give the active ester m.pt. 198°–200° C. with decomposition.

EXAMPLE 120

Synthesis of 17β(N-1-adamantylcarbamoyl)-4-methyl-4-aza-5α-androstan-3-one 100.0 mg of the 4-methyl-4-aza-benzotriazole derivative prepared as described in Example 119, was dissolved in 20.0 ml $CH_2Cl_2$. To the clear solution was added 127 mg of 1-adamantamine. The reaction mixture was stirred overnight at R.T./$N_2$.

Crystallization from EtOAc after filtering the solution through Teflon Acrodisc CR afforded 26.32 mg, m.pt. 210°–217° C. The product was further purified on 1.0 g silica gel column (EM silica gel) with 1:1 (acetone-hexane) as eluant to give after recrystallization (ethyl acetate) 21.75 mg of white needles of the above-titled product, m.pt. 203°–205° C.

Analysis Calculated for $C_{30}H_{46}N_2O_2 \cdot 1.5 H_2O$: C, 73.58; H, 9.68; N, 5.62; Found: C, 73.15; H, 9.30; N, 5.67.

EXAMPLE 121

Diastereomeric Synthesis of 17β(N-exo-2-norbornanyl-carbamoyl)-4-aza-5α-androst-1-en-3-one)

100.0 mg of the corresponding 4-H thiopyridyl ester of Example 107, prepared by the procedure of Example 107, but utilizing the 4-H methyl ester product of Example 1, (See Rasmusson et al. J. Med. Chem. Vol. 29, pp. 2298–2315 (1986), was dissolved in 3.0 ml of dry THF under $N_2$. To the clear solution was added 477 μl of (±) racemic exo-2-aminonorbornane.

Allowed the reaction to proceed for 16 hours at R.T./$N_2$. The reaction mixture was evaporated to dryness in vacuum. The residue was dissolved in chloroform. The organic layer was washed with 2.5N HCl acid (3 times); 3 times with water;, 3 times with saturated NaCl solution, dried over $MgSO_4$, filtered and evaporated to dryness in vacuum to afford 56.3 mg of a racemic diastereomeric mixture.

The crude product was chromatographed on TLC (2 plates, 20 cm×20 cm×500 μm silica gel) eluted with 70:30 ($CHCl_3$:acetone) to yield 43.4 mg. of the above-titled product. Recrystallization from EtOAc yielded 30 mg product, m.pt 245°–245.9° C.

NMR ($CDCl_3$) confirmed the above structure.

FAB mass spectrum calcd. for $C_{26}H_{38}O_2N_2$: m/e 411; Found: 411.

Analysis Calculated for $C_{26}H_{38}O_2N_2 \cdot H_2O$: C, 72.82; H, 9.40; N, 6.58. Found: C, 73.21; H, 9.20; N, 6.25.

EXAMPLE 122

Synthesis of 17β(N-1-adamantylmethylcarbamoyl)-4-aza-5α-androst-1-en-3-one 200.0 mg of the 4-H thiopyridyl aza steroid, used in Example 121, was suspended in 2.0 ml of dry THF.

To the suspension was added 400 μl of 1-aminomethylene adamantane via syringe at R.T./N$_2$. After several minutes, a yellow clear solution resulted and after ½ hr., precipitation occurred. The reaction was allowed to proceed overnight/ N$_2$. Diluted with CH$_2$Cl$_2$, washed with 10% NaOH, two times, then with H$_2$O two times, followed by 10% HCl (two times), H$_2$O (two times), and finally two times with satd. NaCl solution.

The organic layer was dried over MgSO$_4$, filtered, concentrated in vacuo to obtain the product, as shown by NMR, recrystallized from EtOAc, to yield 149.0 mg product, m.pt 255°–257° C. with decomposition.

FAB Mass Spectrum, Calcd: m/e 464+1=465: Found 465.

EXAMPLE 123

Synthesis of 17β(N-2-adamantylcarbamoyl)-4-aza-5α-androstan-3-one

A mixture of 1.09 grams 17β-(N-2-adamantylcarbamoyl)-4-aza-5α-androst-1-en-3-one (See Example 117 for preparation), 150 ml of ethanol, and 1.0 g. of 30%Pd/C was hydrogenated overnight with shaking under 45 psig. hydrogen pressure. The suspension was filtered to remove catalyst, and evaporated to dryness to yield a grey residue. This was chromatographed by elution on a 200 ml silica gel column with 40:60 acetone/methylene chloride eluant to yield 1.0 g of solid, mp. 294°–296° C.

Analysis Calculated for $C_{29}H_{44}N_2O_2 \cdot 0.2H_2O$ C, 76.33; H, 9.80; N, 6.14 Found: C, 76.23; H, 9.86; N, 5.92

Mass Spec. Analysis by electron impact showed MW of 452.

EXAMPLE 124

Synthesis of 17β-(N-2-adamantylcarbamoyl)-4-aza-4-methyl-5α-androst-1-en-3-one

A suspension of 500 mg of 17β-(N-2-adamantylcarbamoyl)-4-aza-5α-androst-1-en-3-one, as prepared in Example 123, 10 ml sieve-dried DMF, 140 mg NaH, were heated and stirred at 70° C. under a nitrogen atmosphere for 18 hours. Cooled to room temperature and then added 0.4 ml methyl iodide dropwise with stirring which was continued at 50° C. for 3 hours. The reaction mixture was then treated by cooling to room temperature, followed by the addition of 15 ml water. The mixture was extracted with 3×20 ml of CH$_2$Cl$_2$. The organic layers were combined, washed with brine, dried and evaporated to yield a white crystalline residue. Recrystallization from ethyl acetate/CH$_2$Cl$_2$ yielded a pure white solid, mp 246°–248° C.

Analysis Calculated for $C_{30}H_{44}N_2O_2 \cdot 0.3H_2O$ C, 76.65; H, 9.56; N, 5.95 Found: C, 76.50; H, 9.75; N, 5.84

Mass spectroscopy showed a molecular weight of 464.

EXAMPLE 125

Synthesis of 17β-(N-2-adamantylcarbamoyl)-3-oxo-4-methyl-4-aza-5α-androstane

17β-(N-2-adamantylcarbamoyl)-4-methyl-4-aza-androsten-1-en-3-one, (200 mg) as prepared in Example 124, were placed into 25 ml absolute ethanol with 200 mg 30% Pd/C hydrogenation catalyst. The suspension was rocked overnight under 40 psig hydrogen pressure. The suspension was filtered, and the filtrate evaporated to dryness. The residue was recrystallized from hot ethyl acetate to give a white crystalline solid, mp. 113°–115° C. Calcd. for $C_{32}H_{50}N_2O_3 \cdot 0.5$ EtOAc Calcd: C, 75.25, H, 9.86, N, 5.48 Found: C, 75.07; H, 9.52; N, 5.28

Mass spectroscopy depicted a molecular weight of 466 for the non-solvated molecule.

EXAMPLE 126

Synthesis of 17β-(N-methyl-N-2-adamantyl)carbamoyl-4-methyl-4-aza-androst-1-en-3-one 17β-(N-2-adamantyl)carbamoyl-4-aza-androst-1-en-3-one (5.0 g) and 1.5 g sodium hydride in 100 ml dry DMF were stirred under dry nitrogen for 3 hours at 40° C. The reaction was cooled to room temperature and about 4 ml of methyl iodide was added dropwise and allowed to stir at room temperature for one hour. The reaction was cooled in an ice bath and a large excess of about 250 ml, water was added. The aqueous mixture was extracted with CH$_2$Cl$_2$ (3×100 ml), the organic extracts combined, washed with H$_2$O, brine, and then evaporated to dryness to yield crude product. The crude product was eluted on an HPLC column (Si gel) with 10/1 acetone/CH$_2$Cl$_2$ to yield 2 peaks having retention times of 3 CV(B) and 3.8 CV(A). Peak (A) was analyzed as per the 4-methylaza titled product of Example 127. The second product (B) was analyzed as the 4-methylaza-17β-(N-methyl-N-2-adamantyl/carbamoyl analog, i.e. the titled compound, mp. 163–165.

Calculated for $C_{31}H_{46}N_2O_2$ C, 77.77; H, 9.68; N, 5.85 Found: C, 77.29; H, 9.79; N, 5.77

Mass spectrometry showed a molecular weight of 478.

EXAMPLE 177

Synthesis of 17β-(N-methyl-N-2-adamantylcarbamoyl)-4-aza-4-methyl-androstan-3-one The crude reaction mixture from Example 126 (4.6 g) was dissolved in 200 ml ethanol and together with 1.0 g 30% Pd/C was hydrogenated under 40–45 Psig a hydrogen atmosphere at room temperature overnight. The mixture was filtered, residue washed with ethanol. The ethanol solution was evaporated to dryness to yield a crude mixture. Recrystallized from CH$_2$Cl$_2$/diethyl ether/hexane to yield 800 mg of the pure monomethyl androstane compound of Example 16, mp 113°–115° C. Second and third crops were combined with mother liquor and treated by HPLC as in Example 124 to yield the dimethylated title compound, mp 180°–182° C.

Analysis Calculated for $C_{31}H_{48}N_2O_2$ C, 77.45; H, 10.06; N, 5.83 Found: C, 77.26; H, 9.87; N, 5.82

Mass spectrometry showed a molecular weight of 480.

EXAMPLES FOR THE CASE WHEN SUBSTITUENT "A" OF GENERAL FORMULA "I" IS AS DEFINED IN GROUP I(A)(2)

EXAMPLE 128

Methyl 3-oxo-4-aza-5a-androst-1-end-17β-carboxylate

A suspension of 83.7 g of methyl 3-oxo-aza-5a-androstane-17-carboxylate* and 126.5 g of benzeneseleninic anhydride in 2.09 l of chlorobenzene was heated at reflux for 2 hours. The reflux condenser was switched to a distillation head and the mixture was distilled slowly to remove water that had formed in the reaction (2 hours). The solution was evaporated to leave 198 g of wet residue. The residue as a solution in dichloromethane was washed with saturated aqueous NaHCO₃ solution and saturated NaCl solution, then dried and evaporated to leave 172.4 g. This material was chromatographed on 2.56 kg of silica gel eluting first with dichloromethane (5 liters) and then with 4:1 dichloromethane-acetone. The desired product was eluted with 8 liters of the above-mixed solvent and evaporated to dryness in vacuo to yield 53.4 g solid. It was washed with diethyl ether and dried to leave 49.5 g of the above-titled product, m.p. 278°–280° C.

*Rasmusson Johnston and Arth. U.S. Pat. No. 4,377,584, Mar. 22, 1983.

EXAMPLE 129

S-(2-Pyridyl)-3-oxo-4-aza-5α-androst-1-ene-17β-thiocarboxylate

A suspension of 25.0 g of the above product from Example 128 was saponified with 12.5 g of KOH in 150.0 ml of 5:1 CH₃OH-H₂O under reflux conditions for 4 hours/N₂. The mixture was cooled to 25° C. and acidified to pH<2. Water (175 ml) was added gradually with stirring to leave a crystalline precipitate which was collected and washed with water.

After drying, the product amounted to 25 g., m.pt 313°–315° C. with decomposition.

The crude dry acid (23.0 g) was suspended in 210 ml of toluene, and to the suspension was added triphenylphosphine (56.0 g) and 2,2'-dipyridyl disulfide (48.3g), and the mixture was stirred at 24° C. overnight/N₂. The reaction mixture was placed on a column of silica gel (1.3 kg) and was eluted with 1:1 (acetone/CH₂Cl₂). The desired thioester eluted slowly, and after rinsing with ether, yielded 36.8 g of the above-titled product, m.p. 232°–235° C.

EXAMPLE 130

22-Methyl-4-aza-21-nor-5α-chol-1-ene-3,20-dione

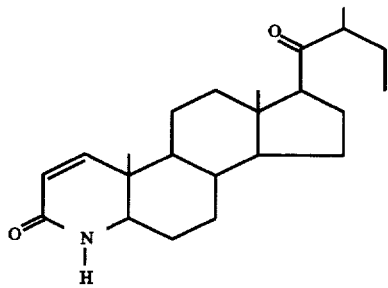

To a solution of 7.2 g of S-(2-pyridyl)-3-oxo-4-aza-5α-androst-1-ene-17β-thiocarboxylate in 288 ml of tetrahydrofuran was added at –78° C. 33.6 ml of 1.3M S-butylmagnesium chloride. After 30 minutes at –78° C. the solution came to room temperature and was treated with saturated aqueous NaCl solution. The product was extracted into dichloromethane and was washed with saturated aqueous NaCl solution and 10% aqueous NaOH solution, then dried and concentrated. The residue was eluted through 430 g of silica gel with 9:1 dichloromethane-acetone to give 4.5 g of the product, m.p. 246°–249° C.

When the procedure is repeated using the following reagents, the indicated product is obtained.

| Starting Material | Reagent | Product |
|---|---|---|
| S-(2-pyridyl)3-oxo-4-aza-5α-androst-1-ene-17β-thiocarboxylate | 2-pyrrolyl magnesium chloride | 17β-(2-pyrrolyl-carbonyl)-4-aza-5α-androst-1-ene-3-one m.p. 294–296° C. |
| S-(2-pyridyl)3-oxo-4-methyl-5α-androst-1-ene-17β-thiocarboxylate | sec-butyl magnesium chloride | 4,22-dimethyl-4-aza-21-nor-5α-chol-1-ene-3,20-dione m.p. 134–136° C. |
| S-(2-pyridyl)3-oxo-4-methyl-4-aza-5α-androst-1-ene-17β-thiocarboxylate | 2-pyrrolyl magnesium chloride | 4-methyl-17β-(2-pyrrolylcarbonyl)-4-aza-5α-androst-1-ene-3-one m.p. 234–238° C. |
| S-(2-pyridyl)3-oxo-4-aza-5α-androst-ene-17β-thiocarboxylate | isobutyl magnesium chloride | 23-methyl-4-aza-21-nor-5α-cholane-3,20-dione m.p. 220–222° C. |

EXAMPLE 131

22-Methyl-4-aza-21-nor-5α-chol-1-ene-3,20-dione

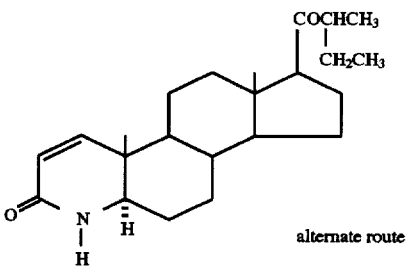

alternate route

A solution of 21 g of 22-methyl-4-aza-21-nor-5α-cholane-3,20-dione and 29.49 g of benzeneseleninic anhydride in 552 ml of chlorobenzene was refluxed with water separation for 4 hours. The mixture was concentrated and the residue was redissolved in dichloromethane. After washing with 10% aqueous sodium hydroxide, then 10% hydrochloric acid and saturated aqueous sodium chloride the solution was dried and concentrated to 45 g of yellow residue. This was chromatographed on 1.5 kg of silica gel packed in dichloromethane and eluted with ethyl acetate to give 10.6 g of the product, m.p. 248°–251° C.

When the procedure is repeated using 23-methyl-4-aza-21-nor-5α-cholane-3,20-dione as starting material the product obtained is 23-methyl-4-aza-21-nor-5α-chol-1-ene-3,20-dione, m.p. 283°–286° C.

EXAMPLE 132

17β-(phenylcarbonyl)-4-aza-5α-androst-1-ene-3-one

To a stirred suspension of 43 g of S-(2-pyridyl)-3-oxo-4-aza-5-alpha-androst-1-ene-17-beta-thiocarboxylate in 500 ml of anhydrous tetra-hydrofuran (THF) was added at –78° C. a THF solution of 157 ml of 2N phenylmagnesium chloride over 60 minutes. After stirring at –78° C. for 60 minutes, the mixture was brought to –30° C. and was quenched by addition of 10% HCl while maintaining the temperature below –20° C. After warming to 0° C., the mixture was diluted with 2000 ml of water and extracted with 4000 ml of dichloromethane in portions. The organic layer was washed sequentially with water, 1N sodium hydroxide, water and saturated sodium chloride solution.

Drying with MgSO$_4$ and concentration afforded 37.5 g of crude product. Recrystallization from dichloromethane/ethyl acetate gave the title phenyl ketone (30.4 g, 77% yield).

m.p. 290°–291° C.

|   | Calc  | Found |
|---|-------|-------|
| N | 3.61  | 3.56  |
| C | 77.48 | 77.16 |
| H | 8.26  | 8.19  |

EXAMPLE 133

17-beta-4-fluorophenycarbonyl-4-aza-5-alpha-androst-1-ene-3-one

The procedure of Example 132 was repeated except using p-fluorophenylmagnesium bromide as the Grignard reagent and the title compound was obtained. m.p. 315°–315.5° C.

EXAMPLE 134

17β-(cyclohexylcarbonyl)-4-aza-5α-androst-1-ene-3-one

To a suspension of 34.8 g of the thiopyridyl ester of Example 2 in 700 ml of anhydrous THF was added at –65 degrees C. 130 ml of a 2M ether solution of cyclohexyl magnesium chloride over a period of 20 minutes. After stirring at –70 degrees C. for 60 minutes the solution was warmed and stirred at –10 degrees C. for 60 minutes. The mixture was diluted with 500 ml of dichloromethane and then dropwise with dichloromethane, the phases were separated and the organic layer was treated sequentially with water, 1N sodium hydroxide, water and saturated sodium chloride solution. The organic solution was decolorized with charcoal, filtered and concentrated to a residue which was crystallized from ethyl acetate to give 28.2 of the title compound, m.p. 271.5–277 degrees C.

EXAMPLE 135

The title compound of Example 134 was also prepared by the following procedure.

To a mixture of 150 g of methyl 3-oxo-4-aza-5-alpha-androst-1-ene-17-beta-carboxylate in 2800 ml of anhydrous THF was added with stirring at less than 0 degrees C. internal temperature 678 ml of a 2N ether solution of cyclohexyl magnesium chloride. The solution was then refluxed for 6 hours. The cooled (less than 10 degrees C.) reaction mixture was acidified with 10% HCl solution and was extracted with dichloromethane. The organic layer was washed sequentially with water, saturated NaHCO3 solution and saturated NaCl solution. Drying (MgSO4) and evaporation left 163 g of crude cyclohexyl ketone. Recrystallization from dichloromethane/ethylacetate gave 131 g of the pure material.

m.p. 269–270 degrees C.

|   | % Calc. | Found |
|---|---------|-------|
| N | 3.61    | 3.61  |
| C | 77.37   | 77.37 |
| H | 9.74    | 10.13 |

EXAMPLE 136

17-beta-(cyclopentylcarbonyl)-4-aza-5-alpha-androst-1-ene-3-one

When the procedure of Example 134 or 135 was repeated using cyclopentylmagnesium chloride, the title compound was obtained:

m.p. 272–273 degrees C.

|   | Calc  | Found |
|---|-------|-------|
| N | 3.66  | 3.78  |
| C | 75.25 | 74.89 |
| H | 9.60  | 9.54  |

EXAMPLE 137

17-beta-(cyclobutylcarbonyl)-4-aza-5-alpha-androst-1-ene-3-one

When the procedure of Example 134 or 135 was repeated using cyclobutylmagnesium chloride, the title compound was obtained:

m.p. 288–289 degrees C.

|   | % Calc | Found |
|---|--------|-------|
| N | 3.94   | 3.87  |
| C | 77.71  | 78.06 |
| H | 9.36   | 9.61  |

EXAMPLE 138

Synthesis of 17-β-(4-Phenylbenzoyl)-4-aza-5a-androst-1-en-3-one

To a suspension of 258.0 mg of dry activated magnesium chips in 5.0 ml of dry THF was added 932.0 mg of 4-bromobiphenyl in 5.0 ml of dry THF under N$_2$. The reaction was run in an ultrasonic bath at a temperature range of 24°–30° C. To the well-agitated mixture was added dropwise 30 ml of 1,2-dibromoethane/N$_2$. The reaction was allowed to proceed for 1–1½ hours at 28° C./N$_2$. The concentration of the Grignard reagent was 4.0 mmoles in 10.0 ml of dry THF.

The steroid from Example 129 (205.0 mg, 0.5 mmol of thiopyridyl ester) was suspended in 2.0 ml of dry THF, cooled to –80° C. and the above Grignard 3.80 ml was added via syringe to the steroidal suspension over 5–10 minutes/N$_2$. The reaction was allowed to proceed for 1 hour at –80° C./N$_2$ and then at –10° C. for an additional hour/N$_2$. The solution was diluted with 10.0 ml of methylene chloride and quenched with saturated aqueous solution of NH$_4$Cl to pH=4. The organic layers were separated, washed 3 times with water, 3 times with saturated sodium chloride, dried over MgSO$_4$, filtered, and evaporated under vacuum to afford 156.2 mg of crude product. Crystallization from EtOAc gave the above-titled product in 98.58 mg, m.pt. 290° C.–290.5° C.

Analysis Calculated for $C_{31}H_{35}NO_2$: C, 82.08; H, 7.78; N, 3.09; Found: C, 81.84; H, 8.01; N, 3.06.

FAB: Calc. for $C_{31}H_{35}NO_2$: 453; Found: 453

EXAMPLE 139

17-β-(3-Phenylbenzoyl)-4-aza-5a-androst-1-en-3-one

To a suspension of 258.0 mg of dry activated magnesium chips in 8.0 ml of dry THF was added 932.0 mg of 3-bromobiphenyl in 2.0 ml of dry THF under N$_2$. The reaction was run in an ultrasonic bath at a temperature range of 24°–30° C. To the well-agitated mixture was added dropwise 30 microliters of 1,2-dibromoethane/N$_2$. The concentration of the Grignard reagent was 4 mmoles in 10.0 ml of dry THF.

The steroid from Example 129, 205.0 mg (0.5 mmoles) was suspended in 2.0 ml of dry THF, cooled to –80° C. and the above prepared Grignard, 3.80 ml, was added via syringe to the steroidal suspension over 5–10 minutes/$N_2$. The reaction was allowed to proceed for 1 hour at –80° C./$N_2$ and then at –10° C. for an additional hour/$N_2$. The solution was diluted with 10.0 ml of methylene chloride and quenched with a saturated aqueous solution of $NH_4Cl$ to pH=4. The organic layers were separated, washed 3 times with water, 3 times with saturated sodium chloride, dried over $MgSO_4$, filtered, and evaporated under vacuum. Crystallization from ethyl acetate afforded 122.84 mg of product. The material was purified on 20.0 g of silica gel column using 70:30 ($CHCl_3$-acetone) as eluant, to give a single spot material 117.0 mg of the above-titled compound, m.pt. 184°–185° C.

Analysis Calculated for $C_{31}H_{35}NO_2$: C, 82.08; H, 7.78; N, 3.09; Found: C, 82.28; H, 8.04; N, 2.98.

FAB: Calcd. for $C_{31}H_{35}NO_2$: 453: Found: 453

EXAMPLE 140

Synthesis of 17-β-(4-Methylthiobenzoyl)-4-aza-5-α-androst-1-en-3-one

To a suspension of 250.0 mg of dry activated magnesium chips in 8.0 ml of dry THF was added 812.0 mg of p-bromophenyl methyl sulfide in 3.0 ml of dry THF under $N_2$. The reaction was run in an ultrasonic bath at a temperature range of 24°–30° C. To the well-agitated mixture was added dropwise 40 µl of 1,2-dibromoethane/$N_2$. The reaction was allowed to proceed for 1 to 1½ hours at 28° C./$N_2$. The concentration of the Grignard reagent was 4.0 mmoles in 10 ml of dry THF.

The steroid from Example 129, i.e. the pyridylthio ester, 205 mg, was suspended in 2.0 ml of dry THF, cooled to –80° C. and the above prepared Grignard was added via syringe to the steroidal suspension in 5–10 minutes/$N_2$. The reaction was allowed to proceed for 1 hour at –80° C./$N_2$ and then at –10° C. for an additional hour/$N_2$. The solution was diluted with 10.0 ml of methylene chloride, and quenched with saturated aqueous solution of $NH_4Cl$ to pH=4. The organic layers were separated, washed 3 times with water; 3 times with saturated sodium chloride, dried over $MgSO_4$, filtered, and evaporated under vacuum to afford 105.0 mg of crude product.

The crude product was chromatographed on TLC (one plate, 20 cm×20 cm×20 cm×1000 µm silica gel) eluted with 80:20 ($CH_2Cl_2$-acetone) to afford 66.0 mg of single spot material. Crystallization from EtOAc afforded 45.0 mg of the above-titled compound, m.pt. 286°–287° C.

FAB for $C_{26}H_{33}NO_2S$ (Calcd.) 424; Found 424.

EXAMPLE 141

Synthesis of 17-β-(4-methylsulfinylbenzoyl) and -(4-methylsulfonylbenzoyl)-4-aza-5α-androst-1-en-3-one
A. Oxidation 19.91 mg of the methylthio product from Example 140 was dissolved in 2.5 ml of $CH_2Cl_2$, cooled to 0°–(–2)°C. and was treated with a solution 9.6 mg of m-chloroperbenzoic acid in 1.0 ml of $CH_2Cl_2$ over a period of 4 minutes. After stirring for 1 hour at 0–(–2)°C., the reaction was diluted with 10 ml. $CH_2Cl_2$. The layers were washed subsequently with 2.5% $NaHCO_3$, $H_2O$ and saturated NaCl solutions. The organic layer was dried over $MgSO_4$ overnight, filtered and evaporated in vacuo to yield 17 mg product. Crystallization from EtOAc gave 11.8 mg of the above-titled compound, a solid, mp. 313°–313.5° C. (with dec.).

Analysis Calculated for $C_{26}H_{33}NO_3S.1/4H_2O$: C, 70.31; H, 7.60; N, 3.15; Found: C, 70.47; H, 7.70; N, 3.00.

FAB for $C_{26}H_{33}NO_3S$ (Calcd. 440); Found 440.
Sulfone

Fifteen percent (15%) of the corresponding sulfone, 17β-(4-methylsulfonyl benzoyl) derivative, was isolated by chromatography from the reaction as a byproduct. Recrystallized from EtOAc to yield a solid, mp. 279°–279.5° C. Molecular weight by FAB showed 456; calculated 456.

Analysis Calculated for $C_{26}H_{33}NO_4S.0.25\ H_2O$ C, 67.87; H, 7.28; N, 3.04. Found: C, 67.96; H, 6.72; N, 2.95.

EXAMPLE 142

Synthesis of 17-β-(4-acetoxymethylthiobenzoyl)-4-aza-5α-androst-1-en-3-one

Trifluoroacetic anhydride (165 µl) was dissolved in 780 µl of acetic anhydride and kept for 5 hours at room temperature (RT).

To 300 µl of the above solution of mixed anhydrides was added 34.15 mg pure sulfoxide from Example 141 with stirring. A few minutes later 54.0 µl of 2,6-lutidine was added and the reaction was allowed to stir at RT/$N_2$ for 17 hours.

The liquid anhydrides were removed under reduced pressure and the remaining residue extracted (4 times with $CHCl_3$). The $CHCl_3$ extracts were washed subsequently with dilute HCl; 5% $NaHCO_3$ solution, 3 times; 3 times with $H_2O$; and finally with saturated NaCl solution, and then dried over $MgSO_4$ filtered and evaporated the solution to dryness in vacuo to yield 42.1 mg of crude product.

The crude product from Step A was purified by chromatography on silica gel using 95:5 ($CHCl_3$-acetone) as eluant and then crystallizing the obtained solid from EtOAc to yield 17.8 mg of the above-titled compound as crystals, m.pt. 235°–236° C. (dec.).

Analysis Calculated for $C_{28}H_{35}O_4NS.1/4\ H_2O$: C, 68.57; H, 7.40; N, 2.86; Found: C, 69.02; H, 7.39; N, 2.73.

FAB for $C_{28}H_{28}O_4NS$ calcd.: 482; Found 482. The NMR (proton) was in agreement with the assigned product structure.

EXAMPLE 143

Synthesis of 17β(4-mercaptobenzoyl)-4-aza-5α-androst-1-en-3one 40.0 mg of the acetoxy-methyl-thio derivative from Example 142 was suspended in 3.0 ml of isopropanol. The reaction mixture was flushed several times with $N_2$, and with vacuum, and the system kept under nitrogen atmosphere. To the above mixture was added 40.0 mg of $K_2CO_3$ in 2.00 ml of water (free of oxygen) via syringe, and the temperature of the reaction mixture was allowed to rise to 80° C. under gentle reflux under slight vacuum for 10 minutes, and then under $N_2$ for 1 hour. After 1 hour, the reaction mixture was a clear yellow solution. It was brought to R.T., cooled to 0°–5° C. and quenched with 2.5N HCl acid/$N_2$. The reaction mixture was extracted 4 times with $CH_2Cl_2$. The organic layer was washed with $H_2O$ 4 times; 3 times with saturated salt solution, and finally dried over $MgSO_4$. Filtered and evaporated to dryness in vacuo to yield 36.9 mg of crude product. The crude product was dissolved in 2.0 ml of $CHCl_3$, filtered through Teflon (Acrodisc CR) and purified by preparative HPLC on silica gel and eluted with 60:40 ($CH_2Cl_2$-acetone). Crystallization, from EtOAc afforded a single spot material, 20.7 mg of the above-titled compound, m.pt. 285°–286° C.

199

Analysis Calculated for $C_{25}H_{31}O_2NS \cdot 1/2\ H_2O$: C, 72.19; H, 7.69; N, 3.24; Found: C, 71.82; H, 7.43; N, 3.26.

FAB: Calcd. for $C_{25}H_{31}O_2NS$: 410; Found: 410.

EXAMPLE 144

Synthesis of 17-β-(4-Dimethylaminobenzoyl)-4-aza-5-a-androst-1-en-3-one

To a suspension of 291.0 mg of dry activated magnesium chips in 8.0 ml of dry THF was added 800.0 mg of 4-bromo-N,N-dimethylaniline in 2.0 ml of dry THF under $N_2$. The reaction was run in an ultrasonic bath at a temperature range of 24°–30° C. To the well-agitated mixture was added dropwise 30 ml of 1,2-dibromoethane/$N_2$. The reaction was allowed to proceed for 1 to 1½ hours at 28° C./$N_2$. The concentration of the Grignard reagent was 4.0 mmoles in 10.0 ml of dry THF.

The steroid from Example 2 (205 mg of pyridyl thioester) was suspended in 2.0 ml of dry THF, cooled to –80° C. and the above Grignard 3.8 ml (3 equivalents) was added via syringe to the steroidal suspension over 5–10 minutes/$N_2$. The reaction was allowed to proceed for 1 hour at –80° C./$N_2$ and then at –10° C. for an additional hour/$N_2$. The solution was diluted with 10.0 ml of methylene chloride and quenched with a saturated aqueous solution of $NH_4Cl$ to pH=4. The organic layers were separated, washed 3 times with water 3 times with saturated sodium chloride, dried over $MgSO_4$, filtered, and evaporated under vacuum to afford 151.3 mg of crude product. Crystallization from ethyl acetate gave 124.5 mg of the above-titled compound, m.pt. 268.5°–269° C.

FAB: Calcd. $C_{27}H_{36}N_2O_2$; 421; Found: 421. The NMR (proton in $CDCl_3$) confirmed the assigned structure.

EXAMPLE 145

General Procedure for Preparing Protected Silyl Derivatives 1.0 mole of phenol or its derivatives, or 1 mole of alcohol is treated with 1.5 liters of dry methylene chloride. To the clear solution is added dry 3.0 moles of imidazole/$N_2$. The clear solution is cooled to 0° C./$N_2$, and 2.0 moles of t-butyl dimethyl chlorosilane in 300.0 ml of dry methylene chloride is added dropwise at 0° C./$N_2$. Towards the end of the addition, precipitation occurs. The ice bath is removed, and the reaction is allowed to proceed overnight at R.T./$N_2$. Filter, wash the cake with cold $CH_2Cl_2$ solution, and the solvent is evaporated in vacuo to afford crude product. The crude product was readily purified by filtering through a silica gel column. (1 gr. of crude product per 100 g of silica gel, using $CH_2Cl_2$ as eluant) This method gives about 99% of pure silyl derivatives of phenols and alcohols.

EXAMPLE 146

Synthesis of 17-β-4-Hydroxybenzoyl)-4-aza-5-α-androst-1-ene-3-one
A. Grignard Reaction To a suspension of 1.22 g of dry activated magnesium chips in 20.0 ml of dry THF was added 5.6 g of 1-bromo-4-(tertiary-butyl dimethyl silyloxy)benzene (prepared from p-bromophenol by the General Procedure detailed above) in 10.0 ml of THF under $N_2$. The reaction was run in an ultrasonic bath at a temperature range of 24°–30° C. To the well-agitated mixture was added dropwise 150 μl–200 μl of 1,2-dibromoethane/$N_2$. The reaction was allowed to proceed for 1–1½ hours at 28° C./$N_2$. The concentration of the Grignard reagent formed was 19.5 mmoles in 30.0 ml of dry THF.

The steroid from Example 129 (1.02 g, 2.49 mmoles) was suspended in 20.0 ml of dry THF, cooled to –80° C. and the above-prepared Grignard (11.5 ml) was added via syringe to the steroidal suspension in 5–10 minutes/$N_2$. The reaction was allowed to proceed for 1 hour at –80° C./$N_2$, and then at –10° C. for an additional hour/$N_2$. The reaction solution was diluted with 10.0 ml of methylene chloride and quenched with a saturated aqueous solution of $NH_4Cl$ to pH=4. Organic layers were separated, washed 3 times with $H_2O$, 3 times with saturated sodium chloride, dried over $MgSO_4$, filtered, and evaporated under a vacuum to a yellow color solid. Crystallization from ethyl acetate afforded 607 mg of product m.p. 248°–249° C.

Analysis Calculated for $C_{31}H_{45}O_3NSi$: C, 73.32; H, 8.93; N, 2.75 Found: C, 73.27; H, 8.99; N, 2.75.

FAB: Found 508; Calc. 508
B. Desilylation

Dissolved 1.3 g of product from above step A in 20.0 ml of dry THF. Cooled to –5° C. and added 437 μl of glacial acetic acid/$N_2$. To the cold solution at –5° C. was added via syringe 3.0 ml tetra-n-butyl-ammonium fluoride dropwise under $N_2$ atmosphere. Allowed the reaction to proceed under stirring for 1½–2 hours at 0° to –5° C./$N_2$. The reaction mixture was poured into a 2-layer mixture of ethyl acetate/ sodium bicarbonate saturated solution at 0° C. The water layer was separated and further extracted with EtOAc 3 times and with $CH_2Cl_2$ (3 times).

The organic layers were combined, washed 3 times with $H_2O$, 1 time with saturated sodium chloride solution, and dried over $MgSO_4$, filtered and evaporated to dryness under vacuum. The crude product was crystallized from ethyl acetate to afford 977.9 mg, and further recrystallized from methanol to afford 842.3 mg of the above-titled product. m.pt. 296°–297° C.

Analysis Calculated for $C_{25}H_{31}NO_3 \cdot 1/3\ H_2O$: C, 75.15; H, 7.98; N, 3.51. Found: C, 75.13; H, 7.76; N, 3.54.

(Mass Spec.) FAB: Found 394; Calcd. 394.

EXAMPLE 147

17-β-(3,5-dimethyl-4-hydroxybenzoyl)-4-aza-5α-androst-1-ene-3-one
A. Preparation of Grignard Reagent To a suspension of 260.0 mg of dry activated magnesium chips in 6.0 ml of dry THF was added 628.0 mg of 1-bromo-3,5-dimethyl-4-tertiary-butyl-dimethylsilyloxybenzene (prepared from 4-bromo-2,6-dimethylphenol by the General Procedure described above) in 4.0 ml of THF/$N_2$. The reaction was conducted in an ultrasonic bath at a temperature range of 24°–30° C. To the well-agitated mixture was added dropwise 40 μl of 1,2-dibromoethane/$N_2$. The reaction was allowed to proceed for 2 hours/$N_2$. The concentration of the Grignard reagent thus formed was 2 mmoles in 10.0 ml of dry THF.

The steroid from Example 129 (205.0 mg (0.5 mmoles) was suspended in 3.0 ml of dry THF, cooled to –80° C., and 7.5 ml (1.50 millieq.) of the above-prepared Grignard was introduced via syringe to the steroidal suspension over a period of 5–10 minutes/$N_2$. The reaction was allowed to proceed for 1 hour at –80° C./$N_2$ and then at –10° C. for additional hour/$N_2$.

The reaction was quenched with 1N HCl, and then diluted with chloroform. The organic layers were combined, washed 3 times with $H_2O$, 3 times with saturated sodium chloride and dried over $MgSO_4$, filtered and concentrated in vacuo. The crude residue was washed with ether to afford 121.7 mg of product.

The crude product was dissolved in 70:30 ($CHCl_3$-acetone), filtered through Teflon (Acrodisc CR) and purified by preparative HPLC (Waters Prep-pak) on silica gel and eluted with 70:30 (CHCl$_3$-acetone).

The major component was recrystallized from ethyl acetate to give 52.0 mg of product m.pt 245°–245.5° C.

Analysis Calculated for C$_{33}$H$_{49}$O$_3$NSi: C, 73.96; H, 9.23; N, 2.61 Found: C, 74.06; H, 9.33; N, 2.64

(Mass Spec.) FAB: Found: 536; Calc.: 536

B. Deblocking the Silyl Derivative

Dissolved 54.0 mg of the above product from A in dry THF (1.3 ml). The clear solution was cooled to 0° C., and 29 μl of glacial HOAc was added via syringe/N$_2$. To the above solution was added dropwise 172 μl of tetra-n-butylammonium fluoride at 0° C. dropwise via syringe/N$_2$. Allowed the reaction to proceed at 0° C./N$_2$ for 1½ hours. The reaction mixture was poured into ice/saturated NaHCO$_3$ solution and EtOAc. Stirred for several minutes. Allow the layers to separate, and the H$_2$O layer was extracted 3 times with EtOAc and 3 times with CHCl$_3$.

Combined the organic layers and washed 3 times with H$_2$O, then 3 times with saturated NaCl, and then dried over MgSO$_4$, filtered and evaporated to dryness in vacuum to afford 52.2 mg.

The product was crystallized from EtOAc to give 22.5 mg of the above-titled product m.pt 305°–306° C.

Analysis Calculated for C$_{27}$H$_{35}$O$_3$N.H$_2$O: C, 73.77; H, 8.49; N, 3.10. Found: C, 73.62; H, 7.90; N, 3.44.

(Mass Spec.) FAB: Calc:422; Found: 422

EXAMPLE 148

Synthesis of 17-β-(4-Methoxybenzoyl)-4-aza-5-α-androst-1-ene-3-one
A. Grignard Reaction To a suspension of 258.0 mg of dry activated Mg chips in 8.0 ml of THF/N$_2$ was added 748.0 mg p-bromoanisole in 2.0 ml of dry THF. The reaction was run in an ultrasonic bath at a temperature range of 24°–30° C./N$_2$. To the well-agitated mixture was added dropwise 30.0 μl of 1,2-dibromoethane as a catalyst. The reaction was allowed to progress for 1–2 hours at 28° C. The formed Grignard reagent had a concentration of 4 mmoles in 10.0 μl of dry THF.

The steroid from Example 129 (205.0 mg (0.50 mml) was suspended in 2.0 ml of THF, cooled to –78° C. and the above-prepared Grignard reagent (3.75 ml; 14 milliequivalents) was added via syringe to the steroidal suspension over 5–10 minutes/N$_2$ and then at –10° C. for an additional hour/N$_2$. The resulting reaction mixture was a clear solution, which was cooled to 0°–5° C., diluted with chloroform and quenched with 1N HCl acid. The organic layers were separated, washed with H$_2$O 2 times, followed with saturated NaCl solution, dried over MgSO$_4$, filtered and evaporated in vacuo. The crude product was washed with ether, and crystallized from EtOAc to give 110 mg of product m.pt 305°–306° C.

Further purification was carried out by chromatographic isolation on a TLC. plate, (20 cm×20 cm×1000 μm), using as eluant, 70:30 (CHCl$_3$:acetone). Recrystallization from EtOAc yielded 78.56 mg of the above-titled product, m.pt 305°–306° C. (dec.).

(Mass Spec) FAB: Calcd., 408; Found 408.

EXAMPLE 149

Synthesis of 17-β-(3-hydroxybenzoyl)-4-aza-5α-androst-1-ene-3 one
A. Preparation of Grignard Reagent To a suspension of 230.0 mg of dry activated Mg chips in 2.0 ml of dry THF was added 722.4 mg of 1-bromo-3-tertiary-butyl dimethyl-silyloxybenzene (prepared from 3-bromophenol by the General Procedure described above) in 8.0 ml of dry THF/N$_2$. The reaction was run in an ultrasonic bath at a temperature range of 24°–30° C./N$_2$. To the well-agitated mixture was added dropwise 20.0 μl of 1,2-dibromoethane/N$_2$. Allowed the reaction to progress for 2½ hours at 28° C./N$_2$. The formed Grignard reagent had a concentration of 2.52 mmoles in 10.0 ml of dry THF.

The steroid from Example 129 (205.0 mg (0.5 mmoles) was suspended in 2.0 ml of THF, cooled to –78° C. and the above-prepared Grignard reagent (6.0 ml, (1.5 milliequivalents) was added via syringe to the steroidal suspension over 5–10 minutes/N$_2$, and then stirred for an additional hour at –10° C./N$_2$. The clear reaction mixture was quenched at 0° to –5° C. with 1N HCl acid for 10.0 minutes and diluted with CHCl$_3$. The combined organic layers were washed 3 times with H$_2$O, 3 times with saturated NaCl, and then dried over MgSO$_4$, filtered and concentrated in vacuo to afford crude product. The product was purified on silica gel column and was eluted with 70:30 (CHCl$_3$-acetone). The desired product amounted to 58.0 mg, as the silyl derivative, 17β-(3-tertiary-butyl-dimethylsilyloxybenzoyl)-4-methyl-4-aza-5α-androst-1-en-3-one.

B. Deblocking 57.6 mg of the above silyl derivative was dissolved in 3.0 ml of dry THF. The solution was cooled to 0° C., and 20 μl of glacial acetic acid was introduced via syringe. To the clear solution was added 130.0 μl of (n-butyl)$_4$NF via syringe, and allowed the reaction to proceed for 1 hour/N$_2$ at 0° C. The reaction mixture was poured into EtOAc/NaHCO$_3$ sat. solution @ 0° C. The water layer was separated, extracted 3 times with EtOAc and then 3 times with chloroform. The organic layers were combined and washed 3 times with H$_2$O, 3 times with saturated NaCl solution, dried over MgSO$_4$, filtered and evaporated in vacuo to give 57.11 mg of crude product. The crude product was chromatographed by TLC (one plate, 20 cm×20 cm×250 μm silica gel), eluted with 70:30 (CHCl$_3$-acetone) to afford 44.5 mg of the above-titled product. Recrystallization from EtOAc gave 29.30 mg m.pt 279°–280° C.

Analysis Calculated for C$_{25}$H$_{31}$NO$_3$: 8H$_2$O: C, 73.60; H, 8.06; N, 3.43. Found: C, 73.26; H, 8.22; N, 3.28.

(Mass Spec.) FAB: Calcd: 394; Found 394.

EXAMPLE 150

Synthesis of 17-β-(4-hydroxymethyl-benzoyl)-4-aza-5α-androst-1-en-3-one A. Preparation of Grignard solution To a suspension of 100.0 mg (4 mmoles) of dry activated Mg chips in 5.0 ml of dry THF/N$_2$, was added 753.0 mg (2.5 mmoles) of 1-bromo-4-tertiary-butyl dimethyl silyloxy methyl benzene (prepared from 4-bromobenzyl alcohol by the General Procedure described above). The reaction was conducted in an ultrasonic bath at a temperature range of 24°–30° C./N$_2$. To the well-agitated mixture was added 20 μl of 1,2-dibromoethane/N$_2$. Allowed the reaction to progress for 2 hours at 28° C./N$_2$. The concentration of formed Grignard was 2.5 mmoles in 5.0 ml of dry THF.

B. Grignard Reaction

The steroid from Example 129 (205.0 mg (0.5 mmoles) was suspended in 2.0 ml of THF, cooled to –78° C., and the above-prepared Grignard (3.0 ml, 3.75 milliequivalents) was introduced via syringe into the steroidal suspension over 5–10 minutes/N$_2$. Allowed the reaction to progress for 1 hour at –80° C./N$_2$, and then for an additional hour at –10° C./N$_2$. The clear reaction solution was quenched with saturated NH$_4$Cl at 0° to –5° C., and then diluted with CH$_2$Cl$_2$.

The organic layers were separated and washed 3 times with water, 3 times with saturated NaCl, dried over $MgSO_4$, filtered and evaporated in vacuo to dryness. Crude product was crystallized from EtOAc to give 137.8 mg of silyl product.

(Mass Spec.) FAB: Calcd for $C_{30}H_{41}O_3NSi$: 521.75 Found: 522.0.

C. Deblocking of Silyl Derivative

The product from Step B above (23.67 mg) was dissolved in 0.5 ml of THF and 0.5 ml of MeOH and cooled to 0° C./$N_2$. To the cold solution was added 10 ml of concentrated sulfuric acid (98%). The reaction was stirred for 45 minutes at 0° C./$N_2$. To the cold solution at 0° C. was slowly added a saturated solution of $NaHCO_3$ and chloroform. Extracted 3 times with $CHCl_3$. The organic layers were washed 3 times with water, 3 times with saturated NaCl, solution dried over $MgSO_4$, filtered and evaporated to dryness in vacuo, to afford 10.18 mg. After chromatography on a TLC plate (elution with 1:1 $CHCl_2$:acetone) The crude product was crystallized from EtOAc to give 6.0 mg of the above-titled product, m.pt 318°–320° C.

Analysis Calculated for $C_{26}H_{33}O_3N.1/3H_2O$: C, 75.41: H, 7.94; N, 3.38. Found: C, 75.61; H, 7.84; N, 3.12.

(Mass Spec.) FAB: Calc.: 408; Found: 408

EXAMPLE 151

Synthesis of 17-β-(4-Carboxybenzoyl)-4-aza-5α-androst-1-en-3-one

A. Oxidation 90.2 mg of the product from Example 150 was dissolved in 2.63 ml of glacial acetic acid and to the clear solution was added 69.0 mg of $CrO_3$ (previously dried over $P_2O_5$ at R.T. for 2 days in vacuo). After stirring overnight, the reaction mixture was diluted with water and allowed to age overnight in the refrigerator. The reaction mixture was filtered and the mother liquor and washes were extracted overnight using a liquid-liquid extractor, ($H_2O$-EtOAc) under reflux conditions. The organic layer was dried over $MgSO_4$, filtered and evaporated in vacuo. The residue was dissolved in hot MeOH, filtered and evaporated in vacuo to afford a product weighing 32.0 mg.

FAB: Calc. for $C_{26}H_{31}O_4N$: 422.0; Found: 422.

B. Purification

The above free acid was purified by dissolving the above product in 1N sodium hydroxide solution. The clear solution was extracted 3 times with EtOAc. The aqueous basic solution was cooled and acidified with 1N HCl acid dropwise to pH=4 with stirring. The reaction mixture was allowed to age for 1 hour at 0° C. It was filtered and the residue was washed with cold water. Dried overnight to 100° C. in vacuum <0.2 mm pressure.

Yield of the above-titled free acid was 9.85 mg.

FAB: Calc. for $C_{25}H_{31}O_4N$: 422; Found 422.

NMR analysis indicated the product to be an acid.

C. Sodium Salt of Above Acid 4.9 mg of the above product acid B was dissolved in 2.0 ml of hot methanol. To the clear solution, was added 11.6 μl of 1N NaOH(aq). To solution after methanol evaporation in vacuo, was added water to reach pH 7.21. The aqueous solution was freeze dried to give 6.3 mg of the sodium salt of the above-titled product.

EXAMPLE 152

Synthesis of 17-β-(4-hydroxyethylbenzoyl)-4-aza-5α-androst-1-en-3-one

A. Grignard Reagent

To a suspension of 252 mg of dry activated Mg chips in 10.0 ml of dry THF was added 1.26 g (4 mmoles) of 1-bromo-4tertiary-butyl dimethyl silyloxy ethyl benzene (prepared from 2-(p-bromophenyl)ethanol by the General Procedure described above). The reaction mixture was vigorously stirred using an ultrasonic vibrator/$N_2$. To the well-agitated mixture was added 40 μl of 1,2-dibromoethane to catalyze the above reaction. Allowed the reaction to progress for 3½–4 hours/$N_2$. The concentration of formed Grignard reagent was 4 mmoles in 10 ml of THF.

B. Grignard Reaction 205.0 mg (0.5 mmoles) of the aza-steroid of Example 129 was suspended in 2.0 ml of dry THF/$N_2$, cooled to –80° C., and the above-prepared Grignard (3.75 ml, 1.5 milliequivalents) via syringe was introduced into the steroidal suspension over 5–10 minutes/$N_2$. The reaction was run at –80° C. for 1 hour/$N_2$ and then for an additional hour at –10° C. The reaction was quenched with a saturated solution of $NH_4Cl$ at 0°–5° C. and diluted with 10.0 ml of $CH_2Cl_2$. The organic layers were washed with water (3 times), saturated NaCl solution (3 times), dried with $MgSO_4$, filtered and evaporated in vacuo to dryness. The crude product was crystallized from EtOAc overnight to give 152.0 mg of product m.pt. 233°–234° C.

Analysis Calculated for $C_{33}H_{49}O_3NSi$: 1/4 $H_2O$: C, 73.55; H, 9.18, N, 2.59. Found: C, 73.45; H, 8.94; N, 3.21

FAB: Calc. 536; Found: 536

C. Desilylation 70.8 mg of product from Step B, was dissolved in 1.45 μl of methanol and 1.45 ml of THF. The solution was cooled to 0°–5° C. and 29 μl of conc. $H_2SO_4$ was added via syringe under $N_2$. The reaction was allowed to proceed for 45 minutes/$N_2$. The reaction was carefully quenched at 0° C. with a saturated solution of $NaHCO_3$, and extracted 3 times with $CH_2Cl_2$. The organic layers were separated, washed with water (3 times), then with saturated NaCl solution, dried over $MgSO_4$, filtered and evaporated in vacuo to give 43.0 mg of crude product. The crude product was placed on a column of silica gel and was eluted with 1:1 acetone-$CH_2Cl_2$. The isolated product was crystallized from anhydrous methanol to afford 20.0 mg of the above-titled product m.pt 292°–293° C. with dec.

Analysis Calculated for $C_{27}H_{35}O_3N.1/4$ $H_2$: C, 75.31; H, 8.25; N, 3.25. Found: C, 75.49; H, 8.29; N, 3.45.

FAB: Calcd 422; Found 422.

EXAMPLE 153

Synthesis of 17-β-(4-carboxymethylbenzoyl)-4-aza-5α-androst-1-en-3-one

A. Oxidation 13.0 mg of the product from Example 152 was dissolved in 1 ml of glacial acetic acid. To the clear solution was added 10.0 mg of $CrO_3$ (previously dried over $P_2O_5$ in vacuum at R.T.). Allowed the reaction to progress overnight at R.T., and then at 0° C. for 48 hours. The addition of 7.0 ml of water caused the product to crystallize overnight in a refrigerator. The crude product was isolated, washed with cold water and dried in a vacuum at 110° C. below 1 mm pressure.

The dried crude product was dissolved in 1N sodium hydroxide and the basic solution was extracted 3 times with methylene chloride (The organic layers were separated, and the aqueous basic solution was cooled and acidified with 1.5N hydrochloric acid. The precipitate was filtered, washed with water dried at 110° C. under vacuum at 0.1 mm pressure.

Yield of above-titled product=7.0 mg.

FAB Calc. $C_{27}H_{33}O_4N$: 436; Found 436.

EXAMPLE 154

Synthesis of 17-β-(3,4-dihydroxybenzoyl)-4-aza-5α-androst-1-en-3-one

A. Grignard

To a suspension of 258.5 mg of dry activated magnesium chips in 10.0 ml of dry THF, was added 482 mg of 4-bromo-1,2-methylenedioxybenzene/$N_2$. (The starting material is commercially available from Aldrich Chemical) The reaction was conducted in an ultrasonic water bath at a temperature range of 24°–30° C. To the well-agitated mixture was added 40 µl of 1,2-dibromoethane as a catalyst/$N_2$, and the reaction was allowed to progress for 1½–2 hours at 28° C./$N_2$. The concentration of the formed Grignard reagent was 3.75 mmoles in 10 ml of dry THF.

The steroid from Example 129 (410 mg, 1 mmole) was suspended in 4.0 ml of dry THF/$N_2$ and cooled to –80° C. and 8.0 ml of the above-prepared Grignard (3.04 milliequivalents) was added via syringe to the steroidal suspension/$N_2$ over a period of 5–10 minutes. The reaction was allowed to proceed for 1 hour at –80° C., and then at –10° C. for an additional hour/$N_2$. The reaction mixture was diluted with $CH_2Cl_2$, and then quenched with 1N HCl at –5° C.

The organic layers were collected and washed with water 3 times, saturated NaCl solution 3 times, dried over $MgSO_4$, filtered and evaporated in vacuo to dryness. Purification of the crude product was carried out on 50.0 g of silica gel using as eluant 1:1 ($CH_2Cl_2$-acetone) to give 347.0 mg.

FAB showed 422; Calcd. 422.

62.4 mg of the above product was crystallized from EtOAc to afford 11.39 mg of product m.pt. 324°–325° C.

Analysis Calculated for $C_{26}H_{31}O_4N \cdot 3/4\ H_2O$: C, 71.78; H, 7.53; N, 3.22. Found: C, 71.90; H, 7.54; N, 3.25.

FAB for $C_{26}H_{31}O_4N$ showed 422; Calcd: 422.

B. Cleavage of Methylene Dioxylan Group 70.0 mg of the product from Step A was dissolved in dry 25.0 ml of 1,2-dichloroethane at R.T./$N_2$. The solution was allowed to cool to –10° C., and 1.03 ml of $BBr_3$ (1.0M solution in dichloromethane) was added dropwise under $N_2$ atmosphere. The reaction was allowed to proceed at R.T. for 3½–4 hours/$N_2$. After 4 hours/$N_2$, the reaction was cooled to (–10° C.) and quenched with 10.0 ml of methanol for 10 minutes at 0° C., and then gradually the temperature was allowed to rise to R.T./$N_2$. The reaction mixture was evaporated in vacuo to dryness. The residue was extracted 3 times with EtOAc. The organic layers were washed with water 3 times, 2 times with saturated $NaHCO_3$ solution, 3 times with water and finally with a saturated solution of NaCl. The organic layers were dried over magnesium sulfate, filtered and concentrated in vacuo. The crude material was chromatographed on 2 silica gel plates, (20 cm×20 cm×20 cm×250 µm) eluted with 1:1 (acetone-methylene chloride). Recrystallization from EtOAc afforded 5.0 mg of the above-titled product m.p. 222°–222.5° C.

Analysis Calculated for $C_{25}H_{31}O_4N \cdot 1/2\ H_2O$: C, 71.78; H, 7.66; N, 3.35. Found: C, 71.71; H, 7.71; N, 3.33.

FAB: Calcd. for $C_{25}H_{31}O_4N$: 410; Found 410.

EXAMPLE 155

Synthesis of 17-β-(2-methoxybenzoyl)-4-aza-5α-androst-1-ene-3-one

A. Grignard

To a suspension of 258.0 mg of dry activated magnesium chips in 8.0 ml of dry THF was added 771.0 mg of o-bromoanisole in 2.0 ml of dry THF/$N_2$. The reaction was conducted in an ultrasonic water bath at a temperature range of 24°–30° C. To the well-agitated mixture was added 30 µl of 1,2-dibromoethane/$N_2$, and the reaction was allowed to progress for 2 hours at 28° C./$N_2$. The concentration of the formed Grignard reagent was 4 mmoles in 10.0 ml of dry THF.

The steroid from Example 129 (205 mg, 0.5 mmoles) was suspended in 2.0 ml of dry THF/$N_2$, cooled to –79° C., and 4.0 ml of the above-prepared Grignard (1.6 milliequivalents) was added via syringe to the steroidal suspension/$N_2$ over a period of 5–10 minutes. The reaction mixture was allowed to proceed for 1 hour at –80° C., and then at 0°–2° C. for an additional hour/$N_2$. The reaction mixture was diluted with $CH_2Cl_2$ and then quenched with 1N HCl solution at 0° C.

The organic layers were combined, washed 3 times with water, 3 times with saturated NaCl solution; and dried over $MgSO_4$. Filtered and evaporated in vacuum to dryness. The crude material was crystallized from EtOAc to give 124.5 mg of product m.pt 228°–230° C. Purification on silica gel column using 70:30 ($CHCl_3$-acetone) gave a single spot material in a yield of 83.0 mg m.pt. 241–241.5.

Analysis Calculated for $C_{26}H_{33}O_3N$: C, 76.91; H, 8.19; N, 3.45 Found: C, 76.36; H, 8.26; N, 3.35.

FAB calcd. for $C_{26}H_{33}O_3N$: 406; Found: 406.

B. Cleavage of Methoxy Group 12.7 mg (0.03 mmoles) of the product from Step A was dissolved in 5.0 ml of dry methylene chloride/$N_2$. To clear solution at –79° C./N, was added 50 µl of 1 mmole/ml of $BBr_3$ in $CH_2Cl_2$ via syringe dropwise. Allowed the reaction to proceed at R.T. overnight/$N_2$ with rapid stirring. Next day, a clear yellow solution was obtained. The reaction mixture was cooled to 0°–2° C. and quenched with water, to hydrolyze excess of $BBr_3$. The organic phase was washed 3 times with dilute sodium hydroxide, 3 times with water, 3 times with dilute HCl, 3 times with water, 3 times with saturated NaCl solution, and dried the organic layer over $MgSO_4$. Filtered, concentrated in a vacuum to dryness. The crude product crystallized from EtOAc to afford 7.0 mg of a pure single spot material being 17-β-(2-hydroxymethyl-benzoyl)-4-aza-5-α-androst-1-en-3-one.

FAB for $C_{25}H_{31}NO_2$; Calcd: 394; Found: 394.

EXAMPLE 156

17β(a-hydroxybenzyl)-4-aza-5α-androst-1-ene-3-one 570 milligrams of 17β-benzoyl-4-aza-5α-androst-1-ene-3-one (prepared from the thiopyridyl ester of Example 129 and commercially available phenyl magnesium bromide, analogously via the procedure in Example 132, to produce the 17-benzoyl derivative, mp. 295°–296° C. crystallized from EtOAc) was suspended in 80 ml of anhydrous isopropanol. To the suspension was added 500.0 mg of $NaBH_4$ in 5 portions. When all the hydride was added, 20.0 ml of dry THF was carefully added, so that the reaction mixture became a clear solution. Allowed the reaction to proceed at R.T./$N_2$ overnight. The reaction was quenched carefully with 1N HCl, and allowed to stir under $N_2$ for an additional hour at R.T. It was then diluted with water, and extracted 3 times with $CHCl_3$. The organic layers were combined, washed 3 times with H$_2$O; 3 times with saturated NaCl solution, and dried over MgSO$_4$. Filtered and evaporated to a white solid weighing 495.0 mg.

The crude material was crystallized from EtOAc to afford 349.5 mg of material. Further purification on a silica gel column, using as eluant, 70:30 (CHCl$_3$-acetone) gave a single spot material, 221 mg, of the above-titled compound, m.pt 296°–297° C.

Analysis Calculated for C$_{25}$H$_{33}$NO$_2$: C, 79.17; H, 8.78; N, 3.70. Found: C, 79.24; H, 8.85; N, 3.48.

FAB Calcd. for C$_{25}$H$_{33}$NO$_2$: 380; Found: 380.

EXAMPLE 157

17β-hydroxymethyl-4aza-5α-androst-1-en-3-one 500.0 mg of S-2-pyridyl-3-oxo-4-aza-5α-androst-1-ene-3 one (Example 2) was dissolved in 40.0 ml of dry THF at R.T./N$_2$. The solution was cooled to –78° C./N$_2$ and 5.5 ml of 1M dibutyl aluminium hydride in THF was slowly added via syringe to the solution, with rapid stirring. Allowed the reaction to proceed at –76° to –78° C. for half an hour under N$_2$. The temperature was gradually brought to R.T. and the reaction mixture kept for 2½ hours/N$_2$. The reaction was then quenched at 0° to 5° C. with 2N HCl acid, and then diluted with CHCl$_3$. The organic layers were separated, washed with H$_2$O 3 times, then with saturated NaCl solution, and finally dried over MgSO$_2$. Filtered, and the organic phase was evaporated under vacuum to give 216.0 mg of crude product.

The crude product was chromatographed on 20.0 g of E.M. silica gel column, using 70:30 (CHCl$_3$-acetone) as eluant.

Yield of single spot material was 126.3 mg of the above-titled compound, m.pt. 271°–271.5° C.

Calcd. for C$_{19}$H$_{29}$O$_2$N: FAB 304; Found 304.

NMR in CDCl$_3$ confirmed the above structure.

EXAMPLE 158

17β-Formyl-4-aza-5α-androst-1-ene-3-one

Into a 100.0 ml dry flask was placed 1.3 ml of oxalyl chloride (2M in CH$_2$Cl$_2$) with 50.0 ml of dry CH$_2$Cl$_2$/N$_2$. The above solution was cooled to –78° C. and 338 μl of DMSO was added dropwise via syringe/N$_2$. The mixture was stirred at –78° C./N$_2$ for 30 minutes, and a solution of above-prepared alcohol from Example 142, i.e. 17β hydroxymethyl-4-aza-5α-androst-1-ene-3-one (256.9 mg in 15.0 ml of dry CH$_2$Cl$_2$/N$_2$ was added via syringe. The reaction was allowed to progress for one hour at –78° C./N$_2$. After an hour at –78° C., was added 1 ml of dry triethylamine at a rapid rate. Reaction was raised slowly to R.T./N$_2$ with stirring, the resulting yellow solution was then poured into 50.0 ml of cold water. The organic layers were washed with a saturated solution of NaHCO$_3$, and then with a saturated solution of NaCl. Dried over MgSO$_4$, evaporated the solvent under vacuum to give 172.4 mg of crude product. The crude product was chromatographed on 60.0 g silica gel column using 70.30 (CHCl$_3$-acetone), to give a single spot material. Crystallization from EtOAc afforded the above-titled compound, 37.7 mg, m.pt. 258°–259° C.

EXAMPLE 159

Synthesis of diastereoisomeric 17β(a-hydroxybenzyl)-4-aza-5α-androst-1-ene-3-ones 26.3 of above-prepared formyl derivative was dissolved in 7.0 ml of dry THF/N$_2$. The solution was cooled to –78° C./N$_2$, and 131 μl of phenyl magnesium bromide (Aldrich reagent) 0.393 milliequivalents) in dry THF was added dropwise via syringe/N$_2$. Allowed the reaction to proceed for 1 hour/N$_2$ at –78° C. and then at R.T. for addition hour/N$_2$.

The reaction was quenched at 0°–5° C. with 2.5N HCl, and then diluted with CHCl$_3$. Organic layers were separated, washed 3 times with water; 3 times with saturated NaCl solution, dried over MgSO$_4$. Filtered and evaporated in vacuum to dryness to afford 28.6 mg of crude product. Analysis of the NMR spectra and peak heights from HPLC indicated this product to be a 1:1 mixture of diastereoisomers. The crude product was filtered through a 1 μm Teflon filter and purified by HPLC on a Whitman Portisil 10 column using 70:30 (CHCl$_3$-acetone). The FAB mass spectrum indicated the same M$^+$+1 for both isomers, being 380 mass units. The faster eluting isomer, m.pt. 289°–289.5° C., was crystallized from EtOAc and showed a single spot material on TLC.

Analysis Calculated for C$_{25}$H$_{33}$NO$_2$•1/4 H$_2$O; C, 78.39; H, 8.81; N, 3.65. Found: C, 78.11; H, 8.65; N, 3.58.

The slower eluting isomer, m.pt. 300°–301° C. showed a single spot material on TLC. The faster isomer showed by NMR(CDCl$_3$): CH$_3$ at C-18 was deshielded (0.89δ) as compared to the slower isomer CH$_3$ at C-18 at (0.69δ). The benzilic proton for the faster isomer was also deshielded (4.5δ) versus (4.95δ). The olefinic proton at C-1 showed deshielding effects for the faster isomer at (6.81δ) to (6.62δ). From the above data, the two isomers showed distinctly different physical properties.

EXAMPLES FOR THE CASE WHEN SUBSTITUENT "A" OF GENERAL FORMULA "I" IS AS DEFINED IN GROUP "II(A)"

EXAMPLE 161

Preparation of 17-(diphenylmethoxymethyl)-4-methyl-5-α-4-azaandro-stan-3-one

To a solution of 17-hydroxymethyl-4-methyl-5-α-4-azaandrostan-3-one (0.096 g, 0.3 mM) and diphenyldiazomethane (0.25 g, 1.28 mM) in anhydrous methylene chloride (8 mL) at ice-bath temperatures was added boron trifluoride etherate (0.05 mL) dropwise over three minutes. The mixture was allowed to stir cold for an additional 25 minutes and then at ambient temperatures for 2 hours. The mixture was transferred to a separatory funnel with methylene chloride, washed with water, dried, and the methylene chloride removed in vacuo. Flash chromatography (silica gel, ethyl acetate as eluant) of the residue thus obtained yielded the title compound as a white waxy solid. Mass Spec (MS) M$^+$ calculated for C$_{33}$H$_{43}$NO$_2$, mw=485.71; observed m/e 485.

EXAMPLE 162

Preparation of 17-(carboethoxymethoxymethyl)-4-methyl-5α-4-azaandro-stan-3-one

Employing substantially the same procedure as described in Example 161, but substituting ethyl diazoacetate for the diphenyldiazomethane used therein, the title compound was obtained. MS M$^+$ calculated for C$_{24}$H$_{39}$NO$_4$, mw=405.58; observed m/e 405.

EXAMPLE 163

Preparation of 17-(carbobenzyloxymethoxymethyl)-4-methyl-5α-4-azaandrostan-3-one Employing substantially the same procedure as described in Example 161, but substituting benzyl diazoacetate for the diphenyldiazomethane used therein, the title compound was obtained. MS MH$^+$ calculated for $C_{29}H_{41}NO_4$, mw=467.66; observed m/e 468.

EXAMPLE 164

Preparation of a) 20-(methoxymethyl)-4-methyl-5α-4-azapregnan-3-one and b) 20-(methoxy)-4-methyl-5α-4-azapregnan-3-one Employing substantially the same procedure as described in Example 161, but substituting 20-(hydroxymethyl)-4-methyl-5-α-4-azapregnan-3-one and diazomethane in place of the corresponding steroid alcohol and diazo compound used in Example 161, title compound (a) was obtained as a white solid. MS M$^+$ calculated for $C_{23}H_{39}NO_2$, mw=361.57; observed m/e 361.

Employing substantially the same procedure as described in Example 161, but substituting 20-hydroxy-4-methyl-5α-4-azapregnan-3-one and diazomethane for the steroid alcohol and diazo compound used therein, title compound (b) was obtained. MS M$^+$ calculated for $C_{22}H_{37}NO_2$, mw=347.54; observed m/e 347.

EXAMPLE 165

Preparation of 17-methoxymethyl-4-methyl-5α-4-azaandrostan-3-one

Employing substantially the same procedure as described in Example 164, but substituting 17-hydroxymethyl-5-α-4-azaandrostan-3-one for the steriod used therein, the title compound was obtained. MS M$^+$ calculated for $C_{21}H_{35}NO_2$, mw=333.53; observed m/e 333.

EXAMPLE 166

Preparation of 17-(ethylthiomethyl)-4-methyl-5α-4-azaandrostan-3-one

The mesylate of 17-hydroxymethyl-4-methyl-5-α-4-azaandrostan-3-one (prepared from the alcohol and methanesulfonyl chloride in methylene chloride with pyridine at room temperature) (0.05 g, 0.125 mM) was heated with sodium thioethoxide (0.121 g, 1.44 mM) in anhydrous 1,2-dimethoxyethane in a nitrogen atmosphere for 73 hours. The solvent was removed in vacuo, the residue taken up in methylene chloride, washed (water) and dried. The residue obtained upon concentration of the methylene chloride was flash chromatographed (silica gel, ethyl acetate as eluant) to yield the title compound as a white waxy solid. MS MH$^+$ calculated for $C_{22}H_{37}NOS$, mw=363.60; observed m/e 364.

EXAMPLE 167

Preparation of 17-carboxymethoxymethyl-4-methyl-5-α-4-azaandrostan-3-one

The title compound was obtained by hydroly-sis of 17-(carboethoxymethoxymethyl)-4-methyl-5-α-4-azaandrostan-3-one using an aqueous-methanolic solution of NaOH. The title compound was also obtained by reduction of 17-(carbobenzyloxy-methoxymethyl)-4-methyl-5-α-4-azaandrostan-3-one with hydrogen using palladium on carbon catalyst. MS MH$^+$ calculated for $C_{22}H_{35}NO_4$, mw=377; observed m/e 378.

EXAMPLE 168

Preparation of a) 20-(diphenylmethoxy)-4-methyl-5α-4-azapregnan-3-one, and b) 20-(diphenylmethoxymethyl)-4-methyl-5α-4-azapregnan-3-one The following compounds of formula 2 were made according to substantially the same procedure as described in Example 161, but substituting the 4-azapregnan-3-one starting material indicated below, for the 17-hydroxymethyl-4-methyl-5α-4-azaandrostan-3-one used therein:

a) 20-hydroxy-4-methyl-5α-4-azapregnan-3-one; MS M$^{+1}$ calculated for $C_{34}H_{45}NO_2$, mw=499.72; observed m/e 499; and b) 20-hydroxymethyl-4-methyl-5α-4-azapregnan-3-one; MS M$^+$ calculated for $C_{35}H_{47}NO_2$, mw=513.76; observed m/e 513.

EXAMPLE 169

Preparation of a) 20-(ethylthiomethyl)-4-methyl-5α-4-azapregnan-3-one, b) 20-(isopropylthiomethyl)-4-methyl-5α-4-azapregnan-3-one, and c) 17a-thiophenoxy-4-methyl-5α-4-azaandrostan-3-one Employing substantially the same procedure as described in Example 166, but substituting the 4-azaandrostan-3-one and thioethoxide starting materials used therein with the starting materials indicated below, the title compounds were obtained:

a) 20-hydroxymethyl-4-methyl-5α-4-azapregnan-3-one and Na$^+$SC$_2$H$_5^-$; MS MH$^{++}$ calculated for $C_{24}H_{41}NOS$, mw=391.66; observed m/e 393;

b) 20-hydroxymethyl-4-methyl-5α-4-azapregnan-3-one and Na$^+$SCH(CH$_3$)$_2^-$; MS MH$^+$ calculated for $C_{25}H_{43}NOS$, mw=405.68; observed m/e 406; and c) 17β-hydroxy-4-methyl-5α-4-azaandrostan-3-one and K$^+$SC$_6$H$_5^-$. M.p. 187°–189° C.

EXAMPLE 170

Preparation of 17β-(4-nitrophenoxy)-4-methyl-5α-4-azaandrostan-3-one

To a stirred solution of 17β-hydroxy-4-methyl-5α-4-azaandrostan-3-one (1.07 g, 3.5 mmole) and p-nitrofluorobenzene (2.0 ml, 14 mmole) in DMF (15 ml) under N$_2$ was added 95% NaH (180 mg, 7 mmole) in two portions during 10 mins. The mixture was stirred for 3 hours at room temperature and poured onto ice (50 g) and water (50 ml). The mixture was extracted with CH$_2$Cl$_2$ (30 ml×2). The organic layer was washed with brine and dried (Na$_2$SO$_4$). Removal of solvent gave the crude product which was purified via a flash silica gel column eluting with 1:1 ethyl acetate-CH$_2$Cl$_2$ to give the desired title product. Mp. 183°–184° C. (recrystallized from CH$_2$Cl$_2$-hexane).

EXAMPLE 171

Employing substantially the same procedure as described in Example 170 using 17β-hydroxy-4-methyl-5α-4-azaandrostan-3-one, compound 7 below, but substituting compound 8 for the p-nitrofluorobenzene used therein, and running the reaction at the temperature indicated, products of formula 9 were made, as defined in 11a–11e:

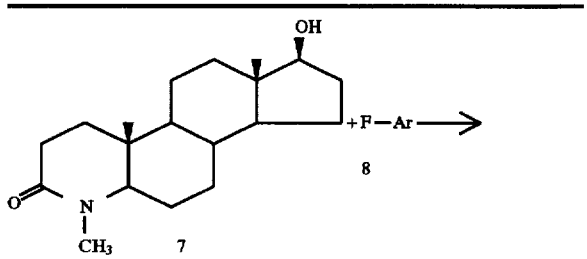

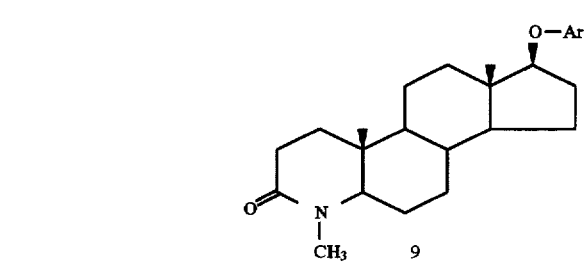

| Ar | temp. (°C.) | |
|---|---|---|
| 11a) —⌬—CN | room temp. | m.p. = 224–225° C. |
| 11b) NO₂—⌬—NO₂ | 70–75 | mass spec. (EI) 471 |
| 11c) —⌬—⌬ | 70–75 | mass spec (EI) 457 |
| 11d) —⌬ (pyridine) | 70–75 | m.p. 172–174° C. |
| 11e) —⌬—CH₂=CH₂ | 70–75 | mass spec. (FAB) 408 |

The following products of formula 9, as defined in 11f–11h, were made using substantially the same procedure as described above, except that in place of NaH/DMF, for 11f KOH/DMF was used, and for 11g–11h KOH/DMSO was used and the reactions were stirred for about 20 hours at 70°–80° C. instead of for 3 hours at room temperature:

| Ar | |
|---|---|
| 11f) —⌬—Br | mass spec. (FAB) 460 |
| 11g) —⌬—Cl | mass spec. (FAB) 416 |
| 11h) —⌬—CH₃ | m.p. 176–179° C. |

EXAMPLE 172

Preparation of 17β-(4-aminophenoxy)-4-methyl-5α-4-azaandrostan-3-one hydrochloride 17β-(4-nitrophenoxy)-4-methyl-5α-4-azaandrostan-3-one (938 mg, 2.2 mmole) in MeOH (70 ml) was hydrogenated at 40 psi in the presence of PtO₂ (400 mg) for 90 mins. To the resulting mixture was added 5% conc. HCl in absolute ethanol (4 ml) under N₂, and then the mixture was filtered through a pad of celite. The filtrate was concentrated, vacuum dried, and then triturated with CH₂Cl₂-hexane to give the title product, mp. 307°–310° C.

EXAMPLE 173

Preparation of 17β-(4-acetamidophenoxy)-4-methyl-5α-4-azaandrostan-3-one

To 17β-(4-aminophenoxy)-4-methyl-5α-4-azaandrostan-3-one hydrochloride (7 mg) in CH₂Cl₂ (100 μl) was added acetic anhydride (30 μl) followed by adding pyridine (50 μl). The mixture was stirred at room temperature for 1 hr and then concentrated to dryness. The residue was purified via a silica gel plate developed with 5% MeOH-EtOAc (Rf=0.3) to give the title product, mp. 340° C.

EXAMPLE 174

Preparation of 17β-(4-carboxamidophenoxy)-4-methyl-5α-4-azaandrostan-3-one

To a solution of 17β-(4-cyanophenoxy)-4-methyl-5α-4-azaandrostan-3-one (102 mg, 0.25 mmole) in absolute ethanol (0.80 ml) and THF (0.40 ml) was added 30% H₂O₂ (0.20 ml) and then 5N NaOH (0.12 ml) dropwise. The resulting mixture was stirred at 48°–50° C. for 5 hr. and concentrated to a residue. The residue was taken up in methylene chloride and purified via preparative silica gel plate (Rf=0.3; 10% MeOH-EtOAc) to yield the title compound, mp 313°–315° C.

EXAMPLE 175

Preparation of
a) 17β-phenoxy-4-methyl-5α-4-azaandrostan-3-one,
b) 17α-phenoxy-4-methyl-5α-4-azaandrostan-3-one and
c) 17α-(4-biphenyloxy)-4-methyl-5α-4-azaandrostan-3-one To a mixture of 17β-(4-aminophenoxy)-4-methyl-5α-4-azaandrostan-3-one hydrochloride (49 mg) in conc. H₂SO₄-95% EtOH (80 ml, 1:4 v/v) at 5°–10° C. was added 95% EtOH (0.75 ml) and ice (0.25 g) with stirring. To this suspension at 5° C. was added a solution of NaNO₂ (12.5 mg) in H₂O (21.5 μl) over 10 min. After stirring at 5° C. for 1 hr, additional 95% EtOH (1.0 ml) was added and the reaction stirred at 5° C. for 20 min to increase the solubility and the diazotization process. To this mixture was added ether washed copper bronze (5 mg) and the mixture was heated at reflux for 5 min. The mixture was then purified on a silica gel plate developed with EtOAc (Rf=0.25, EtOAc) to yield the title product (a). M.p. 169.5°–171° C.

The title product (b) was prepared by combining 17β-hydroxy-4-methyl-5α-4-azaandrostan-3-one (61 mg., 0.20 mmol), phenol (57.4 mg, 0.60 mmol), Ph₃P (68 mg, 0.26 mmol), and DEAD (43 μl, 0.26 mmol) in dry THF (1.0 ml) in a test tube under N₂, and heating the mixture to 80° C. After 2 hours. TLC showed that about 3–5% starting material remained in the reaction mixture. The mixture was purified via preparative TLC in a silica gel plate (1500μ) developed with 4% MeOH/CH₂Cl₂ first and then after drying, with 33% MeOH/CH₂Cl₂, to obtain the crude product (b). The crude material was re-purified via preparative TLC, each on a separate silica gel plate (1000μ) developed with EtOAc. The product was obtained from both plates, and triturated with 5% CH₂Cl₂/hexane to yield the title compound (b).

The title product (c) was prepared using essentially the same procedure as described for making title product (b), except substituting 4-hydroxybiphenyl for the phenol used therein.

Rf=0.3, EtOAc; m.p. 219°–222° C.

EXAMPLE 176

Preparation of 17β-hexoxy-4-methyl-5α-4-azaandrostan-3-one

To a solution of 17β-hydroxy-4-methyl-5α-4-azaandrostan-3-one (102 mg, 0.336 mmol) in DMSO (3 ml) was added powdered KOH (300 mg) followed by n-hexyliodide (400 μl). After stirring the reaction mixture overnight, the reaction was diluted with water and extracted with ethyl acetate. The organic layer was washed with water, then brine, then dried (MgSO₄), and concentrated in vacuo. The residue was then purified by preparative thin layer chromatography to afford the title compound, characterized by H¹ NMR.

Employing substantially the same procedure using KOH/DMSO as described above, but substituting compounds 10 and 11, below, for the steroid and the n-hexyliodide, respectively, used therein, the following products of formula 12 were made, as defined in 16a–16f:

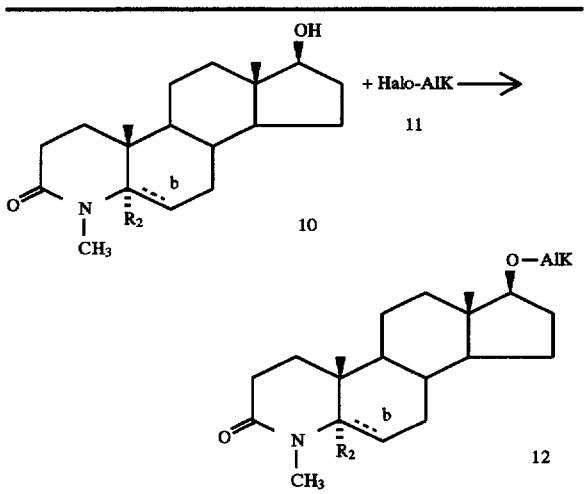

| Halo | AlK | b | R² |
|------|-----|---|-----|
| —I | —(CH₂)₃CH(CH₃)₂ | Single bond | —H |
| —I | —(CH₂)₁₀CH₃ | Single bond | —H |
| —I | —CH₂CH₂CH₃ | Single bond | —H |
| —Br | —CH₂CH=CH₂ | Single bond | —H |
| —Br | —CH₂CH=CH₂ | double bond | absent |
| —I | —(CH₂)₅CH₃ | double bond | absent |

EXAMPLE 177

Preparation of 5α-4-azaandrostan-3-on-17β-yloxyacetic acid

Step A: Preparation of testosterone-seco-acid ethyl ester

Testosterone-seco-acid (24.0 g) and toluenesulfonic acid monohydrate (0.5 g) in absolute ethanol were refluxed for 3 hours. Removal of solvent gave the crude ethyl ester which was used in Step B without purification.

Step B: Preparation of diethyl ester of testosterone-seco-acid-17β-yloxyacetic acid To the ethyl ester (19 g, from Step A) in methylene chloride (200 ml) was added over a 5 hour period a solution of ethyl diazoacetate (7.6 ml) in methylene chloride (40 ml), and solid rhodium diacetate dimer (40 mg) was added in 10 portions during 5 hours, which resulted in ca. 50% conversion to the desired product. The mixture was concentrated to a residue which was purified by two silica gel flash column chromatography to give the liquid title compound.

Step C: Preparation of testosterone-seco-acid-17β-yloxyacetic acid

To the diethyl ester (10.0 g, from Step B) in methanol (210 ml) and THF (210 ml) was added 5N NaOH (50 ml) dropwise during 30 min. This mixture was stirred for another 15 minutes and filtered. The filtrate was concentrated, and extracted with methylene chloride to remove non-acid impurities. The aqueous solution was acidified with 6N HCl to pH 2 and extracted with CH₂Cl₂. The organic layer was dried (Na₂SO₄) and concentrated to give the title diacid.

Step D: Preparation of 4-azaandrost-5-en-3-on-17β-yloxyacetic acid

The diacid (6.0 g, from Step C) in glacial acetic acid (52 ml) and methylene chloride (16 ml) was charged with ammonium acetate (6.4 g). The mixture was heated at 122°–125° C. for 3 hours and distilled off 17 ml of distillate. The reaction solution was stirred at 80° C. while adding deionized (DI) water (70 ml) dropwise during 30 min. The mixture was stirred at 60°–70° C. for 15 minutes, at room temperature for 15 min, and at 0° C. for 30 minutes. The solid product was collected and dried.

Step E: Preparation of 5α-4-azaandrostan-3-on-17β-yloxyacetic acid

The unsaturated acid (3.2 g, from Step D) in glacial acetic acid (200 ml) and platinum oxide (1.0 g) was hydrogenated at 60° C. under 40 psi for 24 hours. The mixture was filtered through a pad of celite, and the filtrate concentrated to dryness. The residue was recrystallized from 5% MeOH in methylene chloride to yield the title acid.

EXAMPLE 178

Preparation of a) 5α-4-azaandrostan-3-on-17β-yloxy-N-(4-acetylphenyl)acetamide, b) 17β-methyleneoxy-[N-cyclohexyl-N-(N-cyclohexylcarbamoyl)-carbamoyl]-5α-4-azaandrostan-3-one, and c) 5α-4-azaandrostan-3-on-17β-yloxy-N-phenylacetamide To a mixture of 5α-4-azaandrostan-3-on-17β-yloxy acetic acid (280 mg) and 4-aminoacetophenone (200 mg) in methylene chloride (50 ml) was added DCC (500 mg) and DMAP (40 mg). The mixture was stirred at ambient temperature for 3 hours, and filtered. The filtrate was concentrated to a residue which was purified via preparative thin layer chromatography (TLC) on three silica gel plates (1000μ) developed with 5.5% MeOH in EtOAc twice to give the title acetamide (a) (Rf=0.33; mp. 252°–254° C.) and the title carbamate (b) (Rf=0.51).

Employing substantially the same procedure, but substituting aniline for the 4-aminoacetophenone, the title acetamide (c) (m.p. 263°–265° C.) and the title carbamate (b) were obtained.

EXAMPLE 179

Preparation of
a) 5α-4-azaandrostan-3-on-17β-yloxy-N-(4-t-butylphenyl)acetamide and
b) 17β-methyleneoxy-[N-isopropyl-N-(N-isopropylcarbamoyl)carbamoyl]-5α-4-azandrostan-3-one To a mixture of 5α-4-azaandrostan-3-on-17β-yloxy acetic acid (90 mg) and 4-t-butylaniline (80 mg) in DMF (3 ml) and methylene chloride (3 ml) was added DIC (100 mg) and DMAP (15 mg). The mixture was stirred at room temperature for 18 hours, and poured onto ice-water. The mixture was extracted with methylene chloride and dried ($Na_2SO_4$). Removal of solvent gave the crude products which were purified via preparative TLC on three silica gel plates (1000μ) developed with 2–5% MeOH in $CH_2Cl_2$ about 5 times to give the title amide (a) (higher Rf; mp 266°–268° C.) and the carbamate (b) (lower Rf; mp 133°–137° C.).

EXAMPLE 180

Preparation of 5α-4-azaandrostan-3-on-17β-yloxy-N-[4-1'(RS)-hydroxyethyl-phenyl]acetamide To 5α-4-azaandrostan-3-on-17β-yloxy-N-(4-acetylphenyl)acetamide (20 mg) in methanol (5 ml) at 10°–15° C. was added $NaBH_4$ (18 mg) in portions during 10 minutes. The mixture was stirred in the cold for 60 minutes and purified using two silica gel plates (1000μ) developed with 9% MeOH in $CH_2Cl_2$ to give the title compound (Rf=0.41; mp 281°–283° C.).

EXAMPLE 181

Preparation of ethyl 5α-4-azaandrostan-3-on-17β-yloxy-acetate

Step A: Preparation of 4-N-benzoyl-17β-t-butyldimethylsilyloxy-4-azaandrost-5-en-3-one To 17β-t-butyldimethylsilyloxy-4-azaandrost-5-en-3-one (2 g) in pyridine (5 ml) at 5°–10° C. was added benzoyl chloride (2 ml) in $CH_2Cl_2$ (10 ml) dropwise. After the addition, the mixture was stirred at 60° C. for 3 hours and poured onto ice-water. The mixture was extracted with methylene chloride, and dried ($Na_2SO_4$). Removal of solvent gave the crude product which was recrystallized from $CH_2Cl_2$-hexane to afford the title product.

Step B: Preparation of 4-N-benzoyl-17β-hydroxy-4-azaandrost-5-en-3-one

To the product of Step A, above, (2.0 g) in THF (80 ml) in a polyethylene bottle was added hydrofluoric acid (2.0 ml) dropwise. The mixture was stirred at room temperature until the reaction was complete. The mixture was neutralized with saturated sodium bicarbonate solution until slightly alkaline. The mixture was concentrated, and extracted with methylene chloride. The organic layer was dried ($Na_2SO_4$), and concentrated to a residue which was purified via flash silica gel column chromatography eluted with 40–50% EtOAc in hexane to give the title product.

Step C: Preparation of 4-N-benzoyl-4-azaandrost-5-en-3-on-17β-yloxyacetic acid ethyl ester To the alcohol product from Step B, above and ethyl diazoacetate (0.5 ml) in methylene chloride (6.5 ml) was added rhodium diacetate dimer (15 mg) intermittently during 2 hours. The mixture was stirred at room temperature for 18 hours. The mixture was concentrated and the residue was purified via preparative TLC using two silica gel plates (2000μ) developed with 40% EtOAc in hexanes to afford the title compound (Rf=0.33).

Step D: Preparation of 4-azaandrost-5-en-3-on-17β-yloxyacetic acid ethyl ester

To the product of Step C, above, (90 mg) in $CH_2Cl_2$ (2.0 ml) was added hydrazine hydrate (0.2 ml). The mixture was shaken for a few minutes and purified via preparative TLC using two silica gel plates (1500μ) developed with EtOAc to give the title product (Rf=0.54).

Step E: Preparation of ethyl 5α-4-azaandrostan-3-on-17β-yloxyacetate

The product of Step D, above, and platinum oxide (35 mg) in glacial acetic acid (2 ml) was hydrogenated at 40 psi for 22.5 hours. The mixture was filtered through a pad of celite. The filtrate was concentrated and the residue purified via preparative TLC using one silica gel plate (1000μ) developed with EtOAc to give the title product (Rf=0.22; mp 170°–172° C.).

EXAMPLE 182

Preparation of ethyl 4-methyl-5α-4-azaandrostan-3-on-17β-yloxyacetate

To a solution of 17β-hydroxy-4-methyl-5α-4-azaandrostan-3-one (2.37 g, 7.75 mmole) in methylene chloride (50 ml) was added ethyl diazoacetate (5.5 g, 48 mmole) and rhodium diacetate dimer (50 mg) intermittently in small portions during 60 hours resulting in ca. 35% conversion to product. The mixture was passed through a flash silica gel column eluted with 1.5% MeOH in $CH_2Cl_2$ to give the semi-purified product which was repurified via another flash silica gel column eluted with 60–95% EtOAc in hexane to give the title product. (Rf=0.3/EtOAc) mp. 39°–41° C.

EXAMPLE 183

Preparation of 4-methyl-5α-4-azaandrostan-3-on-17β-yloxyacetic acid

To ethyl 4-methyl-5α-4-azaandrostan-3-on-17β-yloxyacetate (275 mg) in THF (10 ml) and MeOH (5 ml) under $N_2$ was added 2N NaOH (3.0 ml). The mixture was stirred at room temperature for 2 hours, then concentrated in vacuo. The aqueous residue was extracted with $CH_2Cl_2$. The aqueous layer was then acidified with 3.0N HCl (ca. 2.1 ml) to pH 2, and extracted with $CH_2Cl_2$. The organic layer was washed with brine and dried ($Na_2SO_4$). The solvent was removed, and the crude product recrystallized from $CH_2Cl_2$/hexane to give the title compound. M.p. 180.5°–184° C.

EXAMPLE 184

Preparation of
a) diphenylmethyl 4-methyl-5α-4-aza-androstan-3-on-17β-yloxyacetate and
b) diphenylmethyl5α-4-azaandrostan-3-on-17β-yloxyacetate To 4-methyl-5α-4-azaandrostan-3-on-17β-yloxyacetic acid (3.5 mg) in $CH_2Cl_2$ (0.2 ml) under $N_2$ was added diphenyldiazomethane (ca. 20 mg) in portions during 15 minutes. The reaction stirred at room temperature for 2 hours, then additional diphenyldiazomethane (ca. 5 mg) was added and the reaction was allowed to stir overnight. The mixture was purified via preparative TLC on a silica gel plate (1000μ) developed with EtOAc to yield diphenylmethyl 4-methyl-5α-4-azaandrostan-3-on-17β-yloxyacetate, (Rf=0.4/EtOAc).

Employing substantially the same procedure as described above, but substituting 5α-4-azaandrostan-3-on-17β-yloxyacetic acid for the starting acid used therein, diphenylmethyl 5α-4-azaandrostan-3-on-17β-yloxyacetate was obtained.

EXAMPLE 185

Preparation of a) 4-methyl-5α-4-azaandrostan-3-on-17β-yloxy-N-(3,4-dichlorobenzyl)acetamide and b) 4-methyl-5α-4-azaandrostan-3-on-17β-yloxy-N-phenylace-tamide Ethyl 4-methyl-5α-4-azaandrostan-3-on-17β-yloxyacetate (30mg, ca. 70% pure) and 3,4-dichlorobenzylamine (0.3 ml) were heated together under $N_2$ at 172° C. for 18 hours. The mixture was purified via preparative TLC on a silica gel plate (2000μ) developed with EtOAc to yield the crude dichlorobenzylacetamide compound. The crude product was dissolved in $CH_2Cl_2$ and filtered, and the solvent removed in vacuo, and the residue was re-purified via preparative TLC on a silica gel plate (500μ) to yield the dichlorobenzylacetamide title product (a). MS M+ calculated for $C_{28}H_{38}Cl_2N_2O_3$, MW=521.53; observed m/e 520, 521, 522.

Employing substantially the same procedure as described above, but substituting aniline for the amine used therein, and stirring the mixture for ca. 81 hours instead of 18 hours, the phenylacetamide title product (b) was obtained, (Rf=0.4 in 6:7 acetone:EtOAc), m.p. 221°–223° C.

EXAMPLE 186

Preparation of 5α-4-azaandrostan-3-on-17β-yloxy-N-(4-acetylphenyl)acetamide via mixed anhydride method To a mixture of 5α-4-azaandrostan-3-on-17β-yloxyacetic acid (175 mg) and N-methylmorpholine (60 μl) in dry THF (80 ml) was stirred at room temperature for ½ hour and then cooled to −20° C. under $N_2$. To this mixture was added isobutyl chloroformate (75 ml) dropwise during 5 min. period and stirred at −20° C. for 20 min. followed by adding a solution of 4-aminoacetophenone (100 mg) in THF (3ml) dropwise. The mixture was stirred at −20° C. for ½ hr and then at ambient temperature overnight. The mixture was concentrated and purified via preparative TLC developed with 11% MeOH in EtOAc to give the title product.

EXAMPLE 187

Preparation of a) 4-methyl-17α-phenylsulfonyl-5α-4-azaandrostan-3-one and b) 4-methyl-17α-phenylsulfinyl-5α-4-azaandrostan-3-one isomer a and isomer b To 17α-thiophenoxy-4-methyl-5α-4-azaandrostan-3-one (65 mg) in $CH_2Cl_2$ (5 ml) was added a solution of MCPBA (53 mg) in $CH_2Cl_2$ (1 ml) dropwise. The mixture was stirred at room temperature for 1 hour and subjected to preparative TLC purification using two silica gel plates (2000μ) developed with EtOAc twice (Rf=0.39; 0.18; 0.11/EtOAc×2). Repurification via preparative TLC afforded the title sulfone (a) (Rf=0.44/EtOAc×2; mp. 265°–268° C.) and the title sulfoxide (b) isomer a (Rf=0.19/EtOAc×2; mp. 180°–181.5° C.) and the sulfoxide (b) isomer b (Rf=0.12/EtOAc×2; mp 199°–201° C.).

EXAMPLE 188

Preparation of a) 17β-(2-picolyloxy)-4-methyl-5α-4-azaandrostan-3-one and b) 17β-benzyloxy-4-methyl-5α-4-azaandrostan-3-one To 17β-hydroxy-4-methyl-5α-azaandrostan-3-one (61 mg) in THF (4ml) was added 95% NaH (20mg) and 2-picolyl chloride hydrochloride (82 mg) under $N_2$. The mixture was heated at 70°–80° C. for 18 hours. The mixture was purified via silica gel preparative TLC to give the title compound (a) (Rf=0.20/EtOAc×2; mp. 171°–173° C.).

Using benzyl bromide in place of 2-picolylchloride in the above procedure gave the title benzyloxy compound (b) (Rf=0.39/EtOAc×2; mp. 198°–199° C.).

EXAMPLE 189

Preparation of a) 17β-diphenylmethoxy-4-methyl-5α-4-azaandrostan-3-one and b) 17β-diphenylmethoxy-5α-4-azaandrostan-3-one To a stirred solution of 17β-hydroxy-4-methyl-5α-4-azandrostan-3-one (25 mg) and $BF_3$·etherate (2 drops) in THF (1.5 ml) was added intermittently diphenyldiazomethane (5 mg×4). Preparative TLC purification of the mixture using a silica gel plate developed with EtOAc yielded title compound (a) (Rf=0.4/EtOAc); m.p. 79°–82° C.

Title compound (b) was prepared using substantially the same procedure as described for title compound (a), except 17β-hydroxy-5α-4-azaandrostan-3-one was used as the starting material.

EXAMPLE 190

Preparation of a) 4-methyl-5α-4-azaandrostan-3-on-17β-yloxy-N-(4-acetylphenyl)acetamide, and b) 171β-methyleneoxy-[N-cyclohexyl-N-(N-cyclohexylcarbamoyl)carbamoyl]-4-methyl-5α-4-azaandrostan-3-one To 4-methyl-5α-4-azaandrostan-3-on-17β-yloxy acetic acid (43 mg) and acetylaniline (50 mg) in $CH_2Cl_2$ (2.5 ml) was added DCC (150 mg) and DMAP (5 mg) with stirring at room temperature for 18 hours. Silica gel preparative TLC purification (Rf=0.15/EtOAc) gave title compound (a) with m.p. 171.5°–173° C., and title compound (b) (Rf=0.25/EtOAc).

EXAMPLE 191

Preparation of 4-methyl-5α-4-azaandrostan-3-on-17β-yloxyacetamide 4-Methyl-5α-4-azaandrostan-3-on-17β-yloxy acetic acid (40 mg) and formamide (0.8 ml) were heated at 178°–180° C. under $N_2$ for 18 hours. The mixture was cooled to room temperature and poured onto ice-water. The crude product was extracted with $CH_2Cl_2$ and dried ($Na_2SO_4$). Removal of solvent gave the crude product which was recrystallized from $CH_2Cl_2$-hexane with trace MeOH to give title product, m.p. 222°–225° C.

Additionally, the structures of the compounds made as described in the above examples were satisfactorily confirmed by $H^1$ NMR spectroscopy. Relevant NMR data for compounds made in the above examples is as follows:

| Example | Angular Methyls (ppm) | Miscellaneous (ppm) |
| --- | --- | --- |
| 128 | 0.58, 0.88 | 5.28 (—OC$\underline{H}$(Ph)$_2$) |
| 129 | 0.66, 0.89 | 1.29 (C$\underline{H}_3$C$\underline{H}_2$OCO) |
| 130 | 0.64, 0.89 | 5.49 (—COOC$\underline{H}_2$Ph) |
| 131 | 0.69, 0.88 | 3.31 (—CH$_2$OC$\underline{H}_3$) |
| 131b | 0.69, 0.89 | 3.28 (—OC$\underline{H}_3$) |
| 132 | 0.64, 0.89 | 3.32 (—CH$_2$OC$\underline{H}_3$) |
| 133 | 0.64, 0.89 | 1.25 (—CH$_2$SCH$_2$C$\underline{H}_3$) |
| 134 | 0.67, 0.89 | 4.07 (—CH$_2$OC$\underline{H}_2$COOH) |
| 135 | 0.56, 0.84 | 5.29 (—OC$\underline{H}$(Ph)$_2$ |
| 135b | 0.68, 0.88 | 5.28 (—CH$_2$OC$\underline{H}$(Ph)$_2$ |
| 136 | 0.68, 0.88 | 1.25 (—CH$_2$SCH$_2$C$\underline{H}_3$) |
| 136b | 0.68, 0.88 | 1.24 (—CH$_2$SCH(C$\underline{H}_3$)$_2$) 1.27 |
| 136 | 0.90, 0.93 | 2.94 (-4-NC$\underline{H}_3$) |
| 137 | 0.92, 0.95 | 2.93 (-4-NC$\underline{H}_3$) |
| 138 | 0.91, 0.93 | 2.93 (-4-NC$\underline{H}_3$) |
| 138b | 0.93, 0.99 | 2.94 (-4-NC$\underline{H}_3$) |
| 138c | 0.93, 0.97 | 2.95 (-4-NC$\underline{H}_3$) |
| 138d | 0.91, 0.93 | 2.93 (-4-NC$\underline{H}_3$) |
| 138f | 0.91 (6H) | 2.93 (-4-NC$\underline{H}_3$) |
| 138g | 0.91 (6H) | 2.93 (-4-NC$\underline{H}_3$) |
| 138h | 0.92 (6H) | 2.92 (-4-NC$\underline{H}_3$) |
| 138i | 0.91 (6H) | 2.27 (Ph—C$\underline{H}_3$) |
| 139 | 0.92, 0.94 | 2.98 (-4-NC$\underline{H}_3$) |
| 140 | 0.92 (6H) | 2.15 (—NHCOC$\underline{H}_3$) |
| 141 | 0.91, 0.93 | 2.93 (-4-NC$\underline{H}_3$) |
| 142 | 0.91, 0.93 | 2.93 (-4-NC$\underline{H}_3$) |
| 142b | 0.82, 0.92 | 2.95 (-4-NC$\underline{H}_3$) |
| 142c | 0.83, 0.91 | 2.94 (-4-NC$\underline{H}_3$) |
| 143 (title) | 0.74, 0.87 | 2.91 (-4-NC$\underline{H}_3$) |
| 143a | 0.76, 0.89 | 2.92 (-4-NC$\underline{H}_3$) |
| 176b | 0.76, 0.89 | 2.92 (-4-NC$\underline{H}_3$) |
| 176c | 0.76, 0.88 | 2.92 (-4-NC$\underline{H}_3$) |
| 176d | 0.80, 0.88 | 2.92 (-4-NC$\underline{H}_3$) |
| 176e | 0.80, 1.10 | 3.10 (-4-NC$\underline{H}_3$) |
| 176f | 0.78, 1.10 | 3.10 (-4-NC$\underline{H}_3$) |
| 177, Step A | 0.94, 1.15 | 1.27 (t) (—OCH$_2$C$\underline{H}_3$) |
| 177, Step B | 0.88, 1.14 | 1.27 (t) (—OCH$_2$C$\underline{H}_3$) 1.30 (t) (—OCH$_2$C$\underline{H}_3$) |
| 177, Step C | 0.89, 1.15 | 4.16 (—OC$\underline{H}_2$COOH) |
| 177, Step D | 0.86, 1.10 | 4.12 (dd) (—OC$\underline{H}_2$COOH) |
| 177, Step E | 0.82, 0.90 | 4.11 (dd) (—OC$\underline{H}_2$COOH) |
| 178a | 0.89, 0.94 | 2.60 (—COC$\underline{H}_3$) |
| 178b | 0.81, 0.91 | |
| 178c | 0.86, 0.92 | |
| 179a | 0.86, 0.93 | 1.31 (—C(CH$_3$)$_3$) |
| 179b | 0.82, 0.92 | 1.22 (d) (—CH(CH$_3$)$_2$) 1.44 (d) (—CH(CH$_3$)$_2$) |
| 20 | 0.86, 0.91 | 1.48 (d) (—CH(OH)CH$_3$) |
| 181, Step A | 0.87, 1.31 | 0.91 (—C(C$\underline{H}_3$)$_3$) |
| 181, Step B | 0.80, 1.30 | |
| 181, Step C | 0.85, 1.30 | 4.09 (—OC$\underline{H}_2$CO$_2$Et) |
| 181, Step D | 0.86, 1.12 | 4.10 (—OC$\underline{H}_2$CO$_2$Et) |
| 181, Step E | 0.80, 0.88 | 4.09 (—OC$\underline{H}_2$CO$_2$Et) |
| 182 | 0.82, 0.90 | 2.92 (-4-NC$\underline{H}_3$) |
| 183 | 0.82, 0.90 | 2.94 (-4-NC$\underline{H}_3$) |
| 184a | 0.80, 0.89 | 2.92 (-4-NC$\underline{H}_3$) |
| 184b | 0.79, 0.89 | 4.18 (—OC$\underline{H}_2$CO$_2$CHPh$_2$) |
| 185a | 0.76, 0.87 | 2.91 (-4-NC$\underline{H}_3$) |
| 185b | 0.87, 0.92 | 2.93 (-4-NC$\underline{H}_3$) |
| 186 | 0.89, 0.93 | 4.08 (—OC$\underline{H}_2$CO—) |
| 187a | 0.89, 0.93 | 2.94 (-4-NC$\underline{H}_3$) |
| 187b (Isom. a) | 0.90, 0.92 | 2.94 (-4-NC$\underline{H}_3$) |
| 187b (Isom. b) | 0.92, 0.98 | 2.95 (-4-NC$\underline{H}_3$) |
| 188a | 0.87, 0.91 | 2.93 (-4-NC$\underline{H}_3$) |
| 188b | 0.86, 0.91 | 4.54 (—C$\underline{H}_2$Ph) |
| 189b | 0.91, 0.93 | 5.42 (Ph$_2$C$\underline{H}$O—) |
| 190a | 0.89, 0.93 | 2.60 (—COC$\underline{H}_3$) |
| 190b | 0.80, 0.88 | 2.92 (-4-NC$\underline{H}_3$) |
| 191 | 0.80, 0.89 | 2.93 (-4-NC$\underline{H}_3$) |

While the foregoing specification teaches the principles of the invention, with examples provided for the purpose of illustration, it will be understood that the practice of the invention encompasses all of the usual variations, adaptations, and modifications, as come within the scope of the following claims and its equivalents.

EXAMPLES FOR THE CASE WHEN SUBSTITUENT "A" OF GENERAL FORMULA "I" IS AS DEFINED IN GROUP "III(A)"

EXAMPLE 191

Preparation of 20-(11-(ethylthio)undecanoyloxy)-4-methyl-5α-4-azapregnan-3-one

To a stirred solution of 20-hydroxy-4-methyl-5α-4-azapregnan-3-one (0.66 g, 2.0 mM), 11-ethylthio-undecanoic acid (0.493 g, 2.0 mM), and 4-(dimethylamino)-pyridine (0.242 g, 2.0 mM) in methylene chloride (25 mL) was added N,N'-dicyclohexylcarbodiimide (0.48 g, 2.3 mM) in methylene chloride (3 mL plus 2×3 mL rinses) at room temperature. After stirring overnight two times, the mixture was filtered from the precipitated dicyclohexylurea and concentrated, and the residue flash chromatographed on silica gel using ethyl acetate as eluant to yield the title compound as a thick oil. MS M$^{+1}$ calculated for C$_{34}$H$_{59}$NO$_3$S, mw=561.90; observed m/e 562.

EXAMPLE 192

Preparation of 20-ethoxyacetyloxy-4-methyl-5α-4-azapregnan-3-one

Employing substantially the same procedure as described in Example 191, but substituting ethoxyacetic acid in place of the ethylthioundecanoic acid used therein, the title compound is obtained.

EXAMPLE 193

Preparation of 17-(12-(isopropylthio)dodecanoyloxy)-4-methyl-5α-4-azaandrostan-3-one Employing substantially the same procedure as described in Example 191, but substituting 17-hydroxy-4-methyl-5a-4-azaandrostan-3-one and 12-(isopropylthio)dodecanoic acid for the 20-hydroxy-4-methyl-5α-4-azapregnan-3-one and 11-ethylthioundecanoic acid, respectively, used therein, the title compound was obtained. MS M$^+$ calculated for C$_{34}$H$_{59}$NO$_3$S, mw=561.92: observed m/e 561.

EXAMPLE 194

Preparation of a) 20-(9-(isopropylthio)nonanoyloxy)-5α-4-azapregnan-3-one and b) 20-(12-(isopropylthio)dodecanoyloxy)-5α-4-azapregn-1-ene-3-one Employing substantially the same procedure as described in Example 191, but substituting the steroid alcohol and acid starting materials used therein with the following compounds, both of the title compounds were obtained:

Title compound a): 20-hydroxy-5α-4-azapregnan-3-one and 9-(isopropylthio)nonanoic acid. MS M$^+$ calculated for C$_{32}$H$_{55}$NO$_3$S, mw=533.85; observed m/e 533;

Title compound b): 20-hydroxy-5α-4-azapregn-1-ene-3-one and 12-(isopropylthio)dodecanoic acid. MS M$^+$ calculated for C$_{35}$H$_{59}$NO$_3$S, mw=573.92; observed m/e 573.

EXAMPLE 195

Compounds of formula 3, below, were made employing substantially the same procedure as described in Example 191, but substituting the compounds of formula 1 and 2, below, in place of the 20-hydroxy-4-methyl-5α-4-azapregnan-3-one and 11-ethylthioundecanoic acid respectively, used therein.

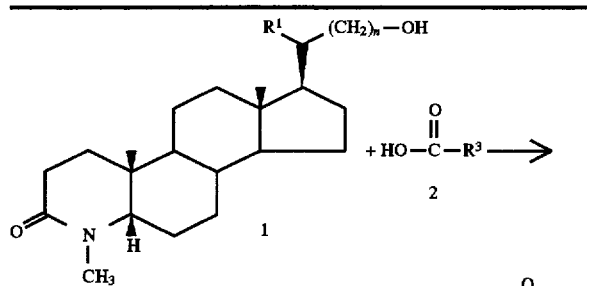

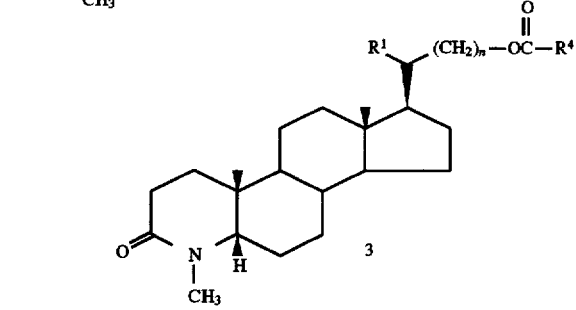

| | R¹ | n | R⁴ |
|---|---|---|---|
| a) | —CH₃ | zero | —(CH₂)₁₁CH₃ |
| b) | —CH₃ | zero | —(CH₂CH(CH₃)CH₂CH₂CH=C(CH₃)₂ |
| c) | —CH₃ | zero | —CH₂-1-adamantyl |
| d) | —CH₃ | zero | —CH₂-2-norbornyl |
| e) | —CH₃ | zero | —CH₂—⟨aryl with 2 OCH₃⟩ |
| f) | —CH₃ | zero | —⟨aryl-isopropyl⟩ |
| g) | —CH₃ | zero | —CH₂—S—CH(CH₃)₂ |
| h) | —CH₃ | zero | —(CH₂)₈—S—CH(CH₃)₂ |
| i) | —CH₃ | zero | —(CH₂)₁₁—S—CH(CH₃)₂ |
| j) | —CH₃ | zero | —(CH₂)₁₁—S—CH(CH₃)₃ |
| k) | —CH₃ | zero | —(CH₂)₃—⟨thienyl⟩ |
| l) | —CH₃ | 1 | —(CH₂)₁₁—S—CH(CH₃)₂ |
| m) | —H | zero | —CH(C₂H₅)—CH₂CH₂CH₂CH₃ |
| n) | —H | zero | —(CH₂)₁₁—S—CH(CH₃)₂ |

The compounds above have the following corresponding mass spectral data:

a) MS M⁺ calculated for $C_{34}H_{59}NO_3$, mw=529.85; observed m/e 529;

b) MS M⁺ calculated for $C_{31}H_{51}NO_3$, mw=485.75; observed m/e 485;

c) MS M⁺ calculated for $C_{33}H_{51}NO_3$, mw=509.78; observed m/e 509;

d) MS M⁺ calculated for $C_{30}H_{47}NO_3$, mw=469.71; observed m/e 469;

e) MS M⁺ calculated for $C_{31}H_{45}NO_5$; mw=511.71; observed m/e 511;

f) MS M⁺ calculated for $C_{31}H_{45}NO_3$; mw=479.71; observed m/e 479;

g) MS M⁺ calculated for $C_{26}H_{43}NO_3S$; mw=449.69; observed m/e 449;

h) MS M⁺ calculated for $C_{33}H_{57}NO_3S$; mw=547.88; observed m/e 548;

i) MS M⁺ calculated for $C_{36}H_{63}NO_3S$; mw=589.94; observed m/e 589;

j) MS M⁺¹ calculated for $C_{37}H_{65}NO_3S$; mw=604.00; observed m/e 605;

k) MS M⁺¹ calculated for $C_{29}H_{43}NO_3S$; mw=485.73; observed m/e 486;

l) MS M⁻¹ calculated for $C_{37}H_{65}NO_3S$; mw=604.00; observed m/e 603;

m) MS M⁺ calculated for $C_{28}H_{47}NO_3$; mw=445.69; observed m/e 445;

n) MS M⁺ calculated for $C_{35}H_{51}NO_3S$; mw=575.92; observed m/e 575.

EXAMPLE 196

Preparation of 4-methyl-20-(10-undecenoyloxy)-5α-4-azapregnan-3-one

To a solution of 20-hydroxy-4-methyl-5α-4-azapregnan-3-one (0.167 g, 0.5 mM) and pyridine (0.1 mL) in anhydrous methylene chloride (4.5 mL) at ice-bath temperatures was added 10-undecenoyl chloride (0.13 mL, 0.6 mM) dropwise. After 10 minutes, the reaction mixture was allowed to warm to room temperature and stir overnight. After diluting further with methylene chloride the mixture was washed with dilute hydrochloric acid, water, and brine, and dried (Na₂SO₄). The residue obtained from concentration of the filtered solution was flash chromatographed on silica gel using ethyl acetate as eluant to give the title compound as a glaze. MS M⁺ calculated for $C_{32}H_{53}NO_3$, mw=499.78; observed m/e 499.

EXAMPLE 197

Compounds of formula 6, below, were made employing substantially the same procedure as described in Example 196, but substituting the compounds of formula 4 and 5, below, in place of the 20-hydroxy-4-methyl-5α-4-azapregnan-3-one and 10-undecenoyl chloride, respectively, used therein.

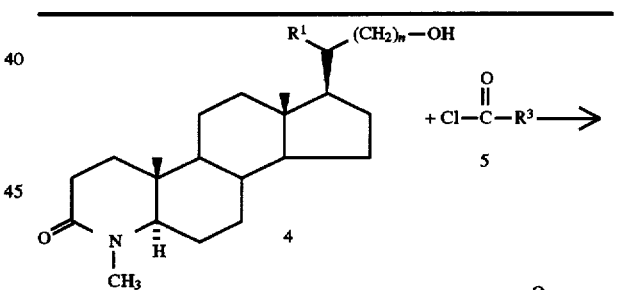

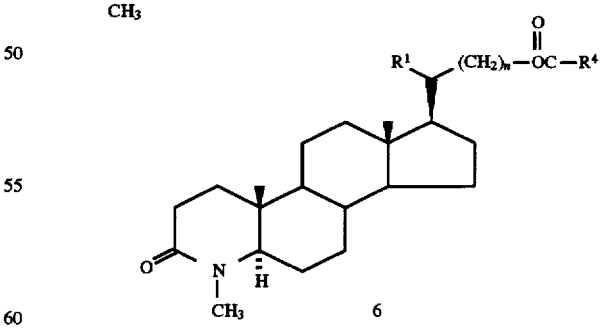

| | R¹ | n | R⁴ |
|---|---|---|---|
| a) | —CH₃ | zero | —CH₂C(CH₃)₃ |
| b) | —CH₃ | zero | —C(CH₃)₃ |
| c) | —CH₃ | zero | —(CH₂)₁₀COOCH₃ |
| d) | —CH₃ | zero | —CH₂CH₂COOCH₂—Ph |
| e) | —CH₃ | 1 | —CH₃ |

| f) | —CH₃ | 1 | —C(CH₃)₃ |
| g) | —H | zero | —CH₃ |
| h) | —H | zero | —C(CH₃)₃ |

The compounds above have the following corresponding mass spectral data:

a) MS M⁺ calculated for C$_{27}$H$_{45}$NO$_3$, mw=431.67; observed m/e 431;

b) MS M⁺¹ calculated for C$_{26}$H$_{43}$NO$_3$, mw=417.64; observed m/e 418;

c) MS M⁺ calculated for C$_{34}$H$_{57}$NO$_5$; mw=559.84: observed m/e 559;

d) MS M⁺² calculated for C$_{32}$H$_{45}$NO$_5$; mw=523.72; observed m/e 525;

e) MS M⁺ calculated for C$_{24}$H$_{39}$NO$_3$; mw=389.59; observed m/e 389;

f) MS M⁺ calculated for C$_{27}$H$_{45}$NO$_3$; mw=431.67; observed m/e 431;

g) MS M⁺ calculated for C$_{22}$H$_{35}$NO$_3$; mw=361.53; observed m/e 361;

h) MS M⁺ calculated for C$_{25}$H$_{41}$NO$_3$; mw=403.61; observed m/e 403.

EXAMPLE 198

Preparation of 20-trimethylacetyloxy-5α-4-azapregn-1-ene-3-one

Employing substantially the same procedure as described in Example 6, but substituting 20-hydroxy-5α-4-azapregn-1-ene-3-one and trimethylacetyl chloride for the 20-hydroxy-4-methyl-5a-4-azapregnan-3-one and 10-undecenoyl chloride, respectively, used therein, the title compound was obtained. MS M⁻¹ calculated for C$_{25}$H$_{39}$NO$_3$, mw=402.53; observed m/e 401.

EXAMPLE 199

Preparation of 20-(11-(ethylsulfinyl)undecanoyloxy)-4-methyl-5α-4-azapregnan-3-one To a stirred solution of 20-(11-(ethylthio)-undecanoyloxy)-4-methyl-5α-4-azapregnan-3-one (0.056 g, 0.1 mM) in acetone (5 mL) at room temperature was added a solution of sodium periodate (0.033 mg, 0.154 mM) in water (3 drops). After prolonged stirring with additional portions of the periodate added (0.046 g total) over 3 days, the solvents were removed in vacuo, and the residue extracted with methylene chloride. The methylene chloride was removed in vacuo, and the resulting residue was flash chromatographed on silica gel (30% acetone/methylene chloride eluant) to give the title compound as a glaze. MS M⁺ calculated for C$_{34}$H$_{59}$NO$_4$S, mw=577.90; observed m/e 577.

EXAMPLE 200

Preparation of 17-(t-butylaminocarbonyloxymethyl)-4-methyl-5α-4-azaandrostan-3-one To a stirred solution of 17-(hydroxymethyl)-4-methyl-5α-4-azaandrostan-3-one (0.048 g, 0.15 mM) in dried benzene (5 mL) was added at room temperature t-butylisocyanate (0.03 mL, 0.23 mM) followed by 1,8-diazabicyclo[5.4.0]undec-7-ene (DBU) (0.023 mL, 0.15 mM). After stirring for two days, the volatiles were removed in vacuo and the residue flash chromatographed on silica gel using ethyl acetate as eluant to give the title compound as a white solid. MS M⁺¹ calculated for C$_{25}$H$_{42}$N$_2$O$_3$, mw=418.55; observed m/e 419.

EXAMPLE 201

Preparation of 20-(t-butylaminocarbonyloxy)-4-methyl-5α-4-azapregnan-3-one

Employing substantially the same procedure as described in Example 200, but substituting 20-hydroxy-4-methyl-5α-4-azapregnan-3-one for the steroid alcohol used therein, the title compound was obtained. MS M⁺¹ calculated for C$_{26}$H$_{44}$N$_2$O$_3$, mw=432.65; observed m/e 433.

EXAMPLE 202

Preparation of 17β-(benzylaminocarbonyloxy)-4-methyl-5α-4-azaandrostan-3-one

To a solution of 17β-hydroxy-4-methyl-5α-4-azaandrostan-3-one (61 mg) in pyridine (0.60 ml) was added benzyl isocyanate (54 mg, 0.40 mmol). The mixture was stirred at 60°–70° C. under N$_2$ for 18 hr and pumped in vacuo to remove pyridine. The residue was purified using a silica gel plate (2000 m) developed with ethyl acetate (Rf=0.37, run in EtOAc) to give the title compound; m.p. is 216°–217° C.

EXAMPLE 203

Preparation of 20-(3-carboxypropionyloxy)-4-methyl-5α-4-azapregnan-3-one 20-(3-(Carbobenzyloxy)propionyloxy)-4-methyl-5a-4-azapregnan-3-one (0.05 g, 0.095 mM) was reduced with hydrogen in ethyl acetate in the presence of 5% palladium on carbon, to obtain the title compound. MS M⁺¹ calculated for C$_{25}$H$_{39}$NO$_5$, mw=433.64; observed m/e 434.

EXAMPLE 204

Preparation of 17-(methylaminocarbonyloxymethyl)-4-methyl-5α-4-azaandrostan-3-one Employing substantially the same procedure as described in Example 202, but substituting methyl isocyanate and 17-(hydroxymethyl)-4-methyl-5α-4-azaandrostan-3-one for the benzyl isocyanate and steroid alcohol, respectively, used therein, the title compound was obtained. MS M⁺² calculated for C$_{22}$H$_{36}$N$_2$O$_3$, mw=376.54; observed m/e 378.

EXAMPLE 205

Preparation of 20-(acetylthiomethyl)-4-methyl-5α-4-azapregnan-3-one

By reacting 20-(hydroxymethyl)-4-methyl-5α-4-azapregnan-3-one with thiolacetic acid as per the procedure of *Tetrahedron Letters* 22 (1981) pp. 3119–3122, the title compound is obtained.

Additionally, the structures of the compounds made as described in the above examples were satisfactorily confirmed by H¹ NMR spectroscopy. NMR data for compounds made in the above examples is as follows:

| NMR DATA (ppm) | | |
|---|---|---|
| Example | Angular Methyls | Miscellaneous |
| 191 | 0.64, 0.88 | 2.94 (-4-NC<u>H</u>₃) |
| 193 | 0.81, 0.91 | 1.24 (—SCH(C<u>H</u>₃)₂) 1.28 |
| 194a | 0.64, 0.90 | 1.25 (—SCH(C<u>H</u>₃)₂) 1.28 |
| 194b | 0.64, 0.94 | 1.22 (—SCH(C<u>H</u>₃)₂) 1.26 |
| 195a | 0.64, 0.88 | 2.95 (-4-NC<u>H</u>₃) |
| 195b | 0.62, 0.86 | 2.92 (-4-NC<u>H</u>₃) |
| 195c | 0.62, 0.87 | 2.92 (-4-NC<u>H</u>₃) |
| 195d | 0.64, 0.88 | 2.92 (-4-NC<u>H</u>₃) |
| 195e | 0.59, 0.88 | 3.80 (Ph—(OC<u>H</u>₃)₂) (Split) |
| 195f | 0.65, 0.82 | 1.22 (Ph—CH(C<u>H</u>₃)₂) 1.25 |
| 195g | 0.65, 0.88 | 3.21 (—SC<u>H</u>₂CO₂—) |
| 195h | 0.63, 0.88 | 1.24 (—SCH(C<u>H</u>₃)₂) 1.28 |
| 195i | 0.63, 0.87 | 1.24 (—SCH(C<u>H</u>₃)₂) 1.27 |
| 195j | 0.64, 0.88 | 1.30 (—C(CH₃)₃ |
| 195k | 0.64, 0.88 | 2.92 (-4-NC<u>H</u>₃) |
| 195l | 0.70, 0.88 | 1.24 (—SCH(C<u>H</u>₃)₂) 1.26 |
| 195m | 0.63, 0.85 | 2.89 (-4-NC<u>H</u>₃) |
| 195n | 0.67, 0.89 | 2.93 (-4-NC<u>H</u>₃) |
| 196 | 0.64, 0.88 | 2.92 (-4-NC<u>H</u>₃) |
| 197a | 0.64, 0.88 | 1.02 (—C(C<u>H</u>₃)₃) |
| 197b | 0.64, 0.87 | 1.13 (—C(C<u>H</u>₃)₃) |
| 197c | 0.64, 0.88 | 3.66 (—CO₂C<u>H</u>₃) |
| 197d | 0.62, 0.87 | 5.14 (—OC<u>H</u>₂Ph) |
| 197e | 0.69, 0.88 | 2.04 (—OCOC<u>H</u>₃) |
| 197f | 0.70, 0.88 | 1.20 (—C(C<u>H</u>₃)₃) |
| 197g | 0.66, 0.90 | 2.02 (—OCOC<u>H</u>₃) |
| 197h | 0.68, 0.89 | 1.18 (—C(C<u>H</u>₃)₃) |
| 198 | 0.64, 0.94 | 1.16 (—C(C<u>H</u>₃)₃) |
| 199 | 0.62, 0.88 | 2.94 (-4-NC<u>H</u>₃) |
| 200 | 0.64, 0.86 | 1.29 (—OCONH—C(CH₃)₃) |
| 201 | 0.69, 0.89 | 1.32 (—OCONH—C(C<u>H</u>₃)₃) |
| 202 | 0.89, 0.92 | 2.94 (4—NC<u>H</u>₃) |
| 203 | 0.62, 0.86 | 2.92 (4—NC<u>H</u>₃) |
| 204 | 0.67, 0.88 | 2.78 (—OCONH—C<u>H</u>₃) 2.82 |

EXAMPLES FOR THE CASE WHEN SUBSTITUENT "A" OF GENERAL FORMULA "I" IS AS DEFINED IN GROUP "VI(A)"

PREPARATION OF STARTING MATERIALS

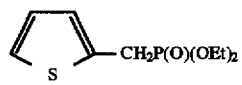

A. Preparation of diethyl 2-thienylmethylphosphonate, (1)

Following the general procedure for carrying out the Arbuzov reaction (reference cite: Chem. Rev. 81, 415, 1981) 0.1 mole (17.5 ml) of triethyl phosphite and 0.1 mole (13.2 g) of 2-chloromethylthiophene were combined and heated under N₂ at 150° C. for 5 hours. The reaction mixture was cooled and partitioned between 100 ml methylene chloride and 50 ml. water. The organic phase was separated, washed with saturated NaHCO₃ solution, dried over magnesium sulfate and concentrated under vacuum to yield 17.5 g. crude liquid product.

The liquid was distilled at 113°–115° C. at 0.5–0.6 mm Hg to yield 5.78 g of the titled product. The proton NMR confirmed the structure of the distilled product.

The following phosphonate reagents were also prepared by the above-described method: diethyl 3-thienylmethylphosphonate, diethyl 2-furanylmethylphosphonate, diethyl 2-fluorobenzylphosphonate.

B. Preparation of Diethyl 4-Pyridylmethyl-phosphonate, (2)

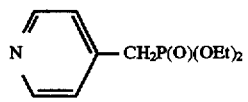

4-Picolyl chloride HCl salt (20 mmol, 3.38 g) was partitioned between 40 milliliters 50% K₂CO₃ and 40 milliliters ethyl acetate. The black aqueous phase was extracted (2×) with ethyl acetate and the combined organic phases were dried over magnesium sulfate, and concentrated under reduced pressure. The residue was dissolved in 20 milliliters of toluene.

Sodium hydride (800 mg., 20 mmol) was washed with (3×) hexane and suspended in 8 milliliters of toluene. Diethyl phosphite (5.15 ml, 40 mmol) was added dropwise with stirring and the mixture heated at 80° C. for 30 minutes to yield a clear solution. The toluene solution of the picolyl chloride was added dropwise and the reaction mixture heated at 80° C. for 30 minutes. After cooling, the mixture was poured into water, saturated with sodium chloride, and extracted (3×) with ethyl acetate. The combined organic phases were dried over magnesium sulfate and concentrated under reduced pressure. The liquid residue was distilled under vacuum to yield 2.45 g. (53.5% of theory), b.pt. 123–125/@0.3 mm Hg. The proton nmr spectrum confirmed the compound structure.

The following phosphonate reagents were also prepared by the above-described method: diethyl 3-chlorobenzylphosphonate, diethyl 2-chlorobenzylphosphonate, diethyl 2-pyridylmethylphosphonate, diethyl 3-pyridylmethylphosphonate, diethyl 4-pyridylmethylphosphonate, diethyl 4-carbethoxybenzylphosphonate, diethyl 4-(N-phenylcarbamoyl)benzyl-phosphonate.

C. Preparation of 4-aza-5a-androst-1-en-3-one-17b-aldehyde (B) and 4-aza-5α-androstan-3-one-17β-aldehyde (C)

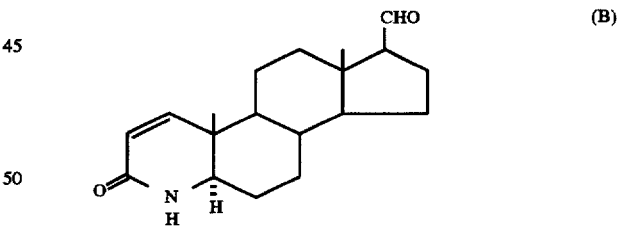

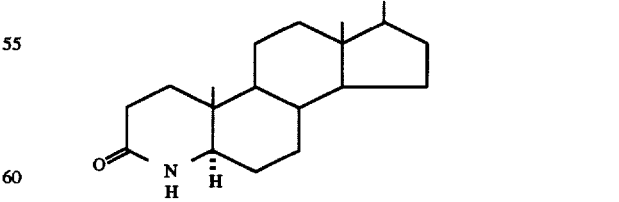

17β-(N-methyl-N-methoxy) carboxamide-5α-4-aza-androst-1-en-3-one (prepared as in following Example D), 3.6g. (10 mmol) was suspended in 100 ml dry THF at 0° C. under dry nitrogen, lithium aluminum hydride (10 ml of 1M lithium aluminum hydride in dry THF) was added slowly dropwise with stirring maintaining temp at <5° C. After addition was complete the reaction was allowed to stir for 20 minutes. 2N HCl was added to the reaction mixture to pH 3, additional water added and the reaction mixture extracted with (3×) chloroform. The organic phases were combined, dried over magnesium sulfate and concentrated to yield 3.2 g. residue. The crude product was flash chromatographed on a 50mm.×7" silica gel column with 4:1 methylene chloride/acetone.

The first fractions eluted (12–22) yielded 1.75 g. (58% of the unsaturated aldehyde (B). m.p. 260°–263°.

Fractions (25–36) yielded 0.70 g. (23%) of the saturated aldehyde (C). m.p. 246°–249°.

Proton NMR confirmed the assigned structures for both compounds.

D. Preparation of (5α,17β)-N-Methoxy-N-methyl-3-oxo-4-azaandrost-1-ene-17β-carboxamide (4)

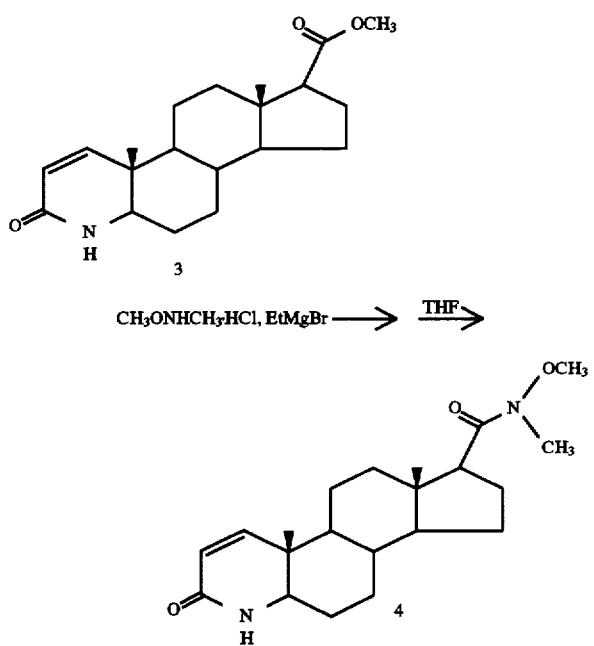

A 2 L three-neck flask equipped with an overhead stirrer, nitrogen inlet, internal thermometer, and/dropping funnel was charged with 800 mL of sieve-dried tetrahydrofuran, 19.72 g (59.6 mmol) of Δ¹-aza ester (Compound 3) (for synthesis, see Rasmusson, Johnston and Arth. U.S. Pat. No. 4,377,584, Mar. 22, 1983.) and 25.6 g (262.4 mmole) of N,O-dimethylhydroxylamine hydrochloride. The resulting slurry was cooled to 0° to 5° C.

A warm solution (30°–40° C.) of ethylmagnesium bromide in dry tetrahydrofuran (252 mL. 2.0 Molar, 504 mmole) was added over fifteen minutes. The pot temperature was maintained at 0°–5° C. during the addition. The reaction mixture was warmed to 25° C. over thirty minutes and aged at 22°–25° C. for one hour. The reaction was cooled to 0°–5° C. and quenched into 650 mL of 25 wt % aqueous ammonium chloride. The mixture was warmed to 40°–45° C. and the layers were separated. The organic solution was cooled to 25° C. and treated with activated carbon.

The THF solution after filtration was concentrated by atmospheric distillation to 200 mL. The resulting slurry was cooled to 35° C. and 1 L of water was added over one hour. The slurry was cooled to 25° C. and aged for 2 hours. The amide was collected by filtration and washed with 200 mL of water then dried at 80° C./house vacuum to yield 19.6 g (91.4%) of amide 4 (98.8 area % pure by LC).

E. Preparation of 4-aza-5α-pregn-1-ene-3,20-dione (E)

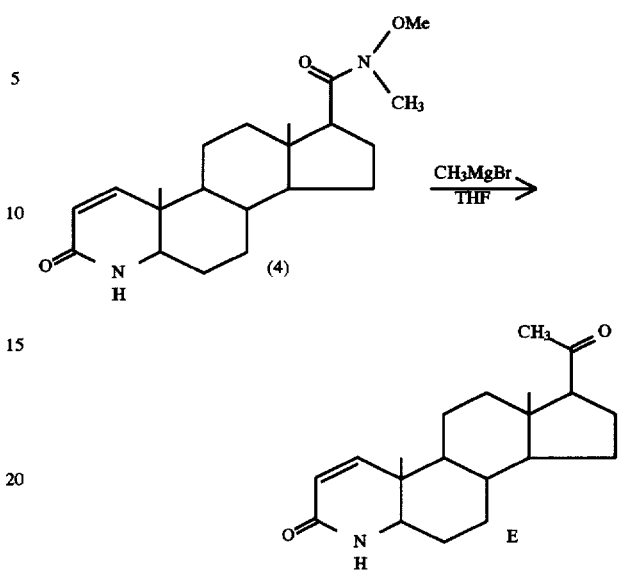

To a slurry of 4 (12 g, 33 mmoles) in 480 ml of dry tetrahydrofuran was added dropwise 83.3 ml (250 mmoles) of 3.0M methylmagnesium bromide in diethyl ether while maintaining the temperature of the reaction <5° with cooling with an ice bath. The mixture was stirred at room temperature for 8 hours. After cooling in an ice bath, 500 ml of aqueous ammonium chloride (1 g/3 ml H₂O) was added. Most of the tetrahydrofuran was removed in vacuo. The slurry was filtered, and the solid washed with H₂O, dried, triturated with Et₂O, filtered and dried to give 10.5 g of 4-aza-5α-pregn-1-ene-3,20-dione, mp. 310°–312°. The NMR spectrum continued the assigned structure.

EXAMPLE 206

Reaction of 17-Carboxaldehyde with Phosphonate Reagent

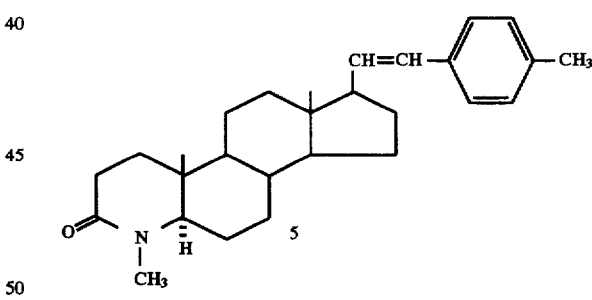

1. Preparation of 17β-(1-(2-(4-tolyl))ethenyl)-4-methyl-4-aza-5α-androstan-3-one, (5).

Following the general procedure of Wadsworth, et al., (see Chem. Rev. 74, 87 (1974) and JACS, Vol. 83, p. 1733 (1961), 5-alpha-4-aza-4-methyl-androstan-3-one-17-aldehyde, Carboxaldehyde A, (245 mg, 0.77 mol), sodium hydride (31 mg, 0.78 mol), diethyl 4-methyl-benzylphosphonate (189 mg., 0.78 mol) in 2 ml. anhydrous dimethylformamide was stirred at 80° C. in a nitrogen atmosphere for 1.5 hours. The reaction was cooled and partitioned with 20 ml. each of 0.1N HCl/methylene chloride. The organic phase was washed with water, dried over magnesium sulfate and concentrated under reduced pressure to yield 391 mg. crude solid. Recrystallization from ethyl acetate yielded a white solid, mp 225°–227° C. The proton NMR and mass spectrum confirmed the assigned structure for 5.

EXAMPLE 207

Following the general procedure described above in Example 206, the following tabulated compounds were prepared.

TABLE 6

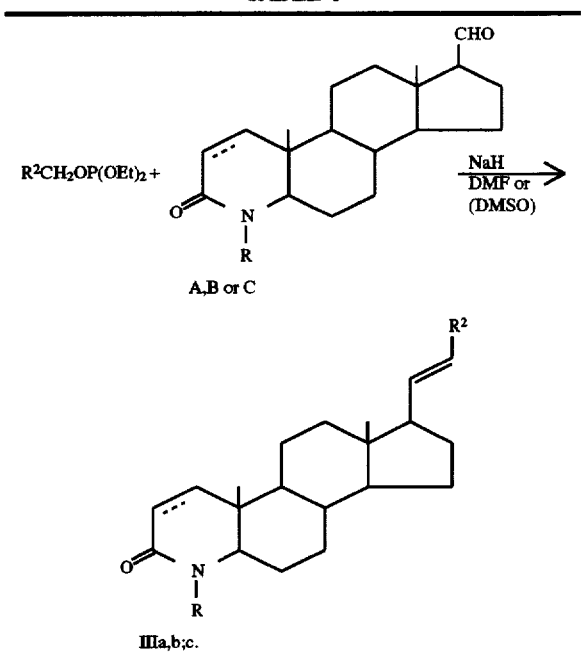

A,B or C

| STRUCTURE | COMPOUND NO. | R | $R^2$ |
|---|---|---|---|
| IIIA | 6 | Me | 4-methoxyphenyl |
| " | 7 | Me | phenyl |
| " | 8 | Me | 4-tolyl |
| " | 9 | Me | 4-chlorophenyl |
| " | 10 | Me | 4-pyridyl |
| " | 11 | Me | 3-chlorophenyl |
| " | 12 | Me | 2-chlorophenyl |
| " | 13 | Me | 2-pyridyl |
| " | 14 | Me | 2-thienyl |
| IIIc | 15 | H | 4-methoxyphenyl |
| IIIa | 16 | Me | 3-thienyl |
| " | 17 | Me | 2-furanyl |
| " | 18 | Me | 2-fluorophenyl |
| IIIb | 19 | H* | 4-pyridyl |
| IIIc | 20 | H | 4-pyridyl |
| IIIb | 21 | H* | 4-methoxyphenyl |
| " | 22 | H* | 2-furanyl |
| " | 23 | H* | 2-pyridyl |
| " | 24 | H* | 3-pyridyl |
| " | 25 | H* | 4-ethoxycarbonyl phenyl |
| " | 26 | H* | 4(N-phenylcarbamoyl) phenyl |
| IIIc | 27 | H | 2-pyridyl |
| " | 28 | H | 3-pyridyl |
| " | 29 | H | 2-thienyl |

| | Mass Spec. method:m/e | | TLC solvent system | Rf |
|---|---|---|---|---|
| IIIA | EI | 421 | A | 0.4 |
| " | EI | 391 | B | 0.5 |
| " | EI | 405 | B | 0.4 |
| " | EI | 425 | B | 0.5 |
| " | EI | 392 | C | 0.25 |
| " | EI | 425 | B | 0.5 |
| " | EI | 425 | B | 0.5 |
| " | EI | 392 | C | 0.3 |
| " | EI | 397 | B | 0.5 |

TABLE 6-continued

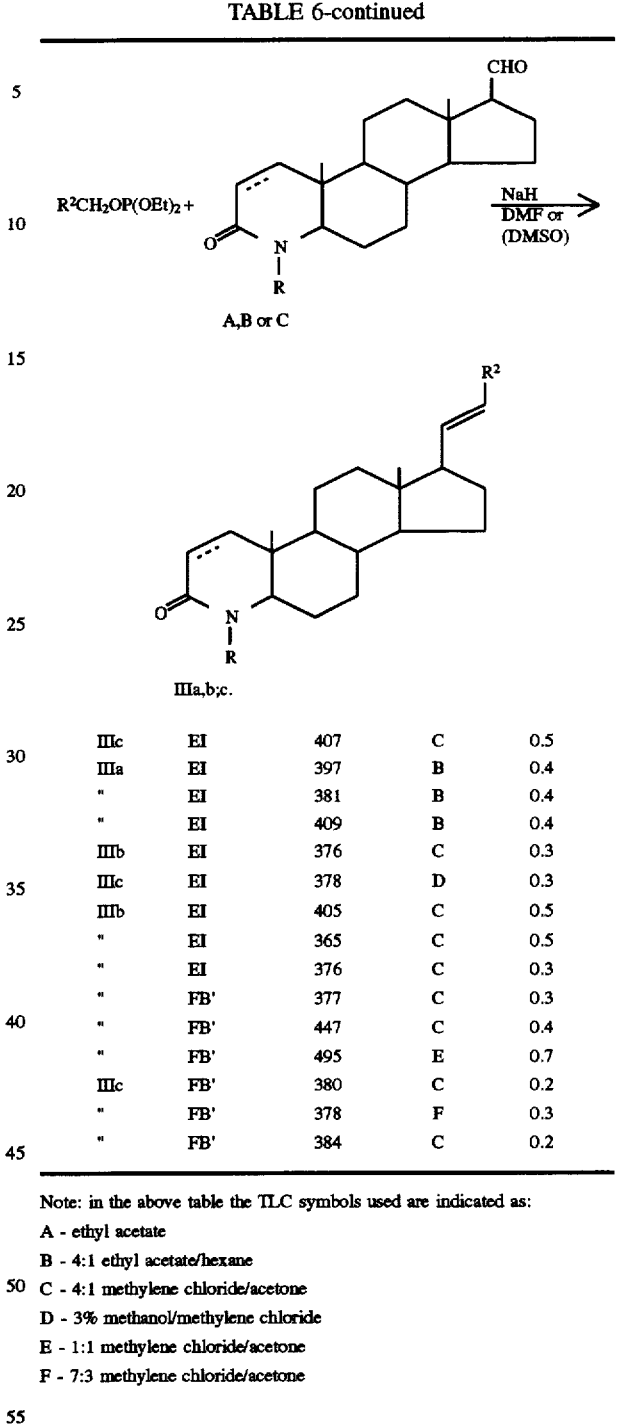

| | | | | |
|---|---|---|---|---|
| IIIc | EI | 407 | C | 0.5 |
| IIIa | EI | 397 | B | 0.4 |
| " | EI | 381 | B | 0.4 |
| " | EI | 409 | B | 0.4 |
| IIIb | EI | 376 | C | 0.3 |
| IIIc | EI | 378 | D | 0.3 |
| IIIb | EI | 405 | C | 0.5 |
| " | EI | 365 | C | 0.5 |
| " | EI | 376 | C | 0.3 |
| " | FB' | 377 | C | 0.3 |
| " | FB' | 447 | C | 0.4 |
| " | FB' | 495 | E | 0.7 |
| IIIc | FB' | 380 | C | 0.2 |
| " | FB' | 378 | F | 0.3 |
| " | FB' | 384 | C | 0.2 |

Note: in the above table the TLC symbols used are indicated as:
A - ethyl acetate
B - 4:1 ethyl acetate/hexane
C - 4:1 methylene chloride/acetone
D - 3% methanol/methylene chloride
E - 1:1 methylene chloride/acetone
F - 7:3 methylene chloride/acetone F—7:3 methylene chloride/acetone The mass spectral data were obtained by either electron impact (EI) or fast atom bombardment (FB) techniques.

The FB recorded results with one prime, $FB^1$, indicates m+1; with two primes, $FB^{11}$, indicates m+2. Also, the asterisk denotes the presence of the 1,2-double bond ($\Delta'$). The starting materials used were the aldehyde, A, for the 4-N-methyl derivatives; C, for 4-NH derivatives; and B, for the 1-ene-4-NH derivatives.

EXAMPLE 208

Reaction of 17-Methyl Ketones with Phosphonate Reagent

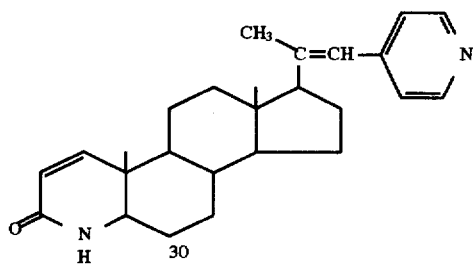

Preparation of: (20E)-20-methyl-21-(4-pyridyl)-4-aza-5α-pregn-1,20-dien-3-one, (30)

Following the general procedure of Wadsworth et al.; cited above, to a solution of 4-aza-5α-pregn-1-ene-3,20-dione (E) (158 mg., 0.5 mmol) and 229 mg (1.0 mol) diethyl 4-pyridylmethylphosphonate in 2 ml. anhydrous DMSO, was added all at once under $N_2$ atmosphere, 50 mg. (1.25 mmol) of sodium hydride (60%). The reaction mixture was stirred and heated at 85° C. under a $N_2$ atmosphere for 3 hours. Hydrogen evolution stopped after 15 minutes. The dark reaction mixture was cooled, poured into 30 ml $H_2O$ and extracted (3×) with methylene chloride. The combined organic phase was washed with water, dried over magnesium sulfate and concentrated under reduced pressure to yield a brown gum. The crude material was chromatographed on silica gel plates with 1:1 methylene chloride/ acetone and the strong UV active band was eluted 2:1 methylene chloride/methanol. The eluate was concentrated to yield pure product after trituration with ether, mp 268°–270° C. (dec.). The proton NMR confirmed the assigned structure for 30.

EXAMPLE 209

Following the general procedure of Example 208, the following tabulated compounds were prepared.

TABLE 7

IIIe,f.

| STRUCTURE | COMPOUND NO. | R | R² | PHYSICAL PROPERTIES |
|---|---|---|---|---|
| IIIe | 31 | Me | Phenyl | NMR* |
| " | 32 | Me | 4-chlorophenyl | mp. 208–211° C. |
| " | 33 | Me | 2-thienyl | mp. 220–222° C. |
| " | 34 | Me | 2-pyridyl | mp. 200–203° C. (dec.) |
| IIIf | 35 | H* | 4-pyridyl | mp. 268–278° C. (dec.) |
| IIIe | 36 | Me | 4-pyridyl | NMR** |
| IIIf | 37 | H* | 2-furyl | m.p. 290–294° C. (dec.) |
| " | 38 | H* | 2-pyridyl | m.p. 255–258° C. (dec.) |

TABLE 7-continued

IIIe,f.

| STRUCTURE | COMPOUND NO. | R | R² | PHYSICAL PROPERTIES |
|---|---|---|---|---|

*NMR(CDCl₃)d 0.65(S, 3H, 18-Me), 0.90(S, 3H, 19-Me), 1.88 (S, 3H, 21-Me), 2.94(S, 3H, N-Me), 6.35(bs, 1H C=CH−), 7.1–7.4(m, 5H, ArH).
**NMR(CDCl₃)d 0.65(S, 3H, 18-Me), 0.91(S, 3H, 19-Me), 1.92(S, 3H, 21-Me), 2.94(S, 3H, N-Me), 6.25(bs, 1H, C=CH−), 7.19(vbs, 2H, pyridyl H), 8.6(vbs. 2H, pyridyl H).

EXAMPLE 210

Reaction of Phosphonate Reagents with 17-Keto Androstanes

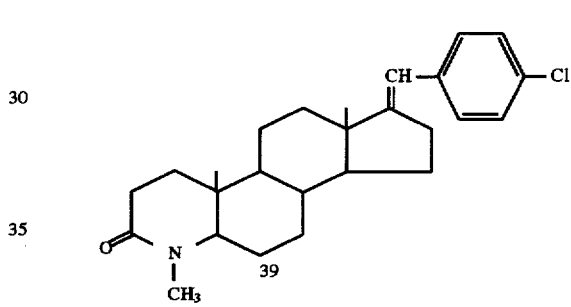

Preparation of 17-[(2-chlorophenyl)methylene]4-methyl-5α-androstan-3-one, (39)

Sodium hydride (60%, 26 mg, 0.66 mmole) was added to a solution of 101 mg. (0.33 mol) of 17-keto-4-methyl-5α-androstan-3-one (F) and 173 mg (0.66 mol) of diethyl 2-chlorobenzylphosphonate in 1.0 ml of dry DMF at room temperature. The mixture was heated at 70° C. in a nitrogen atmosphere with stirring for 110 minutes, cooled poured into 0.5N HCl (20 ml) and extracted with methylene chloride (3×). The organic phases were combined, washed with water (3×), saturated NaCl solution and dried over magnesium sulfate. The organic phase was concentrated under reduced pressure to yield a tan, gummy solid. Flash chromatography of the crude solid was conducted on a silica gel 60×20 mm column, and eluted with 4:1 methylene chloride/acetone in 6 ml. fractions. Fractions 18–24 contained the product which were combined and evaporated to yield a white solid, mp 205°–208° C., yielding one spot on silica gel TLC using 4:1 methylene chloride/acetone. The proton NMR continued the assigned structure for 39.

EXAMPLE 211

Following the general procedure of Example 210 but using different phosphonate reactants, the following compounds were prepared as listed in the following

TABLE 3

[Structure II: steroid with R² substituent on exocyclic vinyl at C-17 and N-R in A-ring lactam]

| No. | R  | R2                          | Physical Properties |
|-----|----|-----------------------------|---------------------|
| 40  | Me | phenyl                      | mp. 193–197° C.     |
| 41  | Me | 4-chlorophenyl              | mp. 138–141° C.     |
| 42  | Me | 3-chlorophenyl              | mp. 236–240° C.     |
| 43  | Me | 2-chlorophenyl              | mp. 205–208° C.     |
| 44  | Me | 4-ethoxycarbonylphenyl      | mp. 178–182° C.     |
| 45  | Me | 4-carboxyphenyl             | mp. >330° C.        |
| 46  | Me | 4-(t-butyl)amino-carbonylphenyl | NMR*            |

*NMR(CDCl$_3$)δ 0.86(S, 3H, 18-Me), 0.90(S, 3H, 19-Me), 1.45(S, 9H, CMe3), 2.92 (S, 3H, N-Me), 5.92(bs, 1H, NH), 6.05(t, 1H, C=CH—), 7.32(d, J=8Hz, 2H, ArH), 7.65 (d, J=8Hz, 2H, ArH).

EXAMPLE 212

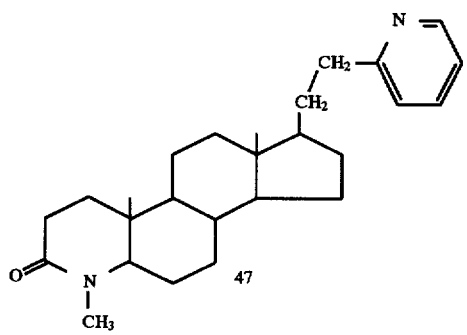

CATALYTIC REDUCTION OF DELTA-17 AND -20 OLEFINS

Preparation of 21-(2-pyridyl)-4-dimethyl-4-aza-5α-pregnan-3-one, (47)

A mixture of 0.075 g. (0.191 mmol) of (20E)-4,20-dimethyl-21-(2-pyridyl)-4-aza-5α-pregn-20-en-3-one, 0.075 mg 10% Pd/C catalyst in 3 ml ethanol were hydrogenated at room temperature under a 45 psig hydrogen atmosphere with shaking for 45 minutes. The reaction mixture was filtered through Celite and concentrated to yield 74 mg of product. The crude solid was chromatographed on a 2000 micron silica gel plate in 4:1 methylene chloride/acetone. The product was eluted using 5% MeOH/methylene chloride and concentrated to yield product 21-(2-pyridyl)-4-methyl-4-aza-5α-pregnan-3-one. The assigned structure for 41 was confirmed by proton NMR. Fast atom bombardment mass spectrum also confirmed a molecular ion peak of M+2=396, and the R$_f$ value on silica gel in 4:1 methylene chloride eluant was 0.2.

EXAMPLE 213

Following the general procedure of Example 212, the following saturated compounds were prepared from the corresponding $\Delta^{17}$ or $\Delta^{20}$ olefin:

[Structure: 4-aza-5α-pregnan-3-one with R¹, R² at C-21; N-CH$_3$]

| Structure   | No. | R¹ | R²                | Physical Properties              |
|-------------|-----|----|-------------------|----------------------------------|
| IVa R² = H  | 48  | H  | CH$_2$—C$_6$H$_4$—OCH$_3$ | M$_+$ 423 m/e (EI); R$_f$ 0.4 EtOAc |
| IVc R = H   | 49  | H  | —C$_6$H$_4$—Cl    | *                                |

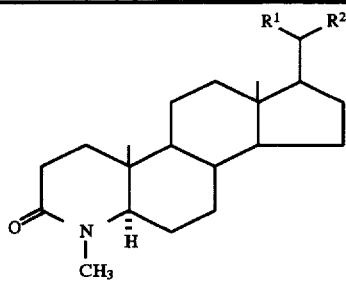

| Structure | No. | R¹ | R² | Physical Properties |
|---|---|---|---|---|
| IVa R² = H | 50 | H | CH₂—(thiophene) | M = 1 400 m/e (FAB); Rf 0.6 CG₂Cl₂-acetone (4:1) |
| IVa R² = H | 51 | H | CH₂—C₆H₄—CONH-t-bu | * |
| IVe R = Me | 52 | H | CH₂—C₆H₅ | *** |

*NMR (CDCl₃) δ 0.69(s, 3H, 18-Me), 0.89(s, 3H, 19-Me), 2.92(s, 3H, N—Me), 7.08(d, 2H, ArH), 7.22(d, 2H, ArH).

**NMR (CDCl₃) δ 0.59(s, 3H, 18-Me), 0.75(s, 3H, 19-Me), 1.44(s, 9H, CMe₃), 2.91(s, 3H, N—Me), 5.90(bs, 1H, NH), 7.19(d, 2H, ArH), 7.61(d, 2H, ArH).

***NMR (CDCl₃) δ 0.68, 0.70, 0.78, 0.80, 0.84, 0.86, 0.91, 0.92(s, 9H, 2 sets of 18- and 19-Me and 2(two) 21-Me doublets), 2.93(s, 3H, N—Me), 7.1–7.3(m, 5H, ArH).

EXAMPLE 214

Preparation of 4-Methyl-17β-[3-(phenyl)propyl]-4-aza-5α-androstan-3-one (53)

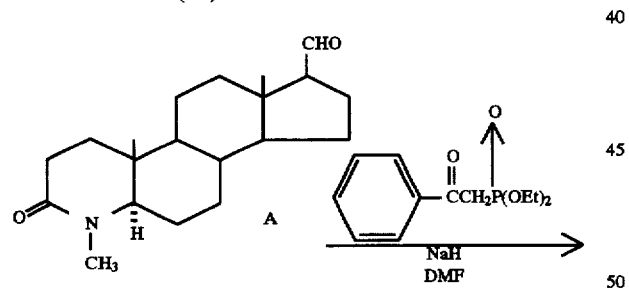

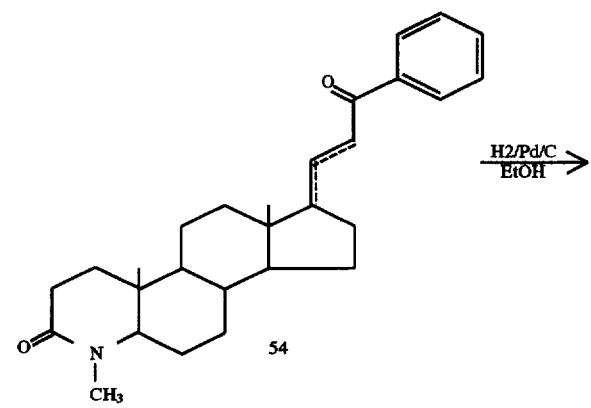

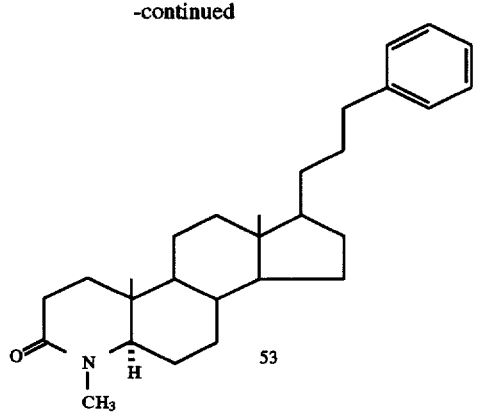

To a solution of 225 mg (0.71 mmoles) of aldehyde A and 185 mg (0.72 mmoles) of diethyl benzoylmethylphosphonate in 2 ml of DMF was added 29 mg (0.72 mmoles) of sodium hydride (60%) and the mixture heated at 80° in a N₂ atmosphere for 1 hour. The cooled reaction was poured into H₂O (50 ml) and extracted with CH₂Cl₂ (3×). The combined extracts were washed with water and brine and dried with magnesium sulfate. Evaporation in vacuo gave an oily solid, which was flash chromatographed on a 20 m×7" silica gel column with 7:3 ethyl acetate-hexane taking 18 ml fractions. Evaporation of fractions 25–42 gave 160 mg of a solid. NMR and TLC indicated it was a 1:1 mixture of Δ¹⁷ and Δ²⁰ olefin isomers (54).

A 60 mg sample of 54 was hydrogenated with 50 mg of 10% palladium on carbon in 3 ml of ethanol at 40 psi for 5 hours. The reaction was filtered through a bed of Celite, and the solid washed with ethanol (3×). The filtrated was evaporated in vacuo to give pure 53. Mass spectrum: m/e 408 (M+1) (FAB) R_f 0.35 EtOAc-hexane (4:1).

EXAMPLE 215

Preparation of 4-Methyl-24-nor-4-aza-5α-cholane-23-nitrile (54)

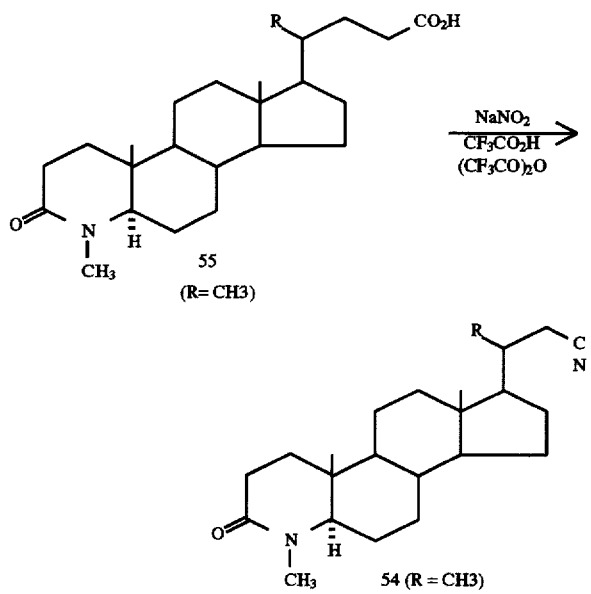

To a solution of 470 mg (1.18 mmoles) of 4-methyl-3-oxo-4-aza-5α-cholan-24-oic acid [G. H. Rasmusson, et al, J. Med. Chem. 1986, 29, 2298 (1986)] in 2.0 ml of trifluoroacetic acid and 0.52 ml of trifluoroacetic anhydride, cooled to 0° C., was added all at once 92 mg (1.33 mmoles) of sodium nitrite. After stirring at 0° for 45 min, the reaction was placed in a 40° oil bath. There was copious evolution of nitrogen, and the reaction darkened. After 20 minutes, the reaction was poured into 2 ml of 2N NaOH and 16 g of ice, extracted with CH$_2$Cl$_2$ (4×). The extracts were washed with H$_2$O and dried with magnesium sulfate. Evaporation in vacuo gave 195 mg of a tan solid. Flash chromatography on a 20 mm×7" column of silica gel with 6:1 CH$_2$Cl$_2$-acetone taking 10 ml fractions. Evaporation in vacuo of fractions 13–30 gave pure 54, m.p. 211°–214°. The NMR spectrum confirmed the assigned structure.

Using the same procedure, 4-methyl-3-oxo-21-nor-4-aza-5α-cholan-24-oic acid (55,R=H) gave 4-methyl-3-oxo-4-aza-5α-pregnane-21-carbonitrile (55,R=H).

Representative compounds included in the invention wherein all of the 7- and 16-substituents, where present, are in the beta configuration are:

7-ethyl-4,16-dimethyl-4-aza-cholestane-3-one
7,16-dimethyl-4-aza-cholestan-3-one
4,7,16-trimethyl-4-aza-5α-cholestan-3-one
4,16-dimethyl-4-aza-5α-cholestan-3,7-dione,
(20E)-20-ethyl-7,16-dimethyl-21-phenyl-4-aza-5α-pregna-1,20-diene-3-one,
(20E)-20-ethyl-7,16-dimethyl-21-(2-pyridyl)-4-aza-5α-pregna-1,20-diene-3-one,
20(E,Z)-4,7,16,21-tetramethyl-21-phenyl-4-aza-5α-pregn-20-en-3-one,
20(E,Z)-4,7,16,21-tetramethyl-21-(2-pyridyl)-4-aza-5α-pregna-1,20-dien-3-one,
20-ethyl-4-16-dimethyl-21-phenyl-4-aza-5α-pregn-20-en-3-one,
4,16,21-Trimethyl-21-(4-pyridyl)-4-aza-5α-pregna-1,20-dien-3-one,
4,7,16-Trimethyl-21-(3-pyridyl)-4-aza-5α-pregn-20-en-3-one,
4,7,16-Trimethyl-21-(2-pyrazinyl)-4-aza-5α-pregn-20-en-3-one,
(17E)-17-[(2-imidazolyl)methylene]-4,16-dimethyl-4-aza-5α-androstan-3-one,
(17E)-17-[(2-thiazolyl)methylene]-16-methyl-4-aza-5α-androst-1-en-3-one,
(17E)-17-[(2-pyrazinyl)methylene]-4,16-dimethyl-4-aza-5α-androstan-3-one,
(17E)-20-phenyl-4,16-dimethyl-4-aza-5a-pregn-17-en-3-one,
(17E)-20-(3-pyridyl)-16-methyl-4-aza-5α-pregna-1,17-dien-3-one,
(17E)-4,16-dimethyl-20-(2-pyrazinyl)-4-aza-5α-pregna-1,17-diene-3-one,
17β-(N'-t-Butylureidomethyl)-4,16-dimethyl-5-α-4-azaandrostan-3-one,
4,16-dimethyl-17β-(N'-phenylureidomethyl-5α-4-azaandrostan-3-one,
4,16-dimethyl-20-(N'-methylureido)-5α-4-azapregnan-3-one,
4,16-dimethyl-17β-(N'-n-propylureidomethyl-5-α-4-azaandrostan-3-one,
4,16-dimethyl-17β-(N'-n-octylureidomethyl)-5-α-4-azaandrostan-3-one,
17β-(N'-isopropylureidomethyl)-4,16-dimethyl-5α-4-azaandrostan-3-one,
4,16-dimethyl-20(trimethylacetamido)5α-4-aza-pregnan-3-one,
4,16-dimethyl-17β(trimethylacetamidomethyl)-4-aza-5α-androstan-3-one,
4,16-dimethyl-17β(2-thiophenesulfonamidomethyl)-4-aza-5α-androstan-3-one,
17β(Carbomethoxyoctanoylamidomethyl)-4,16-dimethyl-4-aza-5α-androstan-3-one,
17β(8-Carboxyoctanoylamidomethyl)-4,16-dimethyl-4-aza-5α-androstan-3-one,
17β(Acetoacetamidomethyl)-4,16-dimethyl-4-aza-5α-androstan-3-one,
20-ethoxyacetyloxy-4,16-dimethyl-5α-4-azapregnan-3-one,
17-acetyloxymethyl-4,16-dimethyl-5a-4-azaandrostan-3-one,
20-(3-carboxypropionyloxy)-4,16-dimethyl-5α-4-azapregnan-3-one,
17β-(phenylcarbonyl)-4-aza-4,16-dimethyl-5α-androst-1-ene-3-one;
17β-(2-tolylcarbonyl)-4-aza-4,16-dimethyl-5α-androst-1-ene-3-one;
17β-(3-tolylcarbonyl)-4-aza-4,16-dimethyl-5α-androst-1-ene-3-one;
17β-(4-tolylcarbonyl)-4-aza-4,16-dimethyl-5α-androst-1-ene-3-one;
17β-(N-tert-butylcarbamoyl)-4-aza-4,7,16-trimethyl-5α-androst-1-en-3-one;
17β-(N-isobutylcarbamoyl)-16-methyl-4-aza-5α-androst-1-en-3-one;
17β-(N-tert-octylcarbamoyl)-4-aza-4,16-dimethyl-5α-androst-1-en-3-one;
17β-(N-1,1-diethylbutylcarbamoyl)-4-aza-4,16-dimethyl-5α-androst-1-en-3-one;
17β-(N-t-butylcarbamoyl)-4,7,16-trimethyl-4-aza-5α-androst-1-en-3-one;
17β-(N-tert-hexylcarbamoyl)-4-aza-4,16-dimethyl-5α-androst-1-en-3-one;
17β-(N-tert-hexylcarbamoyl)-16-methyl-4-aza-5α-androst-1-en-3-one;

17β-(N-2-adamantylcarbamoyl)-16-methyl-4-aza-5α-androst-1-en-3-one,

17β-(N-1-adamantylcarbamoyl)-16-methyl-4-aza-5α-androst-1-en-3-one,

17β-(N-1-adamantylcarbamoyl)-16-methyl-4-aza-5α-androstan-3-one;

17β-(N-1-adamantylcarbamoyl)-4,16-dimethyl-4-aza-5α-androst-1-en-3-one;

17β-(N-1-adamantylcarbamoyl)-4,16-dimethyl-4-aza-5α-androstan-3-one;

17β-(N-1-adamantylmethylcarbamoyl)-16-methyl-4-aza-5α-androst-1-en-3-one;

17β-(N-2-adamantylcarbamoyl)-16-methyl-4-aza-5α-androstan-3-one;

17β-(N-methyl-N-2-adamantylcarbamoyl)-4,16-dimethyl-4-azaandrostan-3-one;

17β-(N-2-adamantylcarbamoyl)-4,16-dimethyl-4-aza-5α-androstane-3-one;

(17E)-17-[(phenyl)methylene]-4,16-dimethyl-4-aza-5α-androstan-3-one, (17E)-17-[(4-carboxyphenyl)methylene]-4,16-dimethyl-4-aza-5α-androstan-3-one, 20-t-butylacetyloxy-4,16-dimethyl-5α-4-azapregnan-3-one, 4,16-dimethyl-20-trimethylacetyloxy-5α-4-azapregnan-3-one, 4,16-dimethyl-20-(10-undecenoyloxy)-5α-4-azapregnan-3-one, 20-(3-carboxypropionyloxy)-4,16-dimethyl-5α-4-azapregnan-3-one, 20-(11-(carbomethoxy)undecanoyloxy)-4,16-dimethyl-5α-4-azapregnan-3-one, 20-(3-(carbobenzyloxy)propionyloxy)-4,16-dimethyl-5α-4-azapregnan-3-one, 20-(1-adamantylacetyloxy)-4,16-dimethyl-5α-4-azapregnan-3-one, 20-(3,4-dimethoxyphenyl)acetyloxy-4,16-dimethyl-5α-4-aza-pregnan-3-one, 20-(4-isopropylphenyl)acetyloxy-4,16-dimethyl-5α-4-azapregnan-3-one, 17-(methoxymethyl)-4,16-dimethyl-5α-4-azaandrostan-3-one, 17-(ethylthiomethyl)-4,16-dimethyl-5α-4-azaandrostan-3-one, 17-(carboxymethoxymethyl)-4,16-dimethyl-5α-4-azaandrostan-3-one, 17-(carboethoxymethoxymethyl)-4,16-dimethyl-5a-4-azaandrostan-3-one, 17-(carbobenzyloxymethoxymethyl)-4,16-dimethyl-5α-4-azaandrostan-3-one, 17-(diphenylmethoxymethyl)-4,16-dimethyl-5α-4-azaandrostan-3-one, 20-(diphenylmethoxy)-4,16-dimethyl-5α-4-azapregnan-3-one, ethyl 4,16-dimethyl-5α-4-azaandrostan-3-on-17β-yloxyacetate, 4,16-dimethyl-5α-4-azaandrostan-3-on-17β-yloxy-N-phenylacetamide, 17β-(N-neopentylcarbamoyl)-4-aza-4,16-dimethyl-5α-androst-1-en-3-one, 17β-(N-1-adamantylcarbamoyl)-16-methyl-4-aza-5α-androstan-3-one;

17β-(N-1-adamantylcarbamoyl)-4,16-dimethyl-4-aza-5α-androst-3-one;

17β-(N-1-adamantylcarbamoyl)-4,16-dimethyl-4-aza-5α-androstan-3-one;

17β-(N-1-adamantylmethylcarbamoyl)-16-methyl-4-aza-5α-androst-3-one;

17β-(N-2-adamantylcarbamoyl)-16-methyl-4-aza-5α-androstan-3-one;

17β-(N-methyl-N-2-adamantylcarbamoyl)-4,16-dimethyl-4-azaandrostan-3-one;

17β-(N-2-adamantylcarbamoyl)-4,16-dimethyl-4-aza-5α-androstane-3-one;

17β-(N-2-adamantylcarbamoyl)-4,16-dimethyl-4-aza-5α-androst-1-en-3-one;

17β-(N-methyl-N-2-adamantyl)carbamoyl-4,16-dimethyl-4-aza-androst-1-en-3-one.

Also included with the scope of this invention are 4-N—X analogs where X is OH, $NH_2$ or $SCH_3$. The 4-N—OH and 4-N—N—$NH_2$ derivatives can be made by incorporating hydroxylamine or hydrazine, respectively, in place of methylamine in the seco acid ring A closure for the starting androstanes herein as described in J. Med. Chem. 29, 2998–2315 (1986) by Rasmusson et al. Further, reaction of the anion of the saturated 4-N—H androstanes, wherein the anion is generated from the 4-N—H precursor by sodium hydride, and methylsulfenyl chloride can produce the corresponding 4-N—$SCH_3$ derivative. Thus, substituent R on the 4-N position also includes OH, $NH_2$ and S—$CH_3$.

There are two general strategies whereby 7,16-disubstituted-5α-4-azaandrostanes with various 17-substituents can be synthesized. The desired 7-substituent is introduced by methods described in Case 18740 (after p. 261 in this case); this 7-substituted intermediate can then be modified to introduce the 16-substituent by methods described in conjunction with the above-presented Flowsheet H, Flowsheet P and Flowsheet S (p. 58). Alternatively, the reversed strategy will also work—the 16-substituent can be introduced by already described methods (vide supra) followed by derivatization at C-7 and introduction of the desired substituent. The nature of the desired 17-substituent will determine which of the two strategies is optimal to one skilled in the art.

The present invention is additionally directed to new 17β-ester, amide, and ketone derivatives of 4-aza-5α-androstan-3-ones and related compounds and the use of such compounds as 5α-reductase inhibitors of the general structural formula (XXVI):

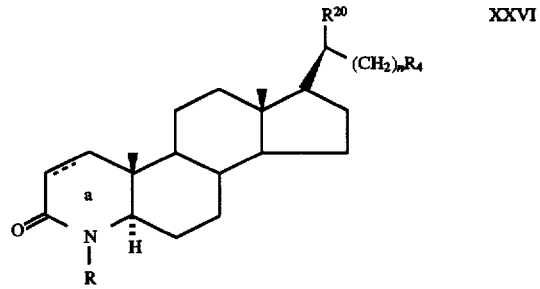

wherein:

dashed line a can represent a double bond when present;

R is selected from hydrogen, methyl, ethyl, hydroxyl, amino, and methylthio;

$R_{20}$ is selected from hydrogen or methyl;

n is an integer from 0 to 10;

$R^4$ is selected from:

(a) $COR_1$, where $R_1$ is $C_6$–$C_{10}$ aryl, substituted $C_6$–$C_{10}$ aryl, and heteroaryl;

(b) $CONHR_2$, where $R_2$ is substituted phenyl, heteroaryl, substituted heteroaryl, or $C_7$ to $C_{12}$ cycloalkyl;

(c) $CO_2R_3$, where $R_3$ is $C_6$–$C_{10}$ aryl, substituted $C_6$–$C_{10}$ aryl, or $C_7$–$C_{12}$ cycloalkyl;

where the above aryl and heteraryl radicals can also be fused with a benzo or another heteroaryl ring and can further be substituted with one or more substituents; and pharmaceutically acceptable salts and esters thereof.

The structure XXVI above encompasses an additional group of preferred embodiments of 5α-reductase inhibitor compounds of this invention. With respect to this structure, the following terms are meant.

By the term $C_1$–$C_4$ alkyl is meant linear or branched alkyl; e.g. methyl, ethyl, isopropyl, propyl, n-butyl, isobutyl, sec-butyl and the like.

Dashed line "a" can independently be a double bond and when present, the compound is a delta-1-ene.

$R_1$ and $R_3$ can be a a $C_6$–$C_{10}$ aryl including phenyl, benzyl, 1- and 2-phenethyl and naphthyl.

$R_2$ can be a phenyl group.

$R_1$ and $R_2$ can also be 5–6 membered heteroaryl radicals being fully unsaturated containing 1–4 nitrogen atoms, e.g. pyridyl, pyrryl, imidazolyl, tetrazolyl, pyrazinyl, pyrimidinyl, pyrazolyl, or triazolyl; containing 1–2 oxygen or sulfur atoms, e.g. thienyl, furanyl; or in combination with 1–2 nitrogen atoms, e.g. isothiazolyl, thiazolyl, isoxazolyl, oxazolyl or thiadiazolyl; or fused with a benzo ring, e.g. quinolyl, isoquinolyl, benzothienyl, isobenzofuryl, indolyl, carbazolyl; or fused with another heteroaryl ring, e.g. purinyl, and the like.

The $C_7$–$C_{12}$ cycloalkyl in $R_2$ and $R_3$ can be 1-, 2-adamantyl, norbornyl, and bicyclo[2.2.2.]octyl.

The aryl or heteroaryl ring in $R_1$ and $R_3$ as well as the phenyl group in $R_2$ can be unsubstituted or substituted with one or more of the following substituents providing the substitution leads to a chemically inert, but biologically active 5α reductase inhibitor:

The ring substituents include:

$C_1$–$C_8$ straight or branched alkyl; e.g. methyl, ethyl, propyl, isopropyl, n-butyl, sec-butyl, isobutyl, t-butyl, n-pentyl, n-hexyl, iso-hexyl, n-butyl, n-octyl, iso-octyl, t-octyl, and the like; $C_2$–$C_8$ straight or branched alkenyl, e.g. ethenyl, 1-propenyl, 2-propenyl, 1-butenyl, 2-butenyl, 3-butenyl, 1-pentenyl, 1-hexenyl, 1-heptenyl, 1-octenyl, 2-octenyl, and the like;

$C_3$–$C_8$ cycloalkyl e.g., cyclopropyl, cyclobutyl, cyclopentyl, cyclohexyl, 1-methyl-cyclobutyl, cyclopentyl, cyclohexyl, 1-methyl-cyclohexyl, 2-methylcyclohexyl, 2-ethylcyclohexyl, and the like;

$C_2$–$C_8$ alkynyl e.g., 1-ethynyl; 1-propynyl, 2-propynyl, 2-butynyl, 2-pentynyl, 1-hexynyl, 1-heptynyl, 1-octynyl;

$CONR^4R^5$ where $R^4$ and $R^5$ independently are H, $C_1$–$C_8$ alkyl, as defined above, $C_3$–$C_8$ cycloalkyl as defined above, $C_1$–$C_4$ perhaloalkyl e.g., trifluoromethyl, perfluoromethyl, trichloromethyl, preferably perfluoroalkyl; phenyl, or substituted phenyl, as described below;

$COR^4$, where $R^4$ is defined above, including acetyl, isobutylcarbonyl, benzoyl and the like;

$S(O)_nR^4$, where n is 0–2 and $R^4$ is defined above, including methylsulfinyl, methylsulfonyl, phenylsulfonyl, 4-chlorophenylsulfinyl and the like;

$OCOR^4$, where $R^4$ is defined above, including acetoxy, propionyloxy, benzoyloxy, 4-chlorobenzoyloxy and the like.

$SO_2NR^4R^5$ where $R^4$ and $R^5$ are described above, including sulfonamido, N-methylsulfonamido, N-phenylsulfonamido, N,N-dimethylsulfonamido and the like;

$NR^4(CO)R^5$, wherein $R^4$ and $R^5$ are defined above, including; acetylamino, benzoylamino, N-methylbenzoylamino and the like;

$NR^4(CO)NHR^5$, wherein $R^4$ and $R^5$ are described above, including; ureido, N-methylureido, N-methyl-$N^1$-phenylureido and the like;

$NHSO_2R^4$, $R^4$ being defined above, including methylsulfonylamino, phenylsulfonylamino and the like;

$OR^4$, where $R^4$ is defined above, including methoxy, phenoxy, 4-chlorophenoxy and the like.

$NR^4R^5$, wherein $R^4$ and $R^5$ are described above, including amino, methylamino, dimethylamino, anilino and the like;

Cyano, nitro, halo, including: fluoro, chloro, bromo and iodo;

Perhalo $C_1$–$C_4$ alkyl, including: trifluoromethyl, perfluoroethyl, trichloromethyl and the like.

$CO_2R^4$, wherein $R^4$ is defined above, including $CO_2CH_3$, $CO_2Ph$, $CO_2$-(1-adamantyl) and the like; phenyl and substituted phenyl of the formula:

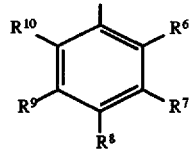

wherein the radicals $R^6$–$R^{10}$ each can represent one or more of the substituents defined above, including; hydrogen, 4-chlorophenyl, 4-fluorophenyl, 4-methoxyphenyl, 4-phenoxy and the like.

Unless otherwise indicated the 17-substituents herein described are assumed to be in the β configuration Representative compounds of the present invention include the following:

21-benzoyl-4-aza-5α-pregnan-3-one,
21-benzoyl-4-methyl-4-aza-5α-pregnan-3-one,
21-(2-methoxybenzoyl)-4-aza-5α-pregn-1-ene-3-one,
4-methyl-21-(2-trifluoromethylbenzoyl)-4-aza-5α-pregn-1-en-3-one,
20-benzoyl-4-methyl-4-aza-5α-pregnan-3-one,
23-(2-fluorobenzoyl)-4-methyl-24-nor-4-aza-5α-cholane-3,23-dione,
23-(3-pyridyl)-24-nor-4-aza-5α-chol-1-ene-3,23-dione,
4-methyl-24-(2-pyridyl)-21-nor-4-aza-5α-cholane-3,24-dione,
17β-[5-(3-chlorobenzoyl)pentyl]-4-aza-5α-androstan-3-one,
17β-(6-benzoylhexyl)-4-methyl-4-aza-5α-androstan-3-one,
17β-(10-benzoyldecyl)-4-aza-5α-androst-1-en-3-one,
4-methyl-21-(2-thienyl)-4-aza-5α-pregnane-3,21-dione,
24-(2-pyrazinyl)-4-aza-5α-chol-1-ene-3,24-dione,
4-ethyl-(2,6-dimethoxybenzoyl)-4-aza-5α-pregnan-3-one,
N-(4-acetylphenyl)-4-methyl-3-oxo-4-aza-5α-pregnane-21-carboxamide,
N-(4-acetylphenyl)-3-oxo-4-aza-5α-pregnane-21-carboxamide,
4-methyl-3-oxo-N-(4-pyridyl)-4-aza-5α-pregnane-21-carboxamide,
3-oxo-N-(4-pyridyl)-4-aza-5α-pregnane-21-carboxamide,
N-(2-adamantyl)-3-oxo-4-aza-5α-pregnane-21-carboxamide,
N-(2-adamantyl)-4-methyl-3-oxo-4-aza-5α-pregnane-21-carboxamide, 3-oxo-N-(4-pyridyl)-4-aza-5α-pregnan-21-amide,
4-methyl-3-oxo-4-(4-pyridyl)-4-aza-21-nor-5α-cholan-24-amide,
4-methyl-3-oxo-N-(3-pyridyl)-4-aza-5α-pregnane-21-carboxamide,
4-methyl-3-oxo-N-(2-pyridyl)-4-aza-5α-pregnane-21-carboxamide,
N-(1-adamantyl)-4-methyl-3-oxo-4-aza-5α-pregnane-20(S)-carboxamide,
N-(4-acetylphenyl)-4-methyl-3-oxo-4-aza-5α-pregnane-20(S)-carboxamide,
N-(4-chlorophenyl)-4-methyl-3-oxo-4-aza-5α-cholan-24-amide,
N-(4-acetylphenyl)-4-methyl-3-oxo-4-aza-5α-cholan-24-amide,
3-oxo-N-(4-trifluoromethylphenyl)-4-aza-5α-cholan-24-amide,
4-methyl-3-oxo-N-(4-pyridyl)-24-nor-4-aza-5α-cholan-24-amide,
N-(1-adamantyl)-11-(4-methyl-3-oxo-4-aza-5α-androstan-17β-yl)undecanamide,
N-(2-pyridyl)-6-(4-methyl-3-oxo-4-aza-5α-androstan-17β-yl)hexanamide,
N-(3-pyridyl)-5-(3-oxo-4-aza-5α-androst-1-en-17β-yl)pentanamide,
N-(2-thienyl)-7-(4-methyl-3-oxo-4-aza-5α-androstan-17β-yl)heptanamide,
3-oxo-N-(2-pyrazinyl)-4-aza-5α-pregnan-21-amide,4-methyl-3-oxo-N-(2-t-butylphenyl)-4-aza-5α-cholane-24-carboxamide,
4-methyl-3-oxo-N-(2-cyanophenyl)-4-aza-chol-1-ene-24-carboxamide,
N-(2-bicyclo[2.2.2]octyl)-9-(3-oxo-4-aza-5α-androstan-17β-yl)nonanamide,
1-adamantyl 4-methyl-3-oxo-4-aza-5α-pregnane-20(S)-carboxylate,
phenyl 4-methyl-3-oxo-4-oxo-4-aza-5α-pregnane-20(S)-carboxylate,
2-(t-butyl)phenyl 4-methyl-3-oxo-4-aza-5α-pregnane-21-carboxylate,
2-methoxyphenyl 4-methyl-3-oxo-4-aza-5α-pregnane-21-carboxylate,
phenyl 3-oxo-4-aza-5α-pregnane-21-carboxylate,
phenyl 4-methyl-3-oxo-4-aza-5α-pregnane-21-carboxylate,
phenyl 5-(4-methyl-3-oxo-4-aza-5α-androstan-17β-yl)pentanoate,
2-(t-butyl)phenyl 3-oxo-4-aza-5α-pregnan-21-oate,
2,6-dimethoxyphenyl 3-oxo-4-aza-5α-pregn-1-en-21-oate,
2-adamantyl 8-(4-methyl-3-oxo-4-aza-5α-androstan-17β-yl)octanoate,
2,6-dimethylphenyl 3-oxo-4-aza-5α-pregn-1-en-21-oate,
2,6-dichlorophenyl 4-methyl-3-oxo-4-aza-5α-pregn-1-en-21-ate,
phenyl 10-(4-methyl-3-oxo-4-aza-5α-androstan-17β-yl)decanoate,
N,4-dimethyl-3-oxo-N-(4-pyridyl)-4-aza-5α-pregnan-21-amide,
N-methyl-3-oxo-N-(4-pyridyl)-4-aza-5α-pregnan-21-amide,
4-methyl-3-oxo-N-(4-pyridyl)-4-aza-5α-pregnane-20-carboxamide,
4-methyl-3-oxo-N-(3-pyridyl)-4-aza-5α-pregnane-20-carboxamide,
4-methyl-3-oxo-N-(2-pyridyl)-4-aza-5α-pregnane-20-carboxamide,
4-methyl-3-oxo-N-(4-pyridyl)-4-aza-5α-cholan-24-amide,
4-methyl-3-oxo-N-(3-pyridyl)-4-aza-5α-cholan-24-amide,
4-methyl-3-oxo-N-(2-pyridyl)-4-aza-5α-cholan-24-amide,
3-oxo-N-(4-pyridyl)-4-aza-5α-pregn-1-ene-20-carboxamide,
3-oxo-N-phenyl-4-aza-5α-pregn-1-ene-21-carboxamide,
N-(4-methoxyphenyl)-3-oxo-4-aza-5α-pregn-1-ene-21-carboxamide,
N-(2-imidazolyl)-3-oxo-4-aza-5α-pregn-1-ene-21-carboxamide,
3-oxo-N-(4-pyridyl)-4-aza-5α-pregn-1-ene-21-carboxamide,
3-oxo-N-(3-pyridyl)-4-aza-5α-pregn-1-ene-21-carboxamide,
3-oxo-N-(2-pyridyl)-4-aza-5α-pregn-1-ene-21-carboxamide,
3-oxo-N-(1,2,4-triazin-3-yl)-4-aza-5α-pregn-1-ene-21-carboxamide,
3-oxo-N-(3-quinolinyl)-4-aza-5α-pregn-1-ene-21-carboxamide,
3-oxo-N-(4-pyridyl)-4-aza-5α-chol-1-en-24-amide,
3-oxo-N-(3-pyridyl)-4-aza-5α-chol-1-en-24-amide,
3-oxo-N-(2-pyridyl)-4-aza-5α-chol-1-en-24-amide,
and also including the corresponding compounds wherein the 4-hydrogen substituent is replaced by a methyl or an ethyl radical, and/or a delta-one double bond is present.

Also included within the scope of this invention are pharmaceutically acceptable salts, i.e. hydrochloride, hydrobromide, acetate, pamoate, and the like, of the compound where a basic heteroaryl radical is present, e.g. 4-pyridyl, which can be used as the dosage form for modifying solubility or hydrolysis characteristics or for use as sustained release or prodrug formulations.

The novel compounds of formula I of the present invention are prepared by methods discussed below. The compounds and intermediates and their physical properties are listed in Table 1, and their preparation is illustrated in Examples 1–11.

The starting materials for these preparations are the appropriate carboxylic acids 1, 2, 9, 16, 17, 34, 37, 40, 45, 63, 64, 68 and 78 (these numbers are with reference to examples 216 through 227). The source of these carboxylic acids is as follows:

The synthesis of acid 1 is published in J. Med. Chem. 1984, Vol. 27, p 1690.

Acid 2 was prepared by the same procedure as acid 1.

The preparation of acid 9 is published in J. Med. Chem. 1984 Vol. 27, p. 1690.

The syntheses of acids 16 and 17 are detailed in Example 1. The aldehyde 50 was reacted with the methyl (diethylphosphono)acetate anion to give the olefinic Horner-Wadsworth reaction product 51. Hydrogenation to the saturated ester 52 and saponification with aqueous KOH in methanol gave 17. The same sequence of reactions starting with the corresponding 4-methyl aldehyde (J. Med. Chem. 1986 Vol. 29, p. 2304, compound 10bg) produced the acid 16.

Acid 34 was prepared as outlined in Example 225, below. The nitrile 58 was transformed into the methyl ester 59 by conversion to the iminoester with anhydrous HCl in methanol followed by treatment with water. KOH saponification produced the acid 34.

The acid 37 was synthesized by the Arndt-Eistert homologation of 16. Activation of 16 as the mixed anhydride with isobutyl chloroformate and N-methyl morpholine and reaction with diazomethane gave the diazoketone 53. Silver benzoate catalyzed decomposition of 53 in methanol gave the homologous methyl ester 54. Saponification have the corresponding acid 37.

The synthesis of the acid 41 and 65 is published in J. Med. Chem. 1986 Vol. 29, p. 2300. The acids 45, 63, and 64 were prepared by the reaction sequence detailed in Example 226. Palladium catalyzed coupling of the $\Delta^{16}$-17-triflate 60 with methyl 4-pentynoate using the procedures published in Synlett. 1991 p. 409; J. Org. Chem. 1992 Vol. 57, p. 973. gave the enyne 61. Hydrogenation catalyzed with palladium on carbon formed the saturated ester 62 and KOH saponification gave 45. Similar reaction sequences using methyl 5-hexynoate and 10-undecynoic acid gave the acids 63 and 64.

Starting with the above acids, the novel ketones, amides, and esters listed in Table 1 were prepared using the procedures discussed below and detailed in the Examples.

The synthesis of the ketones 32 and 33 is given below. Using the procedures published in J. Med. Chem. 1986 Vol. 29, p. 2310, the acids 16 and 17 were converted into the 2-thiopyridyl esters 55 and 56 by reaction with triphenylphosphine and 2,2'-dithiodipyridine. Low temperature reaction of these 2-thiopyridyl esters with phenylmagnesium chloride produced the phenyl ketones 32 and 33 (Example 221).

The amides listed in Table 8 were prepared by a variety of procedures:

For the unhindered acids 16, 17, 34, 37, 41, 62, 63, and 64, 4-dimethylaminopyridine (DMAP) catalyzed carbodiimide mediated condenstion with the appropriate amine or aniline was used. Either dicyclohexylcarbodiimide or the water soluble 1-(3-dimethylaminopropyl)-3-ethylcarbodiimide hydrochloride (Example 223) could be used.

For the more hindered acids 1 and 2, formation of the mixed anhydride with isobutyl chloroformate and N-methylmorpholine followed by reaction with the appropriate amine (Example 219) proved to be the best procedure.

forming the acid chloride with oxalyl chloride (Example 224) or converting it into the 2-thiopyridyl ester (Example 220).

With hindered or unreactive amines such as 1-adamantamine or 4-acetylaniline, reaction of the 2-thiopyridyl ester alone (Example 220) or with silver trifluoromethylsulfonate catalysis (Example 222) was used to form the amide derivatives.

The ester derivatives in Table 8 were formed from the appropriate acid and alcohol or phenol using the same procedures (Examples 218, 222 and 223) used for the formation of the corresponding amide derivatives.

As outlined in Flowchart A the 4-H esters II can be converted into the corresponding $\Delta^1$-4-H esters (III) by the procedure of Dolling,et al using dichlorodicyanobenzoquinone (J. Amer. Chem. Soc. 1988, Vol. 110, p. 3318–3319) or using benzeneselenic anhydride (J. Med. Chem. 1986 Vol. 29, p.2298–2315). Furthermore II and III can be alkylated on the 4-N with methyl or ethyl iodide using sodium hydride in DMF or DMSO to give the 4-methyl- or 4-ethyl-4H esters (IV) or the 4-methyl- or 4-ethyl-$\Delta^1$ esters (V). Also II and III can be converted to the 4-SMe esters IV and V by reaction with sodium hydride and methanesulfenyl chloride (MeSCl). II and III can also be aminated with hydroxylamine-O-sulfonic acid and oxidized with Oxone-acetone reagent to give the 4-NH$_2$ and 4-OH esters IV and V, respectively. After saponification of the esters (II–V), the starting acids containing a 4-hydrogen, methyl, ethyl, hydroxy, amino, or methylthio substituent and either with or without a $\Delta^1$ can be prepared. Using the procedures in Examples 1–11, these acids can be converted into the corresponding ketone, amide, and ester derivatives.

FLOWSHEET LI

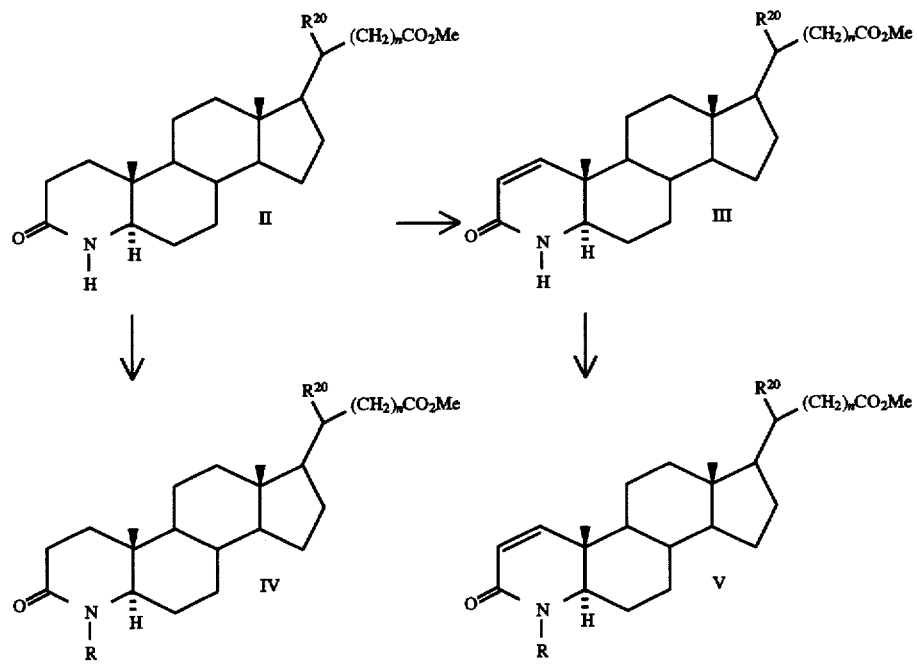

R = Me, Et, OH, NH$_2$, SMe

For the most hindered acid (9), it was necessary to activate the acid for reaction with an amine by either

EXAMPLE 216

3-Oxo-4-aza-5α-pregnan-21-carboxylic acid (17)

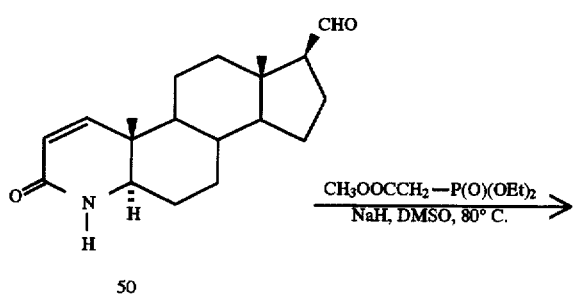

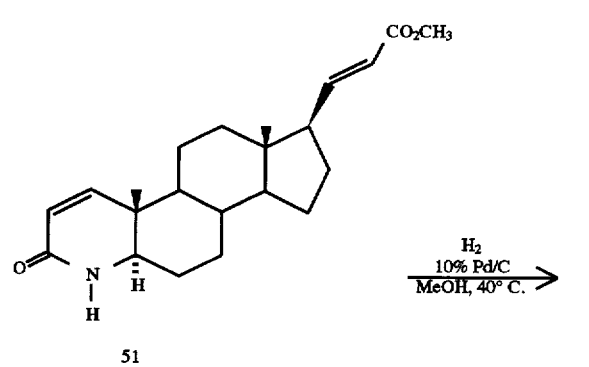

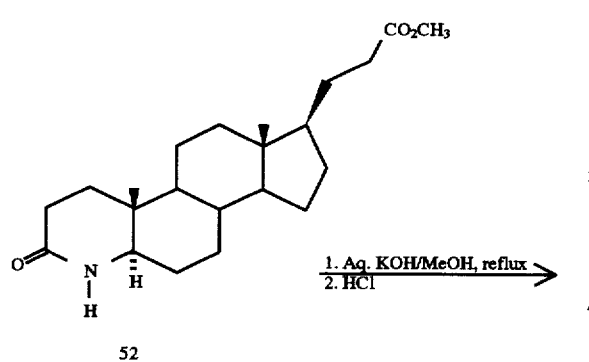

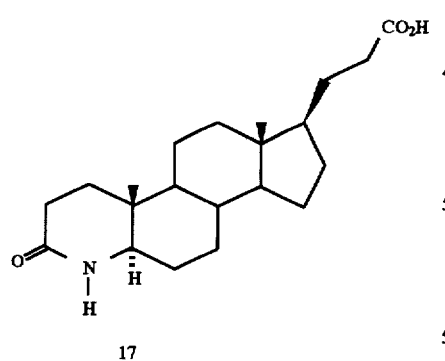

To a suspension of the aldehyde (50), (1.0 g, 3.32 mmole) in 12 ml DMSO was added 14.6 mg (3.65 mmole) sodium hydride (60% in mineral oil) and 698 µl (3.65 mmole) methyl diethylphosphonoacetate. The mixture was heated under $N_2$ atmosphere at 80° C. for 1 hr. The clear solution was cooled and partitioned between dilute HCl and methylene chloride. The organic phase was washed with water, brine, dried over magnesium sulfate and concentrated in vacuo to give 1.2 g crude product. Purification by flash chromatography on silica gel in 4:1 methylene chloride:acetone gave 956 mg of the unsaturated ester [51, NMR, d=0.66 (s, 3H, 18-Me), 0.97 (s, 3H, 19-Me), 3.72 (s, 3H, OMe), 5.7(d, 1H, $\Delta^1$), 5.82(s, 1H, $\Delta^{20}$), 5.96(bs, 1H, NH), 6.79(d, 1H, $\Delta^1$), 6.92 (dd, 1H, $\Delta^{20}$)].

The unsaturated ester (51) (956 mg, 2.67 mmole) was dissolved in 80 ml warm methanol and hydrogenated with 300 mg 10% Pd/C at 40 psi at a temperature of 40° C. for 3 hrs. The mixture was filtered through a pad of Celite, washing with warm methanol. The filtrate was concentrated in vacuo to give 938 mg of the saturated ester (52).

The saturated ester (52) (938 mg, 2.59 mmole) was dissolved in 9 ml methanol containing 863 µl 9M KOH and refluxed for 1 hr. The mixture was concentrated to a small volume and 100 ml water added. The mixture was cooled to 10° C. and brought to pH 1 with concentrated HCl. The resulting precipitate was filtered, washed with water, sucked dry and dried in a vacuum oven at 60° C., 25 in. for 18 hrs, giving 830 mg of the acid (17).

EXAMPLE 217

3-Oxo-4-methyl-4-aza-5α-21-norcholanic acid (37)

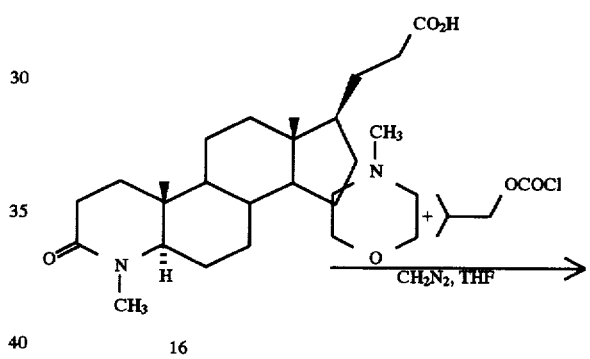

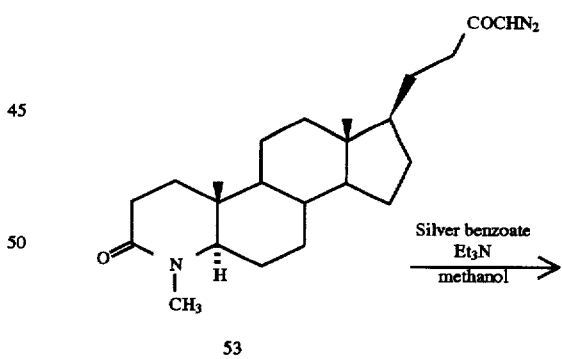

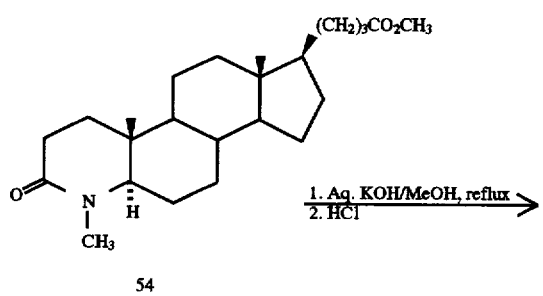

-continued

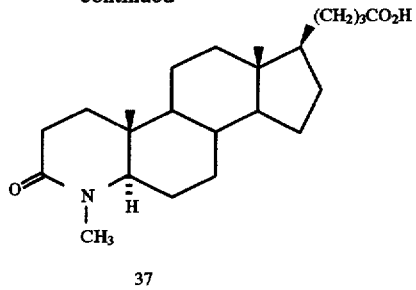

37

To a solution of the acid (16), (763 mg, 2.66 mmole) and N-methyl morpholine (296 ml, 2.66 mmole) in 60 ml THF at −20° C. under $N_2$ atmosphere was added dropwise isobutyl chloroformate (352 µl, 2.66 mmole). The mixture was stirred at −20° C. for 40 minutes, filtered and concentrated in vacuo to about ¼ its volume on a rotary evaporator using no heat. The mixture was cooled to −10° C. under $N_2$ and a freshly prepared ether solution of excess (12 mmole) diazomethane added. After stirring for 18 hours at room temperature, nitrogen was bubbled through the solution for 20 minutes (to remove excess diazomethane) and the mixture concentrated in vacuo. The residue was partitioned with methylene chloride-water and the organic phase washed with 5% acetic acid, water, brine, dried over magnesium sulfate and concentrated in vacuo to give 1.1 g crude product (oil). Purification by flash chromatography on silica gel in 4:1 methylene chloride:acetone gave 350 mg of the diazoketone (53).

The diazoketone (53), (224 mg, 0.681 mmole) was dissolved in 1 ml of methanol and 266 µl of a 0.218M solution of silver benzoate in triethyl amine (50 mg/ml) was added. The mixture was stirred at room temperature for 2 hours and the dark solution concentrated in vacuo. Methylene chloride was added and the mixture filtered. The filtrate was washed with dilute HCl, water, saturated $NaHCO_3$, brine, dried over magnesium sulfate and concentrated in vacuo to give 212 mg crude product (oil). Purification by flash chromatography on silica gel in 4:1 methylene chloride:acetone gave 153 mg of the methyl butyrate (54).

The methyl ester (54) was converted to the free acid (37) using the same conditions as was used in the previous case (52 converted to 17) except that the reflux time was 2 hours.

EXAMPLE 218

3-Oxo-4-methyl-N-phenyl-4-aza-5α-pregnan-21-carboxamide (23)

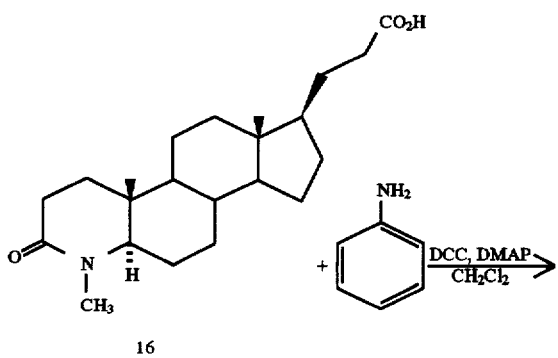

16

-continued

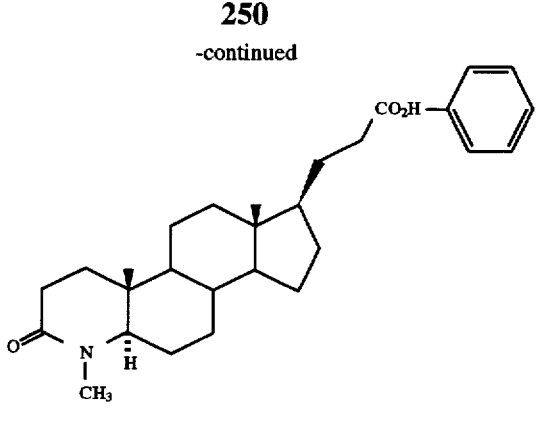

23

To a solution of the acid (16), (57 mg, 0.158 mmole) in 2 ml methylene chloride was added 17 µl (0.190 mmole) aniline, 45 mg (0.220 mmole) dicyclohexylcarbodiimide (DCC) and 1 mg 4-dimethyl-aminopyridine (DMAP). The mixture was stirred at room temperature for 5 hours, filtered and concentrated in vacuo to give 96 mg crude mixture. Purification by preparative thin layer chromatography on a 1500µ silica gel plate in 5% methanol/methylene chloride and trituration with hexane gave 26 mg of the anilide (23).

Compounds 18–20, 24–28, 30, 38–39, 42 and 44 were prepared by the above procedure.

EXAMPLE 219

3-Oxo-4-methyl-N-phenyl-4-aza-5α-pregnan-21-amide (3)

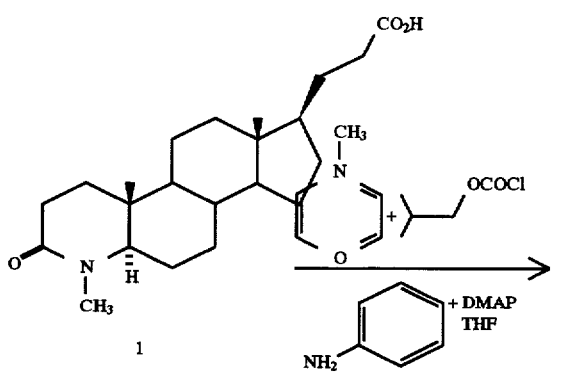

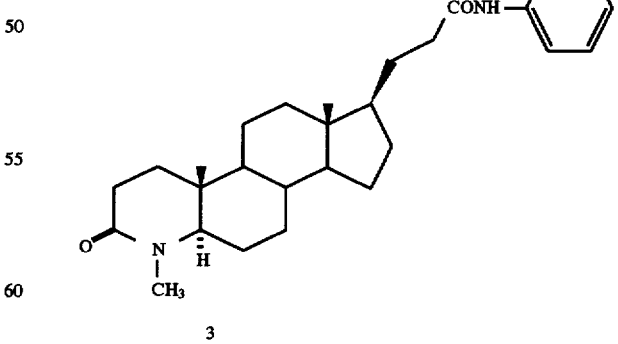

3

To a solution of the acid (1) (174 mg, 0.50 mmole) and N-methyl morpholine (61 µl, 0.55 mmole) in 10 ml THF at −20° C. under a $N_2$ atmosphere was added dropwise isobutyl chloroformate (66 µl, 0.50 mmole). The mixture was stirred at −20° C. for 20 minutes and aniline (64 μl, 0.70 mmoles) plus 4-dimethylaminopyridine (DMAP, 3 mg) was added. The mixture was stirred at −20° C. for 30 minutes and then at room temperature for 18 hours. The mixture was concentrated in vacuo and the residue partitioned with methylene chloride-water. The organic phase was washed with dilute HCl, water, brine, dried over magnesium sulfate and concentrated in vacuo to give 224 mg crude product. Purification by flash chromatography on silica gel in 4:1 methylene chloride:acetone gave 184 mg of the anilide (3).

Compounds 4–8, 29 and 31 were prepared by the above procedure.

EXAMPLE 220

N-2-adamantyl-3-oxo-4-methyl-4-aza-5α-pregnan-21-carboxamide (21)

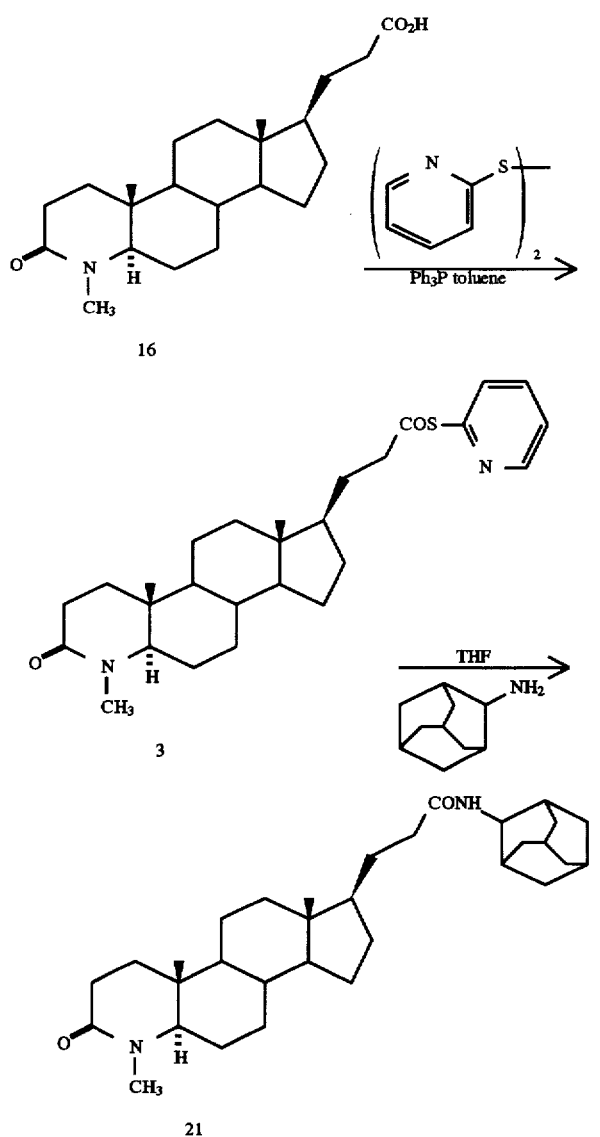

To a suspension of the acid (16), (391 mg, 1.08 mmole) in 3 ml toluene was added 487 mg (2.16 mmole) 2,2'-dithiodipyridine followed by 567 mg (2.16 mmole) triphenylphosphine. The mixture was stirred at room temperature for 18 hours, concentrated in vacuo and the residue flash chromatographed on silica gel in 4:1 methylene chloride-:acetone to give a yellow solid. The solid was washed with ether to give 326 mg of the thiopyridyl ester (55).

Using the same procedure, the thiopyridyl esters 56 and 57 were prepared from the carboxylic acids 17 and 9 respectively.

To a solution of the thiopyridyl ester (55), (105 mg, 0.231 mmole) in 2.5 ml THF was added 262 mg (1.73 mmole) 2-adamantane amine. The mixture was stirred at room temperature for 18 hours, concentrated in vacuo and the residue partitioned with methylene chloride-2N HCl. The organic phase was washed with water, brine, dried over magnesium sulfate and concentrated in vacuo. The residue was flash chromatographed on silica gel in 4:1 methylene chloride:acetone to give 83 mg of the amide (21).

Using the above procedure compounds 14 and 22 were prepared from the thiopyridyl esters 57 and 56 respectively.

EXAMPLE 221

21-Benzoyl-4-aza-5α-pregnan-3-one (33)

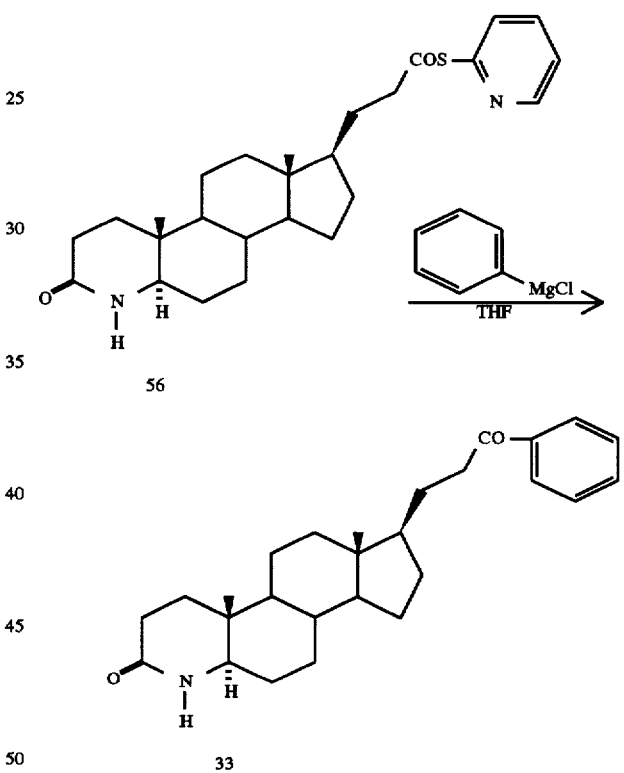

To a suspension of the thiopyridyl ester (56), (100 mg, 0.227 mmole) in 4 ml THF at −78° C. under a $N_2$ atmosphere was added phenyl magnesium chloride (250 μl, 0.499 mmole, 2M in THF). The mixture was stirred at −78° C. for 45 minutes and allowed to warm to 0° C. The reaction was quenched by the careful addition of 5 drops of brine. The mixture filtered and washed with THF and methylene chloride. The filtrate was concentrated in vacuo and the residue dissolved in methylene chloride, washed with 2N NaOH, water, brine, dried over magnesium sulfate and concentrated in vacuo to give 84 mg crude mixture. Purification by preparative thin layer chromatography on a 2000μ silica gel plate in 4:1 methylene chloride:acetone (run up the plate 4 times) gave 20 mg of the phenyl ketone (33).

Compound 32 was prepared by the above procedure.

EXAMPLE 222

N-(4-Acetylphenyl)-4-methyl-3-oxo-4-aza-5α-pregnane-20 (S)-carboxamide (15)

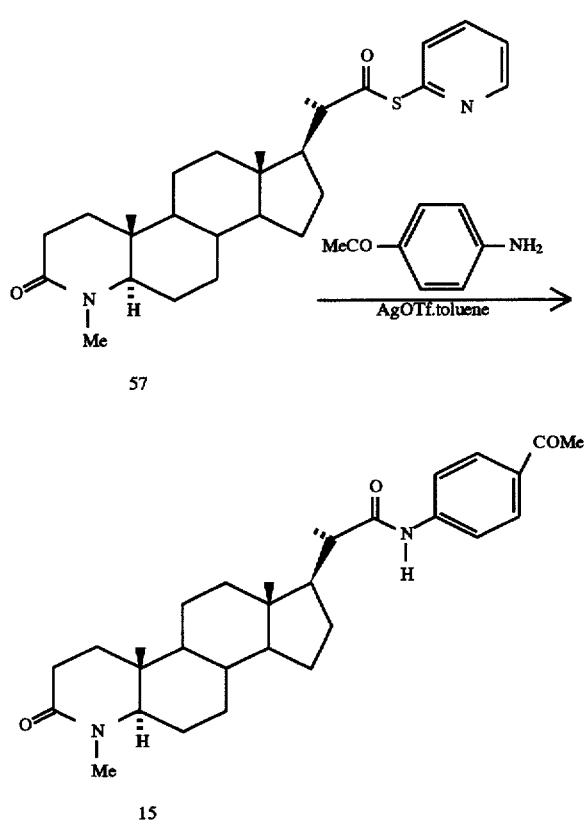

To a suspension of the thiopyridyl ester (57) (136 mg, 0.3 mmoles) and 4-acetylaniline (81 mg, 0.6 mmoles) in 1.5 ml of toluene was added all at once a warm solution of 93 mg (0.36 mmoles) of silver trifluoromethysulfonate in 0.6 ml of toluene. The suspension was stirred at room temperature for 24 hrs. Periodically the gummy precipitate was dispersed with a glass rod. The suspension was diluted with 30 ml of $CH_2Cl_2$ and washed with water, 5% ammonium hydroxide, water, and saturated brine and dried ($MgSO_4$). Evaporation in vacuo gave 117 mg of a pale yellow solid. Preparative TLC on two 20×20 cm. 1000μ, silica gel plates with 4:1 $CH_2Cl_2$-acetone and elution of the strongly UV-active band with 4:1 $CH_2Cl_2$-MeOH gave 32 mg of pure amide 15.

Compounds 10 and 11 were prepared by the above procedure.

EXAMPLE 223

4-Methyl-3-oxo-N-(4-pyridyl)-24-nor-4-aza-5α-cholan-23-amide (36)

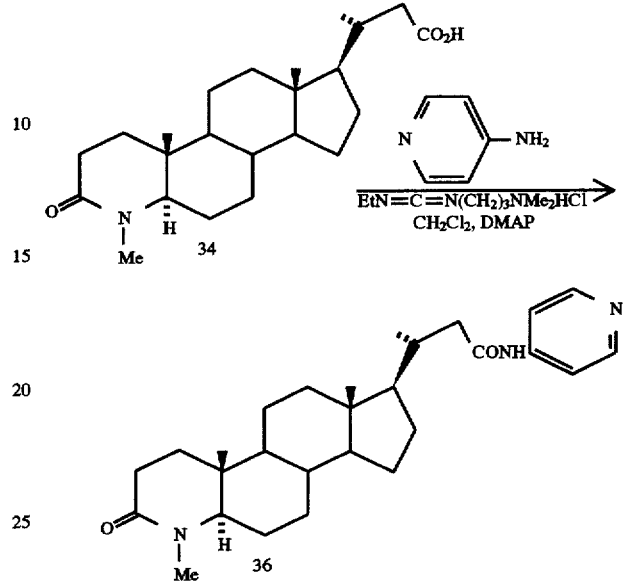

To a solution of 38 mg (0.1 mmole) of the acid 34, 19 mg (0.2 mmoles) of 4-aminopyridine, and 1 mg of 4-dimethlylamino-pyridine in 0.3 ml of $CH_2Cl_2$ was added 38 mg (0.2 mmoles) of 1-(3-dimethylaminopropyl)-3-ethylcarbodiimide hydrochloride. The solution was kept at room temperature for 24 hrs, diluted with $CH_2Cl_2$, washed with water, dilute $K_2CO_3$, water, and saturated brine and dried ($MgSO_4$). Evaporation in vacuo gave 45 mg of a gum. Preparative TLC on a 20×20 cm, 1000μ silica gel plate with 7% MeOH in $CH_2Cl_2$ and elution of the strongly UV-active band with 2:1 $CH_2Cl_2$-MeOH gave 23 mg of pure amide 36.

Compounds 35, 43, 46, 47, 48, and 49 were prepared from the appropriate acids by the above procedure.

EXAMPLE 224

N-(1-Adamantyl)-4-methyl-3-oxo-4-aza-5α-pregnane-20 (S)-carboxamide (13)

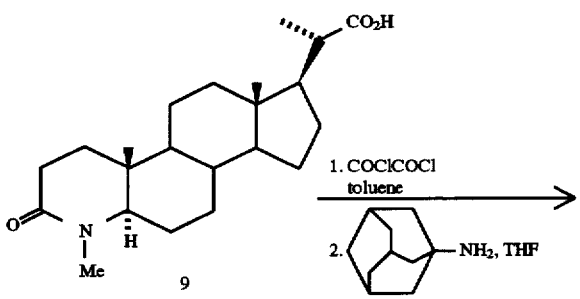

255
-continued

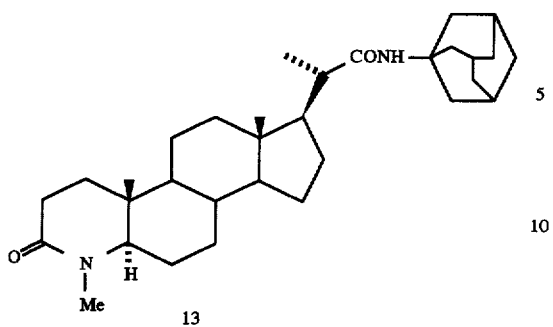

To a suspension of 108 mg (0.3 mmoles) of the acid 9 in 1.3 ml of toluene was added 0.24 ml (2.75 mmoles) of oxalyl chloride at room temperature. After 30 min the volatiles were removed in vacuo, and the residue was dissolved in 1.5 ml of THF. A solution of 181 mg (1.2 mmoles) of 1-adamantanamine and 3 mg of 4-dimethyl-aminopyridine in 1 ml of THF was added, and the mixture allowed to stir at room temperature for 20 hrs. Most of the THF was removed in vacuo, and the residue partitioned between ice water and $CH_2Cl_2$. The aqueous phase was extracted with $CH_2Cl_2$ (2×). The combined organic extracts were washed with 0.5N HCl, water, and dried ($MgSO_4$). Evaporation in vacuo and flash chromatography of the residue on a 10 mm×18 cm column of silica gel with 1:1 ethyl acetate-acetone gave 47 mg of pure amide 13.

EXAMPLE 225

4-Methyl-3-oxo-24-nor-4-aza-5α-cholan-23-oic acid (34)

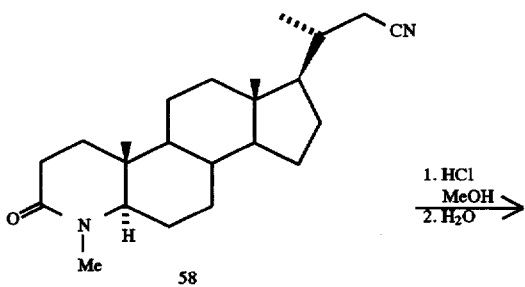

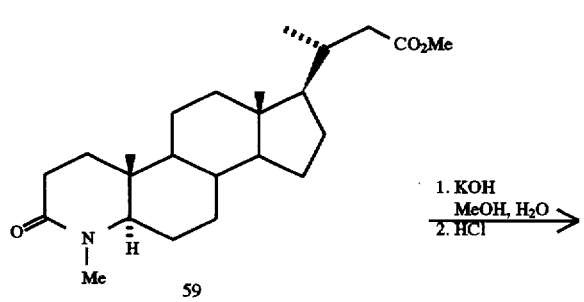

256
-continued

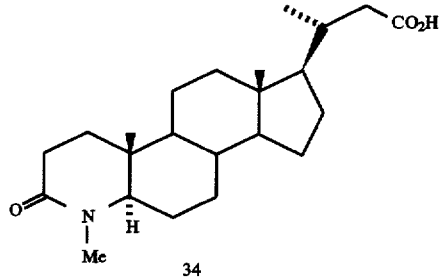

A solution of 144 mg of 4-methyl-3-oxo-24-nor-4-aza-5α-cholano-23-nitrile in 5 ml of methanol saturated with anhydrous HCl was allowed to stand at room temperature for 6 hrs. The residue after evaporation in vacuo was stirred in 10 ml of water for 3 hrs and extracted with $CH_2Cl_2$ (3×). The extracts were washed with water and dried ($MgSO_4$). Evaporation in vacuo and flash chromatography of the residue on silica gel with 4:1 $CH_2Cl_2$-acetone gave 112 mg of methyl 4-methyl-3-oxo-24-nor-4-aza-5α-cholan-23-oate (59).

EXAMPLE 226

4-Methyl-3-oxo-21-nor-4-aza-5α-cholane-24-carboxylic acid (45)

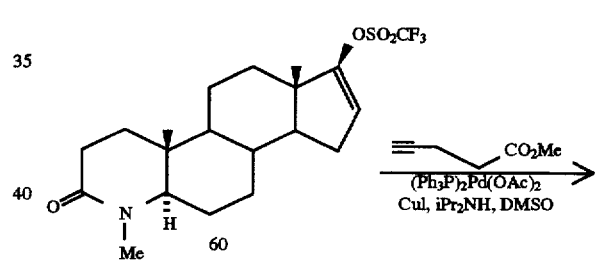

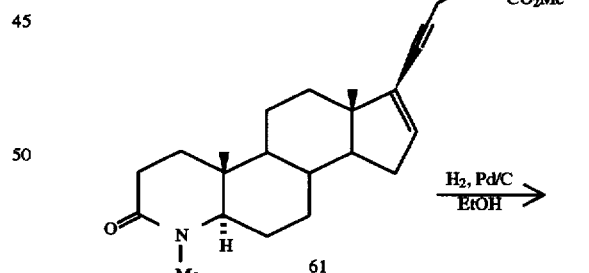

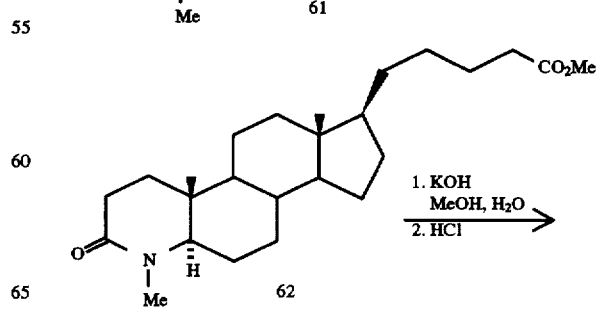

257

-continued

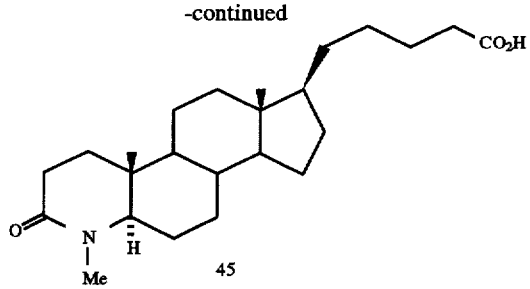

A mixture of 436 mg (1.0 mmole) of 4-methyl-17-triflluoromethylsulfonyloxy-4-aza-5α-androst-16-en-3-one (60) (Case 18730), 168 mg (1.5 mmoles) of methyl 4-pentynoate, 40 mg of bis(triphenylphosphine)palladium (II) acetate, 5 mg of cuprous iodide in 3.0 ml of DMSO and 3.0 ml of N,N-diisopropylamine was stirred at room temperature for 17 hrs. The dark reaction mixture was poured into 50 ml of 0.5M HCl and extracted with $CH_2Cl_2$ (3×). The combined extracts were washed with water (4×) and dried ($MgSO_4$). Evaporation in vacuo and flash chromatography of the residue on silica gel with 6:1 $CH_2Cl_2$-acetone gave 400 mg of enyne 61. The enyne was immediately hydrogenated in 20 ml of EtOH with 150 mg of 10% palladium on carbon catalyst under a hydrogen-filled balloon. After stirring at room temperature for 24 hrs, the reaction mixture was filtered through a bed of Celite., which was washed with EtOH (4×). The filtrate and washes were evaporated in vacuo and the residue flash chromatographed on silica gel with 5:1 $CH_2Cl_2$ to give 345 mg of methyl 4-methyl-3-oxo-21-nor-4-aza-5α-cholane-24-carboxylate (62).

The acids 6-(4-methyl-3-oxo-4-aza-5α-androstan-17β-yl) hexanoic acid (63) and 11-(4-methyl-3-oxo-4-aza-5α-androstan-17β-yl)-undecanoic acid (64) used for the preparation of the anilides 48 and 49 respectively were prepared by the above procedure.

The following table lists the compounds made in this invention and their physical properties.

EXAMPLE 227

3-Oxo-4-aza-5a-pregn-1-ene-21-carboxylic acid

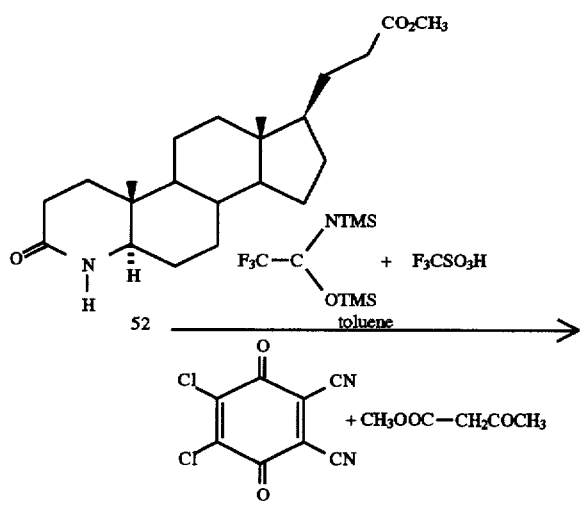

258

-continued

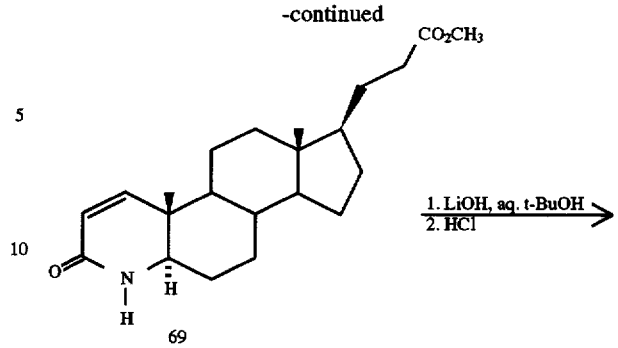

To a dry toluene solution of the ester 52 (361 mg, 1.0 mmole) under $N_2$ was added 2,3-dichloro-5,6-dicyano-1,4-benzoquinone (266 mg, 1.13 mmole), bis(trimethylsilyl) trifluoroacetamide (1.07 ml, 4 mmole) and trifluoromethanesulfonic acid (7 ml, 0.077 mmole) and the clear red solution stirred at room temperature for 24 hours. Methylacetoacetate (11 ml, 0.1 mmole) was added and after stirring for 1 hour at room temperature the solution was refluxed for 24 hours. The reaction mix was concentrated in vacuo to a small volume and the residue dissolved in methylene chloride and extracted with an aqueous solution of 1.5% sodium carbonate plus 0.5% sodium sulfite, 5% sodium bicarbonate, dried over magnesium sulfate and concentrated in vacuo to give 328 mg crude product. Purification by flash chromatography on silica gel in 9:1 methylene chloride:acetone gave 229 mg of the unsaturated ester 69.

The unsaturated ester 69 (215 mg, 0.598 mmole) was dissolved in 2 ml tert-butanol containing lithium hydroxide monohydrate (75 mg, 1.79 mmole) and 200 ml water and refluxed for 1.5 hours. The mixture was concentrated in vacuo to a small volume and 20 ml water added. The mixture was cooled to 10° C. and brought to pH 1 with concentrated HCl. The resulting precipitate was filtered, washed with water, sucked dry and dried in a vacuum oven at 60° C., 25 in. for 18 hours giving 174 mg of the unsaturated acid 68.

Using the above procedures the ester 59a was converted into the ester 79 and the acid 78.

The following tables 6 and 7 list some of the compounds made in this invention and their physical properties. The compound numbers in these two tables are with reference to compounds described in Examples 73 through 84.

TABLE 9

[Structure: steroid core with N-R substituent at bottom ring, ketone, and side chain $R_{20}$-CH-(CH$_2$)$_n$-R$_4$ at top]

| Compd | R | $R_{20}$ | n | $R_4$ | NMR 18-Me |
|---|---|---|---|---|---|
| 1 | Me | H | 0 | CO$_2$H | |
| 2 | H | H | 0 | CO$_2$H | |
| 3 | Me | H | 0 | CONH-phenyl | 0.62 |
| 4 | H | H | 0 | CONH-phenyl | 0.65 |
| 5 | H | H | 0 | CONH-C$_6$H$_4$-COMe | 0.66 |
| 6 | H | H | 0 | CONH-C$_6$H$_4$-COMe | 0.66 |
| 7 | Me | H | 0 | CONH-(4-pyridyl) | 0.64 |
| 7a | Me | H | 0 | CONH(Me)-(4-pyridyl) | 0.44 |
| 8 | H | H | 0 | CONH-(4-pyridyl) | 0.62 |
| 8a | H | H | 0 | CONH(Me)-(4-pyridyl) | 0.45 |
| 9 | Me | Me | 0 | CO$_2$H | |
| 10 | Me | Me | 0 | CO$_2$-phenyl | 0.76 |
| 11 | Me | Me | 0 | CO$_2$-adamantyl | 0.67 |
| 12 | Me | Me | 0 | CONH-C(CH$_3$)$_2$CH$_2$C(CH$_3$)$_3$ | 0.68 |
| 13 | Me | Me | 0 | CONH-adamantyl | 0.68 |
| 14 | Me | Me | 0 | CONH-phenyl | 0.74 |
| 15 | Me | Me | 0 | CONH-C$_6$H$_4$-COMe | 0.72 |
| 15a | Me | Me | 0 | CONH-(4-pyridyl) | 0.71 |
| 15b | Me | Me | 0 | CONH-(3-pyridyl) | 0.72 |
| 15c | Me | Me | 0 | CONH-(2-pyridyl) | 0.71 |
| 16 | Me | H | 1 | CO$_2$H | 0.60 |
| 17 | H | H | 1 | CO$_2$H | |
| 18 | Me | H | 1 | CO$_2$-phenyl | 0.65 |
| 19 | Me | H | 1 | 2-MeO-C$_6$H$_4$-CO$_2$ | 0.64 |
| 20 | Me | H | 1 | 2-tBu-C$_6$H$_4$-CO$_2$ | 0.65 |
| 21 | Me | H | 1 | CONH-adamantyl | 0.62 |
| 22 | H | H | 1 | CONH-adamantyl | 0.62 |
| 23 | Me | H | 1 | CONH-phenyl | 0.63 |
| 24 | H | H | 1 | CONH-phenyl | 0.63 |

TABLE 9-continued

| # | R1 | R2 | n | Group | Value |
|---|----|----|----|-------|-------|
| 25 | Me | H | 1 | CONH–C6H4–COMe | 0.63 |
| 26 | H | H | 1 | CONH–C6H4–COMe | 0.63 |
| 27 | Me | H | 1 | CONH–(4-pyridyl) | 0.64 |
| 28 | H | H | 1 | CONH–(4-pyridyl) | 0.63 |
| 29 | Me | H | 1 | CONH–(3-pyridyl) | 0.63 |
| 30 | H | H | 1 | CONH–(3-pyridyl) | 0.62 |
| 31 | Me | H | 1 | CONH–(2-pyridyl) | 0.62 |
| 32 | Me | H | 1 | CO–C6H5 | 0.64 |
| 33 | H | H | 1 | CO–C6H5 | 0.63 |
| 34 | Me | Me | 1 | $CO_2H$ | 0.69 |
| 35 | Me | Me | 1 | CONH–C6H5 | 0.73 |
| 36 | Me | Me | 1 | CONH–(4-pyridyl) | 0.71 |
| 37 | Me | H | 2 | $CO_2H$ | 0.58 |
| 38 | Me | H | 2 | CONH–C6H5 | |
| 39 | Me | H | 2 | CONH–(4-pyridyl) | 0.59 |
| 40 | Me | Me | 2 | $CO_2H$ | |
| 41 | H | Me | 2 | $CO_2H$ | 0.65 |
| 42 | Me | Me | 2 | CONH–C6H5 | 0.68 |
| 43 | H | Me | 2 | CONH–C6H5 | 0.69 |
| 44 | Me | Me | 2 | CONH–C6H4–COMe | 0.68 |
| 44a | Me | Me | 2 | CONH–(4-pyridyl) | 0.66 |
| 44b | Me | Me | 2 | CONH–(3-pyridyl) | 0.66 |
| 44c | Me | Me | 2 | CONH–(2-pyridyl) | 0.67 |
| 45 | Me | H | 3 | $CO_2H$ | 0.55 |
| 46 | Me | H | 3 | $CO_2$–C6H5 | 0.57 |
| 47 | Me | H | 3 | CONH–C6H5 | 0.56 |
| 48 | Me | H | 4 | CONH–C6H5 | 0.55 |
| 49 | Me | H | 9 | CONH–C6H5 | 0.56 |
| 52 | H | H | 1 | $CO_2Me$ | 0.61 |
| 53 | Me | H | 1 | $COCHN_2$ | |
| 54 | Me | H | 2 | $CO_2Me$ | 0.58 |
| 55 | Me | H | 1 | COS–(2-pyridyl) | 0.62 |
| 56 | H | H | 1 | COS–(2-pyridyl) | 0.64 |
| 57 | Me | Me | 0 | COS–(2-pyridyl) | 0.74 |
| 58 | Me | Me | 1 | CN | |
| 59 | Me | Me | 1 | $CO_2Me$ | 0.70 |
| 59a | H | Me | 2 | $CO_2Me$ | 0.64 |

TABLE 9-continued

| 62 | Me | H | 3 | CO$_2$Me | 0.56 |
| 64 | Me | H | 9 | CO$_2$H | 0.56 |

| Compd | NMR 19-Me | Other | Mass Spectrum | |
|---|---|---|---|---|
| 1 | | J. Med. Chem. 1984. 27. 1690–1701 | | |
| 2 | | | m/e334(M+1) | FAB |
| 3 | 0.84 | 7.04–7.52 (m,5H,ArH) | m/e423(M+1) | FAB |
| 4 | 0.91 | 7.07–7.53 (m,5H,ArH) | m/e409(M+1) | FAB |
| 5 | 0.90 | 2.58(s,3H,COMe); 7.61 (d,2H,ArH); 7.94(d,2H, ArH) | m/e466(M+2) | FAB |
| 6 | 0.90 | 2.57(s,3H,COMe); 7.62 (d,2H,ArH); 7.93(d,2H,ArH) | m/e451(M+1) | FAB |
| 7 | 0.90 | 7.56(d,2H,ArH); 8.46(d, 2H,ArH) | m/e424(M+1) | FAB |
| 7a | 0.85 | 3.30(s,3H,NMe); 7.13(d, 2H,ArH); 8.65(d,2H, ArH) | | |
| 8 | 0.88 | 7.58(d,2H,ArH); 8.44(d, 2H,ArH) | m/e410(M+1) | FAB |
| 8a | 0.87 | 3.27(s,3H,NMe); 7.15(d, 2H,ArH); 8.66(d,2H, ArH) | m/e423(M) | EI |
| 9 | | J. Med. Chem. 1984. 27 1690–1701 | | |
| 10 | 0.91 | 1.36(s,3H,21-Me); 7.0–7.5(m,5H,ArH) | | |
| 11 | 0.88 | 1.3(d,3H,21-Me); 1.64; 2.09; 2.14(bs,15H, adamantylH); | | |
| 12 | 0.90 | 1.03(s,9H,CMe3); 1.12 (d,3H,21-Me); 1.40,1.42 (s,6H,NCMe2); 5.20(s, 1H,NH) | | |
| 13 | 0.89 | 1.14(d,3H,21-Me); 1.67, 1.99,2.06(bs,15H, adamantylH); 5.03(bs, 1H,NH) | | |
| 14 | 0.90 | 1.28(d,3H,21-Me); 7.06–7.70(m,5H,ArH) | | |
| 15 | 0.89 | 1.28(d,3H,21-Me); 2.58 (s,3H,COMe); 7.68(d, 2H,ArH); 7.92(d,2H, ArH); 8.00(bs,1H,NH) | | |
| 15a | 0.89 | 1.27(d,3H,21-Me); 7.64 (d,2H,ArH); 8.44(d,2H, ArH); 8.50(s,1H,NH) | | |
| 15b | 0.89 | 1.29(d,3H,21-Me); 7.28 (m,1H,ArH); 7.92(s,1H, ArH); 8.30(m,2H,ArH); 8.61(bs,1H,NH) | | |
| 15c | 0.88 | 1.28(d,3H,21-Me); 7.04 (m,1H,ArH); 7.78(m,1H, ArH); 8.13(m,3H,ArH+NH) | | |
| 16 | 0.90 | | m/e361(M) | EI |
| 17 | | | m/e347(M) | EI |
| 18 | 0.90 | 7.05–7.41(m,5H,ArH) | m/e347(M) | EI |
| 19 | 0.89 | 3.81(s,3H,OMe); 6.90–7.29(m,4H,ArH) | | |
| 20 | 0.90 | 1.35(s,9H,CMe3); 6.95–7.43(m,4H,ArH) | | |
| 21 | 0.90 | | m/e495(M+1) | FAB |
| 22 | 0.91 | | m/e481(M+1) | FAB |
| 23 | 0.89 | 7.05–7.54(m,5H,ArH) | m/e436(M) | EI |
| 24 | 0.91 | 7.06–7.55(m,5H,ArH) | m/e422(M) | EI |
| 25 | 0.89 | 2.56(s,3H,COMe); 7.64 (d,2H,ArH); 7.93(d,2H, ArH) | m/e478(M) | EI |
| 26 | 0.91 | 2.57(s,3H,COMe); 7.63 (d,2H,ArH); 7.91 (d, 2H,ArH) | m/e464(M) | EI |
| 27 | 0.90 | 7.84(d,2H,ArH); 8.43(d, 2H,ArH) | m/e437(M) | EI |
| 28 | 0.91 | 7.58(d,2H,ArH); 8.46(d, 2H,ArH) | m/e424(M+1) | FAB |
| 29 | 0.89 | 7.30(m,1H,ArH); 8.28 (m,2H,ArH); 8.60(s,1H, ArH) | | |
| 30 | 0.90 | 7.33(m,1H,ArH); 8.32 (m,2H,ArH); 8.62(s,1H, ArH) | m/e424(M+1) | FAB |
| 31 | 0.89 | 7.05(m,1H,ArH); 7.31 (m,1H,ArH); 8.24(m,2H, ArH) | | |
| 32 | 0.91 | 7.38–7.62(m,3H,ArH); 7.95(d,2H,ArH) | | |
| 33 | 0.90 | 7.05–7.54(m,5H,ArH) | m/e408(M+1) | FAB |
| 34 | 0.86 | 1.01(d,2H,21-Me) | | |
| 35 | 0.89 | 1.04(d,3H,21-Me); 7.03–7.62(m,5H,ArH); 7.21 (bs,1H,NH) | | |
| 36 | 0.87 | 1.01(d,3H,21-Me); 7.60 (bs,2H,ArH); 8.40(s,1H, NH);8.44(bs,2H,ArH) | | |
| 37 | 0.90 | | m/e376(M+1) | FAB |
| 38 | 0.87 | 7.07–7.49(m,5H,ArH) | m/e451(M+1) | FAB |
| 39 | 0.89 | 7.58(d,2H,ArH); 8.46(d, 2H,ArH) | m/e451(M+1) | FAB |
| 40 | | J. Med. Chem. 1986, 29 2298–2315 | | |
| 41 | 0.88 | 0.91(d,3H,21-Me) | | |
| 42 | 0.89 | 0.96(d,3H,21-Me); 7.03–7.56(m,5H,ArH); 7.48(bs,1H,NH) | | |
| 43 | 0.91 | 0.96(d,3H,21-Me); 5.92 (bs,1H,NH); 7.04–7.64 (m,5H,ArH) | | |
| 44 | 0.89 | 0.96(d,3H,21-Me); 2.57 (s,3H,COMe); 7.66(d, 2H,ArH); 7.90(d,2H, ArH); 8.16(bs,1H,NH) | | |
| 44a | 0.88 | 0.94(d,3H,21-Me); 7.60 (d,2H,ArH); 8.37(s, 1H,NH); 8.44(d,2H,ArH) | | |
| 44b | 0.88 | 0.96(d,3H,21-Me); 7.33 (m,1H,ArH); 8.02(bs, 1H,ArH); 8.33(m,2H, ArH); 8.64(s,1H,NH) | | |
| 44c | 0.87 | 0.95(d,3H,21-Me); 7.08 (m,1H,ArH); 7.78(m, 1H,ArH); 8.25(m,2H, ArH); 8.68(bs,1H,NH) | | |
| 45 | 0.87 | 2.31(t,2H,CH2CO2) | | |
| 46 | 0.88 | 2.53(t,2H,CH2CO2); 7.02–7.38(m,5H,ArH) | | |
| 47 | 0.87 | 2.33(t,2H,CH2CO2); 7.05–7.52(m,5H,ArH); 7.21(s,1H,NH) | | |
| 48 | 0.87 | 2.33(t,2H,CH2CO2); 7.05–7.52(m,5H,ArH); 7.23(s,1H,NH) | | |
| 49 | 0.88 | 2.33(t,2H,CH2CO2); 7.05–7.54(m,5H,ArH) | | |
| 52 | 0.90 | 3.66(s,3H,OMe); 5.83 (bs,1H,NH) | | |
| 53 | | IR,2140 cm−1 N2 | | |
| 54 | 0.90 | 2.30(t,2H,CH2CO2); 3.69(s,3H,OMe) | | |
| 55 | 0.90 | 7.30(m,1H,ArH); 7.70 (m,2H,ArH); 8.62(m, 1H,ArH) | | |
| 56 | 0.92 | 5.7(bs,1H,NH); 7.31(m, 1H,ArH); 7.71(m,2H, ArH); 8.63(m,1H,ArH) | | |
| 57 | 0.90 | 1.32(d,3H,21-Me); 7.32(m,1H,ArH); 7.72 (m,2H,ArH); 8.63(m, 1H,ArH) | | |
| 59 | 0.88 | 0.97(d,3H,21-Me); 3.65 (s,3H,OMe) | | |
| 59a | 0.88 | 0.91(d,3H,21-Me); 3.65 (s,3H,OMe); 5.77(s, 1H,NH) | | |

TABLE 9-continued

| 62 | 0.88 | 2.29(t,2H,CH2CO2);<br>3.66(s,3H,OMe) |
| 64 | 0.86 | 2.33(t,2H,CH2CO2) |

TABLE 10

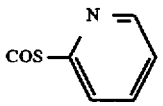

| Compd | R20 | n | R4 | NMR 18-Me | 19-Me | Other | Mass Spectrum |
|---|---|---|---|---|---|---|---|
| 65 | Me | 0 | CO2H | | | | |
| 66 | Me | 0 | 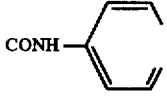 | 0.63 | 0.95 | 1.33(d,3H,21-Me); 5.81(d,1H,1-H); 6.03(bs,1H,NH); 6.79(d,1H,2-H); 7.34, 7.63, 7.79, 8.64(m,1H ea,ArH) | |
| 67 | Me | 0 | 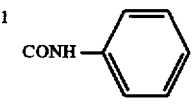 | 0.72 | 0.94 | 1.25(d,3H,21-Me); 5.78(d,1H,1-H); 6.79(d,1H,2-H); 7.62(d,2H,ArH); 8.39(d,2H,ArH) | |
| 68 | H | 1 | CO2H | 0.57 | 0.87 | 5.59(d,1H,1-H); 6.82(d,1H,2-H) | |
| 69 | H | 1 | CO2Me | 0.62 | 0.98 | 3.66(s,3H,OMe); 5.82(d,1H,1-H); 6.82(d,1H,2-H); | m/e359(M+) EI |
| 70 | H | 1 | 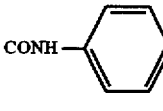 | 0.64 | 0.98 | 5.81(d,1H,1-H); 6.82(d,1H,2-H); 7.05–7.54(m,5H,ArH) | m/e420(M+) EI |
| 71 | H | 1 | 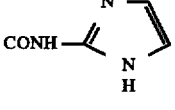 | 0.64 | 0.97 | 3.79(s,3H,OMe); 5.82(d,1H,1-H); 6.82(d,1H,2-H); 6.86(d,2H,ArH); 7.42(d,2H,ArH) | m/e451(M + 1) FAB |
| 72 | H | 1 | 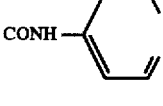 | 0.62 | 0.97 | 5.81(d,1H,1-H); 6.81(d,1H,2-H); 6.78(s,2H,ArH) | m/e410(M+) EI |
| 73 | H | 1 | 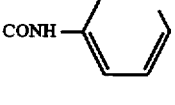 | 0.64 | 0.97 | 5.78(d,1H,1-H); 6.83(d,1H,2-H); 7.58(d,2H,ArH); 8.39(d,2H,ArH) | m/e(421(M+) EI |
| 74 | H | 1 | 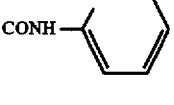 | 0.63 | 0.96 | 5.79(d,1H,1-H); 6.79(d,1H,2-H); 7.28(m,1H,ArH); 8.27(m,2H,ArH); 8.58(s,1H,ArH) | m/e422(M + 1) FAB |
| 75 | H | 1 |  | 0.64 | 0.98 | 5.81(d,1H,1-H); 6.81(d,1H,2H); 7.04(m,1H,ArH); 7.96(m,1H,ArH); 8.24(m,2H,ArH) | m/e422(M + 1) FAB |

TABLE 10-continued

| Compd | R20 | n | R4 | NMR 18-Me | 19-Me | Other | Mass Spectrum |
|---|---|---|---|---|---|---|---|
| 76 | H | 1 | CONH—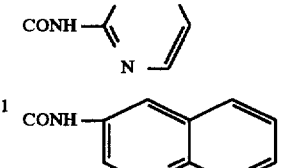 (tetrazole/triazole ring with N=N) | 0.64 | 0.97 | 5.81(d,1H,1-H); 6.80(d,1H,2-H); 8.51(d,1H,ArH); 8.96(d,1H,ArH) | m/e423(M+) EI |
| 77 | H | 1 | CONH—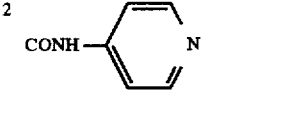 (quinolinyl) | 0.64 | 0.95 | 5.82(d,1H,1-H); 6.86(d,1H,2-H); 7.52–8.06(m,4H,ArH); 8.71–8.95(m,2H,ArH) | m/e472(M + 1) FAB |
| 78 | Me | 2 | CO2H | 0.63 | 0.83 | 0.87(d,3H,21-Me); 5.59(d,1H,1-H); 6.78(d,1H,2-H); | |
| 79 | Me | 2 | CO2Me | 0.66 | 0.95 | 0.91(s,3H,21-Me); 3.64(s,3H,OMe); 5.41(s,1H,4-NH); 5.78(d,1H,1-H); 6.77(d,1H,2-H) | |
| 80 | Me | 2 | CONH—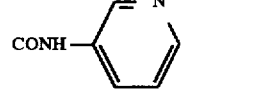 (pyridyl) | 0.68 | 0.97 | 0.95(d,3H,21-Me); 5.46(s,1H,4-NH); 5.81(d,1H,1-H); 6.80(d,1H,2-H); 7.56(d,2H,ArH); 8.13(bs,1H,CONH); 8.46(d,2H,ArH) | |
| 81 | Me | 2 | CONH—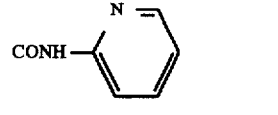 (pyridyl) | 0.68 | 0.96 | 0.94(d,3H,21-Me); 5.58(bs,1H,4-NH); 5.81(d,1H,1-H); 6.80(d,1H,2-H); 7.24(m,1H,ArH); 8.03(m,1H,ArH); 8.22(d,1H,ArH); 8.32(bs,1H,ArH); 8.58(bs,1H,CONH) | |
| 82 | Me | 2 | CONH—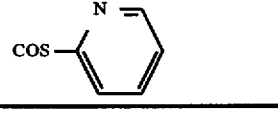 (pyridyl) | 0.69 | 0.96 | 0.97(d,3H,21-Me); 5.54(bs,1H,4-NH); 5.81(d,1H,1-H); 6.79(d,1H,2-H); 7.08(m,1H,ArH); 7.76(m,1H,ArH); 8.26(m,2H,ArH); 8.71(bs,1H,CONH) | |
| 83 | H | 1 | COS—(pyridyl) | 0.62 | 0.97 | 5.80(d,1H,1-H); 6.80(d,1H,2-H); 7.18–7.78(m,3H,ArH); 8.60(d,1H,ArH) | |

Another preferred embodiment of this invention is a series of compounds characterized in having ether moieties at the 17 position, and which can be synthesized according to the following flowsheet:

Flowsheet XXXXVI

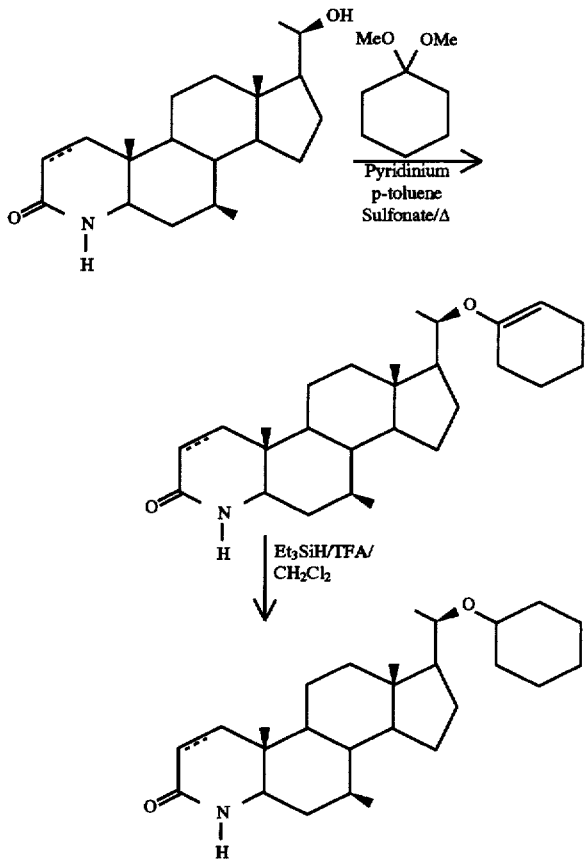

EXAMPLE 228

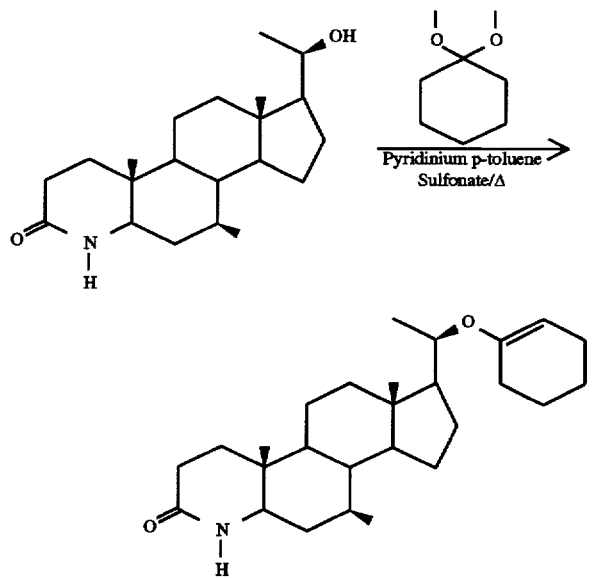

To a solution of Azasteroid (250 mg) in dimethoxycyclohexane (10 ml) was added pyridinum p-toluenesulfonate and reaction mixture was heated at 140° for 2hrs. The temperature of reaction was increased and dimethoxycyclohexane was removed slowly by distillation over 4 hrs. Finally all the dimethoxycyclohexane was distilled off and residue taken in ethyl acetate, washed with aqueous sodium bicarbonate, brine, dried and concentrated to give 2. MS calculated for $C_{27}H_{43}NO_2$, 413.65. Observed 413 (EI).

EXAMPLE 229

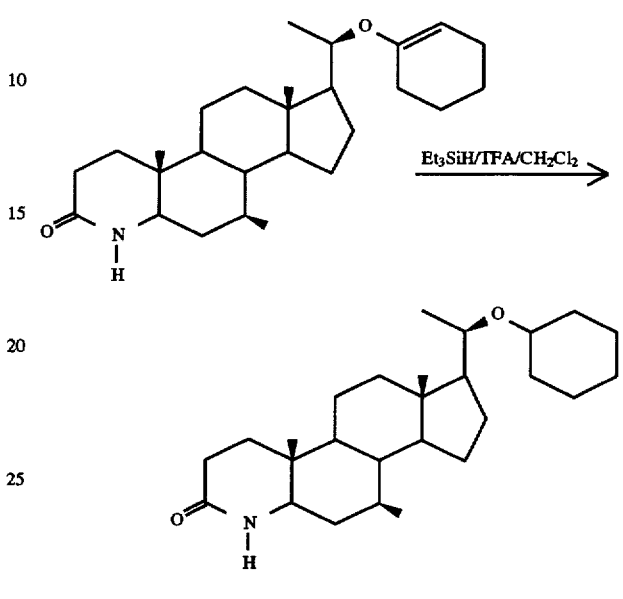

To a solution of Enol Ether (150 mg) in $CH_2Cl_2$ (2 ml) was added triethylsilane (418.6 mg, 10 eq.) followed by slow dropwise addition of TFA (2.07 g). After stirring the reaction for overnight at room temperature, the reaction mixture was diluted with $CH_2Cl_2$, washed with aq. $NaHCO_3$, brine, dried and concentrated. The residue was purified by prep. tlc over silica gel using 30% acetone/ $CH_2Cl_2$ as solvent. MS calculated for $C_{27}H_{45}NO_2$, 415.66. Observed 415(EI).

An additional preferred embodiment of the invention is presented in the following Table 8, in which compounds are presented that are readily synthesizeable by one of ordinary skill in this art by following the procedures previously presented and exemplified:

TABLE 11

| $R_4$ | $R_{17}$ |
|---|---|
| $CH_3$ | β-(R) — $CH(CH_3)(CH_2)_3CH(CH_3)_2$ |
| $CH_3$ | β-$COCH_3$ |
| $CH_3$ | β-(E) — $C(CH_3)$ = CH(4-Pyridyl) |
| $CH_3$ | β-(S) — $CH(CH_3)CH_2CN$ |
| $CH_3$ | β-(R))$CH(CH_3)CH_2CN$ |
| $CH_3$ | β-$(CH_2)_2CF_3$ |
| $CH_3$ | β-$OCONHCH(CH_3)_2$ |
| $CH_3$ | β-$(CH_2)_2CO_2$ — Ph |
| $CH_3$ | β-$(CH_2)_2$-(1-Phenyltetrazol-5-yl) |

TABLE 11-continued

| | | |
|---|---|---|
| CH₃ | | β-(CH₂)₂-(2-Methyl-1,3,4-oxadiazol-5-yl) |
| CH₃ | | β-CH₂CONH-(4-Pyridyl) |
| CH₃ | | β-CH₂CH₃ |
| CH₃ | | Δ¹⁶ |
| CH₃ | | 17-H |
| Me | | 3-thiophenecarboxamido |
| Me | | 2-methyl-3-fluorobenzamido |
| Me | | phenylthioacetamido |
| Me | | t-butylthioacetamido |
| Me | | phenylthioacetamido |
| Me | | 2-fluorobenzamido |
| Me | | 2-thiophenesulfonamido |
| Me | | 2,3-difluorobenzamido |
| Me | | isopropylthioacetamido |
| Me | | O-((isopropylthio)acetyl)oximino |
| Me | | 9-(isopropylthio)nonanoylamido |
| Me | | β-O-phenyl-p-cyano |
| Me | | β-O—CH₂COOEt |
| Me | | β-O—CH₂COOH |
| Me | | β-O—CH₂CONHPh |
| Me | | β-O—CH₂CONHPh-p-COMe |
| Me | | exo-methylene |
| Me | | 17α-OH, 17β-CH₂N₃ |
| Me | | β-Me |
| Me | | α-OH, β-CH₂NHCMe₃ |
| Me | | α-OH, β-CH₂NH₂ |
| Me | | cyclopropyl-16-ene | part 2

| C₁₈ | C₁₉ | 7β-CH₃ | other | °C. | M⁺ or M + 1⁺ |
|---|---|---|---|---|---|
| 0.93 | 0.89 | 1.15 d | 1.2 d | 63–65 | 415 (M+) |
| 0.63 | 0.85 | 1.06 d | 2.13(s,3H,COMe) | | |
| 0.64 | 0.84 | 1.09 d | 1.91(s,3H, C=CMe); 6.23(s,1H,C=CH); 7.17(bs,2H,ArH); 8.55(bs,2H,ArH) | | |
| 0.71 | 0.85 | 1.05 d | 1.19(d,3H,21-Me) | | |
| 0.70 | 0.84 | 1.05 d | 1.08(d,3H,21-Me) | | |
| 0.62 | 0.85 | 1.06 d | | | |
| 0.76 | 0.84 | 1.04 d | 1.15(d,6H,CHMe₂); 4.49(t,1H,17-H) | | |
| 0.64 | 0.84 | 1.05 d | 7.04–7.39(m,5H,Ar) | | 451(M⁺) |
| 0.56 | 0.85 | 1.04 d | 7.43–7.63(m,5H,Ar) | | 476(M + 1)⁺ |
| 0.63 | 0.85 | 1.05 d | 2.49(s,3H, C(CH₃)=N | | 413(M⁺) |
| 0.64 | 0.86 | 1.06 d | 7.54(d,2H,Ar); 8.48(d,2H,Ar) | | 437(M⁺) |
| 0.55 | 0.83 | 1.02 d | 0.84(t,3H,CH₃) | | 332(M⁺) |
| 0.74 | 0.85 | 1.04 d | 5.65(m,1H,16-H); 5.78(m,1H,17H) | | |
| 0.70 | 0.83 | 1.05 d | 2.92(s,3H,N—Me) | | 304(M⁺) |
| 0.755 | 0.833 | 1.033 | 2.904(N—Me) | | M+ = 428 |
| 0.76 | 0.85 | 1.04 | 2.82(N—Me) | | M+ = 454 |
| 0.441 | 0.784 | 0.975 | 2.879(N—Me) | | M+ = 468 |
| 0.719 | 0.820 | 1.011 | 2.891(N—Me) | | M+ = 448 |
| 0.446 | 0.784 | | 2.879(N—Me) | | M+ = 524 |
| 0.777 | 0.839 | 1.037 | 2.907(N—Me) | | M + 1 = 440 |
| 0.688 | 0.812 | 0.975 | 2.884(N—Me) | | M+ = 464 |
| 0.799 | 0.858 | 1.048 | 2.923(N—Me) | | M+ = 458 |
| 0.88 | 0.94 | 1.07 | 2.93(N—Me), 4.14(t,17α) | 200–202 | M⁺ = 420 |
| 0.82 | 0.86 | 1.05 | 2.92, 3.38(t,17α), 4.09(OCH₂) | | M⁺ = 405 |
| 0.84 | 0.86 | 1.05 | 2.92, 3.42(t,17α), 4.10(OCH₂) | 163–166 | M + 1⁺ = 378 |
| 0.88 | 0.89 | 1.06 | 2.92, 3.42(t,17α), 4.06(OCH₂) | 175.5–178.5 | M + 1⁺ = 453 |
| 0.89 | 0.90 | 1.07 | 2.58(MeCO), 2.93, 3.44(t,17α), 4.07 (OCH₂) | 212–216 | M + 1⁺ = 495 |
| 0.82 | 0.88 | 1.10 | 2.92, 4.67(m, =CH₂) | 85–87.5 | M⁺ = 315 |
| 0.78 | 0.88 | 1.07 | 2.93, 3.49(ABq, CH₂N) | 243.5–246 | M + 1⁺ = 375 |
| 0.57 | 0.87 | 1.06 | 0.83(d,17β-Me) | 98–100 | M⁺ = 318 |
| 0.75 | 0.89 | 1.07 | 1.28(CMe₃), 2.76 (ABq, CH₂N) | | M⁺ = 404 |
| 0.76 | 0.87 | 1.09 | | 272–277 | M⁺ = 348 |
| 0.83 | 0.89 | 1.06 | 0.39(m,2H, cyclopropyl), 0.64 (m, 2H,cyclopropyl), 5.11(m,=CH—) | | M⁺ = 341 |

In this specifications, Rf values cited were carried out on standard thin layer chromatographic Silica gel plates. The elution solvent system used is given in the parentheses following the Rf value.

The mass spectral values cited are given as FAB, i.e., fast atom bombardment, and are reported as (M+1) molecular ion peaks, being the molecular weight plus one atomic mass unit. The electron impact (EI) mass spectrum values cited are reported as molecular ion peaks and are indicated in parentheses, either being (M) or (M+2), the molecular weight, MW, or the MW plus two atomic units.

The nuclear magnetic resonance data was taken at 400 MHz in CDCl₃ and is tabulated for representative unique proton values. The coupling constant J is given in Hertz, Hz.

The present invention has the objective of providing suitable topical, oral and parenteral pharmaceutical formulations for use in the novel methods of treatment of the present invention.

The compositions containing the compounds of the present invention as the active ingredient for use in the treatment of e.g., benign prostatic hypertrophy, prostatitis, and treatment of prostatic carcinoma, hyperandrogenic conditions, can be administered in a wide variety of therapeutic dosage forms in conventional vehicles for systemic administration, as, for example, by oral administration in the form of tablets, capsules, solutions, or suspensions, or by injection. The daily dosage of the products may be varied over a wide range varying from 0.5 to 1,000 mg per adult human/per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. For the treatment of androgenic alopecia, acne vulgaris, seborrhea, female hirsutism, the compounds of the present invention are administered in a pharmaceutical composition comprising the active compound in combination with a pharmacologically acceptable carrier adapted for topical, oral or parenteral administration.

These topical pharmaceutical compositions may be in the form of a cream, ointment, ge or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a 5α-reductase agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

Oral dosages of the present invention, when used for the indicated effects, will range between about Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

BIOLOGICAL ASSAYS

Preparation of Human prostatic and scalp 5a-reductases.

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay.

The reaction mixture contained in a final volume of 100 μl is: 40 mM buffer (human scalp, potassium phosphate, pH 6.5; human prostatic 5α-reductase, sodium citrate, pH 5.5), 0.3–10 μM $^{14}$C-T (or $^3$H-T), 1 mM DTT, and 500 μM NADPH. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate: retention times DHT, 6.8–7.2 min; androstanediol, 7.6–8.0; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Stumptail macaque protocol

The following protocol is utilized with the stumptail macaque monkey to demonstrate the effect of compounds of the present invention for promoting hair growth.

Twenty-one male stumptail macaque monkeys of species *Macaca speciosa* are assigned to vehicle control and drug treatment groups on the basis of baseline hair weight data. This assignment procedure is necessary to insure that the average baseline hair growth for each control and experimental group is comparable. The control and drug treatment groups are as follows:

1. Topical 50:30:20 vehicle (N=6)
2. Oral 5α-reductase and topical 50:30:20 vehicle (N=5)

3. Oral placebo (N=5)
4. 5α-reductase in vehicle (N=5)

The vehicle consists of 50% propylene glycol, 30% ethanol and 20% water. A 100 mM concentration of topical 5α-reductase is formulated in this vehicle. The same 5α-reductase is administered as an oral dose of 0.5 mg per monkey. Immediately prior to the dosing phase of the study, hair is removed from a 1 inch square area (identified by four tatoos) in the center of the balding scalp. This hair collection is the baseline hair growth determination prior to the beginning of treatment. Approximately 250 µL of vehicle and 5α-reductase in vehicle is prepared and topically administered to the tatooed area of the scalp. The selected 5α-reductase and placebo is ingested by the monkeys at the same time as the topical doses are administered. The monkeys are dosed once per day, seven days per week for twenty weeks.

At four week intervals throughout the dosing phase of the study, each monkey is shaved and the hair is collected and weighed. The body weight data (at baseline and during assay) is analyzed by the nonparametric Wilcoxon rank-sum test. Differences are significant at p<0.05. Hair weight data at each week collection for vehicle, placebo and treatment groups are expressed as the change from baseline. Statistical analysis is performed on the rank of the data to show overall differences among groups at each four week collection.

While the invention has been described and illustrated with reference to certain preferred embodiments thereof, those skilled in the an will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound selected from:
   20(R)-methoxy-4,16β-dimethyl-5α-4-aza-pregnan-3-one,
   20(R)-allyloxy-4,16β-dimethyl-5α-4-aza-pregnan-3-one,
   20(R)-n-propyloxy-4,16β-dimethyl-5α-4-aza-pregnan-3-one, and
   20(R)-(3-methyl-2-butenyloxy)-4,16β-dimethyl-5α-4-aza-pregnan-3-one.

* * * * *